US010415052B2

(12) United States Patent
Loque et al.

(10) Patent No.: US 10,415,052 B2
(45) Date of Patent: Sep. 17, 2019

(54) TISSUE SPECIFIC REDUCTION OF LIGNIN

(71) Applicant: THE REGENTS OF THE UNIVERSITY OF CALIFORNIA, Oakland, CA (US)

(72) Inventors: Dominique Loque, Albany, CA (US); Aymerick Eudes, Emeryville, CA (US)

(73) Assignee: The Regents of the University of California, Oakland, CA (US)

( * ) Notice: Subject to any disclaimer, the term of this patent is extended or adjusted under 35 U.S.C. 154(b) by 361 days.

(21) Appl. No.: 14/774,614

(22) PCT Filed: Mar. 11, 2014

(86) PCT No.: PCT/US2014/023443
§ 371 (c)(1),
(2) Date: Sep. 10, 2015

(87) PCT Pub. No.: WO2014/150504
PCT Pub. Date: Sep. 25, 2014

(65) Prior Publication Data
US 2016/0017355 A1 Jan. 21, 2016

Related U.S. Application Data

(60) Provisional application No. 61/792,864, filed on Mar. 15, 2013.

(51) Int. Cl.
C12N 9/88 (2006.01)
C12N 15/82 (2006.01)

(52) U.S. Cl.
CPC .......... C12N 15/8255 (2013.01); C12N 9/88 (2013.01); C12Y 402/01118 (2013.01)

(58) Field of Classification Search
CPC ... C12N 9/88; C12N 15/8246; C12N 15/8255
See application file for complete search history.

(56) References Cited

U.S. PATENT DOCUMENTS

| | | | |
|---|---|---|---|
| 6,087,557 A | 7/2000 | Clausen et al. | |
| 2007/0118916 A1 | 5/2007 | Puzio et al. | |
| 2010/0319091 A1 | 12/2010 | Vainstein et al. | |
| 2014/0245496 A1* | 8/2014 | Hansen | C12Y 402/01118 800/298 |

FOREIGN PATENT DOCUMENTS

| | | | |
|---|---|---|---|
| WO | 2013/010124 A1 | 1/2013 | |
| WO | WO/2013/010124 | * | 1/2013 |

OTHER PUBLICATIONS

Withers et al (The Journal of Biological Chemistry vol. 287, No. 11, pp. 8347-8355, Mar. 9, 2012) (Year: 2012).*
Eudes et al (Plant Biotechnology Journal (2012) 10, pp. 609-620) (Year: 2012).*
Wang et al (2013). Plant cell wall lignification and monolignol metabolism. Front Plant Sci. 4. (Year: 2013).*
Abe et al., "Benzalaceton synthase a novel polyketide synthase that plays a crucial role in the biosynthesis of phenylbutanones in *Rheum palmatum*," Eur. J. Biochem., 2001, vol. 268, pp. 3354-3359.
Baucher et al., "Lignin: Genetic engineering and impact on pulping," Crit. Rev. Biochem. and Mol. Biol., 2003, vol. 38(4), pp. 305-350.
Boerjan et al., "Lignin biosynthesis," Annu Rev. Plant. Biol., 2003, vol. 54, pp. 519-546.
Bonawitz et al., "Can genetic engineering of lignin deposition be accomplished without an unacceptable yield penalty?" Curr. Opin. Biotechnol., 2013, vol. 24(2), pp. 336-343.
Chen et al., "Lignin modification improves fermentable sugar yields biofuel production," Nat. Biotechnol., Jul. 2007, vol. 25(7), pp. 759-761.
Dao et al., "Chalcone synthase and its functions in plant resistance," Phytochem Rev., Sep. 2011, vol. 10, pp. 397-412.
Duncan et al., "The pentafunctional arom enzyme of *Saccharomyces cerevisiae* is a mosaic of monofunctional domains," Biochem. J., 1987, vol. 246, pp. 375-386.
Eudes et al., "Lignin bioengineering," Curr Opin. Biotechnol., Apr. 2014, vol. 26, pp. 189-198, doi: 10.1016/j.copbio.2014.01.002.
Eudes et al., "Biosynthesis and incorporation of side-chain-truncated lignin monomers to reduce lignin polymerization and enhance saccharification," Plant Biotech Journal, 2012, vol. 10(5), pp. 609-620.
Farhi et al., "Identification of rose phenylacetaldehyde synthase by functional complementation in yeast," Plant Mol. Biol., 2010, vol. 72, pp. 235-245.
Feng et al., "Mechanistic, Mutational, and Structural Evaluation of a *Taxus* Phenylalanine Aminomutase," Biochemistry, 2011, vol. 50, pp. 2919-2930.
Franke et al., "The *Arabidopsis* REF8 gene encodes the 3-hydroxylase of phenylpropanoid metabolism," The Plant J., 2002, vol. 30(1), pp. 33-45.
Gu et al., "Crystal Structure of Shikimate Kinase from *Mycobacterium tuberculosis* Reveals the Dynamic Role of the LID Domain in Catalysis," J. Mol. Biol., 2002, vol. 319, pp. 779-789.
Hansen et al., "De Novo Biosynthesis of Vanillin in Fission Yeast (*Schizosaccharomyces pombe*) and Baker's Yeast (*Saccharomyces cerevisiae*)," Appl. Environ. Microbiol., May 2009, vol. 75, pp. 2765-2774.
Jorgensen et al., "Enzymatic conversion of lignocellulose into fermentable sugars: challenges and opportunities," Biofuel Bioprod. Bior., 2007, vol. 1, pp. 119-134.

(Continued)

Primary Examiner — Lee A Visone
(74) Attorney, Agent, or Firm — Kilpatrick Townsend & Stockton LLP

(57) ABSTRACT

The present invention provides an expression cassette comprising a polynucleotide that encodes a protein that diverts a monolignol precursor from a lignin biosynthesis pathway in the plant, which is operably linked to a heterologous promoter. Also provided are methods of engineering a plant having reduced lignin content, as well as plant cells, plant parts, and plant tissues from such engineered plants.

15 Claims, 28 Drawing Sheets

Specification includes a Sequence Listing.

(56) References Cited

OTHER PUBLICATIONS

Kaminaga et al., "Plant Phenylacetaldehyde Synthase Is a Bifunctional Homotetrameric Enzyme That Catalyzes Phenylalanine Decarboxylation and Oxidation," J. Biol. Chem., Aug. 2006, vol. 281(33), pp. 23357-23366.

Kapteyn et al., "Evolution of Cinnamate/p-coumarate carboxyl methyltransferases and their role in the biosynthesis of methylcinnamate," The Plant Cell, Oct. 2007, vol. 19, pp. 3212-3229.

Katsuyama et al., "In vitro synthesis of curcuminoids by type III polyketide synthase from *Oryza sativa*," J. Biol. Chem., Dec. 2007, vol. 282, pp. 37702-37709.

McKenna et al., "Styrene biosynthesis from glucose by engineered *E. coli*," Metab. Eng., 2011, vol. 13, pp. 544-554, doi:10.1016/j.ymben.2011.06.005.

Shadle et al., "Down-regulation of hydroxycinnamoyl CoA: Shikimate hydroxycinnamoyl transferase in transgenic alfalfa affects lignification, development and forage quality," Phytochemistry, 2007, vol. 68, pp. 1521-1529.

Teramoto et al., "Regulation of expression of genes involved in quinate and shikimate utilization in Corynebacterium glutamicum," Appl. Environ. Microbiol., Jun. 2009, vol. 75, pp. 3461-3468.

Vialart et al., "A 2-oxoglutarate-dependent dioxygenase from *Ruta graveolens* L. exhibits p-coumaroyl CoA 2'-hydroxylase activity (C2'H): a missing step in the synthesis of umbelliferone in plants," The Plant J., 2012, vol. 70, pp. 460-470.

Vinzant et al., "Simultaneous Saccharification and Fermentation of Pretreated Hardwoods, Effect of Native Lignin Content," Appl. Biochem. and Biotechnol., 1997, vol. 62, pp. 99-104.

Voelker et al., "Antisense down-regulation of 4CL expression alters lignification, tree growth, and saccharification potential of field-grown poplar," Plant Physiol., Oct. 2010, vol. 154, pp. 874-886.

Voelker et al., "Transgenic poplars with reduced lignin show impaired xylem conductivity, growth efficiency and survival," Plant, Cell & Environ., 2011, vol. 34(4), pp. 655-668.

Yan et al., "The heterologous expression in *Arabidopsis thaliana* of sorghum transcription factor SbbHLHa downregulates lignin synthesis," J. Exp. Bot., 2013, vol. 64(10), pp. 3021-3302.

Yang et al., "Engineering secondary cell wall deposition in plants," Plant Biotechnol J., 2013, vol. 11(3), pp. 325-335.

Zhang et al., "An engineered monolignol 4-o-methyltransferase depresses lignin biosynthesis and confers novel metabolic capability in *Arabidopsis*," Plant Cell, 2012, vol. 24(7), pp. 3135-3152.

International Search Report and Written Opinion, dated Sep. 10, 2014, PCT application No. PCT/US14/23443, 18 pages.

\* cited by examiner

FIG. 2

PRECURSOR DEPLETION STRATEGY TO REPRESS ENZYMATIC STEPS:
*Depletion of phenylalanine: PAL substrate*
(1) Cytosolic depletion of phenylalanine
TcPAM: Taxus phenylalanine aminomutase
(2) Plastidial depletion of phenylalanine
TcPAM + plastid targeting signal TcOAM: Taxus phenylalanine aminomutase
(PAM catalyst isomerizes (S)-alpha-phenylalanine to the (R)-beta-isomer)

FIG. 5

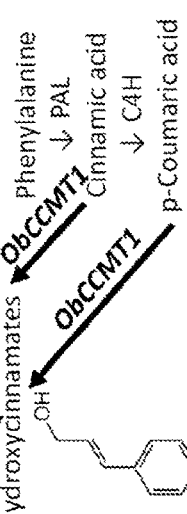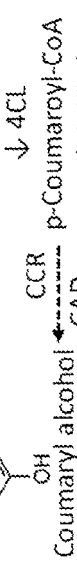
FIG. 6

PRECURSOR DEPLETION STRATEGY TO REPRESS ENZYMATIC STEPS:
*Depletion of coumaroyl-CoA: HCT substrate*
Cytosolic depletion of coumaroyl-CoA Chalcone, Trihydroxychalcone,
CHS/SPS/CUS/BAS: Stilbene, Curuminoid,
Chalcone synthase, stilbene synthase, benzalacetone
curcuminoid synthase, benzalacetone
synthase

FIG. 9

FIG. 19
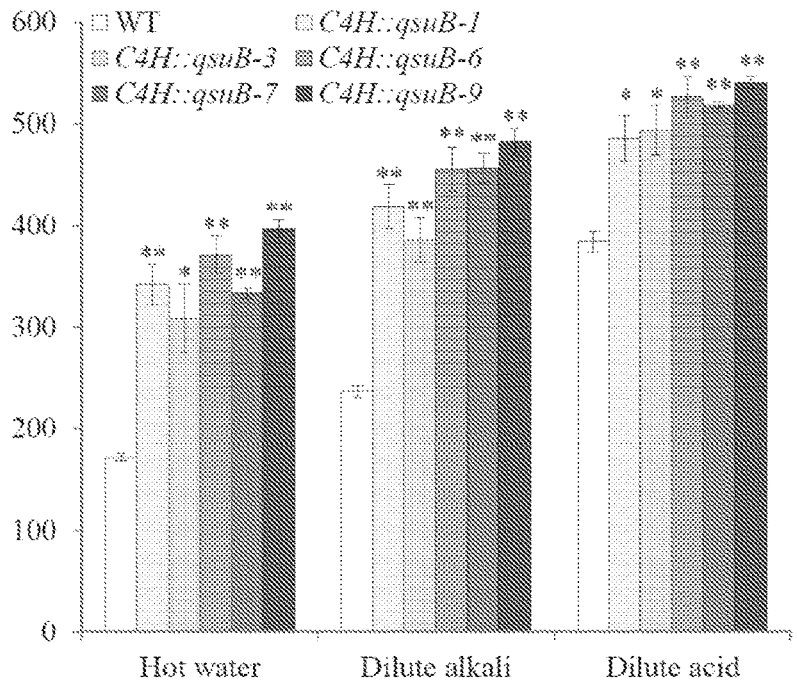
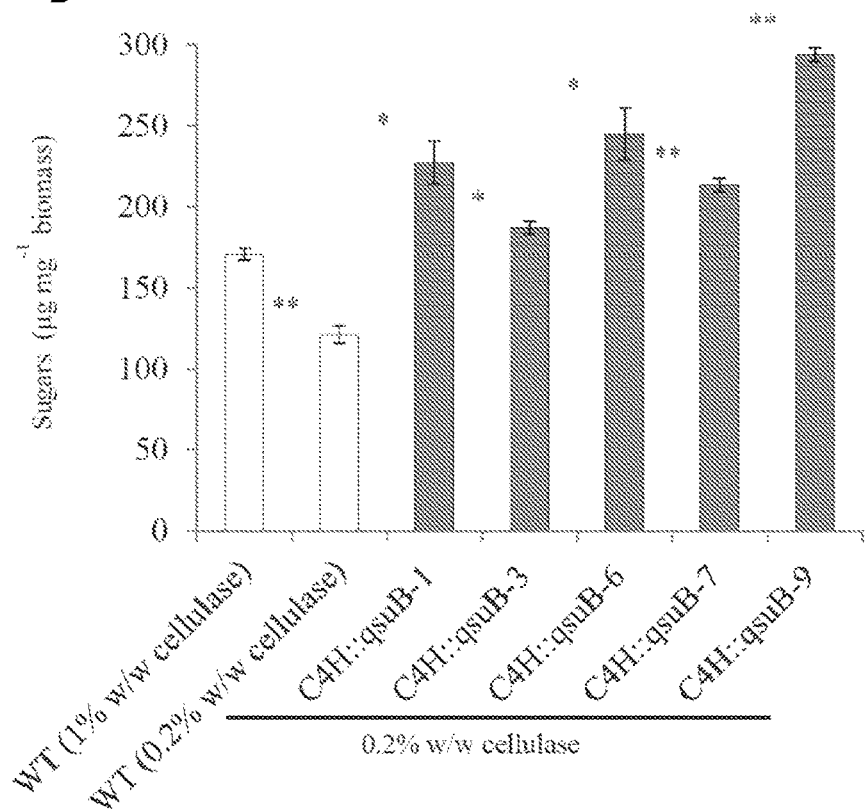

FIG. 28

| Compound name | Origin | Formula | Molecular mass | Main mass fragments | Elution time (min) | WT (%) | C4H-cpsuB-1 (%) | C4H-cpsuB-9 (%) |
|---|---|---|---|---|---|---|---|---|
| Phenol | H | C₆H₆O | 94 | 65, 66, 94 | 4.28 | 1.3 (0.1) | 5.1 (0.1) | 10.5 (0.3) |
| 2-Methylphenol | H | C₇H₈O | 108 | 77, 107, 108 | 4.96 | 0.6 (0.0) | 1.5 (0.1) | 5.7 (0.0) |
| 3-Methylphenol | H | C₇H₈O | 108 | 77, 107, 108 | 5.16 | 1.4 (0.2) | 4.6 (0.5) | 10.9 (0.9) |
| 2-Methoxyphenol | G | C₇H₈O₂ | 124 | 81, 109, 124 | 5.34 | 5.6 (0.0) | 3.7 (0.1) | 3.1 (0.4) |
| 2,5-Dimethylphenol | H | C₈H₁₀O | 122 | 77, 107, 122 | 5.93 | 0.4 (0.1) | 1.7 (0.1) | 4.1 (0.2) |
| 4-Ethylphenol | H | C₈H₁₀O | 122 | 77, 107, 122 | 6.15 | nd | nd | 5.3 (0.3) |
| 2-Methoxy-5-methylphenol | G | C₈H₁₀O₂ | 138 | 95, 123, 138 | 6.45 | 7.6 (0.3) | 9.0 (0.8) | 4.0 (0.1) |
| 4-Ethyl-2-methoxyphenol | G | C₉H₁₂O₂ | 152 | 123, 137, 152 | 7.45 | 3.3 (0.1) | 1.6 (0.2) | 4.2 (0.1) |
| 4-Ethenyl-2-methoxyphenol | G | C₉H₁₀O₂ | 150 | 107, 135, 150 | 7.88 | 18.9 (0.4) | 18.9 (0.2) | 12.3 (0.2) |
| 2,6-Dimethoxyphenol | S | C₈H₁₀O₃ | 154 | 111, 139, 154 | 8.36 | 2.1 (0.1) | 1.4 (0.1) | 4.4 (0.3) |
| 2-Methoxy-4-propenylphenol | G | C₁₀H₁₂O₂ | 164 | 131, 149, 164 | 8.41 | 3.3 (0.0) | 2.6 (0.6) | nd |
| 4-hydroxy-3-methoxyphenylacetaldehyde | G | C₁₀H₁₄O₂ | 166 | 122, 137, 166 | 8.82 | 0.4 (0.0) | 0.6 (0.0) | nd |
| Hydroxy-3-methoxybenzaldehyde | G | C₈H₈O₃ | 152 | 109, 151, 152 | 9.02 | 8.6 (0.3) | nd | 0.3 (0.1) |
| 4-Methyl-2,6-dimethoxyphenol | S | C₉H₁₂O₃ | 168 | 125, 153, 168 | 9.47 | 3.1 (0.1) | 3.1 (0.0) | 1.9 (0.1) |
| 2-Methoxy-4-propenylphenol | G | C₁₀H₁₂O₂ | 164 | 131, 149, 164 | 9.52 | 11.4 (0.2) | 8.9 (0.2) | 5.3 (0.4) |
| 4-Ethyl-2,6-dimethoxyphenol | S | C₁₀H₁₄O₃ | 182 | 167, 182 | 10.42 | 1.1 (0.1) | 0.9 (0.3) | 2.2 (0.1) |
| 4-Hydroxy-3-methoxyphenyl acetone | G | C₁₀H₁₂O₃ | 180 | 122, 137, 180 | 10.56 | 2.1 (0.1) | nd | nd |
| 4-Hydroxy-3,5-dimethoxystyrene | S | C₁₀H₁₂O₃ | 180 | 137, 165, 180 | 10.88 | 10.5 (0.3) | 16.5 (0.5) | 12.7 (0.2) |
| 4-Allyl-2,6-dimetoxyphenol | S | C₁₁H₁₄O₃ | 194 | 167, 179, 194 | 11.32 | 2.3 (0.2) | 3.6 (0.3) | 1.0 (0.3) |
| 4-Hydroxy-3,5-dimethoxybenzaldehyde | S | C₉H₁₀O₄ | 182 | 167, 181, 182 | 12.07 | 2.6 (0.1) | nd | 1.4 (0.3) |
| 4-Propinyl-2,6-dimethoxyphenol | S | C₁₁H₁₄O₃ | 192 | 106, 131, 177, 192 | 12.23 | 0.9 (0.1) | 1.1 (0.4) | nd |
| Propenyl-2,6-dimethoxyphenol | S | C₁₁H₁₄O₃ | 194 | 162, 179, 194 | 12.43 | 7.8 (0.5) | 9.1 (0.3) | 6.6 (1.2) |
| 4-Hydroxy-3,5-dimethoxyacetophenone | S | C₁₀H₁₂O₄ | 196 | 153, 181, 196 | 12.88 | 0.8 (0.1) | 0.9 (0.6) | 0.4 (0.2) |
| 4-hydroxy-3-methoxycinnamaldehyde | G | C₁₀H₁₀O₃ | 178 | 107, 135, 147, 178 | 13.00 | 2.2 (0.4) | nd | nd |
| 4-hydroxy-3,5-dimethoxyphenyllactone | S | C₁₁H₁₄O₄ | 210 | 123, 167, 210 | 13.26 | 1.3 (0.0) | 2.2 (0.2) | 3.9 (0.5) |
| 4-Hydroxy-3,5-dimethoxyphenylethanone | S | C₁₀H₁₂O₄ | 196 | 153, 181, 196 | 13.83 | 0.5 (0.0) | nd | nd |
| % H-units | | | | | | 3.7 (0.2) | 13.2 (0.7) | 36.8 (1.3) |
| % G-units | | | | | | 63.3 (0.3) | 46.8 (0.9) | 29.3 (0.3) |
| % S-units | | | | | | 32.7 (0.7) | 40.0 (0.2) | 33.9 (1.0) |

TISSUE SPECIFIC REDUCTION OF LIGNIN

CROSS-REFERENCE TO RELATED APPLICATIONS

This application is a national stage application under 35 U.S.C. § 371 of PCT/US2014/023443, filed Mar. 11, 2014, which claims the benefit of U.S. Provisional Application No. 61/792,864, filed Mar. 15, 2013, each of which is incorporated by reference herein for all purposes.

STATEMENT AS TO RIGHTS TO INVENTIONS MADE UNDER FEDERALLY SPONSORED RESEARCH AND DEVELOPMENT

This invention was made with government support under Contract No. DE-AC02-05CH11231 awarded by the U.S. Department of Energy. The government has certain rights in this invention.

REFERENCE TO A SEQUENCE LISTING

The Sequence Listing written in file 07742-011610US-0957057 SequenceListing.txt, created on Sep. 10, 2015, 158,485 bytes, machine format IBM-PC, MS-Windows operating system, is hereby incorporated by reference in its entirety for all purposes.

BACKGROUND OF THE INVENTION

Plant lignocellulosic biomass is used as a renewable feedstock for biofuel production and is a promising alternative to fossil fuel consumption. However, a major bottleneck in biofuel production is the quality of available feedstocks. Available feedstocks have a high resistance (recalcitrance) to being reduced into simple sugars that can in turn be converted into fuel. Therefore, improving the composition and/or digestibility of the raw biomass will have an important beneficial impact on lignocellulosic biofuels production.

Lignocellulosic biomass is mainly composed of secondary cell walls, which comprise polysaccharide polymers embedded in lignin. The embedding of the polysaccharide polymers in lignin reduces their extractability and accessibility to hydrolytic enzymes, resulting in cell wall recalcitrance to enzymatic hydrolysis. Lignin content and saccharification efficiency of plant cell wall usually are highly negatively correlated. See, e.g., Chen and Dixon, *Nat. Biotechnol.* 25:759-761 (2007); Jorgensen et al., *Biofuel Bioprod. Bior.* 1:119-134 (2007); and Vinzant et al., *Appl. Biochem. Biotechnol.* 62:99-104 (1997). However, most attempts at reducing lignin content during plant development have resulted in severe biomass yield reduction (Franke et al., *Plant J.* 30:33-45 (2002); Shadle et al., *Phytochemistry* 68:1521-1529 (2007); and Voelker et al., *Plant Physiol.* 154:874-886 (2010)) and therefore, there are few crops having significant lignin reduction. Although silencing strategies have been used to reduce the amount of lignin in plants, there remains a need for methods of reducing lignin in specific cell and tissue types that reduce cell wall recalcitrance, thus improving the extractability and hydrolysis of fermentable sugars from plant biomass.

BRIEF SUMMARY OF THE INVENTION

In one aspect, the present invention provides methods of engineering a plant having reduced lignin content. In some embodiments, the method comprises:

introducing into the plant an expression cassette comprising a polynucleotide that encodes a protein that diverts a monolignol precursor from a lignin biosynthesis pathway (e.g., a p-coumaryl alcohol, sinapyl alcohol, and/or coniferyl alcohol biosynthesis pathway) in the plant, and wherein the polynucleotide is operably linked to a heterologous promoter; and culturing the plant under conditions in which the protein that diverts the monolignol precursor from the lignin biosynthesis pathway is expressed.

In some embodiments, the protein reduces the amount of cytosolic and/or plastidial shikimate that is available for the lignin biosynthesis pathway. In some embodiments, the protein is shikimate kinase (AroK), pentafunctional AROM polypeptide (ARO1), dehydroshikimate dehydratase (DsDH), or dehydroshikimate dehydratase (QsuB). In some embodiments, the protein is substantially identical to an amino acid sequence of SEQ ID NO:2, SEQ ID NO:4, SEQ ID NO:6, or SEQ ID NO:8.

In some embodiments, the protein reduces the amount of cytosolic and/or plastidial phenylalanine that is available for the lignin biosynthesis pathway. In some embodiments, wherein the protein is phenylacetaldehyde synthase (PAAS) or phenylalanine aminomutase (PAM). In some embodiments, the protein is substantially identical to an amino acid sequence of SEQ ID NO:10 SEQ ID NO:29.

In some embodiments, the protein reduces the amount of cinnamate and/or coumarate that is available for the lignin biosynthesis pathway. In some embodiments, the protein is p-coumarate/cinnamate carboxylmethltransferase (CCMT1) or phenylacrylic acid decarboxylase (PDC). In some embodiments, the protein is substantially identical to an amino acid sequence of SEQ ID NO:12 or SEQ ID NO:30.

In some embodiments, the protein reduces the amount of coumaroyl-CoA, caffeoyl-CoA, and/or feruloyl-CoA that is available for the lignin biosynthesis pathway. In some embodiments, the protein is 2-oxoglutarate-dependent dioxygenase (C2'H), chalcone synthase (CHS), stilbene synthase (SPS), cucuminoid synthase (CUS), or benzalacetone (BAS). In some embodiments, the protein is substantially identical to an amino acid sequence of SEQ ID NO:14, SEQ ID NO:31, SEQ ID NO:32, SEQ ID NO:33, SEQ ID NO:34, SEQ ID NO;35, or SEQ ID NO:36.

In some embodiments, the protein activates or potentiates a metabolic pathway that competes with the lignin biosynthesis pathway for the use of monolignol precursors. In some embodiments, the metabolic pathway is a stilbene biosynthesis pathway, a flavonoid biosynthesis pathway, a curcuminoid biosynthesis pathway, or a bensalacetone biosynthesis pathway. In some embodiments, the protein is a transcription factor that activates or potentiates the flavonoid biosynthesis pathway. In some embodiments, the protein is substantially identical to an amino acid sequence of SEQ ID NO:37, SEQ ID NO:38, SEQ ID NO:39, SEQ ID NO:40, SEQ ID NO:41, SEQ ID NO:42, SEQ ID NO:43, SEQ ID NO:44, or SEQ ID NO:45.

In some embodiments, the promoter is a tissue-specific promoter. In some embodiments, the promoter is a secondary cell wall-specific promoter or a fiber cell-specific promoter. In some embodiments, the promoter is an IRX5 promoter. In some embodiments, the promoter is from a gene that is co-expressed in the lignin biosynthesis pathway (phenylpropanoid pathway), e.g., a promoter from a gene expressed in the pathway shown in FIG. 1. In some embodiments, the promoter is a C4H, C3H, HCT, CCR1, CAD4, CAD5, F5H, PAL1, PAL2, 4CL1, or CCoAMT promoter.

In some embodiments, the protein that diverts a monolignol precursor from a lignin biosynthesis pathway is targeted to a plastid in the plant. In some embodiments, the polynucleotide comprises a plastid targeting signal that is substantially identical to the polynucleotide sequence of SEQ ID NO:15.

In some embodiments, the protein diverts a monolignol precursor from a sinapyl alcohol and/or coniferyl alcohol biosynthesis pathway. In some embodiments, the plant has reduced content of guaiacyl (G) and syringyl (S) lignin units.

In some embodiments, the plant (or plant part, or seed, flower, leaf, or fruit from the plant) is selected from the group consisting of *Arabidopsis*, poplar, eucalyptus, rice, corn, switchgrass, sorghum, millet, miscanthus, sugarcane, pine, alfalfa, wheat, soy, barley, turfgrass, tobacco, hemp, bamboo, rape, sunflower, willow, and *Brachypodium*.

In another aspect, the present invention provides a plant cell comprising a polynucleotide that encodes a protein that diverts a monolignol precursor from a lignin biosynthesis pathway in the plant, wherein the polynucleotide is operably linked to a heterologous promoter.

In some embodiments, the plant cell comprises a polynucleotide that encodes a protein that reduces the amount of cytosolic and/or plastidial shikimate that is available for the lignin biosynthesis pathway. In some embodiments, the protein is shikimate kinase (AroK), pentafunctional AROM polypeptide (ARO1), dehydroshikimate dehydratase (DsDH), or dehydroshikimate dehydratase (QsuB). In some embodiments, the protein is substantially identical to an amino acid sequence of SEQ ID NO:2, SEQ ID NO:4, SEQ ID NO:6, or SEQ ID NO:8.

In some embodiments, the plant cell comprises a polynucleotide that encodes a protein that reduces the amount of cytosolic and/or plastidial phenylalanine that is available for the lignin biosynthesis pathway. In some embodiments, wherein the protein is phenylacetaldehyde synthase (PAAS) or phenylalanine aminomutase (PAM). In some embodiments, the protein is substantially identical to an amino acid sequence of SEQ ID NO:10 or SEQ ID NO:29.

In some embodiments, the plant cell comprises a polynucleotide that encodes a protein that reduces the amount of cinnamate and/or coumarate that is available for the lignin biosynthesis pathway. In some embodiments, the protein is p-coumarate/cinnamate carboxylmethltransferase (CCMT1) or phenylacrylic decarboxylase (PDC). In some embodiments, the protein is substantially identical to an amino acid sequence of SEQ ID NO:12 or SEQ ID NO:30.

In some embodiments, the plant cell comprises a polynucleotide that encodes a protein that reduces the amount of coumaroyl-CoA, caffeoyl-CoA, and/or feruloyl-CoA that is available for the lignin biosynthesis pathway. In some embodiments, the protein is 2-oxoglutarate-dependent dioxygenase (C2'H), chalcone synthase (CHS), stilbene synthase (SPS), cucuminoid synthase (CUS), or benzalacetone (BAS). In some embodiments, the protein is substantially identical to an amino acid sequence of SEQ ID NO:14, SEQ ID NO:31, SEQ ID NO:32, SEQ ID NO:33, SEQ ID NO:34, SEQ ID NO;35, or SEQ ID NO:36.

In some embodiments, the plant cell comprises a polynucleotide that encodes a protein activates or potentiates a metabolic pathway that competes with the lignin biosynthesis pathway for the use of monolignol precursors. In some embodiments, the metabolic pathway is a stilbene biosynthesis pathway, a flavonoid biosynthesis pathway, a curcuminoid biosynthesis pathway, or a bensalacetone biosynthesis pathway. In some embodiments, the protein is a transcription factor that activates or potentiates the flavonoid biosynthesis pathway. In some embodiments, the protein is substantially identical to an amino acid sequence of SEQ ID NO:37, SEQ ID NO:38, SEQ ID NO:39, SEQ ID NO:40, SEQ ID NO:41, SEQ ID NO:42, SEQ ID NO:43, SEQ ID NO:44, or SEQ ID NO:45.

In some embodiments, the plant cell comprises a tissue-specific promoter. In some embodiments, the promoter is a secondary cell wall-specific promoter or a fiber cell-specific promoter. In some embodiments, the promoter is an IRX5 promoter. In some embodiments, the plant cell comprises a promoter from a gene that is co-expressed in the lignin biosynthesis pathway (phenylpropanoid pathway), e.g., a promoter from a gene expressed in the pathway shown in FIG. 1. In some embodiments, the promoter is a C4H, C3H, HCT, CCR1, CAD4, CAD5, F5H, PAL1, PAL2, 4CL1, or CCoAMT promoter.

In some embodiments, the plant cell comprises a polynucleotide encoding a protein that diverts a monolignol precursor from a lignin biosynthesis pathway that is targeted to a plastid in the plant. In some embodiments, the polynucleotide comprises a plastid targeting signal that is substantially identical to the polynucleotide sequence of SEQ ID NO:15.

In another aspect, the present invention provides plants comprising a plant cell as described herein. In some embodiments, the plant has reduced lignin content that is substantially localized to secondary cell wall tissue or fiber cells of the plant.

In yet another aspect, the present invention provides methods of engineering a plant having reduced lignin content by expressing or overexpressing a competitive inhibitor of a lignin biosynthesis pathway enzyme. In some embodiments, the method comprises:
  introducing into the plant an expression cassette comprising a polynucleotide that encodes a protein that produces a competitive inhibitor of hydroxycinnamoyl-CoA shikimate/quinate hydroxycinnamoyltransferase (HCT) in the plant, wherein the polynucleotide is operably linked to a heterologous promoter; and
  culturing the plant under conditions in which the protein that produces a competitive inhibitor of HCT is expressed.

In some embodiments, the protein produces one or more of the competitive inhibitors protocatechuate, gentisate, catechol, 2,3-dihydroxybenzoate, 3,6-dihydroxybenzoate, or 3-hydroxy-2-aminobenzoate. In some embodiments, the protein produces the competitive inhibitor of HCT protocatechuate. In some embodiments, the protein is dehydroshikimate dehydratase (QsuB), dehydroshikimate dehydratase (DsDH), isochorismate synthase (ICS), salicylic acid 3-hydroxylase (S3H), salicylate hydroxylase (nahG), or salicylate 5-hydroxylase (nagGH).

In some embodiments, the polynucleotide that encodes a protein that produces a competitive inhibitor of HCT is operably linked to a tissue-specific promoter. In some embodiments, the promoter is a secondary cell wall-specific promoter or a fiber cell-specific promoter. In some embodiments, the promoter is an IRX5 promoter. In some embodiments, the promoter is from a gene that is expressed in the lignin biosynthesis pathway (phenylpropanoid pathway), e.g., a promoter from a gene expressed in the pathway shown in FIG. 1. In some embodiments, the promoter is a C4H, C3H, CCR1, CAD4, CAD5, F5H, PAL1, PAL2, 4CL1, or CCoAMT promoter.

In still another aspect, the present invention provides a plant, plant part, or seed, flower, leaf, or fruit from the plant, or a plant cell comprising a polynucleotide that encodes a protein that produces a competitive inhibitor of HCT in the plant, wherein the polynucleotide is operably linked to a heterologous promoter.

In still another aspect, the present invention provides biomass comprising plant tissue from a plant or part of a plant as described herein.

In yet another aspect, the present invention provides methods of obtaining an increased amount of soluble sugars from a plant in a saccharification reaction. In some embodiments, the method comprises subjecting a plant as described herein to a saccharification reaction, thereby increasing the amount of soluble sugars that can be obtained from the plant as compared to a wild-type plant.

In still another aspect, the present invention provides methods of increasing the digestibility of the biomass for ruminants. In some embodiments, the method comprises introducing an expression cassette as described herein into a plant, culturing the plant under conditions in which the protein that diverts the monolignol precursor from the lignin biosynthesis pathway, or the protein that produces a competitive inhibitor of HCT, is expressed; and obtaining biomass from the plant, thereby increasing the digestibility of the biomass for ruminants.

BRIEF DESCRIPTION OF THE DRAWINGS

FIG. 2. Lignin reduction via depletion of shikimate (HCT co-substrate). Strategies for reducing or depleting the amount of shikimate that is available for the lignin biosynthesis pathway are shown. (1) The amount of cytosolic shikimate that is available for the lignin biosynthesis pathway can be reduced or depleted by expressing a shikimate kinase such as *M. tuberculosis* shikimate kinase ("MtAroK"). (2) The amount of plastidial shikimate that is available for the lignin biosynthesis pathway can be reduced or depleted by expressing a pentafunctional arom protein such as *S. cerevisiae* pentafunctional arom protein ("ScAro1"). Plastidial expression of the protein can be accomplished via a plastid targeting signal, e.g., as described herein.

FIG. 5. Lignin reduction via depletion of phenylalanine (PAL substrate). Strategies for reducing or depleting the amount of phenylalanine that is available for the lignin biosynthesis pathway are shown. For example, the amount of (1) cytosolic and/or (2) plastidial phenylalanine that is available for the lignin biosynthesis pathway can be reduced or depleted by expressing a phenylalanine aminomutase such as *T. canadensis* phenylalanine aminomutase ("Tc-PAM"). Plastidial expression of the protein can be accomplished via a plastid targeting signal, e.g., as described herein.

FIG. 6. Lignin reduction via depletion of cinnamate (C4H substrate) and coumarate (4CL substrate). Strategies for reducing or depleting the amount of cinnamate and/or p-coumarate that is available for the lignin biosynthesis pathway are shown. For example, the amount of cytosolic cinnamate and/or p-coumarate that is available for the lignin biosynthesis pathway can be reduced or depleted by expressing a cinnamate/p-coumarate carboxyl methyltransferase such as *O. basilicum* cinnamate/p-coumarate carboxyl methyltransferase ("ObCCMT1").

FIG. 9. Lignin reduction via depletion of coumaroyl-CoA (HCT substrate). Strategies for reducing or depleting the amount of coumaroyl-CoA that is available for the lignin biosynthesis pathway are shown. For example, the amount of cytosolic coumaroyl-CoA that is available for the lignin biosynthesis pathway can be reduced or depleted by expressing a chalcone synthase (CHS), stilbene synthase (SPS), cucuminoid synthase (CUS), or benzalacetone (BAS).

FIG. 19. Saccharification of biomass from mature senesced stems of wild-type (WT) and pC4H::schl::qsuB (C4H::qsuB) lines. (A) Amounts of sugars released from biomass after various pretreatments and 72-h enzymatic digestion with cellulase (1% w/w). Values are means±SE of four biological replicates (n=4). Asterisks indicate significant differences from the wild type using the unpaired Student's t-test (*P<0.05; **P<0.005). (B) Amounts of sugars released from biomass after hot water pretreatment and 72-h enzymatic digestion using two different cellulase loadings (1% or 0.2% w/w). Values are means SE of four biological replicates (a 4). Asterisks indicate significant differences from the wild type at 1% cellulase loading using the unpaired Student's t-test (*P<0.05; **P<0.005).

FIG. 28. Characteristics and relative molar abundances (%) of the compounds released after pyro-GC/MS of extractive-free senesced mature stems from wild-type (WT) and pC4H::schl::qsuB (C4H::qsuB) plants. Values in brackets are the SE from duplicate analyses. nd, not detected.

DETAILED DESCRIPTION OF THE INVENTION

I. Definitions

Figure 1:
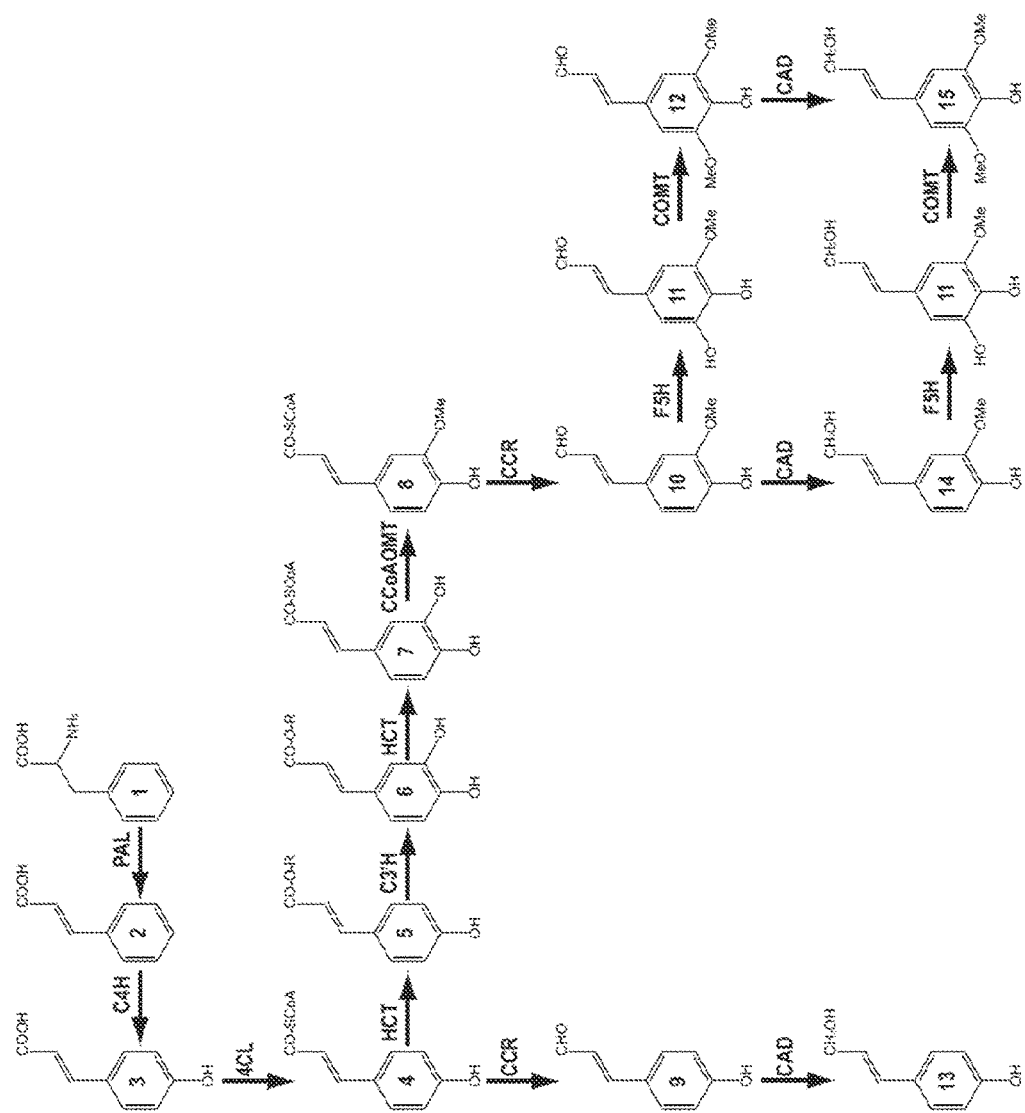
FIG. 1. Representation of the lignin biosynthesis pathway. Modified lignin biosynthesis pathway from Fraser and Chapple (2011). Enzyme descriptions: PAL: phenylalanine ammonia-lyase; C4H: cinnamate-4-hydroxylase; 4CL: 4-hydroxycinnamate CoA-ligase; HCT: hydroxycinnamoyl-CoA shikimate/quinate hydroxycinnamoyltransferase; C3H: 4-hydroxycinnamate 3-hydroxylase; CCoAOMT: caffeoyl-CoA O-methyltransferase; CCR: hydroxycinnamoyl-CoA NADPH oxidoreductase; COMT: caffeate O-methyltransferase; CAD: hydroxycinnamyl alcohol dehydrogenase; F5H: ferulate 5-hydroxylase. Name of the lignin precursors: 1, phenylalanine; 2, cinnamate; 3, p-coumarate; 4, p-coumaroyl-CoA; 5, p-coumaroyl-shikimate/quinate (R=shikimate/quinate); 6, caffeoyl-shikimate/quinate; 7, caffeoyl-CoA; 8, feruloyl-CoA; 9, p-coumaraldehyde; 10, coniferaldehyde; 11, 5-hydroxy-coniferaldehyde; 12, sinapaldehyde; 13, p-coumaryl alcohol; 14, coniferyl alcohol; 15, sinapyl alcohol.

As used herein, the term "lignin biosynthesis pathway" refers to an enzymatic pathway (the phenylpropanoid pathway) in plants in which the lignin monomers (p-coumaryl (4-hydroxycinnamyl) alcohol, coniferyl (3-methoxy 4-hydroxycinnamyl) alcohol, and sinapyl (3,5-dimethoxy 4-hydroxycinnamyl) alcohol) are synthesized from phenylalanine. The lignin biosynthesis pathway and enzymatic components of the pathway are depicted, for example, in FIG. 1.

As used herein, the term "monolignol precursor" refers to a substrate of the lignin biosynthesis pathway that is directly or indirectly synthesized into a lignin monomer. In some embodiments, a monolignol precursor is a substrate of the lignin biosynthesis pathway that is identified in any of FIGS. 1-11.

As used herein, the term "protein that diverts a monolignol precursor from a lignin biosynthesis pathway" refers to a protein that activates, promotes, potentiates, or enhances expression of an enzymatic reaction or metabolic pathway that decreases the amount of monolignol precursor that is available for the synthesis of a lignin monomer. The term includes polymorphic variants, alleles, mutants, and inter-species homologs to the specific proteins (e.g., enzymes) described herein. A nucleic acid that encodes a protein that diverts a monolignol precursor from a lignin biosynthesis pathway (or a nucleic acid that encodes a protein that diverts a monolignol precursor from a p-coumaryl alcohol, sinapyl alcohol, and/or coniferyl alcohol pathway) refers to a gene, pre-mRNA, mRNA, and the like, including nucleic acids encoding polymorphic variants, alleles, mutants, and inter-species homologs of the particular proteins (e.g., enzymes) described herein. In some embodiments, a nucleic acid that encodes a protein that diverts a monolignol precursor from a lignin biosynthesis pathway (1) has a nucleic acid sequence that has greater than about 50% nucleotide sequence identity, 55%, 60%, 65%, 70%, 75%, 80%, 85%, 90%, preferably 91%, 92%, 93%, 94%, 95%, 96%, 97%, 98% or 99% or higher nucleotide sequence identity, preferably over a region of at least about 10, 15, 20, 25, 50, 100, 200, 500 or more nucleotides or over the length of the entire polynucleotide, to a nucleic acid sequence of any of SEQ ID NOs:1, 3, 5, 7, 9, 11, or 13; or (2) encodes a polypeptide having an amino acid sequence that has greater than about 50% amino acid sequence identity, 55%, 60%, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200 or more amino acids or over the length of the entire polypeptide, to a polypeptide encoded by a nucleic acid sequence of any of SEQ ID NOs:1, 3, 5, 7, 9, 11, or 13, or to an amino acid sequence of any of SEQ ID NOs:2, 4, 6, 8, 10, 12, 14, 29, 30, 31, 32, 33, 34, 35, 36, 37, 38, 39, 40, 41, 42, 42, 43, 44, or 45. In some embodiments, a protein that diverts a monolignol precursor from a lignin biosynthesis pathway has an amino acid sequence having greater than about 50% amino acid sequence identity, 55%, 60%, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200 or more amino acids or over the length of the entire polypeptide, to an amino acid sequence of any of SEQ ID NOs:2, 4, 6, 8, 10, 12, 14, 29, 30, 31, 32, 33, 34, 35, 36, 37, 38, 39, 40, 41, 42, 42, 43, 44, or 45.

Figure 27:
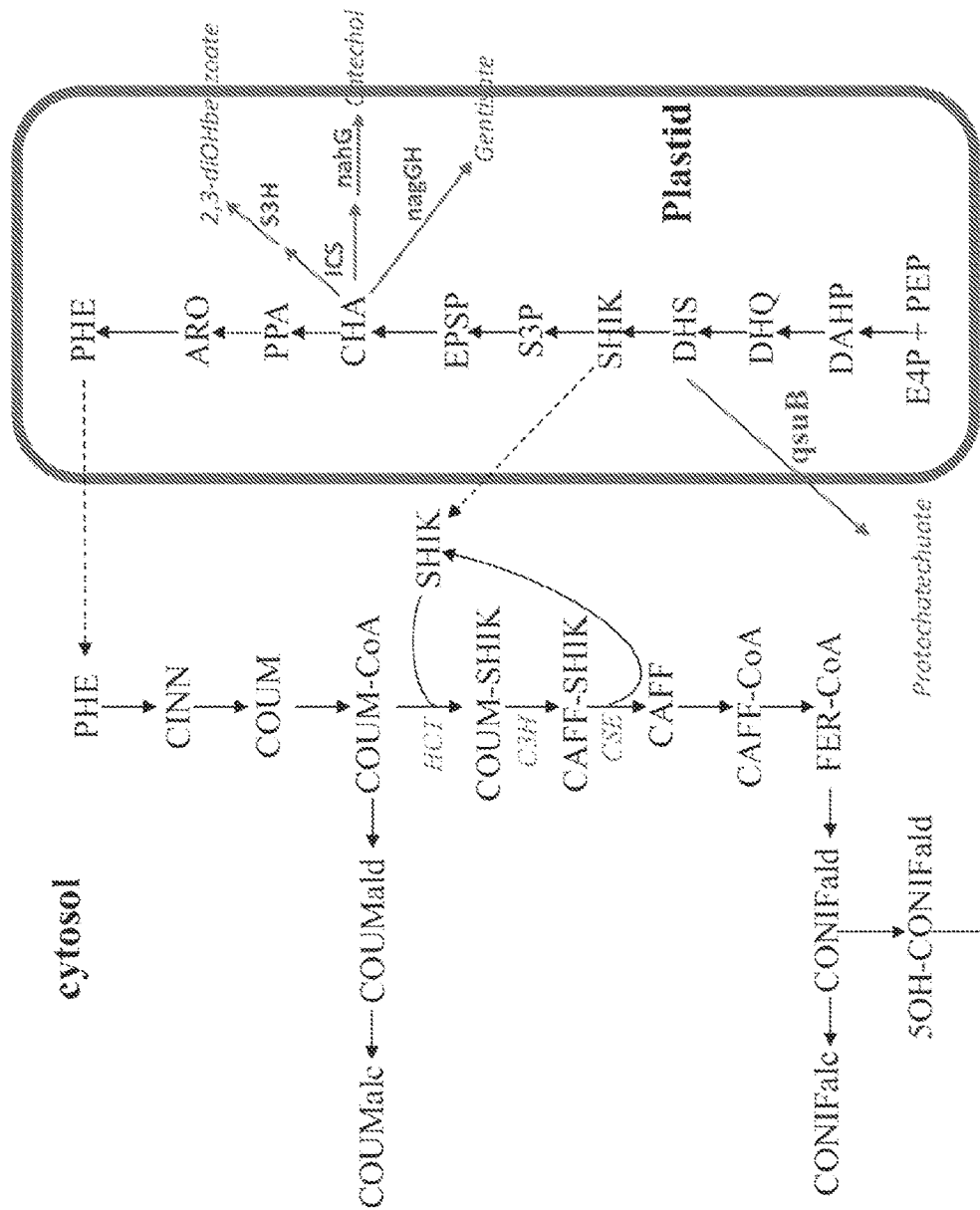
FIG. 27. Competitive inhibitor pathways.

The term "protein that produces a competitive inhibitor of HCT" refers to a protein that directly or indirectly produces a molecule that can compete with p-coumaroyl-CoA and/or shikimate as a substrate for hydroxycinnamoyl-CoA shikimate/quinate hydroxycinnamoyltransferase (HCT), thereby acting as a competitive inhibitor of HCT. Non-limiting examples of molecules (e.g., metabolites) that can act as competitive inhibitors of HCT are shown in FIG. 27. In some embodiments, the competitive inhibitor of HCT is protocatechuate, catechol, 3,6-dihydroxybenzoate, 3-hydroxy-2-aminobenzoate, or 2,3-dihydroxybenzoate. Thus, in some embodiments, the protein that produces a competitive inhibitor of HCT is a protein (e.g., an enzyme) that directly or indirectly produces protocatechuate, catechol, 3,6-dihydroxybenzoate, 3-hydroxy-2-aminobenzoate, or 2,3-dihydroxybenzoate, including but not limited to the enzymes dehydroshikimate dehydratase (QsuB), dehydroshikimate dehydratase (DsDH), isochorismate synthase (ICS), salicylic acid 3-hydroxylase (S3H), salicylate hydroxylase (nahG), and salicylate 5-hydroxylase (nagGH). In some embodiments, an in vivo enzymatic assay, for example as described in the Examples section below, can be used to determine whether a molecule can compete with p-coumaroyl-CoA and/or shikimate as a substrate for HCT.

The terms "polynucleotide" and "nucleic acid" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonueleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "substantially identical," used in the context of two nucleic acids or polypeptides, refers to a sequence that has at least 50% sequence identity with a reference sequence. Percent identity can be any integer from 50% to 100%. Some embodiments include at least: 50%, 55%, 60%, 65%, 70%, 75%, 80%, 85%, 90%, 91%, 92%, 93%, 94%, 95%, 96%, 97%, 98%, or 99%, compared to a reference sequence using the programs described herein; preferably BLAST using standard parameters, as described below. For example, a first polynueleotide is substantially identical to a second polynucleotide sequence if the first polynucleotide sequence is at least 50%, 55%, 60%, 65%, 70%, 75%, 80%, 85%, 90%, 91%, 92%, 93%, 94%, 95%, 96%, 97%, 98%, or 99% identical to the second polynucleotide sequence.

Two nucleic acid sequences or polypeptide sequences are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, Computer Applic. Biol. Sci. 4:11-17 (1988) e.g., as implemented in the program PC/GENE (Intelligenetics, Mountain View, Calif., USA).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2,0 algorithms, which are described in Altschul et al. (1990) J. Mol. Biol. 215: 403-410 and Altschul et al. (1977) Nucleic Acids Res. 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, Proc. Natl. Acad. Sci. USA 89:10915 (1989)).

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

Nucleic acid or protein sequences that are substantially identical to a reference sequence include "conservatively modified variants." With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid.

One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, *Proteins* (1984)).

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. For example, stringent conditions for hybridization, such as RNA-DNA hybridizations in a blotting technique are those which include at least one wash in 0.2×SSC at 55° C. for 20 minutes, or equivalent conditions.

As used herein, the term "promoter" refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. Promoters are located 5' to the transcribed gene, and as used herein, include the sequence 5' from the translation start codon (i.e., including the 5' untranslated region of the mRNA, typically comprising 100-200 bp). Most often the core promoter sequences lie within 1-5 kb of the translation start site, more often within 1 kbp and often within 500 bp of the translation start site. By convention, the promoter sequence is usually provided as the sequence on the coding strand of the gene it controls.

A "constitutive promoter" is one that is capable of initiating transcription in nearly all cell types, whereas a "cell type-specific promoter" initiates transcription only in one or a few particular cell types or groups of cells forming a tissue. In some embodiments, the promoter is secondary cell wall-specific and/or fiber cell-specific. A "fiber cell-specific promoter" refers to a promoter that initiates substantially higher levels of transcription in fiber cells as compared to other non-fiber cells of the plant. A "secondary cell wall-specific promoter" refers to a promoter that initiates substantially higher levels of transcription in cell types that have secondary cell walls, e.g., lignified tissues such as vessels and fibers, which may be found in wood and bark cells of a tree, as well as other parts of plants such as the leaf stalk. In some embodiments, a promoter is fiber cell-specific or secondary cell wall-specific if the transcription levels initiated by the promoter in fiber cells or secondary cell walls, respectively, are at least 3-fold, 4-fold, 5-fold, 6-fold, 7-fold, 8-fold, 9-fold, 10-fold, 50-fold, 100-fold, 500-fold, 000-fold higher or more as compared to the transcription levels initiated by the promoter in other tissues, resulting in the encoded protein substantially localized in plant cells that possess fiber cells or secondary cell wall, e.g., the stem of a plant. Non-limiting examples of fiber cell and/or secondary cell wall specific promoters include the promoters directing expression of the genes IRX1, IRX3, IRX5, IRX7, IRX8, IRX9, IRX10, IRX14, NST1, NST2, NST3, MYB46, MYB58, MYB63, MYB83, MYB85, MYB103, PAL1, PAL2, C3H, CcOAMT, CCR1, F5H, LAC4, LAC17, CADc, and CADd. See, e.g., Turner et al 1997; Meyer et al 1998; Jones et al 2001; Franke et al 2002; Ha et al 2002; Rohde et al 2004; Chen et al 2005; Stobout et al 2005; Brown et al 2005; Mitsuda et al 2005; Zhong et al 2006; Mitsuda et al 2007; Zhong et al 2007a, 2007b; Zhou et al 2009; Brown et al 2009; McCarthy et al 2009; Ko et al 2009; Wu et al 2010; Berthet et al 2011. In some embodiments, a promoter is substantially identical to a promoter from the lignin biosynthesis pathway (e.g., a promoter for a gene encoding a protein shown in FIG. 1). Non-limiting examples of promoter sequences are provided herein as SEQ ID NOs:17-28. A promoter originated from one plant species may be used to direct gene expression in another plant species.

A polynucleotide is "heterologous" to an organism or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety, or a gene that is not naturally expressed in the target tissue).

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" refers to a nucleic acid construct that, when introduced into a host cell, results in transcription and/or translation of an RNA or polypeptide, respectively. Antisense or sense constructs that are not or cannot be translated are expressly included by this definition. In the case of both expression of transgenes and suppression of endogenous genes (e.g., by antisense, RNAi, or sense suppression) one of skill will recognize that the inserted polynucleotide sequence need not be identical, but may be only substantially identical to a sequence of the gene from which it was derived. As explained herein, these substantially identical variants are specifically covered by reference to a specific nucleic acid sequence.

The term "plant," as used herein, refers to whole plants and includes plants of a variety of a ploidy levels, including aneuploid, polyploid, diploid, and haploid. The term "plant part," as used herein, refers to shoot vegetative organs and/or structures (e.g., leaves, stems and tubers), branches, roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, and plant tissue (e.g., vascular tissue, ground tissue, and the like), as well as individual plant cells, groups of plant cells (e.g., cultured plant cells), protoplasts, plant extracts, and seeds. The class of plants that can be used in the methods of the invention is generally as broad as the class of higher and lower plants amenable to transformation techniques, including angiosperms (monocotyledonous and dicotyledonous plants), gymnosperms, ferns, and multicellular algae.

The term "biomass," as used herein, refers to plant material that is processed to provide a product, e.g., a biofuel such as ethanol, or livestock feed, or a cellulose for paper and pulp industry products. Such plant material can include whole plants, or parts of plants, e.g., stems, leaves, branches, shoots, roots, tubers, and the like.

The term "reduced lignin content" encompasses reduced amount of lignin polymer, reduced amount of either or both of the guaiacyl (G) and/or syringyl (S) lignin units, reduced size of a lignin polymer, e.g., a shorter lignin polymer chain due to a smaller number of monolignols being incorporated into the polymer, a reduced degree of branching of the lignin polymer, or a reduced space filling (also called a reduced pervaded volume). In some embodiments, a reduced lignin polymer can be shown by detecting a decrease in the molecular weight of the polymer or a decrease in the number of monolignols by at least 2%, 5%, 10%, 20%, 25%, 30%, 40%, 50%, or more, when compared to the average lignin molecule in a control plant (e.g., a non-transgenic plant). In some embodiments, reduced lignin content can be shown by detecting a decrease in the number or amount of guaiacyl (G) and/or syringyl (S) lignin units in the plant as compared to a control plant (e.g, a non-transgenic plant). In some embodiments, a plant as described herein has reduced lignin content if the amount of guaiacyl (G) and/or syringyl (S) lignin units in the plant is decreased by at least about 2%, 5%, 10%, 20%, 25%, 30%, 40%, 50% or more, as compared to a control plant. Methods for detecting reduced lignin content are described in detail below.

II. Introduction

Plant cell walls constitute a polysaccharidic network of cellulose microfibrils and hemicellulose embedded in an aromatic polymer known as lignin. This ramified polymer is mainly composed of three phenylpropanoid-derived phenolics (i.e., monolignols) named p-coumaryl, coniferyl, and sinapyl alcohols which represent the p-hydroxyphenyl (H), guaiacyl (G) and syringyl (S) lignin units (Boerjan et al., 2003). Monolignols have a $C_6C_3$ carbon skeleton which consists of a phenyl ring ($C_6$) and a propane ($C_3$) side chain. Lignin is crucial for the development of terrestrial plants as it confers recalcitrance to plant cell walls. It also provides mechanical strength for upright growth, confers hydrophobicity to vessels that transport water, and acts as a physical barrier against pathogens that degrade cell walls (Boudet, 2007). Notably, lignin content and composition are finely regulated in response to environmental biotic and abiotic stresses (Moura et al., 2010).

Economically, lignocellulosic biomass from plant cell walls is widely used as raw material for the production of pulp in paper industry and as ruminant livestock feed. Plant feedstocks also represent a source of fermentable sugars for the production of synthetic molecules such as pharmaceuticals and transportation fuels using engineered microorganisms (Keasling, 2010). However, negative correlations exist between lignin content in plant biomass and pulp yield, forage digestibility, or polysaccharides enzymatic hydrolysis (de Vrije et al., 2002; Reddy et al., 2005; Dien et al., 2006; Chen and Dixon, 2007; Dien et al., 2009; Taboada et al., 2010; Elissetche et al., 2011; Studer et al., 2011). Consequently, reducing lignin recalcitrance in plant feedstocks is a major focus of interest, especially in the lignocellulosic biofuels field for which efficient enzymatic conversion of polysaccharides into monosaccharides is crucial to achieve economically and environmentally sustainable production (Carroll and Somerville, 2009).

Lignin biosynthesis is well characterized and well conserved across land plants (Weng and Chapple 2010). Genetic modifications such as silencing of genes involved in particular steps of this pathway or its regulation have been employed to reduce lignin content (Simmons et al., 2010; Umezawa, 2010) but this approach often results in undesired phenotypes such as dwarfism, sterility, reduction of plant biomass, and increased susceptibly to environmental stress and pathogens (Bonawitz and Chapple, 2010). These pleiotropic effects are generally the consequences of a loss of secondary cell wall integrity, accumulation of toxic intermediates, constitutive activation of defense responses, or depletion of other phenylpropanoid-derived metabolites which are essential for plant development and defense (Li et al., 2008; Naoumkina et al., 2010, Gallego-Giraldo et al., 2011). Alternatively, changing the recalcitrant structure and physico-chemical properties of lignin can be achieved by modifying its monomer composition. For example, incorporation of coniferyl ferulate into lignin improves enzymatic degradation of cell wall polysaccharides (Grabber et al., 2008). Recently, it has been demonstrated that enrichment in 5-hydroxy-G units and reduction in S units in lignin contribute to enhanced saccharification efficiencies without affecting drastically biomass yields and lignin content (Weng et al., 2010; Dien et al., 2011; Fu et al., 2011).

The present invention provides an alternative strategy to reduce lignin content (e.g., reducing the amount of p-hydroxyphenyl (H), guaiacyl (G) and/or syringyl (S) lignin units, or any combination of H-lignin, G-lignin, and S-lignin units). In this strategy, the plant is engineered to express one or more proteins that diverts or shunts a monolignol precursor from a lignin biosynthesis pathway (e.g., p-coumaryl alcohol, sinapyl alcohol, and/or coniferyl alcohol biosynthesis pathway) into a competitive pathway. By diverting or shunting the production of monolignol precursors from p-hydroxyphenyl (H), guaiacyl (G) and/or syringyl (S) lignin unit production to the production of alternative products (e.g., stilbenes, flavonoids, curcuminoids, or bensalacetones, protocatechuates, aromatic amino acids, vitamins, quinones, or volatile compounds) as described herein, the amount of lignin content or its composition, e.g., in specific cell or tissue types such as in secondary cell wall, can be altered in order to enhance saccharification efficiencies without dramatically affecting biomass yield. The present invention also provides plants that are engineered by the method described herein, as well as a plant cell from such a plant, a seed, flower, leaf, or fruit from such a plant, a plant cell that contains an expression cassette described herein for expressing a protein diverts or shunts a monolignol precursor from a lignin biosynthesis pathway into a competitive pathway, and biomass comprising plant tissue from the plant or part of e plant described herein.

III. Plants Having Reduced Lignin Content

A. Expression of a Protein That Diverts a Monolignol Precursor From a Lignin Biosynthesis Pathway In one aspect, the present invention provides a method of engineering a plant having reduced lignin content (e.g., reduced amount of lignin polymers, reduced size of lignin polymers, reduced degree of branching of lignin polymers, or reduced space filling). In some embodiments, the plant has reduced lignin content that is substantially localized to specific cell and/or tissue types in the plant. For example, in some embodiments the plant has reduced lignin content that is substantially localized to secondary cell walls and/or fiber cells. In some embodiments, the method comprises:
  introducing into the plant an expression cassette comprising a polynucleotide that encodes a protein that diverts a monolignol precursor from a lignin biosynthesis pathway (e.g., a p-coumaryl alcohol, sinapyl alcohol, and/or coniferyl alcohol biosynthesis pathway) in the plant, and wherein the polynucleotide is operably linked to a heterologous tissue-specific promoter; and
  culturing the plant under conditions in which the protein that diverts the monolignol precursor from the lignin biosynthesis pathway (e.g., the p-coumaryl alcohol, sinapyl alcohol, or coniferyl alcohol biosynthesis pathway) is expressed.

In some embodiments, the gene that encodes a protein that diverts a monolignol precursor from a lignin biosynthesis pathway (e.g., a p-coumaryl alcohol, sinapyl alcohol, and/or coniferyl alcohol biosynthesis pathway) reduces the amount of cytosolic and/or plastidial shikimate that is available for the p-coumaryl alcohol, sinapyl alcohol, or coniferyl alcohol biosynthesis pathway; reduces the amount of cytosolic and/or plastidial phenylalanine that is available for the p-coumaryl alcohol, sinapyl alcohol, or coniferyl alcohol biosynthesis pathway; reduces the amount of cinnamate and/or coumarate that is available for the p-coumaryl alcohol, sinapyl alcohol, or coniferyl alcohol biosynthesis pathway; and/or reduces the amount of coumaroyl-CoA, caffeoyl-CoA, and/or feruloyl-CoA that is available for the p-coumaryl alcohol, sinapyl alcohol, or coniferyl alcohol biosynthesis pathway. In some embodiments, the gene that encodes a protein that diverts a monolignol precursor from a lignin biosynthesis pathway (e.g., a p-coumaryl alcohol, sinapyl alcohol, and/or coniferyl alcohol biosynthesis pathway) activates or potentiates a metabolic pathway that competes with the p-coumaryl alcohol, sinapyl alcohol, or coniferyl alcohol biosynthesis pathway biosynthesis pathway for the use of monolignol precursors, including but not limited to a metabolic pathway selected from a stilbene biosynthesis pathway, a flavonoid biosynthesis pathway, and an anthocyanin biosynthesis pathway.

An expression cassette as described herein, when introduced into a plant, results in the plant having reduced lignin content (e.g., reduced amount of lignin polymers, reduced size of lignin polymers, reduced degree of branching of lignin polymers, or reduced space filling) that is specifically localized to certain cell and/or tissue types (e.g., specifically localized to secondary cell walls and/or fiber cells), thus reducing cell wall recalcitrance to enzymatic hydrolysis while avoiding defects in plant growth or reductions in biomass yield.

One of skill in the art will understand that the protein that diverts a monolignol precursor from a lignin biosynthesis pathway that is introduced into the plant by an expression cassette described herein does not have to be identical to the protein sequences described herein (e.g., the protein sequences of SEQ ID NOs:2, 4, 6, 8, 10, 12, or 14). In some embodiments, the protein that is introduced into the plant by an expression cassette is substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to a protein sequence described herein (e.g., a protein sequence of SEQ ID NOs:2, 4, 6, 8, 10, 12, or 14). In some embodiments, the protein that is introduced into the plant by an expression cassette is a homolog, ortholog, or paralog of a protein that diverts a monolignol precursor from a lignin biosynthesis pathway as described herein (e.g., a protein sequence of SEQ ID NOs:2, 4, 6, 8, 10, 12, or 14).

Gene and protein sequences for enzymes that divert a monolignol precursor from a lignin biosynthesis pathway are described in the Sequence Listing herein. Additionally, gene and protein sequences for these proteins, and methods for obtaining the genes or proteins, are known and described in the art. One of skill in the art will recognize that these gene or protein sequences known in the art and/or as described herein can be modified to make substantially identical enzymes, e.g., by making conservative substitutions at one or more amino acid residues. One of skill will also recognize that the known sequences provide guidance as to what amino acids may be varied to make a substantially identical enzyme. For example, using an amino acid sequence alignment between two or more protein sequences, one of skill will recognize which amino acid residues are not highly conserved and thus can likely be changed without resulting in a significant effect on the function of the enzyme.

Proteins that Reduce the Amount of Shikimate

Figure 2:
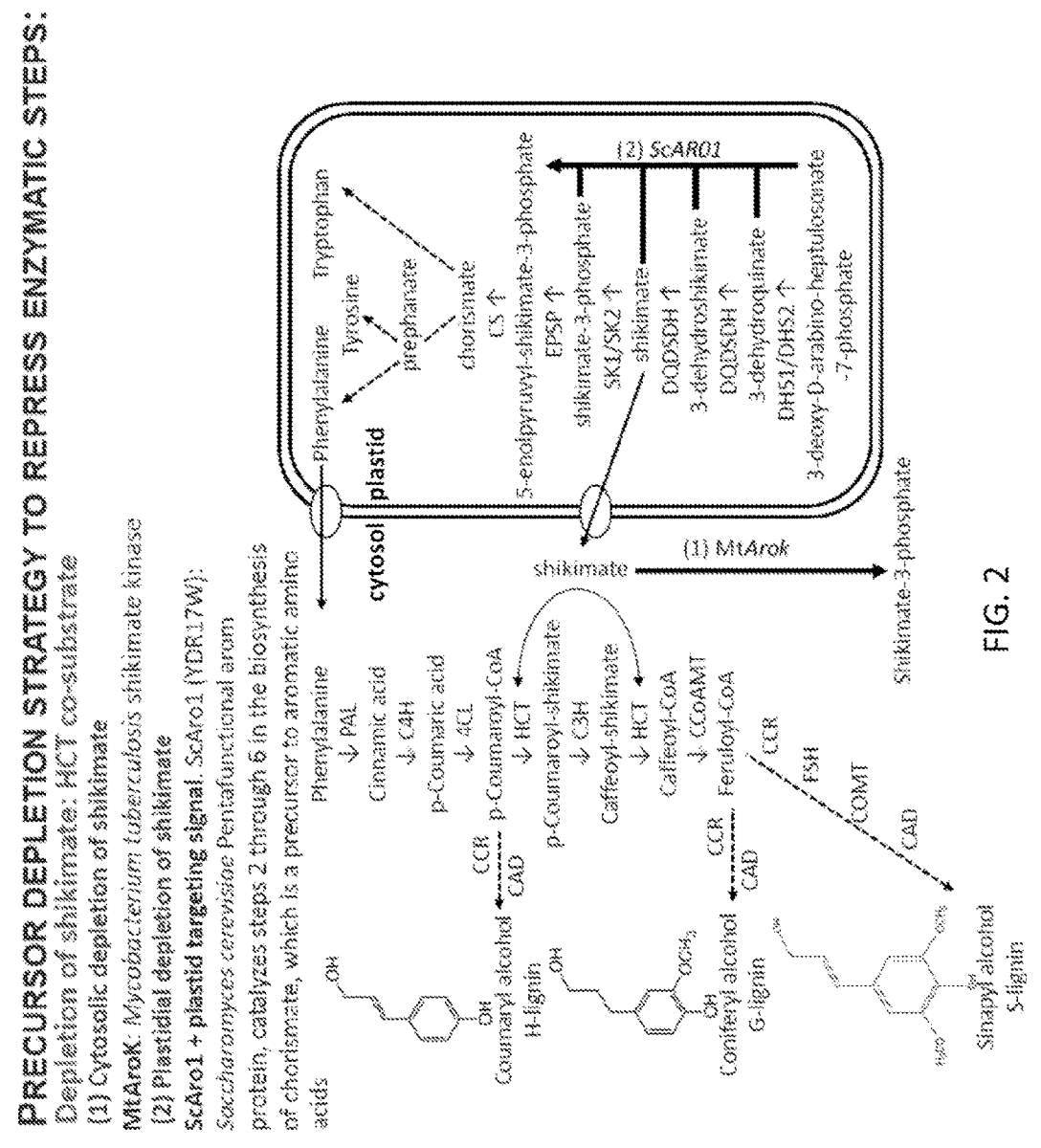
Figure 3:
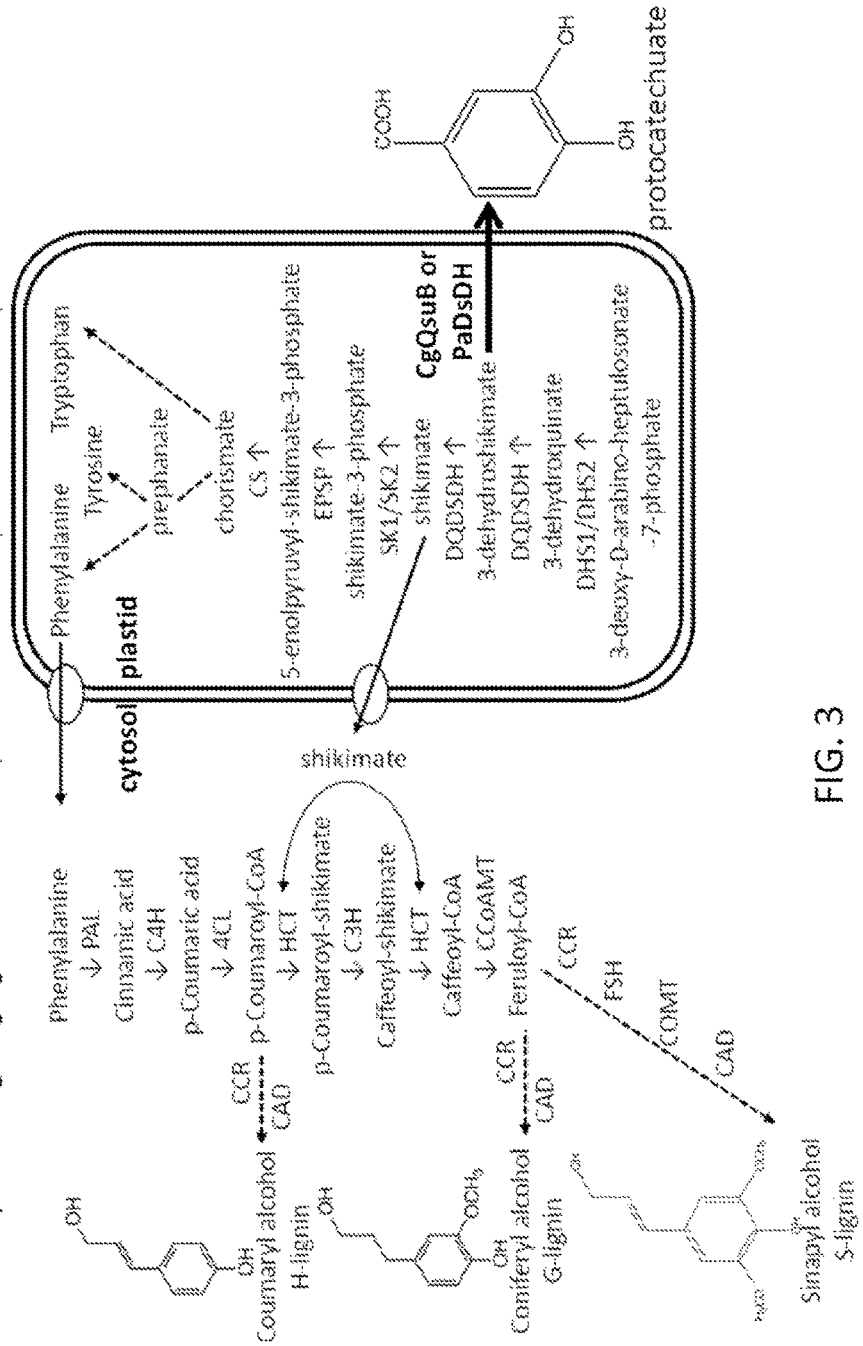
FIG. 3. Lignin reduction via depletion of shikimate and production of new stoppers. Strategies for reducing or depleting the amount of shikimate that is available for the lignin biosynthesis pathway are shown. For example, the amount of plastidial shikimate that is available for the lignin biosynthesis pathway can be reduced or depleted by expressing a dehydroshikimate dehydratase such as *C. glutamicum* dehydroshikimate dehydratase ("CgQsuB") or *P. anserina* dehydroshikimate dehydratase ("PaDsDH"). Plastidial expression of the protein can be accomplished via a plastid targeting signal, e.g., as described herein.

In some embodiments, a protein that diverts a monolignol precursor from a lignin biosynthesis pathway reduces the amount of cytosolic and/or plastidial shikimate that is available for the lignin biosynthesis pathway. Examples of such a protein are shown in FIGS. 2 and 3. In some embodiments, the protein is an enzyme that modifies a shikimate substrate, e.g., a shikimate kinase or a pentafunctional arom protein. In some embodiments, the protein is an enzyme that utilizes shikimate in the synthesis of another compound (e.g., a protocatechuate, an aromatic amino acid, a vitamin, or a quinone), e.g., a dehydroshikimate dehydratase.

Non-limiting examples of a shikimate kinase enzyme are described in Gu et al., *J. Mol. Biol.* 319:779-789 (2002). In some embodiments, the protein is a *Mycobacterium tuberculosis* shikimate kinase (AroK) having the amino acid sequence set forth in SEQ ID NO:2. In some embodiments, the protein is substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to the amino acid sequence of SEQ ID NO:2. In some embodiments, the protein is a homolog of a *Mycobacterium tuberculosis* shikimate kinase (AroK) having the amino acid sequence set forth in SEQ ID NO:2. In some embodiments, a polynucleotide encoding the shikiniate kinase comprises a polynucleotide sequence that is identical or substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to SEQ ID NO:1.

Non-limiting examples of a pentafunctional arom protein are described in Duncan et al., *Biochem. J.* 246:375-386 (1987). In some embodiments, the protein is a *Saccharomyces cerevisiae* pentafunctional arom enzyme (Aro1) having the amino acid sequence set forth in SEQ ID NO:4. In some embodiments, the protein is substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to the amino acid sequence of SEQ ID NO:4. In some embodiments, the protein is a homolog of a *Saccharomyces cerevisiae* pentafunctional arom enzyme (Aro1) having the amino acid sequence set forth in SEQ ID NO:4. In some embodiments, a polynucleotide encoding the pentafunctional arom protein comprises a polynucleotide sequence that is identical or substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to SEQ ID NO:3.

Non-limiting examples of a dehydroshikimate dchydryoshikimatc dehydratase are described in Teramoto et al., *Appl. Environ. Microbiol.* 75:3461-3468 (2009) and Hansen et al., *Appl. Environ. Microbiol.* 75:2765-2774 (2009). In some embodiments, the protein is a *Corynebacterium glutamicum* dehydroshikimate dehydratase (QsuB) having the amino acid sequence set forth in SEQ ID NO:6 or a *Podospora anserina* dehydroshikimate dehydratase (DsDH) having the amino acid sequence set forth in SEQ ID NO:8. In some embodiments, the protein is substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to the amino acid sequence of SEQ ID NO:6 or SEQ ID NO:8. In some embodiments, the protein is a homolog of a *Corynebacterium glutamicum* dehydroshikimate dehydratase (QsuB) having the amino acid sequence set forth in SEQ ID NO:6 or a homolog of the *Podospora anserina* dehydroshikimate dehydratase (DsDH) having the amino acid sequence set forth in SEQ ID NO:8. In some embodiments, a polynucleotide encoding the dehydroshikimate dehydratase comprises a polynucleotide sequence that is identical or substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to SEQ ID NO:5 or SEQ ID NO:7.

Proteins that Reduce the Amount of Phenylalanine

Figure 4:
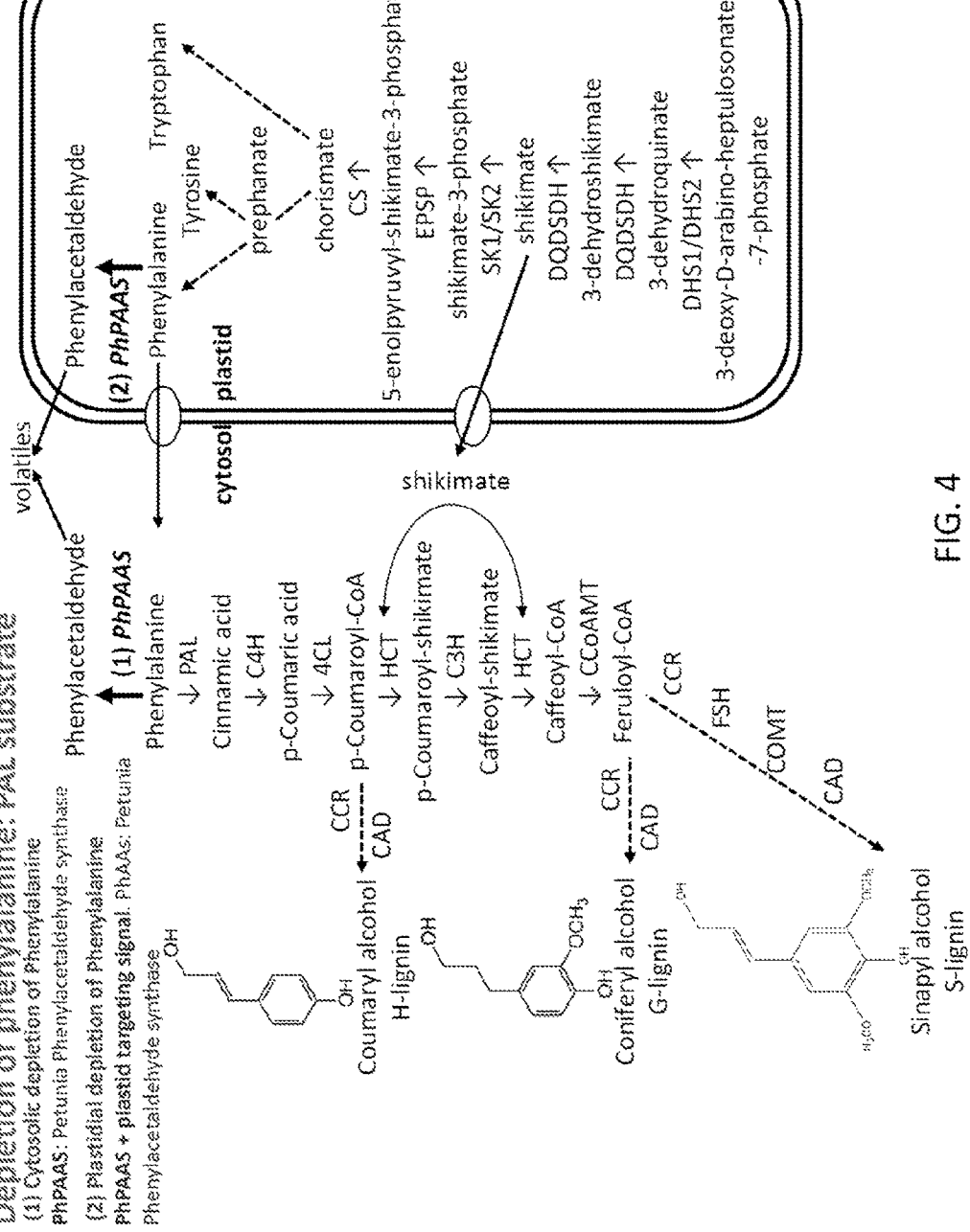
FIG. 4. Lignin reduction via depletion of phenylalanine (PAL substrate). Strategies for reducing or depleting the amount of phenylalanine that is available for the lignin biosynthesis pathway are shown. For example, the amount of (1) cytosolic and/or (2) plastidial phenylalanine that is available for the lignin biosynthesis pathway can be reduced or depleted by expressing a phenylacetaldehyde such as *P. hybrida* phenylacetaldehyde synthase ("PhPAAS"). Plastidial expression of the protein can be accomplished via a plastid targeting signal, e.g., as described herein.

In some embodiments, a protein that diverts a monolignol precursor from a lignin biosynthesis pathway reduces the amount of cytosolic and/or plastidial phenylalanine that is available for the lignin biosynthesis pathway. Examples of such a protein are shown in FIGS. 4 and 5. In some embodiments, the protein is an enzyme that modifies a phenylalanine substrate. In some embodiments, the protein is an enzyme that utilizes phenylalanine in the synthesis of another compound (e.g., a volatile compound), e.g., a phenylacetaldehyde synthase or a phenylalanine aminomutase.

Non-limiting examples of a phenylacetaldehyde synthase are described in Kaminaga et al., *J. Biol. Chem.* 281:23357-23366 (2006) and in Farhi et al., *Plant Mol. Biol.* 72:235-245 (2010). In some embodiments, the protein is a *Petunia hybrida* phenylacetaldehyde synthase (PAAS) having the amino acid sequence set forth in SEQ ID NO:10. In some embodiments, the protein is substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to the amino acid sequence of SEQ ID NO:10. In some embodiments, the protein is a homolog of a *Petunia hybrida* phenylacetaldehyde synthase (PAAS) having the amino acid sequence set forth in SEQ ID NO:10. In some embodiments, a polynucleotide encoding the phenylacetaldehyde synthase comprises a polynucleotide sequence that is identical or substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to SEQ ID NO:9.

Non-limiting examples of a phenylalanine aminomutase are described in Feng et al., *Biochemistry* 50:2919-2930 (2011). In some embodiments, the protein is a *T. canadensis* phenylalanine aminomutase (PAM) having the amino acid sequence set forth in SEQ ID NO:29. In some embodiments, the protein is substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to the amino acid sequence of SEQ ID NO:29. In some embodiments, the protein is a homolog of a *T. canadensis* phenylalanine aminomutase (PAM) having the amino acid sequence set forth in SEQ ID NO:29.

Proteins that Reduce the Amount of Cinnamate and/or Coumarate

Figure 7:
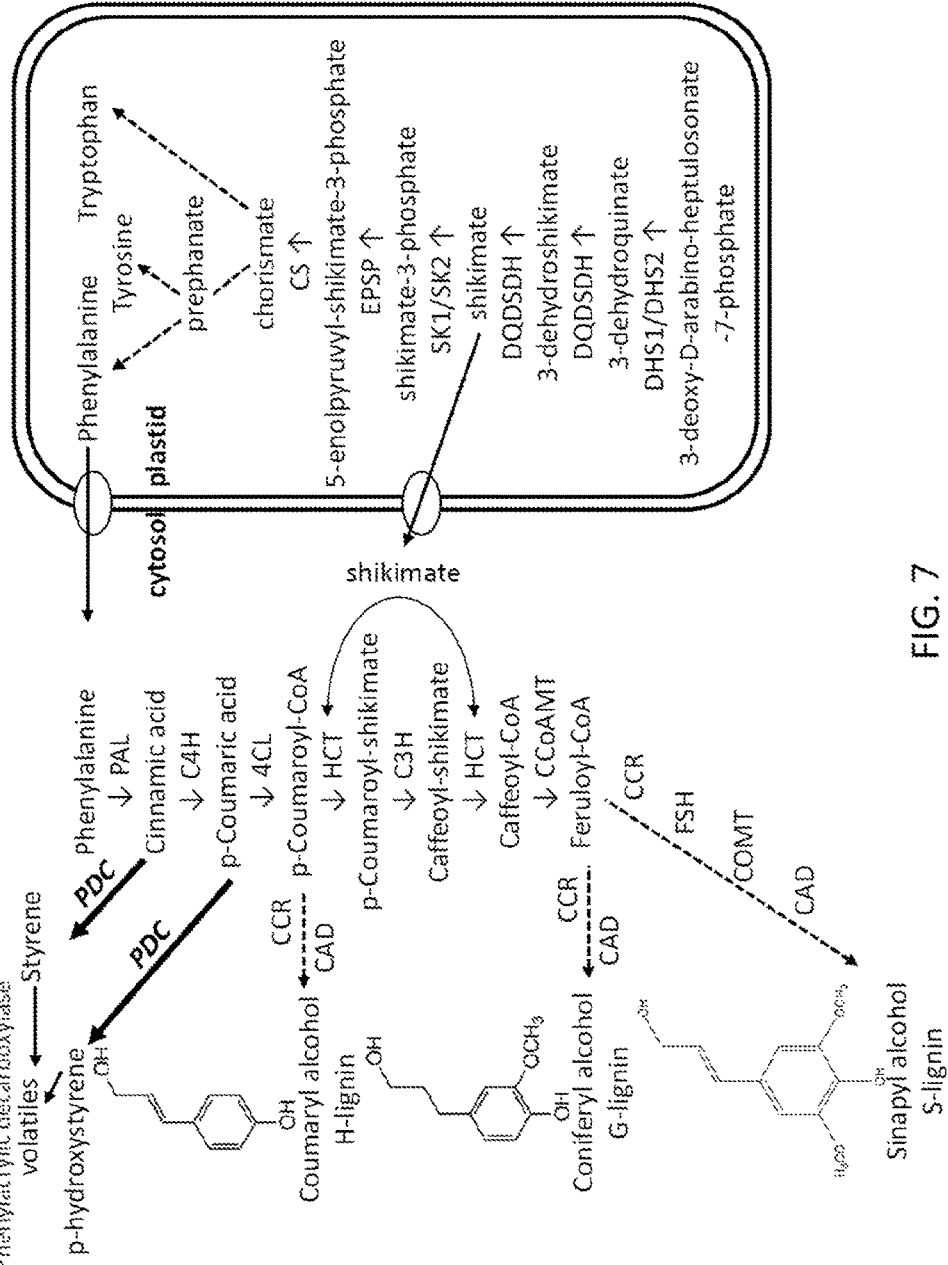
FIG. 7. Lignin reduction via depletion of cinnamate (C4H substrate) and coumarate (4CL substrate). Strategies for reducing or depleting the amount of cinnamate and/or p-coumarate that is available for the lignin biosynthesis pathway are shown. For example, the amount of cytosolic cinnamate and/or p-coumarate that is available for the lignin biosynthesis pathway can be reduced or depleted by expressing a phenylacrylic decarboxylase (PDC or PAD).
Figure 8:
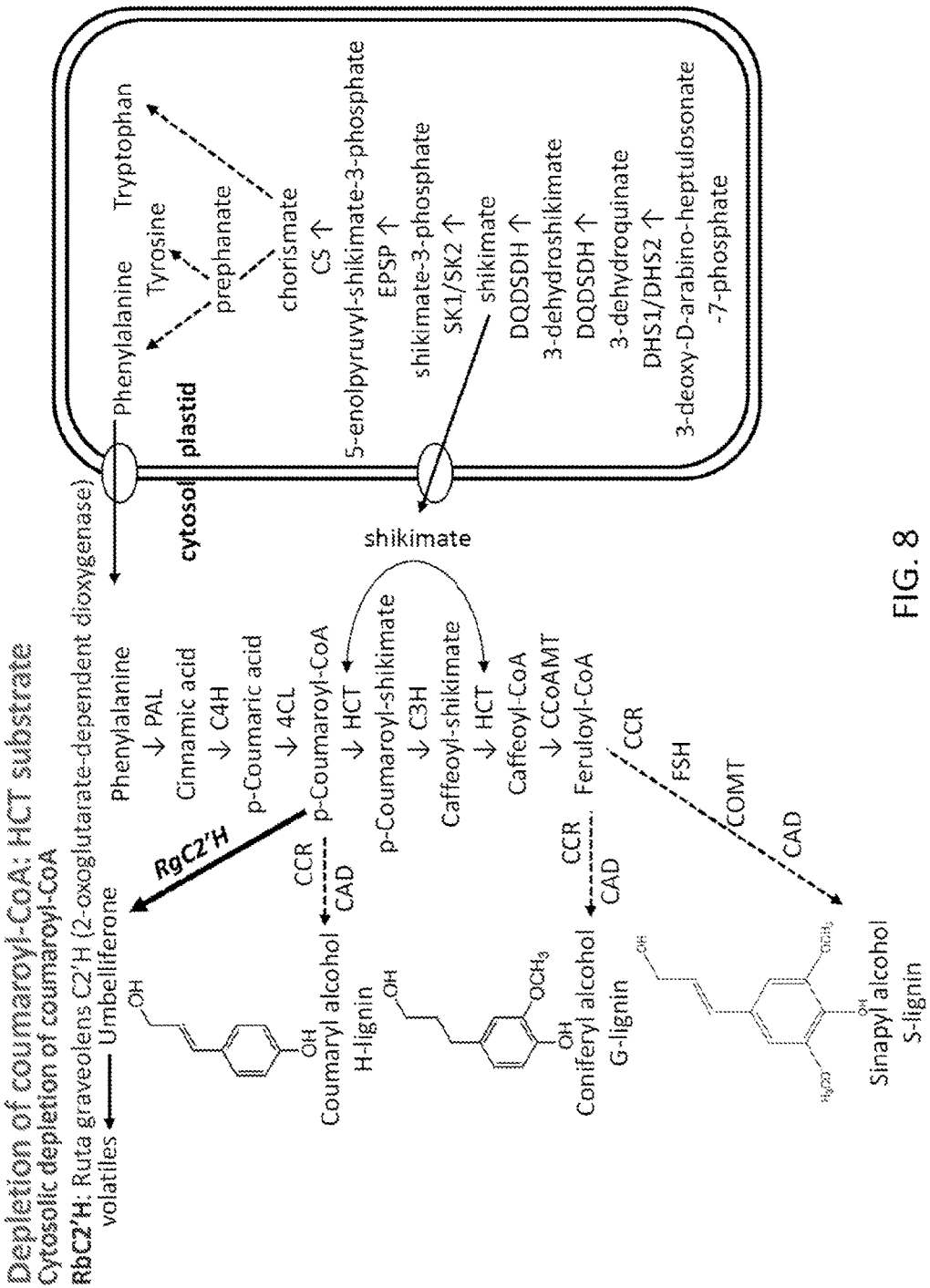
FIG. 8. Lignin reduction via depletion of coumaroyl-CoA (HCT substrate). Strategies for reducing or depleting the amount of coumaroyl-CoA that is available for the lignin biosynthesis pathway are shown. For example, the amount of cytosolic coumaroyl-CoA that is available for the lignin biosynthesis pathway can be reduced or depleted by expressing a 2-oxoglutarate-dependent dioxygenase such as *R. graveolens* C2'H (2-oxoglutarate-dependent dioxygenase) ("RbC2'H").
Figure 10:
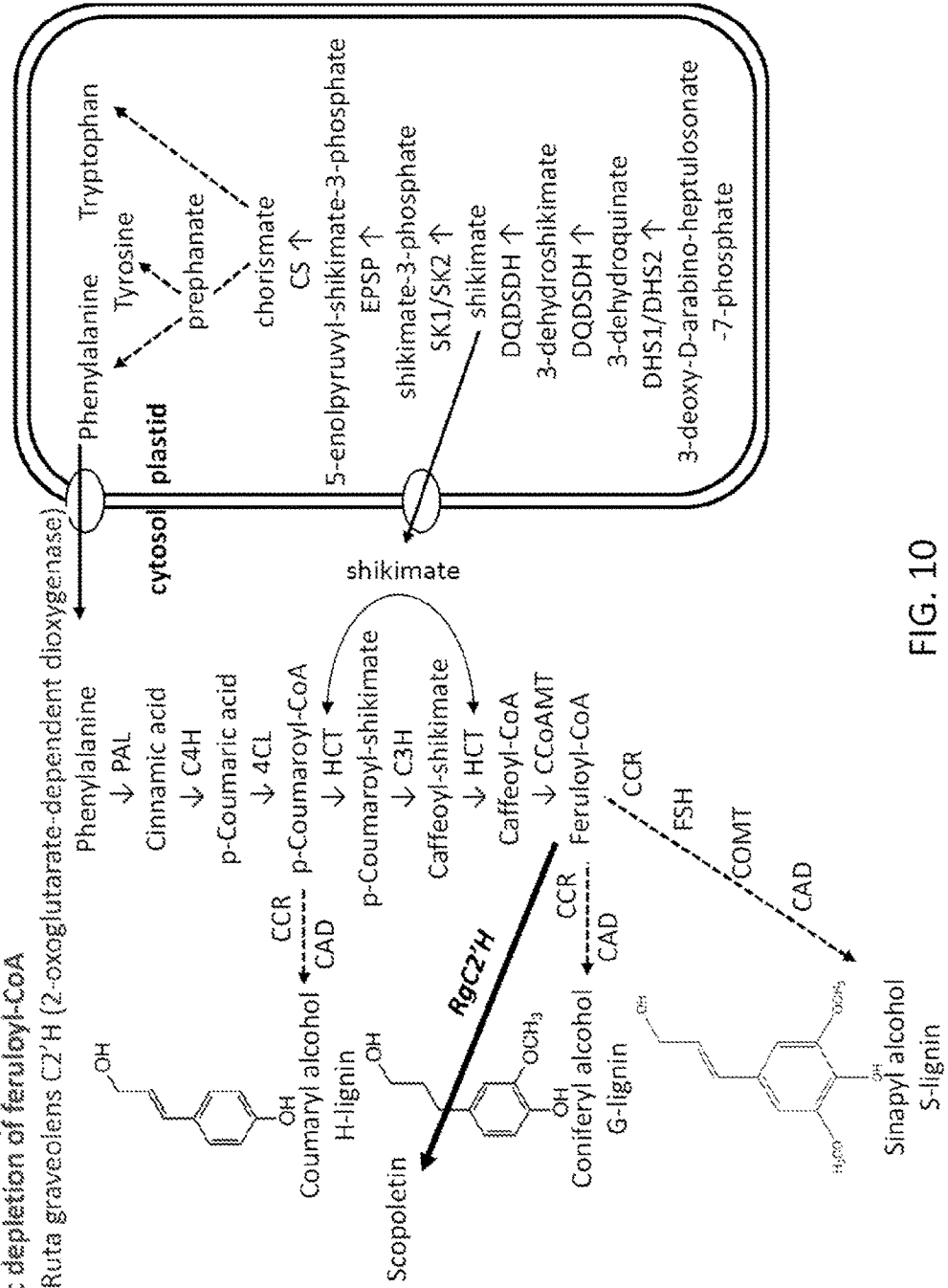
FIG. 10. Lignin reduction via depletion of feruloyl-CoA (CCR substrate). Strategies for reducing or depleting the amount of feruloyl-CoA that is available for the lignin biosynthesis pathway are shown. For example, the amount of cytosolic feruloyl-CoA that is available for the lignin biosynthesis pathway can be reduced or depleted by expressing a 2-oxoglutarate-dependent dioxygenase such as *R. graveolens* C2'H (2-oxoglutarate-dependent dioxygenase) ("RbC2'H").

In some embodiments, a protein that diverts a monolignol precursor from a lignin biosynthesis pathway reduces the amount of cinnamate and/or coumarate that is available for the lignin biosynthesis pathway. Examples of such a protein are shown in FIGS. 6 and 7. In some embodiments, the protein is an enzyme that modifies a cinnamate and/or coumarate substrate, e.g., a cinnamate/p-coumarate carboxyl methyltransferase. In some embodiments, the protein is an enzyme that utilizes cinnamate and/or coumarate in the synthesis of another compound (e.g., a volatile compound, e.g., styrene or p-hydroxystyrene), e.g., phenylacrylic acid decarboxylase or ferulic acid decarboxylase.

Non-limiting examples of a cinnamate/p-coumarate carboxyl methyltransferase enzyme are described in Kapteyn et al., *Plant Cell* 19:3212-3229 (2007). In some embodiments, the protein is a *Ocimum basilicum* cinnamate/p-coumarate carboxyl methyltransferase (CCMT) having the amino acid sequence set forth in SEQ ID NO:12. In some embodiments, the protein is substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to the amino acid sequence of SEQ ID NO:12. In some embodiments, the protein is a homolog of a Ocimum basilicum cinnamate/p-coumarate carboxyl methyltransferase (CCMT) having the amino acid sequence set forth in SEQ ID NO:12. In some embodiments, a polynucleotide encoding the cinnamate/p-coumarate carboxyl methyltransferase comprises a polynucleotide sequence that is identical or substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to SEQ ID NO:11.

Non-limiting examples of a phenylacrylic acid decarboxylase are described in McKenna et al., Metab Eng 13:544-554 (2011). In some embodiments, the protein is a P. penosaceus phenylacrylic aicd decarbaxylase (PDC) having the amino acid sequence set forth in SEQ ID NO:30. In some embodiments, the protein is substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to the amino acid sequence of SEQ ID NO:30. In some embodiments, the protein is a homolog of a P. penosaceus phenylacrylic acid decarboxylase (PDC) having the amino acid sequence set forth in SEQ ID NO:30.

Proteins that Reduce the Amount of Coumaroyl-CoA, Caffeoyl-CoA, and/or Feruloyl-CoA In some embodiments, a protein that diverts a monolignol precursor from a lignin biosynthesis pathway reduces the amount of coumaroyl-CoA and/or feruloyl-CoA that is available for the lignin biosynthesis pathway. Examples of such a protein are shown in FIGS. 8-11. In some embodiments, the protein is an enzyme that modifies a coumaroyl-CoA and/or feruloyl-CoA substrate. In some embodiments, the protein is an enzyme that utilizes coumaroyl-CoA and/or feruloyl-CoA in the synthesis of another compound (e.g., umbelliferone, a volatile compound, scopoletin, chalcone, trihydroxychalcone, stilbene, curuminoid, or benzylacetone), e.g., 2-oxoglutarase-dependent dioxygenase, chalcone synthase, stilbene synthase, cucuminoid synthase, benzalacetone synthase.

A non-limiting example of a 2-oxoglutarase-dependent dioxygenase enzyme is described in Viatart et al., Plant J. 70:460-470 (2012). In some embodiments, the protein is a Ruta graveolens 2-oxoglutarase-dependent dioxygenase (C2'H) having the amino acid sequence set forth in SEQ ID NO:14. In some embodiments, the protein is substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to the amino acid sequence of SEQ ID NO:14. In some embodiments, the protein is a homolog of a Ruta graveolens 2-oxoglutarase-dependent dioxygenase (C2'H) having the amino acid sequence set forth in SEQ ID NO:14. In some embodiments, a polynucleotide encoding the oxogiutarase-dependent dioxygenase comprises a polynucleotide sequence that is identical or substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to SEQ ID NO:13.

Other non-limiting examples of proteins that reduce the amount of coumaroyl-CoA, caffeoyl-CoA, and/or feruloyl-CoA that is available for the lignin biosynthesis pathway chalcone synthase (CHS), stilbene synthase (SPS), cucuminoid synthase (CUS), or benzalacetone synthase (BAS), described in Katsuyama et al., J. Biol. Chem. 282:37702-37709 (2007); Sydor et al., Appl. Environ. Microbiol. 76:3361-3363 (2010); Jiang et al., Phytochemistry 67:2531-2540 (2006); Abe and Morita, Nat. Prod. Rep. 27:809 (2010); Dao et al., Phytochem Rev. 10:397-412(2011); Suh et al., Biochem J. 350:229-235 (2000); Tropf et al., J. Biol. Chem. 270:7922-7928 (1995); Knogge et al., Arch. Biochem. Biophys. 250:364-372 (1986); Ferrer et al., Nat. Struct. Biol. 6:775-784 (1999); Miyazono et al., Proteins 79:669-673 (2010); and Abe et al., Eur. J. Biochem. 268: 3354-3359 (2001). In some embodiments, the protein is a Physcomitrella patens CHS having the amino acid sequence set forth in SEQ ID NO:31; an Arabidopsis thaliana CHS having the amino acid sequence set forth in SEQ ID NO:32; a Vitis vinifera SPS having the amino acid sequence set forth in SEQ ID NO:33; an Oryza sativa CUS having the amino acid sequence set forth in SEQ ID NO:34 or SEQ ID NO:35; or a Rheum palmatum BAS having the amino acid sequence set forth in SEQ ID NO:36; or a homolog thereof. In some embodiments, the protein is substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to the amino acid sequence of any of SEQ ID NOs:31, 32, 33, 34, 35, or 36.

Proteins that Activate Competitive Metabolic Pathway

In some embodiments, a protein that diverts a monolignol precursor from a lignin biosynthesis pathway activates, upregulates, or potentiates a metabolic pathway that competes with the lignin biosynthesis pathway biosynthesis pathway for the use of monolignol precursors. Non-limiting examples of metabolic pathways that are competitive with the lignin biosynthesis pathway include the stilbene biosynthesis pathway, the flavonoid biosynthesis pathway, the curcuminoid biosynthesis pathway, and the bensalacetone biosynthesis pathway. Thus, in some embodiments, the protein that diverts a monolignol precursor from a lignin biosynthesis pathway is a protein (e.g., a transcription factor, a TALE-based artificial transcription factor (see Zhang et al., Nat. Biotechnol. 29:149-153 (2011)), or an enzyme) that activates, upregulates, induces, or potentiates a stilbene biosynthesis pathway, a flavonoid biosynthesis pathway, a curcuminoid biosynthesis pathway, or a bensalacetone biosynthesis pathway As one non-limiting example, a protein can be expressed that activates, upregulates, induces, or potentiates a flavonoid biosynthesis pathway. The flavonoid biosynthesis pathway utilizes monolignol precursors such as coumaroyl-CoA, caffeoyl-CoA, and feruloyl-CoA from the lignin biosynthesis pathway for the synthesis of flavonoids such as chalcones, flavonones, dihydroflavonols, flavonols, and anthocyanins. See FIGS. 9 and 11. In some embodiments, the protein that diverts a monolignol precursor from a lignin biosynthesis pathway is a protein that activates, upregulates, induces, or potentiates the expression and/or activity of an enzyme in the flavonoid biosynthesis pathway (e.g., an enzyme such as chalcone synthase or flavonol synthase). In some embodiments, the protein that diverts a monolignol precursor from a lignin biosynthesis pathway is a transcription factor. Transcription factors in the flavonoid biosynthesis pathway are known in the art. See, e.g., Bovy et al., *Plant Cell* 14:2509-2526 (2002); Tohge et al., *Plant* 42:218-235 (2005); Peel et al., *Plant J.* 59:136-149 (2009); Pattanaik et al., *Planta* 231:1061-1076 (2010); and Hichri et al., *J Exp Botany* 62:2465-2483 (2011); incorporated by reference herein. Non-limiting examples of transcription factors in the flavonoid biosynthesis pathway include MYB transcription factors, basic helix-loop-helix (bHLH) transcription factors, and WD40 transcription factors. In some embodiments, the protein is an *Arabidopsis thaliana* PAP1 R2R3 MYB transcription factor having the amino acid sequence set forth in SEQ ID NO:37; an *Arabidopsis thaliana* PAP2 R2R3 MYB transcription factor having the amino acid sequence set forth in SEQ ID NO:38; an *Arabidopsis thaliana* TT2 R2R3 MYB transcription factor having the amino acid sequence set forth in SEQ ID NO:39; a *Nicotiana tabacum* NtAn2 R2R3 MYB transcription factor having the amino acid sequence set forth in SEQ ID NO:40; a *Medicago truncatula* LAP1 R2R3 MYB transcription factor having the amino acid sequence set forth in SEQ ID NO:41; a *Zea mays* MYR-C R2R3 transcription factor having the amino acid sequence set forth in SEQ ID NO:42; a *Zea mays* MYC-Lc BHLH transcription factor having the amino acid sequence set forth in SEQ ID NO:43; an *Arabidopsis thaliana* TT8 BHLH transcription factor having the amino acid sequence set forth in SEQ ID NO:44; or a *Vitis vinifera* Myc1 BHLH transcription factor having the amino acid sequence set forth in SEQ ID NO:45; or a homolog thereof. In some embodiments, the protein is substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to the amino acid sequence of any of SEQ ID NOs:37, 38, 39, 40, 41, 42, 43, 44, or 45.

In some embodiments, a plant is engineered to express two, three, four or more proteins as described herein. In some embodiments, the plant expresses two or more proteins, each of which is identical or substantially identical to SEQ ID NOs:2, 4, 6, 8, 10, 12, 14, 29, 30, 31, 32, 33, 34, 35, 36, 37, 38, 39, 40, 41, 42, 42, 43, 44, or 45. In some embodiments, the two or more proteins utilize different substrates or activate different pathways; for example, in some embodiments the plant expresses a first protein that reduces the amount of shikimate that is available for the lignin biosynthesis pathway and a second protein that reduces the amount of phenylalanine that is available for the lignin biosynthesis pathway. In some embodiments, the two or more proteins potentiate or activate the same pathway; for example, in some embodiments the plant expresses a first transcription factor and a second transcription factor that function cooperatively to induce the flavonoid biosynthesis pathway.

Proteins that Produce a Competitive Inhibitor of HCT

In some embodiments, a plant having reduced lignin content is engineered by expressing or overexpressing a competitive inhibitor of a lignin biosynthesis pathway enzyme (e.g., a molecule that competes with p-coumaroyl-CoA and/or shikimate as a substrate for hydroxycinnamoyl-CoA shikimate/quinate hydroxycinnamoyltransferase (HCT)). In some embodiments, the method comprises:

introducing into the plant an expression cassette comprising a polynucleotide that encodes a protein that produces a competitive inhibitor of hydroxycinnamoyl-CoA shikimate/quinate hydroxycinnamoyltransferase (HCT) in the plant, wherein the polynucleotide is operably linked to a heterologous promoter; and culturing the plant under conditions in which the protein that produces a competitive inhibitor of HCT is expressed.

In some embodiments, the protein directly or indirectly produces one or more of the competitive inhibitors protocatechuate, gentisate, catechol, 2,3-dihydroxybenzoate, 3,6-dihydroxybenzoate, 3-hydroxy-2-aminobenzoate (e.g., by catalyzing the formation of the competitive inhibitor or by catalyzing the formation of a precursor to the competitive inhibitor). Examples of pathways to produce competitive inhibitors of HCT are shown in FIG. 27.

As a non-limiting example, in some embodiments, the competitive inhibitor of HCT is protocatechuate. As shown in FIG. 27, protocatechuate can be produced by the enzyme dehydroshikimate dehydratase (QsuB) or by the enzyme dehydroshikimate dehydratase (DsDH). In some embodiments, the protein that produces a competitive inhibitor of HCT is a *Corynebacterium glutamicum* dehydroshikimate dehydratase (QsuB) having the amino acid sequence set forth in SEQ ID NO:6 or a *Podospora anserina* dehydroshikimate dehydratase (DsDH) having the amino acid sequence set forth in SEQ ID NO:8. In some embodiments, the protein is substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to the amino acid sequence of SEQ ID NO:6 or SEQ ID NO:8. In some embodiments, the protein is a homolog of a *Corynebacterium glutamicum* dehydroshikimate dehydratase (QsuB) having the amino acid sequence set forth in SEQ ID NO:6 or a homolog of the *Podospora anserina* dehydroshikimate dehydratase (DsDH) having the amino acid sequence set forth in SEQ ID NO:8. In some embodiments, a polynucleotide encoding the dehydroshikimate dehydratase comprises a polynucleotide sequence that is identical or substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to SEQ ID NO:5 or SEQ ID NO:7.

B. Plastidial Expression of Proteins

In some embodiments, the protein that diverts a monolignol precursor from a lignin biosynthesis pathway as described herein is expressed in one or more specific organelles of the plant, e.g., in the plastid of the plant. The polynucleotide sequence encoding the protein that diverts a monolignol precursor from a lignin biosynthesis pathway (e.g., a polynucleotide encoding shikimate kinase (AroK), pentafunctional AROM polypeptide (ARO1), dehydroshikimate dehydratase dehydroshikimate dehydratase (QsuB), phenylacetaldehyde synthase (PAAS), or phenylalanine aminomutase (PAM), e.g., a polynucleotide comprising a sequence that is identical or substantially identical to a polynucleotide sequence of SEQ ID NO:1, 3, 5, 7, or 9, or a polynucleotide comprising a sequence that encodes a polypeptide is identical or substantially identical to an amino acid sequence of SEQ ID NO:2, 4, 6, 8, 10, or 29) can be engineered to include a sequence that encodes a targeting or transit signal for the organelle, e.g., a targeting or transit signal for the plastid. Targeting or transit signals act by facilitating transport of proteins through intracellular membranes, e.g., vacuole, vesicle, plastid, and mitochondrial membranes.

In some embodiments, the plastid targeting signal is a targeting signal described in U.S. Pat. No. 5,510,471, incorporated by reference herein. In some embodiments, the plastid targeting signal is identical or substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to an amino acid sequence of SEQ ID NO:16. In some embodiments, the plastid targeting signal is identical or substantially identical e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to a polynucleotide sequence of SEQ ID NO:15. In some embodiments, the organelle targeting signal (e.g., the plastid targeting signal) is linked in-frame with the coding sequence for the protein that diverts a monolignol precursor from a lignin biosynthesis pathway.

C. Promoters

In some embodiments, the polynueleotide encoding the protein that diverts a monolignol precursor from the lignin biosynthesis pathway, or the protein that produces a competitive inhibitor of HCT, is operably linked to a heterologous promoter. In some embodiments, the promoter is a cell- or tissue-specific promoter as described below. In some embodiments, the promoter is from a gene in the lignin biosynthesis pathway (e.g., a promoter from a gene expressed in the pathway shown in FIG. 1). In some embodiments, the promoter is from a gene in the lignin biosynthesis pathway, with the proviso that the promoter is not the native promoter of the polynucleotide encoding the protein that diverts a monolignol precursor from the lignin biosynthesis pathway or the native promoter of the polynucleotide encoding the protein that produces a competitive inhibitor of HCT to be expressed in the plant. In some embodiments, the promoter is a C4H, C3H, HCT, CCR1, CAD4, CAD5, PAL1, PAL2, 4CL1, or CCoAMT promoter. In some embodiments, the promoter is identical or substantially identical to a polynucleotide sequence of any of SEQ ID NOs:18, 19, 20, 21, 22, 23, 24, 25, 26, 27, or 28.

Cell- or Tissue-Specific Promoters

In some embodiments, the polynucleotide encoding the protein that diverts a monolignol precursor from the lignin biosynthesis pathway, or the protein that produces a competitive inhibitor of HCT, is operably linked to a tissue-specific or cell-specific promoter. In some embodiments, the promoter is a secondary cell wall-specific promoter or a fiber cell-specific promoter. The secondary cell wall-specific promoter is heterologous to the polynucleotide encoding the protein that diverts a monolignol precursor from the lignin biosynthesis pathway, e.g., the promoter and the promoter coding sequence are derived from two different species. A promoter is suitable for use as a secondary cell wall-specific promoter if the promoter is expressed strongly in the secondary cell wall, e.g., in vessel and fiber cells of the plant, but is expressed at a much lower level or not expressed in cells without the secondary cell wall. A promoter is suitable for use as a fiber cell-specific promoter if the promoter is expressed strongly in fiber cells as compared to other non-fiber cells of the plant.

In some embodiments, the promoter is an IRX5 promoter. IRX5 is a gene encoding a secondary cell wall cellulose synthase Cesa4/IRX5, (Genbank Accession No. AF458083_1). In some embodiments, the promoter is identical or substantially identical to the pIRX5 polynucleotide sequence of SEQ ID NO:17.

Secondary cell wall-specific promoters are also described in the art. See, for example, Mitsuda et al., *Plant Cell* 17:2993-3006 (2005); Mitsuda et al., *Plant Cell* 19:270-280 (2007); and Ohtani et al., *Plant Journal* 67:499-512 (2011).

It will be appreciated by one of skill in the art that a promoter region can tolerate considerable variation without diminution of activity. Thus, in some embodiments, a promoter (e.g., a promoter from the lignin biosynthesis pathway, a secondary cell wall-specific promoter, or a fiber cell-specific promoter) is substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to a polynucleotide sequence of any of SEQ ID NOs:17, 18, 19, 20, 21, 22, 23, 24, 25, 26, 27, or 28. The effectiveness of a promoter may be confirmed using a reporter gene (e.g., 1.3-$\beta$-glucuronidase or GUS) assay known in the art.

D. Preparation of Recombinant Expression Vectors

Once the promoter sequence and the coding sequence for the gene of interest (e.g., coding for a protein that diverts a monolignol precursor from the lignin biosynthesis pathway) are obtained, the sequences can be used to prepare an expression cassette for expressing the gene of interest in a transgenic plant. Typically, plant transformation vectors include one or more cloned plant coding sequences (genomic or cDNA) under the transcriptional control of 5' and 3' regulatory sequences and a dominant selectable marker. Such plant transformation vectors may also contain a promoter (e.g., a secondary cell wall-specific promoter or fiber cell-specific promoter as described herein), a transcription initiation start site, an RNA processing signal (such as intron splice sites), a transcription termination site, and/or a polyadenylation signal.

The plant expression vectors may include RNA processing signals that may be positioned within, upstream, or downstream of the coding sequence. In addition, the expression vectors may include regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Plant expression vectors routinely also include dominant selectable marker genes to allow for the ready selection of transformants. Such genes include those encoding antibiotic resistance genes (e.g., resistance to hygromycin, kanamycin, bleomycin, G418, streptomycin or spectinomycin), herbicide resistance genes (e.g., phosphinothricin acetyltransferase), and genes encoding positive selection enzymes (e.g. mannose isomerase).

Once an expression cassette comprising a polynucleotide encoding the protein that diverts a monolignol precursor from the lignin biosynthesis pathway and operably linked to a promoter as described herein has been constructed, standard techniques may be used to introduce the polynucleotide into a plant in order to modify gene expression. See, e.g., protocols described in Ammirato et al. (1984) Handbook of Plant Cell Culture—Crop Species. Macmillan Publ. Co. Shimamoto et al. (1989) Nature 338:274-276; Fromm et al. (1990) Bio/Technology 8:833-839; and Vasil et al. (1990) Bio/Technology 8:429-434.

Transformation and regeneration of plants are known in the art, and the selection of the most appropriate transformation technique will be determined by the practitioner. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumeficiens* mediated transformation. Transformation means introducing a nucleotide sequence in a plant in a manner to cause stable or transient expression of the sequence. Examples of these methods in various plants include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042.

Following transformation, plants can be selected using a dominant selectable marker incorporated into the transformation vector. Typically, such a marker will confer antibiotic or herbicide resistance on the transformed plants or the ability to grow on a specific substrate, and selection of transformants can be accomplished by exposing the plants to appropriate concentrations of the antibiotic, herbicide, or substrate.

The polynucleotides coding for a protein that diverts a monolignol precursor from the lignin biosynthesis pathway, as well as the polynucleotides comprising promoter sequences for secondary cell wall-specific promoters or fiber cell-specific promoters, can be obtained according to any method known in the art. Such methods can involve amplification reactions such as PCR and other hybridization-based reactions or can be directly synthesized.

E. Plants in Which Lignin Content Can Be Reduced

An expression cassette comprising a polynucleotide encoding the protein that diverts a monolignol precursor from the lignin biosynthesis pathway and operably linked to a promoter, or comprising a polynucleotide encoding the protein that produces a competitive inhibitor of HCT and operably linked to a promoter, as described herein, can be expressed in various kinds of plants. The plant may be a monocotyledonous plant or a dicotyledonous plant. In some embodiments of the invention, the plant is a green field plant. In some embodiments, the plant is a gymnosperm or conifer.

In some embodiments, the plant is a plant that is suitable for generating biomass. Examples of suitable plants include, but are not limited to, *Arabidopsis*, poplar, eucalyptus, rice, corn, switchgrass, sorghum, millet, miscanthus, sugarcane, pine, alfalfa, wheat, soy, barley, turfgrass, tobacco, hemp, bamboo, rape, sunflower, willow, *Jatropha*, and *Brachypodium*.

In some embodiments, the plant into which the expression cassette is introduced is the same species of plant as the promoter and/or as the polynucleotide encoding the protein that diverts a monolignol precursor from the lignin biosynthesis pathway or encoding the protein that produces a competitive inhibitor of HCT (e.g., a polynucleotide encoding the protein that diverts a monolignol precursor from the lignin biosynthesis pathway and a secondary cell wall-specific or fiber cell-specific promoter from *Arabidopsis* is expressed in an *Arabidopsis* plant). In some embodiments, the plant into which the expression cassette is introduced is a different species of plant than the promoter and/or than the polynucleotide encoding the protein that diverts a monolignol precursor from the lignin biosynthesis pathway (e.g., a polynucleotide encoding the protein that diverts a monolignol precursor from the lignin biosynthesis pathway and/or a secondary cell wall-specific or fiber cell-specific promoter from *Arabidopsis* is expressed in a poplar plant). See, e.g., McCarthy et al., *Plant Cell Physiol.* 51:1084-90 (2010); and Thong et al., *Plant Physiol.* 152:1044-55 (2010).

F. Screening for Plants Having Reduced Lignin Content

After transformed plants are selected, the plants or parts of the plants can be evaluated to determine whether expression of the protein that diverts a monolignol precursor from the lignin biosynthesis pathway, or expression of the protein that produces a competitive inhibitor of HCT, e.g., under the control of a secondary cell wall-specific promoter or a fiber cell-specific promoter, can be detected, e.g., by evaluating the level of RNA or protein, by measuring enzymatic activity of the protein, and/or by evaluating the size, molecular weight, content, or degree of branching in the lignin molecules found in the plants. These analyses can be performed using any number of methods known in the art.

In some embodiments, plants are screened by evaluating the level of RNA or protein. Methods of measuring RNA expression are known in the art and include, for example, PCR, northern analysis, reverse-transcriptase polymerase chain reaction (RT-PCR), and microarrays. Methods of measuring protein levels are also known in the art and include, for example, mass spectroscopy or antibody-based techniques such as ELISA, Western blotting, flow cytometry, immunofluorescence, and immunohistochemistry.

In some embodiments, plants are screened by assessing for activity of the protein being expressed, and also by evaluating lignin size and composition. Enzymatic assays for the proteins described herein (e.g., shikimate kinase (AroK), pentafunctional AROM polypeptide (ARO1), dehydroshikimate dehydratase (DsDH), dehydroshikimate dehydratase (QsuB), phenylacetaldehyde synthase (PAAS), phenylalanine aminomutase (PAM), p-coumarate/cinnamate carboxylmethltransferase (CCMT1), ferulic acid decarboxylase (FDC1), phenylacrylic acid decarboxylase (PDC1), 2-oxoglutarate-dependent dioxygenase (C2'H), chalcone synthase (CHS), stilbene synthase (SPS), cucuminoid synthase (CUS), or benzalacetone (BAS)) are well known in the art. Lignin molecules can be assessed, for example, by nuclear magnetic resonance (NMR), spectrophotometry, microscopy, klason lignin assays, thioacidolysis, acetylbromide reagent or by histochemical staining (e.g., with phloroglucinol).

As a non-limiting example, any of several methods known in the art can be used for quantification and/or composition analysis of lignin in a plant or plant part as described herein. Lignin content can be determined from extract free cell wall residues using acetyl bromide or Klason methods. See, e.g., Eudes et al., *Plant Biotech. J.* 10:609-620 (2012); Yang et al., *Plant Biotech. J.* (2013) (in press); and Deuce et al. (eds) *Lignin determination*. Berlin: SpringerVerlag (1992); each of which is incorporated by reference herein. Extract free cell wall residues correspond to raw biomass, which has been extensively washed to remove the ethanol soluble component. Eudes et al., *Plant Biotech. J.* 10:609-620 (2012); Yang et al., *Plant Biotech. J.* (2013) (in press); Sluiter et al., Determination of structural carbohydrates and lignin in biomass. In: *Laboratory Analytical Procedure*. National Renewable Energy Laboratory, Golden, Colo., USA; and Kim et al., *Bio. Res.* 1:56-66 (2008). Lignin composition analysis and G/S lignin subunit determination can be performed using any of various techniques known in the art such as 2D 13C-H1 HSQC NMR spectroscopy (Kim and Ralph, *Org. Biomol. Chem.* 8:576-591 (2010); Kim et al., *Bio. Res.* 1:56-66 (2008)); thioacidolysis method (Lapierre et al., *Plant Physiol.* 119:153-164

(1999); Lapierre et al., *Res. Chem. Intermed.* 21:397-412 (1995); Eudes et al., *Plant Biotech. J.* 10:609-620 (2012)); derivatization followed by reductive cleavage method (DFRC method; Lu and Ralph, *J. Agr. Food Chem* 46:547-552 (1998) and Lu and Ralph, *J. Agr. Food Chem* 45:2590-2592 (1997)) and pyrolysis-gas chromatograph method (Py-GC method; Sonoda et al., *Anal. Chem.* 73:5429-5435 (2001)) directly from extract free cell wall residues or from cellulolytic enzyme lignin (CEL lignin). CEL lignin derives from cell wall residues, which were hydrolyzed with crude cellulases to deplete the polysaccharide fraction and enrich the lignin one (Eudes et al., *Plant Biotech. J.* 10:609-620 (2012)).

IV. Methods of Using Plants Having Reduced Lignin Content

Plants, parts of plants, or plant biomass material from plants having reduced lignification due to the expression of a protein that diverts a monolignol precursor from the lignin biosynthesis pathway or due to the expression of a protein that produces a competitive inhibitor of HCT, e.g., under the control of a secondary cell wall-specific promoter or a fiber cell-specific promoter, can be used for a variety of methods. In some embodiments, the plants, parts of plants, or plant biomass material generate less recalcitrant biomass for use in a conversion reaction as compared to wild-type plants. In some embodiments, the plants, parts of plants, or plant biomass material are used in a saccharification reaction, e.g., enzymatic saccharification, to generate soluble sugars at an increased level of efficiency as compared to wild-type plants. In some embodiments, the plants, parts of plants, or plant biomass material are used to increase biomass yield or simplify downstream processing for wood industries (such as paper, pulping, and construction) as compared to wild-type plants. In some embodiments, the plants, parts of plants, or plant biomass material are used to increase the quality of wood for construction purposes. In some embodiments the plants, parts of plants, or plant biomass material can be used in a combustion reaction, gasification, pyrolysis, or polysaccharide hydrolysis (enzymatic or chemical). In some embodiments, the plants, parts of plants, or plant biomass material are used as feed for animals (e.g., ruminants).

Methods of conversion, for example biomass gasification, are known in the art. Briefly, in gasification plants or plant biomass material (e.g., leaves and stems) are ground into small particles and enter the gasifier along with a controlled amount of air or oxygen and steam. The heat and pressure of the reaction break apart the chemical bonds of the biomass, forming syngas, which is subsequently cleaned to remove impurities such as sulfur, mercury, particulates, and trace materials. Syngas can then be converted to products such as ethanol or other biofuels.

Methods of enzymatic saccharification are also known in the art. Briefly, plants or plant biomass material (e.g., leaves and stems) are optionally pre-treated with hot water, dilute alkaline, AFEX (Ammonia Fiber Explosion), ionic liquid or dilute acid, followed by enzymatic saccharification using a mixture of cell wall hydrolytic enzymes (such as hemicellulases, cellulases and beta-glucosidases) in buffer and incubation of the plants or plant biomass material with the enzymatic mixture. Following incubation, the yield of the saccharification reaction can be readily determined by measuring the amount of reducing sugar released, using a standard method for sugar detection, e.g. the dinitrosalicylic acid method well known to those skilled in the art. Plants engineered in accordance with the invention provide a higher saccharification efficiency as compared to wild-type plants, while the plants' growth, development, or disease resistance is not negatively impacted.

EXAMPLES

The following examples are provided to illustrate, but not limited the claimed invention.

Example 1: Strategies for Diverting a Monolignol Precursor from the Lignin Biosynthesis Pathway The engineered plants of the present invention express one or more genes encoding a protein that diverts a precursor component from the lignin biosynthesis pathway (FIG. 1) to a competitive pathway. This diversion reduces the amount of lignin that is produced and increases the amount of product produced by the competitive pathway.

FIGS. 2-11 provide exemplary strategies for diverting a precursor component from the lignin biosynthesis pathway. In one strategy (FIGS. 2 and 3), the monolignol precursor shikimate can be reduced or depleted. For example, the amount of cytosolic and/or plastidial shikimate that is available for the lignin biosynthesis pathway can be reduced or depleted by expressing a shikimate kinase such as *M. tuberculosis* shikimate kinase ("MtAroK"), a pentafunctional arom protein such as *S. cerevisiae* pentafunctional arom protein ("ScAro1"), a dehydroshikimate dehydratase such as *C. glutamicum* dehydroshikimate dehydratase ("CgQsuB"), or a *P. anserina* dehydroshikimate dehydratase ("PaDsDH").

In another strategy (FIGS. 4 and 5), the monolignol precursor phenylalanine can be reduced or depleted. For example, the amount of cytosolic and/or plastidial phenylalanine that is available for the lignin biosynthesis pathway can be reduced or depleted by expressing a phenylacetaldehyde such as *P. hybrida* phenylacetaldehyde synthase ("PhPAAS") or a phenylalanine aminomutase such as *T. canadensis* phenylalanine aminomutase ("TcPAM").

In another strategy (FIGS. 6 and 7), the monolignol precursors cinnamate and/or p-coumarate are reduced or depleted. For example, the amount of cytosolic cinnamate and/or p-coumarate that is available for the lignin biosynthesis pathway can be reduced or depleted by expressing a cinnamate/p-coumarate carboxyl methyltransferase such as *O. basilicum* cinnamate/p-coumarate carboxyl methyltransferase ("ObCCMT1") or a phenylacrylic acid decarboxylase such as *P. pentosaceus* phenylacrylic decarboxylase ("PDC").

In another strategy (FIGS. 8-11), the monolignol precursors coumaroyl-CoA, caffeoyl-CoA, and/or feruloyl-CoA are reduced or depleted. For example, the amount of cytosolic coumaroyl-CoA, caffeoyl-CoA, and/or feruloyl-CoA that is available for the lignin biosynthesis pathway can be reduced or depleted by expressing a 2-oxoglutarate-dependent dioxygenase such as *R. graveolens* C2'H (2-oxoglutarate-dependent dioxygenase) ("RbC2'H"), a chalcone synthase (CHS), a stilbene synthase (SPS), a cucuminoid synthase (CUS), or a benzalacetone (BAS).

Example 2: Generation of Transgenic Lines Expressing QsuB or DsDH in Plastids

The promoter (pC4H) of the lignin C4H gene from *Arabidopsis* was synthesized with flanking SmaI and AvrII restriction sites at the 3' and 5' ends respectively (Genscript).

The encoding sequence of the chloroplastic targeting signal peptide sequence (ctss; U.S. Pat. No. 5,510,471) was codon optimized and synthesized (Genscript), then amplified by PCR and inserted into the AvrII restriction site located at the 5' end of pC4H using In-Fusion cloning (Clontech). The pC4Hctss DNA fusion was then used to replace the IRX5 promoter from pTKan-pIRX5 (Eudes et al. *Plant Biotechnol J* 10, 609-620 (2012)) using Gateway technology (Invitrogen) and to generate a new pTkan-pC4Hctss-GWR3R2 vector. This vector is designed to clone in-frame with the ctss sequence any gene of interest previously cloned into a pDONR221.P3-P2 vector according to the manufacturer instruction (Invitrogen).

Codon-optimized nucleotide sequences encoding for the dehydroshikimate dehydratases QsuB from *Corynebacterium glutamicum* (accession number A4QB63) and DsDH from *Podospora anserina* (accession number CAD60599) were synthesized for expression in *Arabidopsis* (Genescript), cloned in pDONR221.P3-P2 gateway vector according the manufacturer instruction (Invitrogen), and transferred into pTkan-pC4Hctss-GWR3R2 by LR clonase reaction (invitrogen) to generate the pTKan-pC4Hctss-QsuB and pTKan-pC4Hctss-DsDH binary vectors respectively. The in-frame fusions of cttss with QsuB and DsDH encoding sequences were verified by sequencing.

Both constructs were introduced independently into WT *Arabidopsis* plants (ecotype Co10) via *Agrobacterium tumefaciens*-mediated transformation (Bechtold and Pelletier, *Methods Mol Biol* 82:259-266 (1998)) and several independent S-QsuB and S-DsDH lines harboring ctss::QsuB and ctss::DsDH gene fusions respectively were generated.

Results

Figure 11:
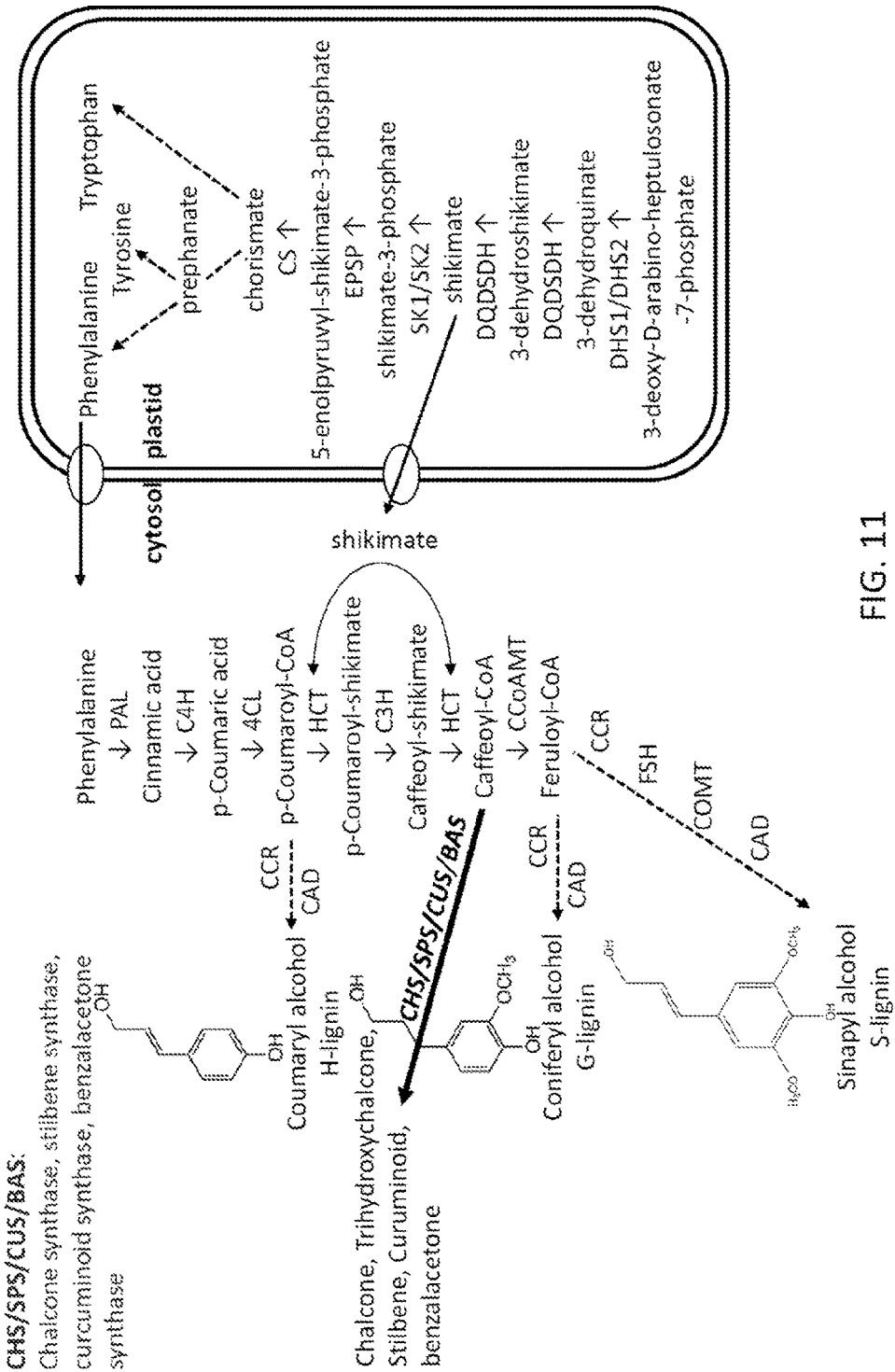
FIG. 11. Lignin reduction via depletion of caffeoyl-CoA feruloyl-CoA (CCR substrate). Strategies for reducing or depleting the amount of caffeoyl-CoA and/or feruloyl-CoA that is available for the lignin biosynthesis pathway are shown. For example, the amount of cytosolic caffeoyl-CoA and/or feruloyl-CoA that is available for the lignin biosynthesis pathway can be reduced or depleted by expressing a chalcone synthase (CHS), synthase (SPS), cucuminoid synthase (GUS), or benzalacetone (BAS).
Figure 12:
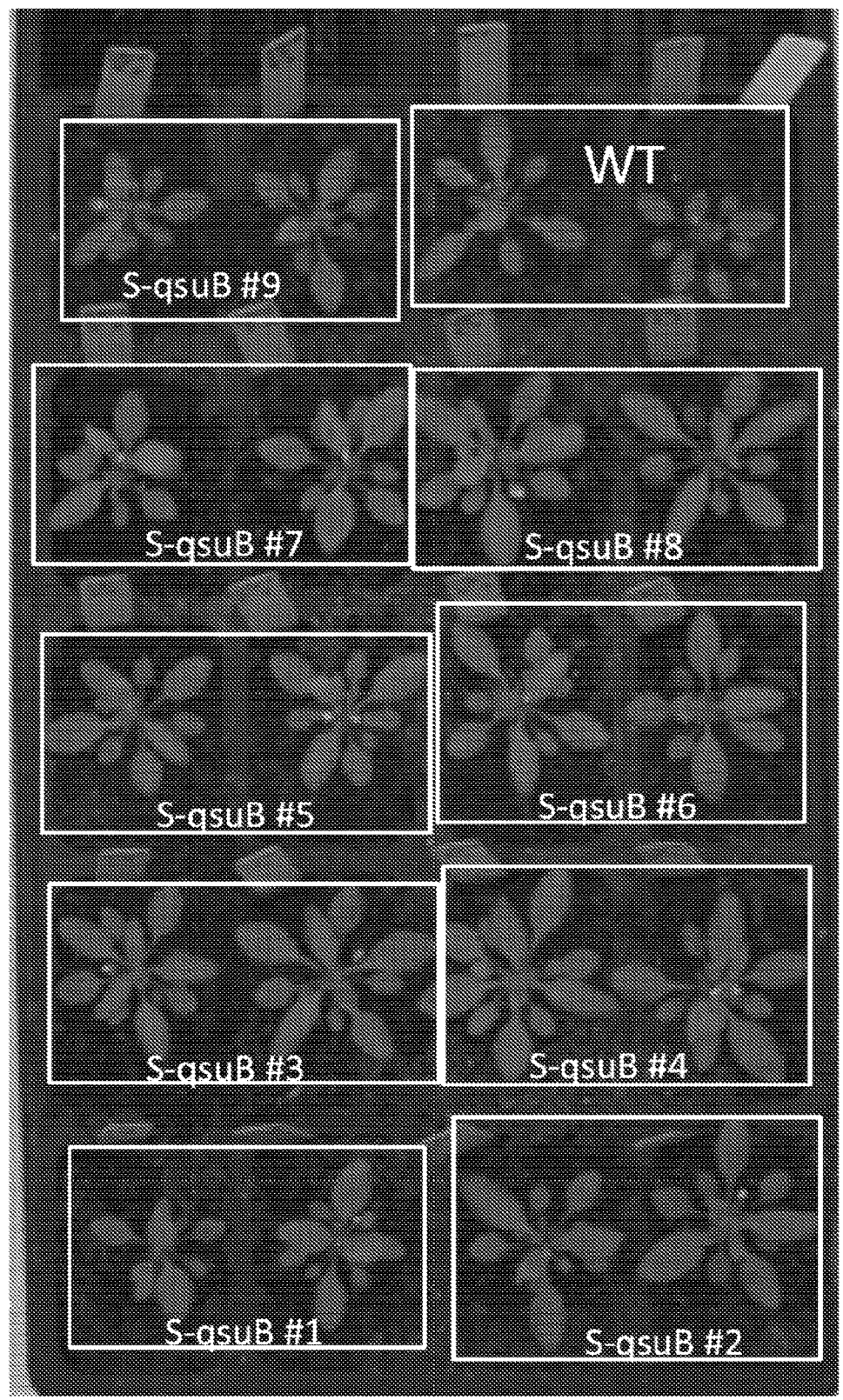
FIG. 12. Growth phenotype analysis of S-QsuB lines. Picture of 3 weeks-old plants at rosette stage. No phenotypic differences could be observed between S-QsuB lines and WT plants at the rosette stage.
Figure 13:
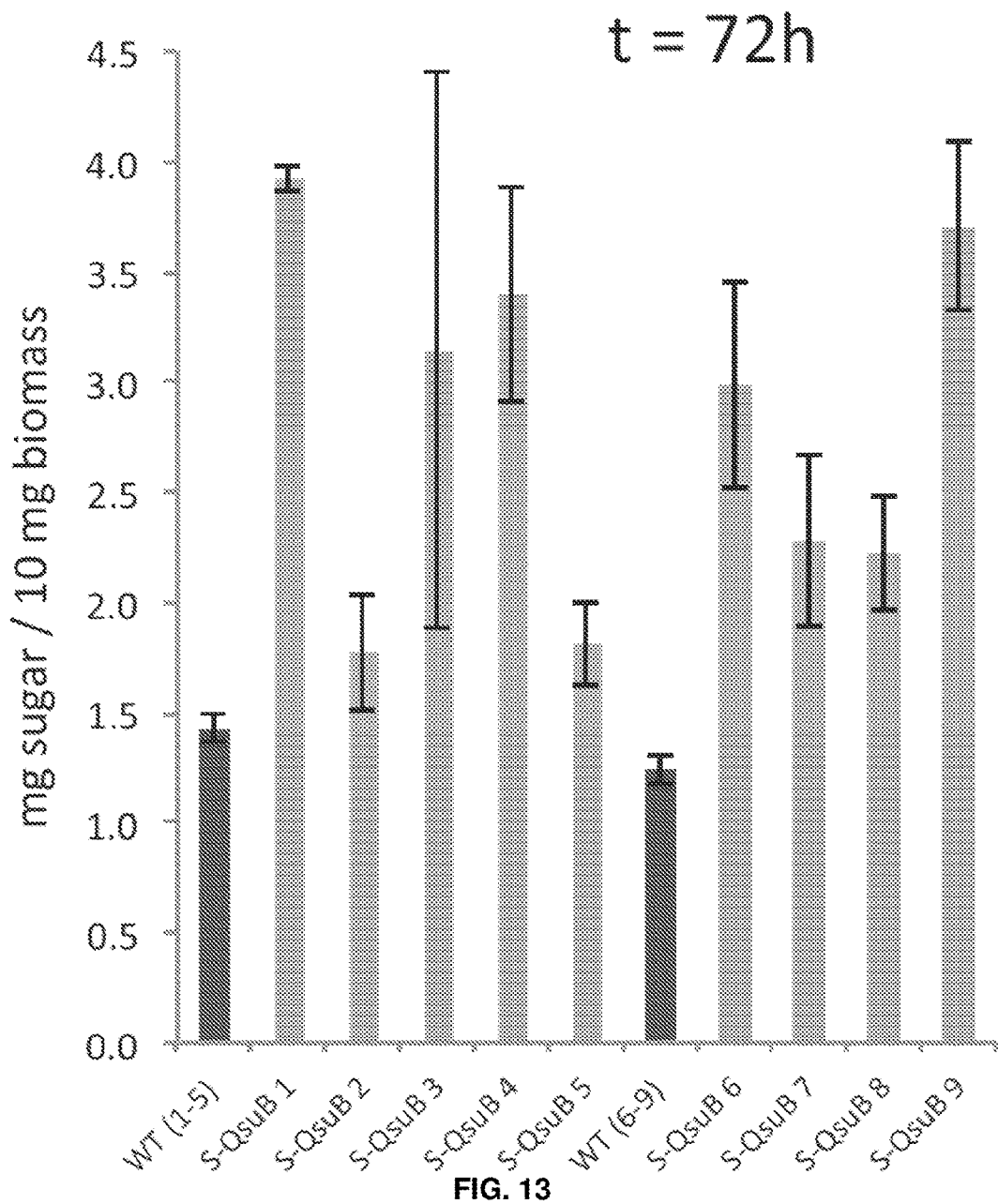
FIG. 13. Total reducing-sugars released from stem biomass of S-QsuB lines and WT plants after 72 h incubation with a cellulolytic enzyme cocktail. Total reducing-sugars released from biomass after hot-water pretreatment (1 h at 120 C) and incubation with a cellulolytic enzyme cocktail (Novozymes Cellic® CTec2) at a loading of 0.88% (g enzyme/g biomass) were measured using the 3,5-Dinitrosalicylic acid assay as described in Eudes et al. 2012 (*Plant Biotech Journal* 10(5):609-620).

Nine independent lines resistant to kanamycin and therefore harboring the pTKan-pC4Hctss-QsuB construct (S-QsuB lines) were selected and analyzed at the T2 generation. These lines express the dehydroshikimate dehydratase QsuB protein from *Corynebacterium glutamicum* fused to a plastid targeting signal peptide to address the QsuB protein in their plastids. At the rosette stage (3-week-old), S-QsuB lines were phenotypically indistinguishable from wild-type (WT) plants (FIG. 11). The biomass from dried senesced stems collected from S-QsuB lines and WT plants was used to perform saccharification analysis. As shown on FIG. 12, the amount of reducing sugars released from the biomass of all the S-QsuB lines was higher compared to the amount released from WT plants. In particular, using similar amount of cellulolytic enzyme, the S-QsuB lines #1, 4, and 9 showed improved saccharification efficiencies of up to 3.0 fold compared to WT plants (FIG. 12). Moreover, the amount of reducing sugars released from the biomass of S-QsuB lines #1, #4, #9) and WT plants using different loadings of cellulolytic enzyme cocktail was investigated. As shown on FIG. 13, the saccharification efficiency was on average 75% higher for the three S-QsuB lines although 10 times less enzyme was used compared to WT biomass. This result shows that much less cellulolytic enzyme is required to release similar amount of sugars from the biomass of S-QsuB lines compared to that of WT plants.

Figure 14:
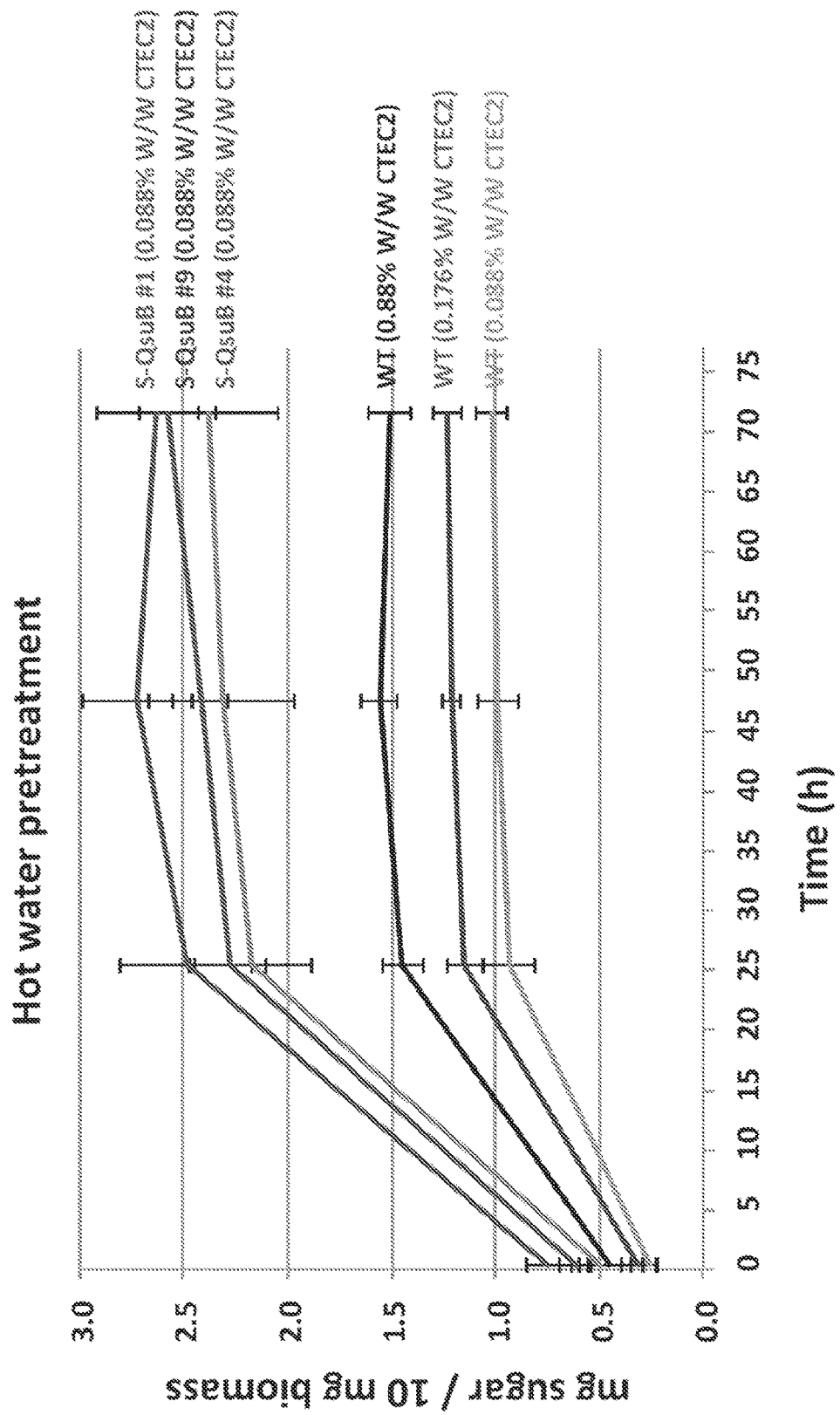
FIG. 14. Time course for total reducing-sugars released from stem biomass of S-QsuB lines and WT plants after incubation with different loadings of a cellulolytic enzyme cocktail. Time course for total reducing-sugars released from biomass after hot-water pretreatment (1 h at 120 C) and incubation with different loadings (0.88%, 0.176% or 0.088%; g of enzyme/g of biomass) of a cellulolytic enzyme cocktail (Novozymes Cellic® CTec2). Measurements were performed as described in (Eudes et al. 2012 Plant Biotech Journal 10(5):609-620).
Figure 15:
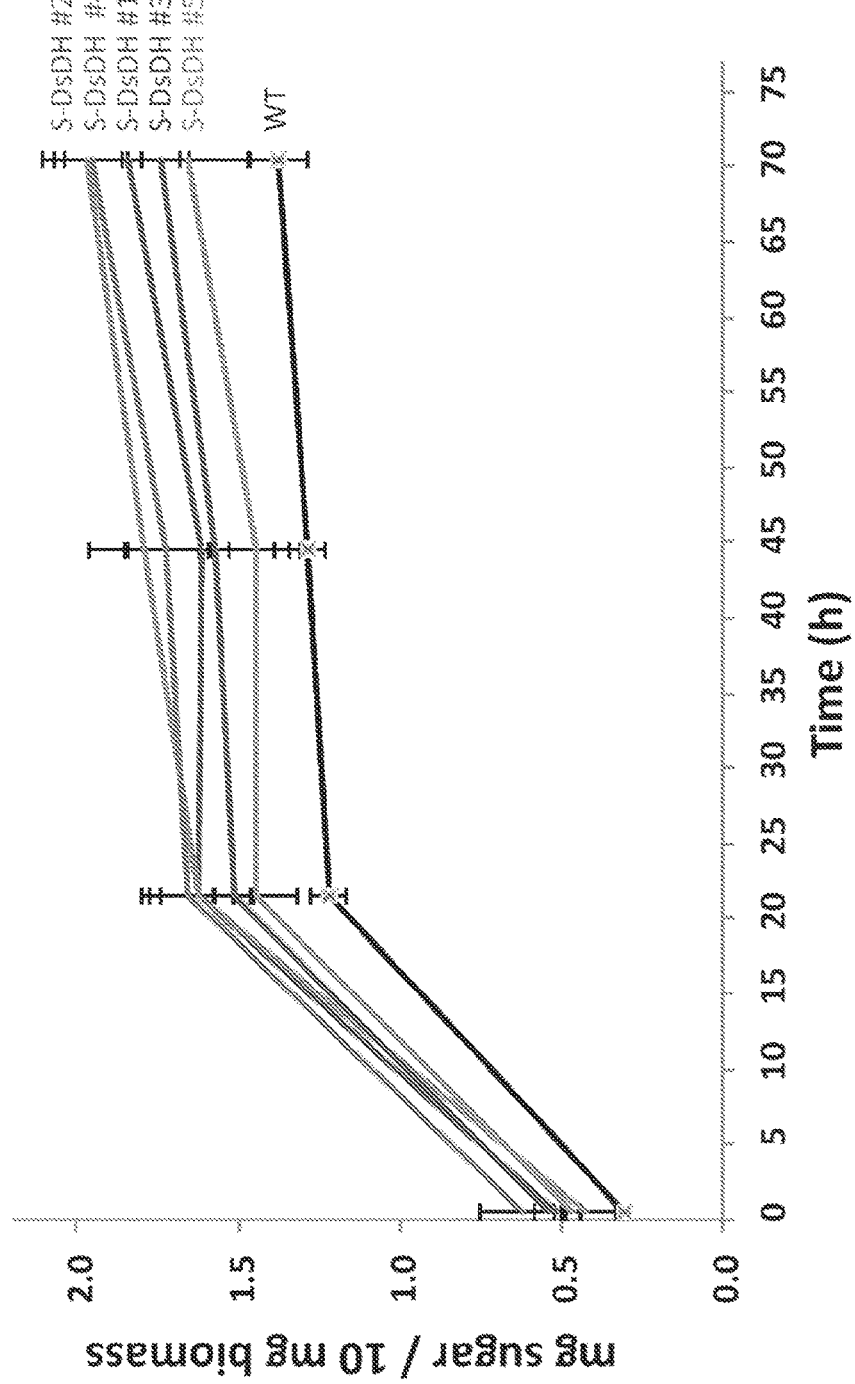
FIG. 15. Total reducing-sugars released from stem biomass of S-DsDH lines after 72 h incubation with a cellulolytic enzyme cocktail. Time course for total reducing-sugar released from biomass after hot-water pretreatment (1 h at 120 C) and incubation with a cellulolytic enzyme cocktail (Novozymes Cellic® CTec2) at a loading of 0.88% (g enzyme/g biomass). Measurements were performed as described in (Eudes et al. 2012 Plant Biotech Journal 10(5): 609-620).

Alternatively, five independent lines resistant to kanamycin and therefore harboring the pTKan-pC4Hctss-DsDH construct (S-DsDH lines) were selected and analyzed at the T2 generation. These lines express the dehydroshikimate dehydratase DsDH protein from *Podospora anserina* fused to a plastid targeting signal peptide to address the QsuB protein in their plastids. The biomass from dried senesced stems collected from S-DsDH lines and WT plants was used to perform saccharification analysis. As shown on FIG. 14, using identical amount of cellulolytic enzyme, the amount of reducing sugars released over time from the biomass of all the S-DsDH lines was higher compared to the amount released from WT plants, representing an improvement of up to 1.4 fold after 72 h of hydrolysis. Similarly to the S-QsuB lines, this result indicates that the biomass of S-DsDH lines is less recalcitrant to polysaccharide enzymatic digestion compared to WT plants.

Example 3: Expression of a Bacterial 3-dehydroshikimate Dehydratase Reduces Lignin Content and Improves Biomass Saccharification Efficiency Abstract Lignin confers recalcitrance to plant biomass used as feedstocks in agro-processing industries or as a source of renewable sugars for the production of bioproducts. The metabolic steps for the synthesis of lignin building blocks belong to the shikimate and phenylpropanoid pathways. Genetic engineering efforts to reduce lignin content typically employ gene-knockout or gene-silencing techniques to constitutively repress one of these metabolic pathways. In this study, we report that expression of a 3-dehydroshikimate dehydratase (QsuB from *Corynebacterium glutamicum*) reduces lignin deposition in *Arabidopsis* cell walls. QsuB was targeted to the plastids to convert 3-dehydroshikimate an intermediate of the shikimate pathway into protocatechuate. Compared to wild-type plants, lines expressing QsuB contain higher amounts of protocatechuate, cinnamate, p-coumarate, p-coumaraldehyde, and coumaryl alcohol. 2D-NMR spectroscopy, thioacidolysis, and pyrolysis-gas chromatography/mass spectrometry (pyro-GC/MS) reveal an increase of p-hydroxyphenyl units and a reduction of guaiacyl units in the lignin of QsuB lines, while size-exclusion chromatography indicates a lower degree of lignin polymerization. Our data show that the expression of QsuB primarily affects one of the key enzymatic steps within the lignin biosynthetic pathway. Finally, biomass from these lines exhibits more than a twofold improvement in saccharification efficiency. We conclude that the expression of QsuB in plants, in combination with specific promoters, is a promising gain-of-function strategy for spatio-temporal reduction of lignin in plant biomass.

Significance

Lignin is a complex aromatic polymer found in plant cells walls that is largely responsible for the strength and toughness of wood. These properties also confer "recalcitrance" to biomass, so materials high in lignin content are more difficult to break down in processes such as production of biofuels. Efforts to reduce lignin content through altering plant gene expression often result in reduced biomass yield and compromise plant fitness. In this study, we present an effective alternative strategy: reducing lignin content and biomass recalcitrance through expression of a bacterial 3-dehydroshikimate dehydratase in plants. We demonstrate that this strategy achieved dramatic changes in the lignin composition and structure in transgenic plants, as well as improved conversion of biomass into fermentable sugars.

Introduction

Plant cells walls are the primary source of terrestrial biomass and mainly consist of cellulosic and hemicellulosic polysaccharides impregnated with lignins. Lignins are polymers of p-hydroxycinnamyl alcohols (i.e., monolignols), which are synthesized inside the cells, exported to the cell wall, and ultimately undergo oxidative polymerization via laccase and peroxidase activities. The main monolignols—p-coumaryl, coniferyl, and sinapyl alcohols—give rise to the p-hydroxyphenyl (H), guaiacyl (G), and syringyl (S) lignin units, respectively (1). Lignification generally confers mechanical strength and hydrophobicity in tissues that develop secondary cell walls, such as sclerenchyma (i.e., fibers) and xylem vessels. In addition to its essential role for upright growth, lignin also serves as a physical barrier against pathogens that degrade cell walls (2).

Lignocellulosic biomass is used for pulp and paper manufacture, ruminant livestock feeding, and more recently has been considered an important source of simple sugars for fermentative production of intermediate or specialty chemicals and biofuels (3). It is well-documented that lignin in plant biomass negatively affects pulp yield, forage digestibility, and polysaccharide saccharification (4-6). This has prompted major interest in developing a better understanding of lignin biosynthesis to reduce biomass recalcitrance by modifying lignin content and/or composition.

Figure 20:
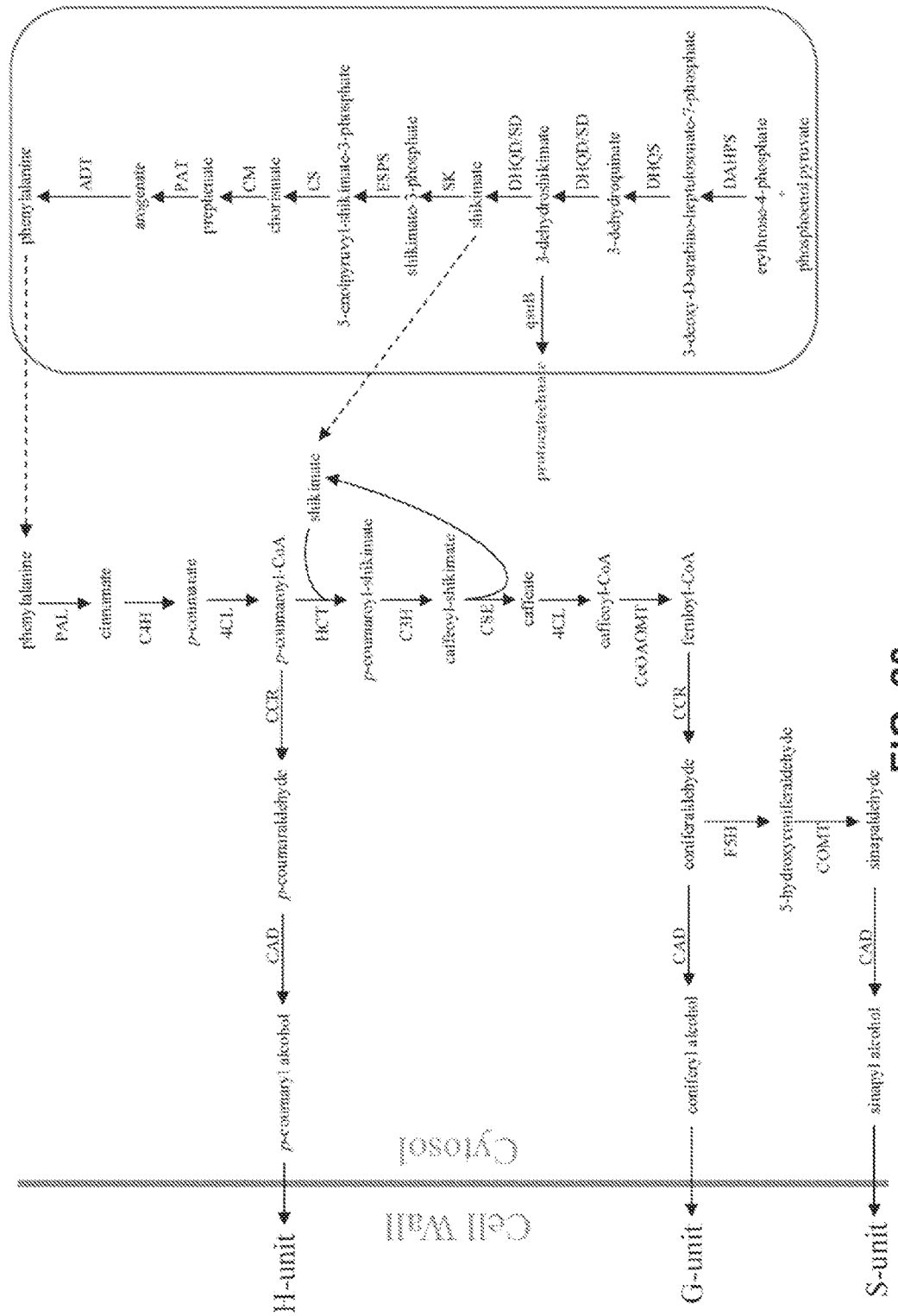
FIG. 20. The lignin biosynthetic pathway. Abbreviations: DAHPS, 3-deoxy-D-arabino-heptulosonate 7-phosphate synthase; DHQS, 3-dehydroquinate synthase; DHQD/SD, 3-dehydroquinate dehydratase; SK, shikimate kinase; ESPS, 3-phosphoshikimate 1-carboxyvinyltransferase; CS, chorismate synthase; CM, chorismate mutase; PAT, prephenate aminotransferase; ADT, arogenate dehydratase; PAL, phenylalanine ammonia-lyase; C4H, cinnamate 4-hydroxylase; CSE, caffeoyl shikimate esterase; 4CL, 4-coumarate CoA ligase; CAD, cinnamyl alcohol dehydrogenase; F5H, ferulate 5-hydroxylase; C3H, coumarate 3-hydroxylase; COMT, caffeic acid 3-O-methyltransferase; CCR, cinnamoyl-CoA reduetase; HCT, hydroxycinnamoyl-Coenzyme A shikimate/quinate hydroxycinnamoyltransferase; CCoAOMT, caffeoyl/CoA-3-O-methyltransferase; qsuB, 3-dehydroshikimate dehydratase from *Corynebacterium glutamicum*.

The shikimate pathway, which is located in plastids in plants, provides a carbon skeleton for the synthesis of phenylalanine, the precursor of the cytosolic phenylpropanoid pathway responsible for the biosynthesis of monolignols (FIG. 20). All the metabolic steps and corresponding enzymes for both pathways are known and well-conserved across land plants (7-10). Classic approaches to lignin reduction have relied on genetic modifications, such as transcript reduction and allelic variation of specific genes from the phenylpropanoid pathway (11, 12). However, these strategies often result in undesired phenotypes—including dwarfism, sterility, and increased susceptibly to environmental stresses—due to loss of cell-wall integrity, depletion of other phenylpropanoid-related metabolites, accumulation of pathway intermediates, or the constitutive activation of defense responses (13, 14). Such negative effects are unfortunately difficult to avoid because of the non-tissue specificity of the strategies employed: allelic variations are transmitted to every cell of the plant during cell divisions, and small interfering RNAs generated for gene silencing generally move from cell-to-cell and over long distance in vegetative tissues (15).

Alternatively, there are novel and promising gain-of-function strategies that involve expression of specific proteins to reduce the production of the three main monolignols change their ratios. Using specific promoters with restricted expression patterns, these strategies would enable the alteration of lignin at later developmental stages or, for example, only in certain tissues such as fibers—without compromising the functionality of conductive vessels for the transport of water (14). Examples of such expressed proteins are transcription factors that act as negative regulators of lignin biosynthesis (16-19); enzymes that use intermediates of the lignin pathway for the synthesis of derived metabolites (20-22); engineered enzymes that modify monolignols into their non-oxidizable forms (23): or proteins that mediate the post-transcriptional degradation of enzymes from the lignin biosynthetic pathway (24).

In this study, we report for the first time on the expression of a bacterial 3-dehydroshikimate dehydratase in *Arabidopsis* (25). We selected QsuB from *C. glutamicum* and targeted it to the plastids to convert the shikimate precursor 3-dehydroshikimate into protocatechuate, with the aim of reducing lignin content and modifying its composition and structure in the biomass of transgenic lines. Metabolomic analysis of plants expressing QsuB revealed higher amounts of cinnamate, p-coumarate, and of the two direct precursors of H-lignin units: p-coumaraldehyde and p-coumaryl alcohol. Conversely, the direct precursors of G and S units—coniferaldehyde, coniferyl alcohol, sinapaldehyde, and sinapyl alcohol—were reduced. Lignin content was severely reduced in these transgenic lines and exhibited an enrichment of H units at the expense of G units and a lower polymerization degree. Compared to those of wild-type plants, cell walls from lines expressing QsuB released significantly higher amounts of simple sugars after cellulose treatment and required less enzyme for saccharification. Collectively, these results support the hypothesis that expression of a plastidic QsuB affects one of the enzymatic steps within the lignin biosynthetic pathway.

Results

Targeted Expression of QsuB *Arabidopsis*

Figure 16:
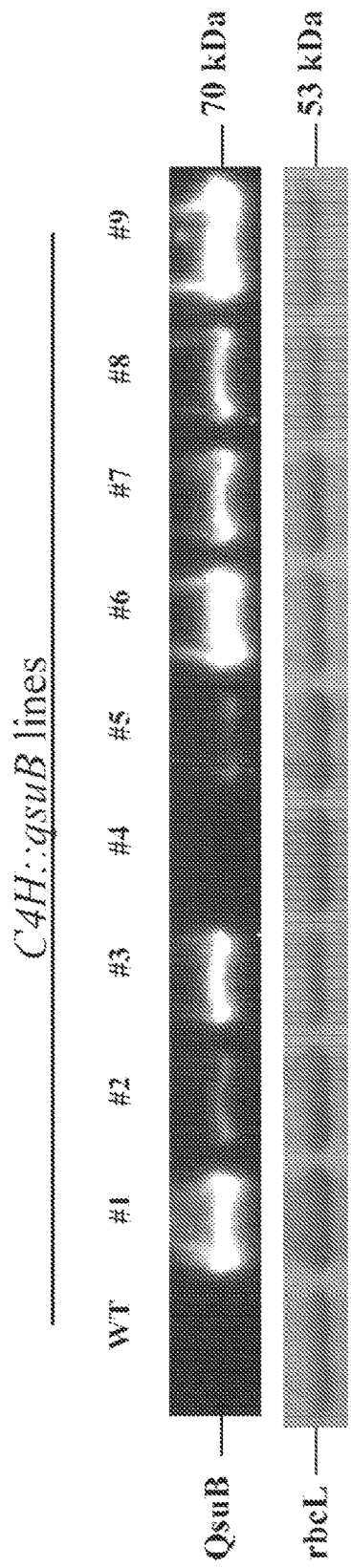
FIG. 16. QsuB expression in *Arabidopsis* stems. Detection by Western blot of QsuB tagged with the AttB2 peptide (approximate size 70 kDa) using the "universal antibody" and stem proteins from nine independent 6-wk-old pC4H::schl::qsuB (C4H::qsuB) T2 transformants. A stem protein extract from wild type was used as a negative control (WT) and a Ponceau staining of Rubisco large subunit (rbcL) is shown as a loading control.
Figure 21:
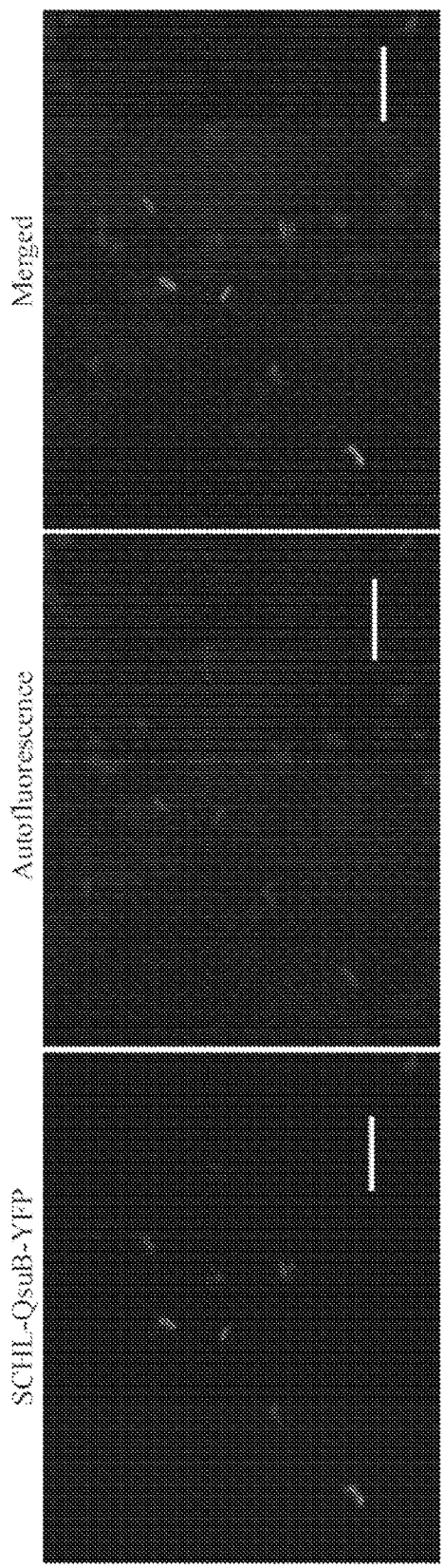
FIG. 21. Subcellular localization of SCHL-QsuB. The left panel displays the transient expression of SCHL-QsuB-YFP fusion protein expressed under the control of the 35S promoter in epidermal cells of *N. benthamiana* and imaged by confocal laser scanning microscopy. The central panel displays fluorescing chloroplasts and the right panel shows the merged images (colocalizations are visible as yellow dots). Scale bars=20 μm.

A sequence encoding QsuB was cloned downstream of the sequence encoding for a plastid-targeting signal peptide (SCHL) for expression in plastids. Using transient expression in tobacco, we first confirmed that QsuB was correctly targeted to the plastids by analyzing its subcellular localization when fused at the C-terminus to a YFP marker (FIG. 21). The schl-qsuB sequence was cloned downstream of the *Arabidopsis* C4H promoter for expression in lignifying tissues of *Arabidopsis*. Western blot analysis confirmed that QsuB was expressed in stems of several T2 plants homozygous for the pC4H::schl::qsuB construct (FIG. 16). Based on the migration of molecular weight markers, QsuB was detected at around 70 kDa, which corresponds to the theoretical size of its native sequence after cleavage of the chloroplast transit peptide (FIG. 16). Five lines with different QsuB expression levels (C4H::qsuB-1, -3, -6, -7, and -9) were selected for biomass measurement. Although a height reduction was observed for these lines, only two of them (C4H::qsuB-1 and -9) showed a slight decrease of biomass yield (stem dry weight) by 18% and 21%, respectively (Table 1).

TABLE 1

Height and dry weight of the main inflorescence stem of senesced mature wild-type (WT) and pC4H::schl::qsuB (C4H::qsuB) plants.

| Plant line | Height (cm) Mean ± SE | Dry weight (mg) Mean ± SE | n |
|---|---|---|---|
| WT | 47.3 ± 0.8 | 271.0 ± 11.1 | 24 |
| C4H::qsuB-1 | 36.6 ± 1.0*** | 221.3 ± 11.0** | 20 |
| C4H::qsuB-3 | 38.8 ± 0.7*** | 244.4 ± 13.4 | 20 |
| C4H::qsuB-6 | 35.9 ± 0.9*** | 254.1 ± 12.7 | 20 |
| C4H:qsuB-7 | 41.0 ± 0.9*** | 251.3 ± 17.4 | 20 |
| C4H::qsuB-9 | 31.8 ± 0.7* | 214.4 ± 14.2 | 20 | n = number of plants analyzed.
Asterisks indicate significant differences from the wild-type using the unpaired Student's t-test (*P < 0.05; P < 0.005; *P < 0.001).

Metabolite Analysis of C4H::qsuB Lines

Figure 22:
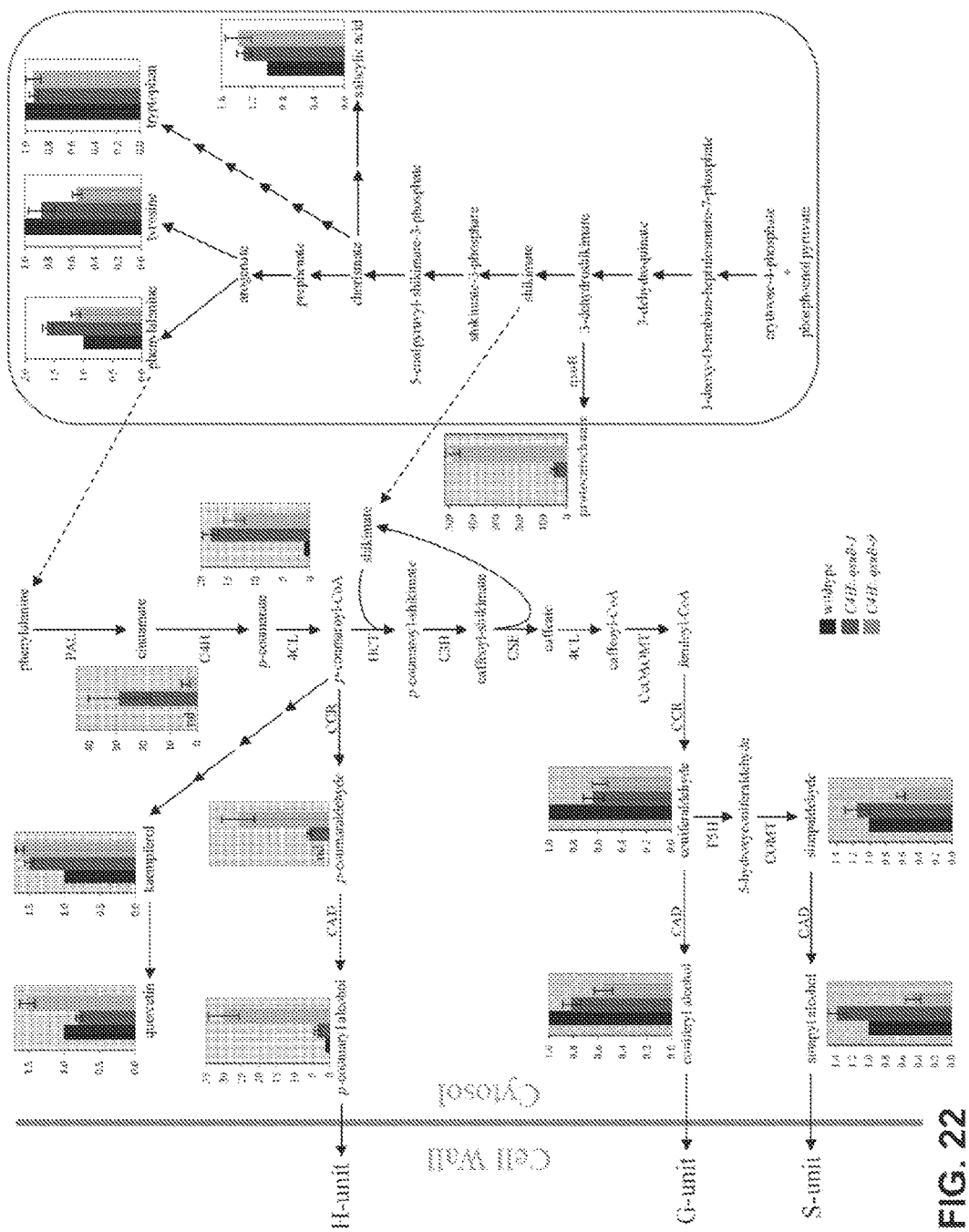
FIG. 22. Summary of the fold changes observed for the methanol-soluble metabolites extracted from plants expressing QsuB.

Methanol soluble metabolites from stems of the C4H::qsuB-1 and C4H::qsuB-9 lines were extracted for analysis (Table 2, FIG. 22). Compared to wild-type plants, protocatechuate content was increased 53- and 485-fold in those two transgenic lines, respectively. However, except for tyrosine in line C4H::qsuB-9, no significant reduction was observed for the content of several metabolites derived from the shikimate pathway in plastids such as salicylate and aromatic amino acids. Instead, salicylate was slightly increased, 1.3-1.4-fold, in both lines and phenylalanine was 1.6-fold higher in line C4H::qsuB-1. Interestingly, several metabolites from the phenylpropanoid pathway were increased in the transgenic lines. Cinnamate and p-coumaraldehyde were detected only in transgenic lines; while p-coumarate and p-coumaryl alcohol contents were increased, compared to those of wild type, 14-18-fold and 3.5-30-fold, respectively. Kaempferol and quercetin, two flavonols derived from p-coumaroyl-CoA, were also found in higher amounts in both C4H::qsuB lines. The direct precursors of G- and S-lignin units were negatively altered; coniferaldehyde was reduced 40% in both transgenic lines, while coniferyl alcohol, sinapaldehyde, and sinapyl alcohol were decreased twofold in C4H::qsuB-9 (Table 2).

Cell wall-bound metabolites released from cell wall residues by mild alkaline hydrolysis were also analyzed (Table 3). Protocatechuate was found in cell walls of the C4H::qsuB lines but not in those from wild-type plants. The content of p-coumarate was significantly increased in line C4H::qsuB-1, whereas ferulate was reduced in both transgenic lines.

TABLE 2

Quantitative analysis of methanol-soluble metabolites in stems from 6-wk-old wild-type (WT) and pC4H:schl::qsuB (C4H::qsuB) plants.

| | Mean ± SE | | |
|---|---|---|---|
| Metabolites | WT | C4H::qsuB-1 | C4H::qsuB-9 |
| Protocatechuate$^\alpha$ | 2.04 ± 0.4 | 108.0 ± 24.8**** | 991.9 ± 60.7**** |
| Tryptophan$^\alpha$ | 3.7 ± 0.5 | 3.4 ± 0.2 | 3.4 ± 0.2 |
| Phenylalanine$^\alpha$ | 2.9 ± 0.2 | 4.7 ± 0.2*** | 3.3 ± 0.2 |
| Tyrosine$^\alpha$ | 5.0 ± 1.1 | 4.2 ± 0.6 | 2.7 ± 0.2* |
| Sinapyl alcohol$^\alpha$ | 4.1 ± 0.3 | 5.7 ± 0.4** | 1.9 ± 0.4*** |
| Quercetin$^\alpha$ | 16.1 ± 3.6 | 12.8 ± 0.6 | 24.6 ± 1.8* |
| Kaempferol$^\alpha$ | 159.4 ± 31.6 | 239.8 ± 9.7** | 260.2 ± 8.8** |
| p-Coumarate$^\beta$ | 6.8 ± 1.2 | 123.1 ± 9.9**** | 93.7 ± 12.8**** |
| p-Coumaryl alcohol$^\beta$ | 7.6 ± 1.9 | 26.8 ± 4.8** | 229.6 ± 32.8**** |
| Coniferyl aldehyde$^\beta$ | 28.6 ± 1.8 | 18.1 ± 2.3** | 16.6 ± 1.8*** |
| Coniferyl alcohol$^\beta$ | 828.5 ± 99.2 | 671.0 ± 63.2 | 457.0 ± 62.2** |
| Sinapyl aldehyde$^\beta$ | 59.2 ± 3.9 | 68.1 ± 8.7 | 36.4 ± 3.1*** |
| Salicylate$^\beta$ | 655.3 ± 30.7 | 854.4 ± 63.1** | 905.7 ± 111.5* |
| Cinnamate$^\beta$ | nd$^\varphi$ | 977.2 ± 389.1 | 144.3 ± 50.5 |

$^\alpha$(µg/g fresh weight)
$^\beta$(µg/g fresh weight)
$^\varphi$Using a detection limit of 34 ng/g fresh weight
Values are means of four biological replicates (n = 4).
nd, not detected.
Asterisks indicate significant differences from the wild type using the unpaired Student's t-test (*P < 0.1; P < 0.05; *P < 0.005; ****P < 0.001).

TABLE 3

Quantitative analysis of cell wall-bound aromatics in stems from extractive-free senesced mature wild-type (WT) and pC4H::schl::qsuB (C4H::qsuB) plants.

| | Mean ± SE (µg/g dry weight) | | |
|---|---|---|---|
| Metabolite | WT | C4H:qsuB-1 | C4H::qsuB-9 |
| Protocatechuate | nd | 6.3 ± 0.4 | 6.7 ± 1.4 |
| p-Coumarate | 15.8 ± 3.0 | 37.4 ± 2.5* | 20.4 ± 1.0 |
| Ferulate | 18.1 ± 0.7 | 7.8 ± 0.5** | 5.3 ± 0.1** |

Values are means of four biological replicates (n = 3).
nd, not detected.
Asterisks indicate significant differences from the wild type using the unpaired Student's t-test (*P < 0.05; P < 0.005; *P < 0.001).

Compositional Analysis of Cell Wall from C4H::qsuB Lines

Using the Klason method, the lignin content measured in the stem of lines C4H::qsuB-1 and C4H::qsuB-9 was reduced 50% and 64%, respectively, compared to that of wild type (Table 4). Analysis of the cell-wall monosaccharide composition showed higher amounts of glucose (+4-10%), xylose (+13-19%), and other less abundant sugars in the transgenic lines, resulting in 8% increase in total cell-wall sugars for the C4H::qsuB-1 line and an 11% increase for C4H::qsuB-9 line (Table 4).

TABLE 4

Chemical composition of senesced mature stems from wild-type (WT) and pC4H::schl::qsuB (C4H::qsuB) plants.

| | Mean ± SE (mg/g cell wall) | | |
|---|---|---|---|
| Component | WT | C4H::qsuB-1 | C4H::qsuB-9 |
| Glucose | 376.7 ± 5.0 | 391.6 ± 2.9* | 416.0 ± 0.9** |
| Xylose | 173.0 ± 2.0 | 199.5 ± 2.2** | 212.9 ± 0.2** |
| Galacturonic acid | 60.8 ± 2.0 | 70.8 ± 0.5* | 63.1 ± 0.8 |
| Galactose | 20.5 ± 0.5 | 23.3 ± 0.1* | 20.2 ± 0.3 |
| Arabinose | 17.1 ± 0.4 | 19.4 ± 0.1* | 16.8 ± 0.3 |
| Rhamnose | 12.1 ± 0.3 | 14.1 ± 0.2** | 13.0 ± 0.2 |
| Fucose | 1.8 ± 0.1 | 2.3 ± 0.1 | 2.0 ± 0.1 |
| Glucuronic acid | 7.1 ± 0.1 | 7.3 ± 0.1 | 8.2 ± 0.2* |
| Total sugars | 669.1 ± 6.8 | 728.4 ± 5.1** | 752.3 ± 2.8** |
| Klason lignin | 191.5 ± 9.5 | 96.2 ± 8.0** | 68.4 ± 5.8** |
| Acid soluble lignin | 4.5 ± 0.4 | 5.0 ± 0.7 | 4.7 ± 0.9 |

Values are means ± SE of triplicate analyses (n = 3).
Asterisks indicate significant differences from the wild type using the unpaired Student's t-test (*P < 0.05; **P < 0.005).

Lignin Monomeric Composition and Structure in C4H::qsuB Lines

Determination of the lignin monomer composition, using thioacidolysis, indicated an increase in the relative amount of H units in transgenic lines. H units represented 12.7% and 27.9% of the total lignin monomers in lines C4H::qsuB-1 and C4H::qsuB-9, which corresponds to 21- and 46-fold increases compared to that of wild type, respectively (Table 5). The relative amount of G units in transgenics (~45%) was also reduced compared to wild type (~64%), whereas S units were higher in C4H::qsuB-1 and lower in C4H::qsuB-9 (Table 5).

Figure 17:
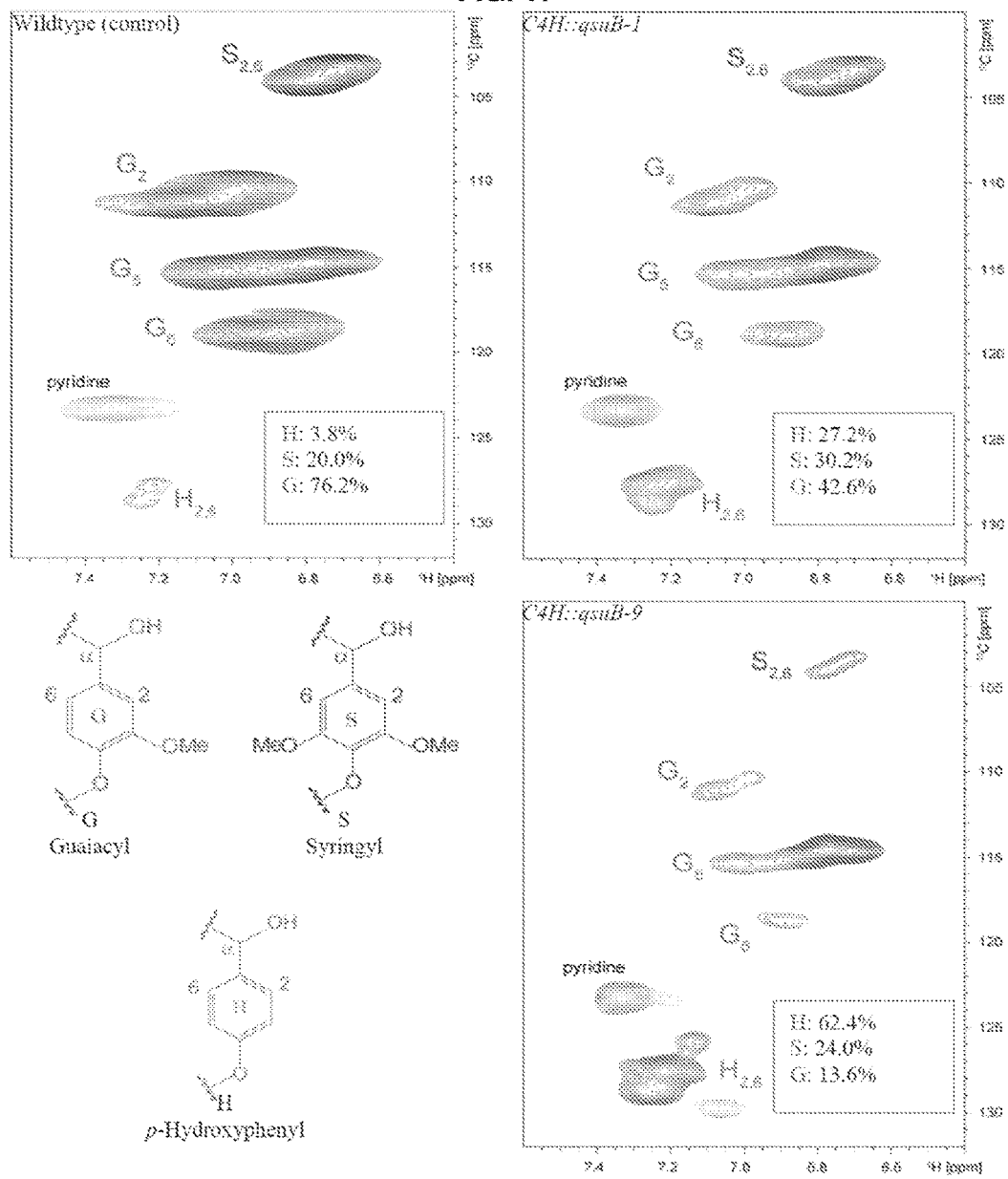
FIG. 17. Partial short-range $^{13}$C-$^1$H (HSQC) spectra (aromatic region) of cell-wall material from mature senesced stems of wild-type (WT), pC4H::schl::qsuB-1 (C4H::qsuB-1) and pC4H::schl::qsuB-9 (C4H::qsuB-9) plants. Lignin monomer ratios are provided on the figures.
Figure 23:
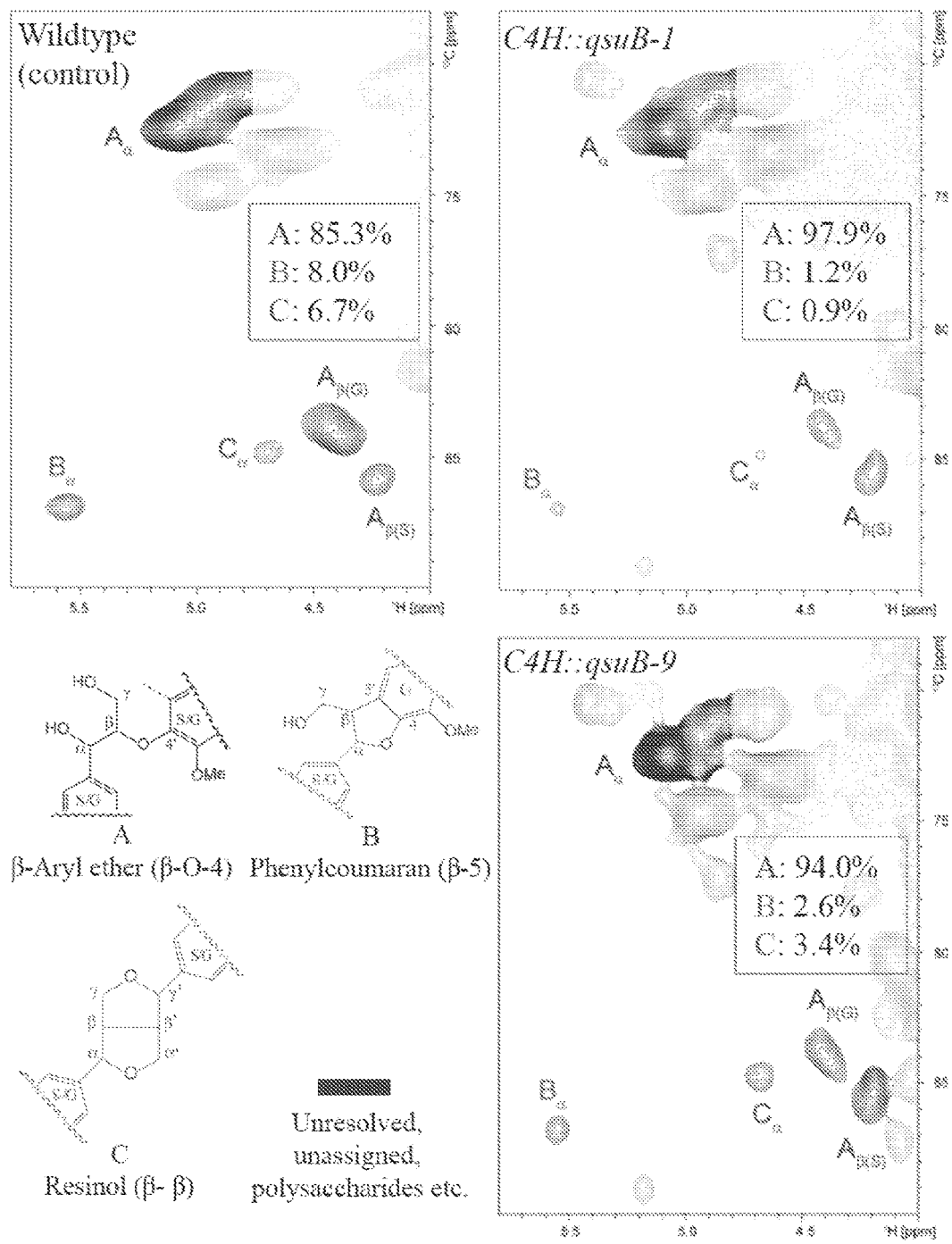
FIG. 23. Partial short-range $^{13}$C-$^1$H (HSQC) spectra (aliphatic region) of cell wall material from mature senesced stems of wild-type (WT), pC4H::schl::qsuB-1 (C4H::qsuB-1) and pC4H::schl::qsuB-9 (C4H::qsuB-9) plants.

NMR (2D $^{13}$C-$^1$H-correlated, HSQC) spectra of cell-wall material from C4H::qsuB-1 and C4H::qsuB-9 lines were also obtained for determination of lignin composition and structure. Analysis of the aromatic region of the spectra confirmed the higher relative amount of H units in both C4H::qsuB lines (29% and 64.4% respectively) compared to that in wild type (3.6%), as well as a reduction of G units (FIG. 17). Moreover, analysis of the aliphatic reaion of the spectra indicated a strong reduction of phenylcoumaran (β-5) and resinol (β-β) linkages in the lignin of the transgenic lines (FIG. 23).

Finally, cell-wall material from stems of wild-type and C4H::qsuB lines were analyzed by pyro-GC/MS. For each line, identification and relative quantification of the pyrolysis products derived from H, G, or S units allowed determination of H/G/S ratios (FIG. 28). Compared to wild type, H units were increased 3.5- and 10-fold, and G units were reduced 1.4- and 2.2-fold, in lines C4H::qsuB1 and C4H::qsuB-9, respectively.

TABLE 5

Main H, G, and S lignin-derived monomers obtained by thioacidolysis of extractive-free senesced mature stems from wild-type (WT) and pC4H::schl::qsuB (C4H::qsuB) plants.

| | WT | C4H::qsuB-1 | C4H::qsuB-9 |
|---|---|---|---|
| Total yield (µmol/g CWR) | 263.5 (22.7) | 116.3 (11.8)* | 73.5 (2.1)** |
| Total yield (µmol/g KL) | 1372.5 (118.5) | 1211.8 (122.6) | 1081.2 (30.7)* |

TABLE 5-continued

Main H, G, and S lignin-derived monomers obtained by thioacidolysis of extractive-free senesced mature stems from wild-type (WT) and pC4H::schl::qsuB (C4H::qsuB) plants.

|     | WT          | C4H::qsuB-1   | C4H::qsuB-9   |
|-----|-------------|---------------|---------------|
| % H | 0.6 (0.03)  | 12.7 (0.78)** | 27.9 (0.38)** |
| % G | 63.7 (0.46) | 46.5 (1.94)*  | 44.9 (0.40)*  |
| % S | 35.7 (0.43) | 40.8 (1.16)*  | 27.2 (0.02)*  |

Values in parentheses are the SE from duplicate analyses.
Asterisks indicate significant differences from the wild type using the unpaired Student's t-test (*P < 0.05; **P < 0.01).

Lignins from C4H::qsuB Lines Have a Lower Polymerization Degree

Figure 18:
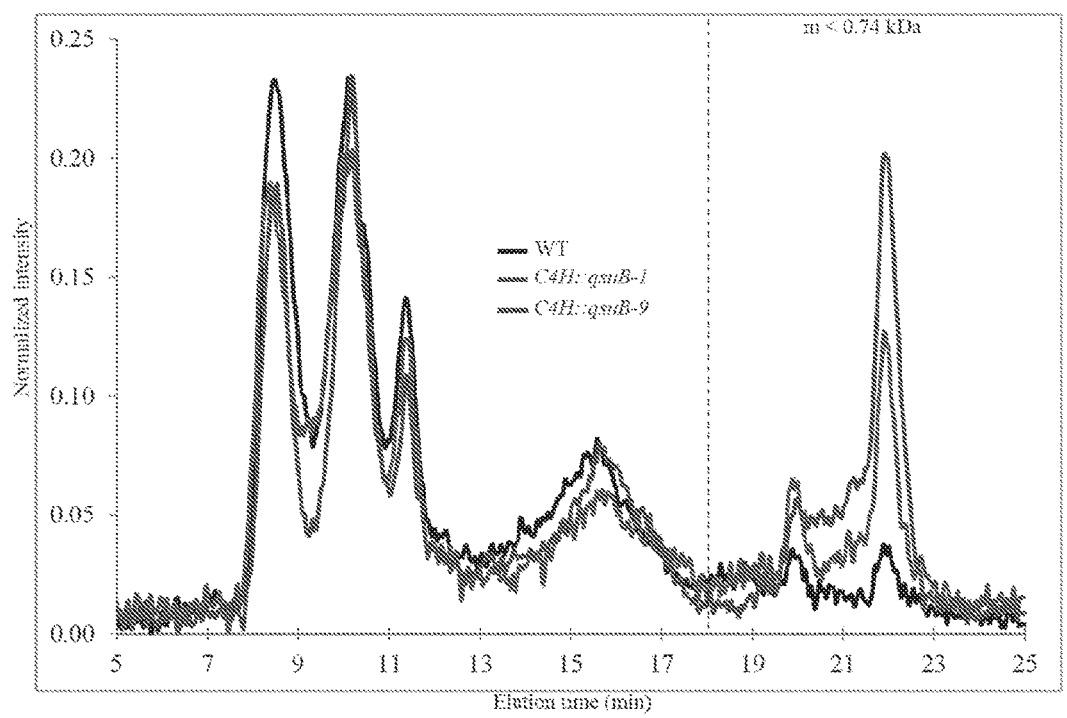
FIG. 18. Polydispersity of cellulolytic enzyme lignins from wild-type and C4H::qsuB lines. Cellulolytic enzyme lignins were purified from mature senesced stems of wild-type (WT, black line), pC4H::qsuB-1(C4H::qsuB-1, red line) and pC4H::qsuB-9 (C4H::qsuB-9, purple line) plants and analyzed for polydispersity by size-exclusion chromatography (SEC). SEC chromatograms were obtained using UV-F fluorescence ($Ex_{250}/Em_{450}$). m, molecular weight.

Lignin fractions were isolated from wild-type and C4H::qsuB lines for analysis of their polydispersity using size-exclusion chromatography (SEC). Elution profiles acquired by monitoring UV-F fluorescence of the dissolved lignin revealed differences between wild-type and transgenic lines (FIG. 18). The total area of the three mass peaks, corresponding to the largest lignin fragments detected between 7.8 min and 12.5 min, was significantly reduced in C4H::qsuB lines compared to wild type. Similarly, intermediate molecular mass material, which elutes in a fourth peak between 12.5 min and 18 min, was also less abundant in C4H::qsuB lines. Conversely, the area corresponding to the smallest lignin fragments, detected between 18 min and 23.5 min, was increased in the transgenic lines. These results demonstrate a reduction in the degree of polymerization of lignins purified from plants expressing QsuB compared to that of wild type.

Biomass from C4H::qsuB Lines Shows Improved Saccharification

Saccharification assays on stem material were conducted to evaluate the cell-wall recalcitrance of the C4H::qsuB lines. As shown in FIG. 19A, higher amounts of sugars were released after 72 hr enzymatic hydrolysis of biomass from the C4H::qsuB lines (−1, −3, −6, −7 and −9) compared to those of wild type in all pretreatments tested. Saccharification improvements ranged between 79-130% after hot water; 63-104% after dilute alkali; and 26-40% after dilute acid pretreatments (FIG. 19A). Moreover, similar saccharification experiments using hot water pretreated biomass, at 5× lower cellulase loadings, revealed that biomass from all C4H::qsuB lines releases more sugar than that of wild type hydrolyzed with a typical enzyme loading (FIG. 19B). Taken together, these data demonstrate that cellulose from the C4H::qsuB lines is less recalcitrant to cellulase digestion and requires a lower amount of enzyme to be converted into high yields of fermentable sugars.

Discussion

Gain-of-function strategies have several advantages for the manipulation of metabolic pathways. For example, they can be used to bioengineer lignin deposition in plants via better spatio-temporal control of monolignol production in lignifying cells, and to adjust lignin composition and its biophysical properties (26). Therefore, identification of proteins in which in planta-expression results in modifications of lignin content or composition is of particular interest and presents novel opportunities. In this work, we demonstrate that expression of the 3-dehydroshikimate dehydratase QsuB in plastids leads to drastic reduction and compositional changes of lignin in Arabidopsis (Table 4). As a result, biomass from these transgenic plants exhibits much higher saccharification efficiency after pretreatment (FIG. 19A), which is a highly desired trait for several agro-industries and the bioenergy sector. Moreover, the efficiency of this approach to decrease lignin content in plant biomass allows a reduction of hydrolytic enzyme loadings by at least five-fold, while retaining greater saccharification potential than control plants hydrolyzed at standard enzyme loading (FIG. 19B). Consequently, the transfer of this technology to energy crops should have a great impact on the cost-effectiveness of cellulosic biofuels production, since enzyme cost is the major barrier in this process (27).

Figure 24:
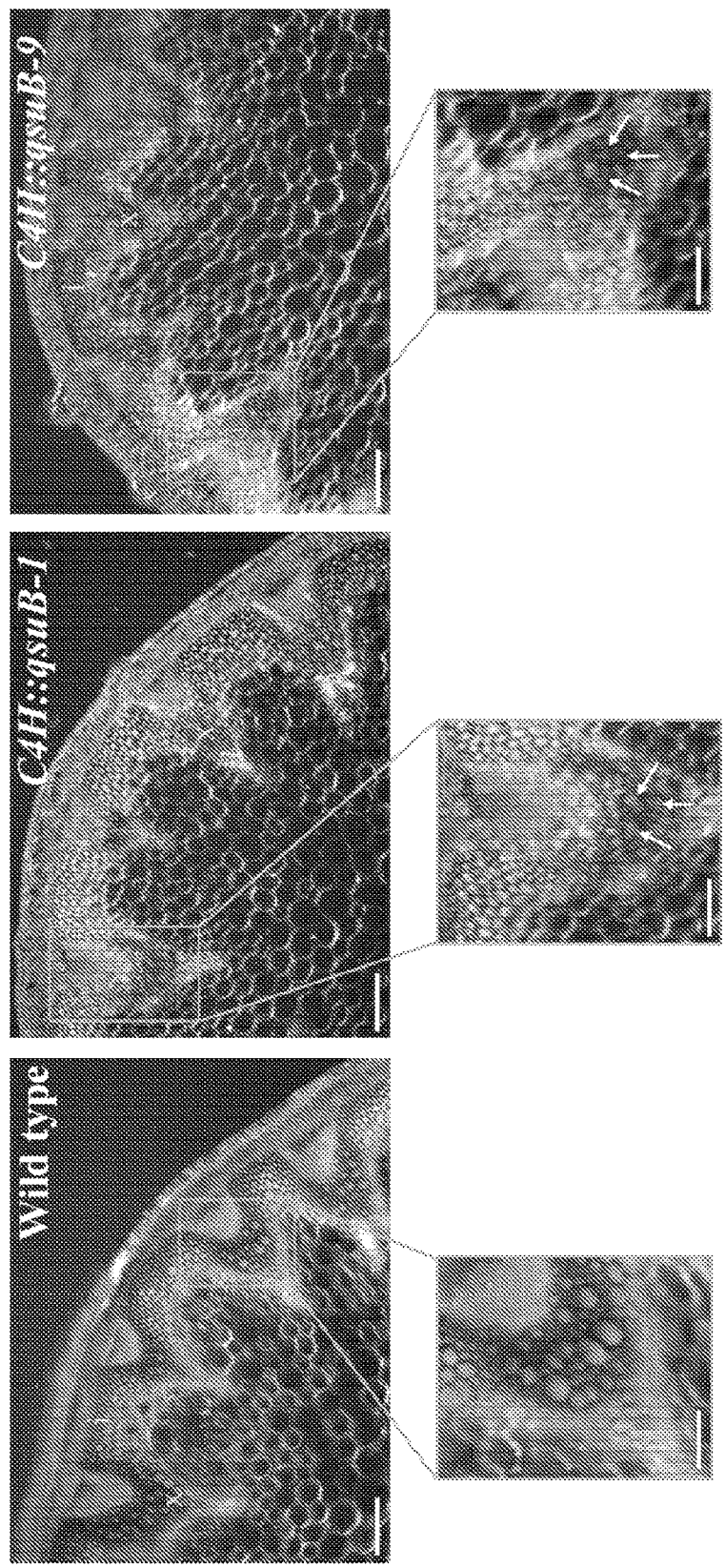
FIG. 24. Lignin staining by phloroglucinol-HCl of stem sections from 5-wk-old wild-type (WT) and pC4H::schl:: qsuB (C4H::qsuB) plants.

In this study, as a proof of concept, we used the promoter of the AtC4H gene to ensure strong QsuB expression in all tissues of the plant. This resulted in a slight decrease of plant height for all the lines; but no significant reductions in biomass yield except for that of two transgenic lines, which expressed QsuB very strongly (Table 1; FIG. 16) and exhibited—in some stem transverse sections (FIG. 24)—evidence of vessel collapse that could impair xylem conductivity (14). Nevertheless, our strategy offers the potential to overcome these defects by selecting more stringent promoters (e.g., fiber-specific) that would exclude QsuB expression from xylem-conductive elements (26, 28). Moreover, translation of our technology from model plant to crops is expected to be straightforward: it is based solely on the expression of QsuB, does not require any particular genetic backgrounds, and the lignin and shikimate pathways are well-conserved among vascular plants.

A direct consequence of QsuB expression is the accumulation of protocatechuate in the biomass of transgenic plants (~1% dry weight in line C4H::qsuB-9; Table 2). Considering the beneficial properties of protocatechuate in the bin-based polymer industry and human health sector, such de novo production adds extra commercial value to the biomass of plants expressing QsuB (29, 30). Much higher amounts of protocatechuate were recovered after acid treatment of the methanol-soluble extracts from transgenic plants (data not shown), which suggests its conjugation in the cytosol after export from the plastids. Interestingly, QsuB expression did not affect substantially the level of metabolites derived from the shikimate pathway, such as aromatic amino acids and salicylate, suggesting that plastidic 3-dehydroshikimate is not limiting (Table 2). On the other hand, a buildup of cinnamate and p-coumarate was observed in these lines, accompanied by an accumulation of p-coumaraldehyde and p-coumaryl alcohol pools (Table 2 and FIG. 22).

Analysis of the lignin monomeric composition—using 2D NMR spectroscopy, thioacidolysis, and pyro-GC/MS—unequivocally demonstrated an increase in H units in plants expressing QsuB (FIG. 17 and FIG. 28; Table 5). These data could explain the reduced degree of polymerization of these lignins, which has been previously observed in various lignin mutants that exhibit high content of H units, incorporation of which typically slows or stops lignin-chain elongation (31, 32; FIG. 18). Therefore, reduced lignin-polysaccharide crosslinking within the biomass of the transgenic lines is expected, and this could contribute to its superior enzymatic digestibility.

Figure 25:
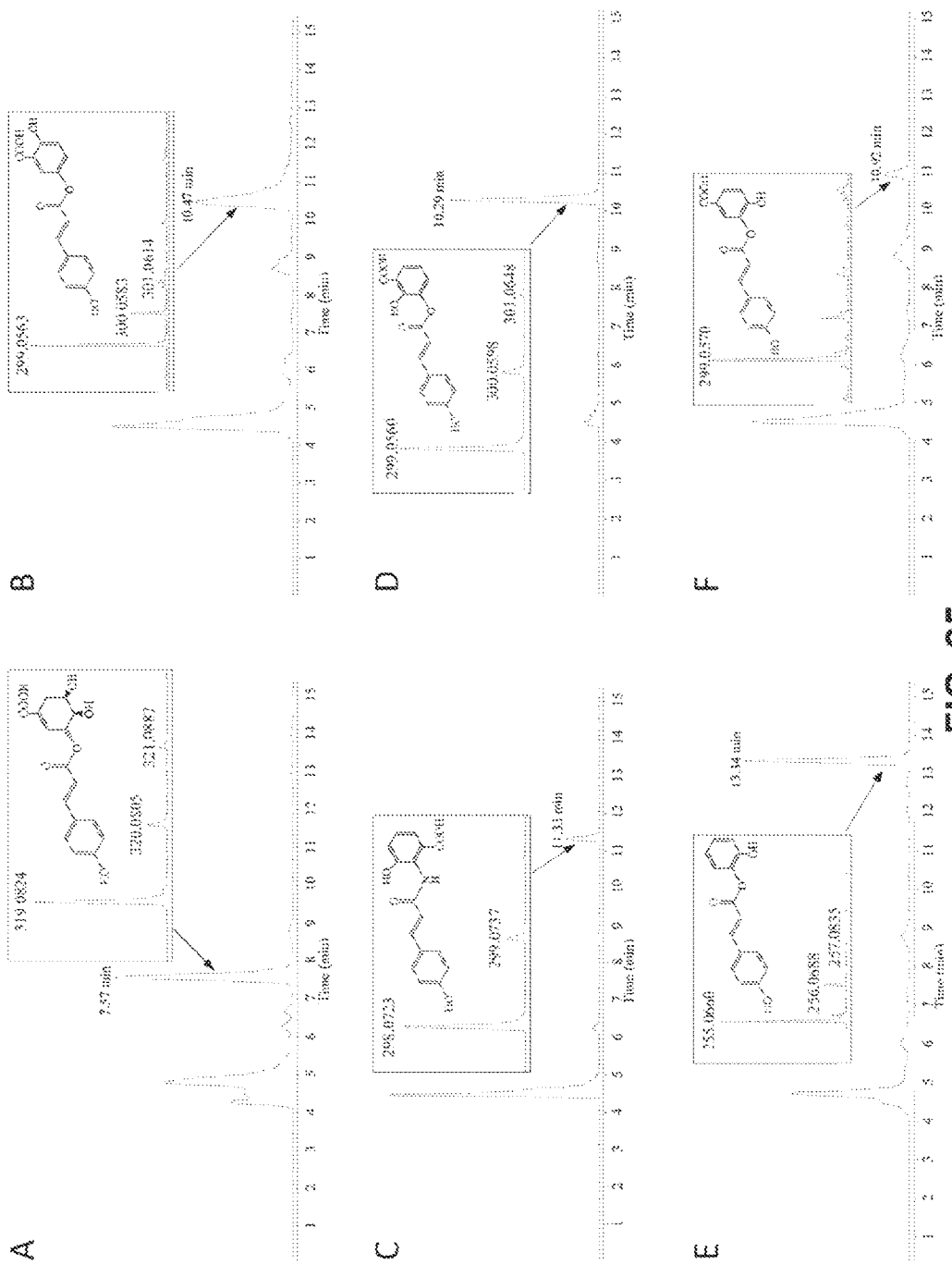
FIG. 25. LC-MS chromatograms from AtHCT in-vivo activity assays. LC-MS chromatograms of coumarate conjugates produced by AtHCT after feeding a recombinant yeast strain co-expressing At4CL5 and AtHCT with p-coumarate and (A) shikimate, (B) 3,6-dihydroxybenzoate, (C) 3-hydroxy-2-amino benzoate, (D) 2,3-dihydroxybenzoate, (E) catechol, or (F) protocatechuate are presented. Structures of coumarate-dihydroxybenzoate esters are arbitrary shown with an ester linkage at the 3-hydroxy position of the dihydroxybenzoate ring. The structure of coumaroyl-3-hydroxyanthranilate (C) is represented as determined in Moglia et al. (34).

A low lignin content rich in H-units corresponds to a phenotype previously characterized in plants down-regulated for hydroxycinnamoyl-CoA shikimate/quinate hydroxycinnamoyl transferase (HCT), p-coumarate 3-hydroxylase (C3H), or caffeoyl shikimate esterase (CSE). This suggests that an alteration of these biosynthetic steps has occurred in the C4H::qsuB lines (10, 32, 33). A possible explanation is that QsuB activity in plastids affects the export of shikimate from the plastids to the cytosol. This would indirectly limit the availability of cytosolic shikimate used for the enzymatic step catalyzed by HCT. The distribution of shikimate between plastids and the cytosol is still poorly understood, and shikimate levels were below the detection limit in our stem extracts from wild-type and transgenic plants. Alternatively, because previous studies reported a substrate flexibility of HCTs (34, 35), the large accumulation of protocatechuate could act as inhibitor of AtHCT, which couples p-coumaroyl-CoA and shikimate. Using an in vivo enzymatic assay to determine the substrate preference of AtHCT, we confirmed its affinity for p-coumaroyl-CoA and shikimate, but also demonstrated its capacity to accept protocatechuate and several other substrates such as catechol, 3,6-dihydroxybenzoate, 3-hydroxy-2-aminobenzoate, and 2,3-dihydroxybenzoate (FIG. 25). Therefore, we cannot exclude the possibility that the protocatechuate pool accumulated in C4H::qsuB plants exerts a competitive inhibition of HCT and limits the synthesis of coumaroyl shikimate required for the production of G- and S-lignin units.

Material and Methods

Plant Material and Growth Conditions

*Arabidopsis thaliana* (ecotype Columbia, Col-0) seeds were germinated directly on soil. Growing conditions were 150 µmol/m$^2$/s, 22° C., 60% humidity, and 10 h of light per day for the first 4-5 wk, followed by 14 h of light per day until senescence. Selection of T1 and T2 transgenic plants was made on Murashige and Skoog vitamin medium (PhytoTechnology Laboratories, Shawnee Mission, Kans.), supplemented with 1% sucrose, 1.5% agar, and 50 µg/mL kanamycin.

Generation of Binary Vectors

The promoter p35S, with a single enhancer, was amplified by PCR from pRT100 with phosphorylated primers F-p35S (5'-GTCAACATGGTGGAGCACGACAC-3'; SEQ ID NO:46) and R-p35S (5'-CGAGAATCTAGATTGTC-CTCTCCAAATGAAATGAACTTC-3'; SEQ ID NO:47), and cloned into a SmaI-digested dephosphorylated pTkan vector (36) to generate a pTKan-p35S vector. Subsequently, a GW-YFP cassette was extracted from the pX-YFP vector (37) by XhoI SpeI digestion, and ligated into a XhoI/SpeI-digested pTkan-p35S vector to generate the pTkan-p35S-GWR1R2-YFP vector.

A chimeric DNA construct was synthesized (GenScript, Piscatway, N.J.): it was flanked by the gateway sequences attB4r (5'-end) and attB3r (3'-end), and contained, in the following order, the tG7 terminator; the restriction sites SmaI, KpnI, HindIII and XhoI; a 2.9-Kb sequence corresponding to the *Arabidopsis* C4H promoter (pC4H); and a sequence encoding a plastid targeting signal (SCHL; 38). This attB4r-tG7-pC4H-schl-attB3r construct was then subcloned into the Gateway pDONR221-P4rP3r entry vector by BP recombination (Life technologies, Foster City, Calif., USA) to generate pENTR-L4-tG7-pC4H-schl-L3. An LR recombination reaction was performed with pTkan-pIRX5-GW (21), pENTR-L1-pLac-lacZalpha-L4 (Life technologies, Foster City, Calif., USA), pENTR-L3-pLac-Tet-L2 (Life technologies, Foster City, Calif., USA), and pENTR-L4-tG7-pC4H::schl-L3. The obtained construct was subsequently digested by SmaI to remove the pLac-lacZalpha and tG7 fragments. The pLac-Tet fragment was replaced by the gateway cassette using BP recombination to generate the pTKan-pC4H::schl-GWR3R2 vector.

Generation of a pTkan-pC4H::schl-qsuB Plasmid and Plant Transformation

A gene sequence encoding QsuB from *C. glutamicum* (GenBank accession number YP_001137362.1) without stop codon and flanked with the Gateway attB3 (5'-end) and attB2 (3'-end) recombination sites was synthesized for expression in *Arabidopsis* (GenScript, Piscatway, N.J.) and cloned into the Gateway pDONR221-P3P2 entry vector by BP recombination (Life technologies, Foster City, Calif., USA). A sequence-verified entry clone was LR recombined with the pTKan-pC4H::schl-GWR3R2 vector to generate the pTKan-pC4H::schl-qsuB construct, which was introduced into wild-type *Arabidopsis* plants (ecotype Col-0) via *Agrobacterium*-mediated transformation (39).

Western Blot Analysis

Proteins from *Arabidopsis* stems were extracted using a buffer containing 250 mM Tris-HCl pH 8.5, 25 mM EDTA, 2 mM DTT, 5 mM β-mercaptoethanol, and 10% sucrose; and were quantified using the Bradford method (40). Proteins (15 µg) were separated by SDS-PAGE, blotted, and immunodetected using a universal antibody, as previously described (41).

Methanol-Soluble Metabolites Extraction

*Arabidopsis* stems of 6-wk-old wild-type and transgenic lines were collected in liquid nitrogen and stored at −80° C. until further utilization. Prior the metabolite extraction, collected stems were pulverized in liquid nitrogen. For extraction of methanol-soluble metabolites, 700-1,000 mg of frozen stem powder was mixed with 2 ml of 80% (v/v) methanol-water and mixed (1,400 rpm) for 15 min at 70° C. This step was repeated four times. Pooled extracts were cleared by centrifugation (5 min, 20,000×g, at room temperature), mixed with 4 mL of analytical grade water and filtered using Amicon Ultra centrifugal filters (10,000 Da MW cutoff regenerated cellulose membrane; EMD Millipore, Billerica, Mass.). Filtered extracts were lyophilized and the resulting pellets dissolved in 50% (v/v) methanol-water prior to LC-MS analysis. An acid-hydrolysis of the samples was performed for the quantification of protocatechuate, salicylate, and flavonols; an aliquot of the filtered extracts was dried under vacuum, resuspended with 1 N HCl and incubated at 95° C. for 3 h. The mixture was subjected to three ethyl acetate partitioning steps. Ethyl acetate fractions were pooled, dried in vacuo, and resuspended in 50% (v/v) methanol-water prior to LC-MS analysis.

Cell-Wall Bound Aromatics Extraction

Senesced stems were ball-milled using a Mixer Mill MM 400 (Retsch Inc., Newtown, Pa.) and stainless steel balls for 2 min at 30 s$^{-1}$. Extractive-free cell-wall residues (CWR) were obtained by sequentially washing 60 mg of ball-milled stems with 1 mL of 96% ethanol at 95° C. twice for 30 min and mixing with 1 mL of 70% ethanol twice for 30 sec. The resulting CWR were dried in vacuo overnight at 30° C. The CWR (6 mg) were mixed with 500 µL of 2 M NaOH and shaken at 1,400 rpm for 24 h at 30° C. The mixture was acidified with 100 µL of concentrated HCl, and subjected to three ethyl acetate partitioning steps. Ethyl acetate fractions were pooled, dried in vacuo, and suspended in 50% (v/v) methanol-water prior to LC-MS analysis.

LC-MS Analysis

Figure 26:
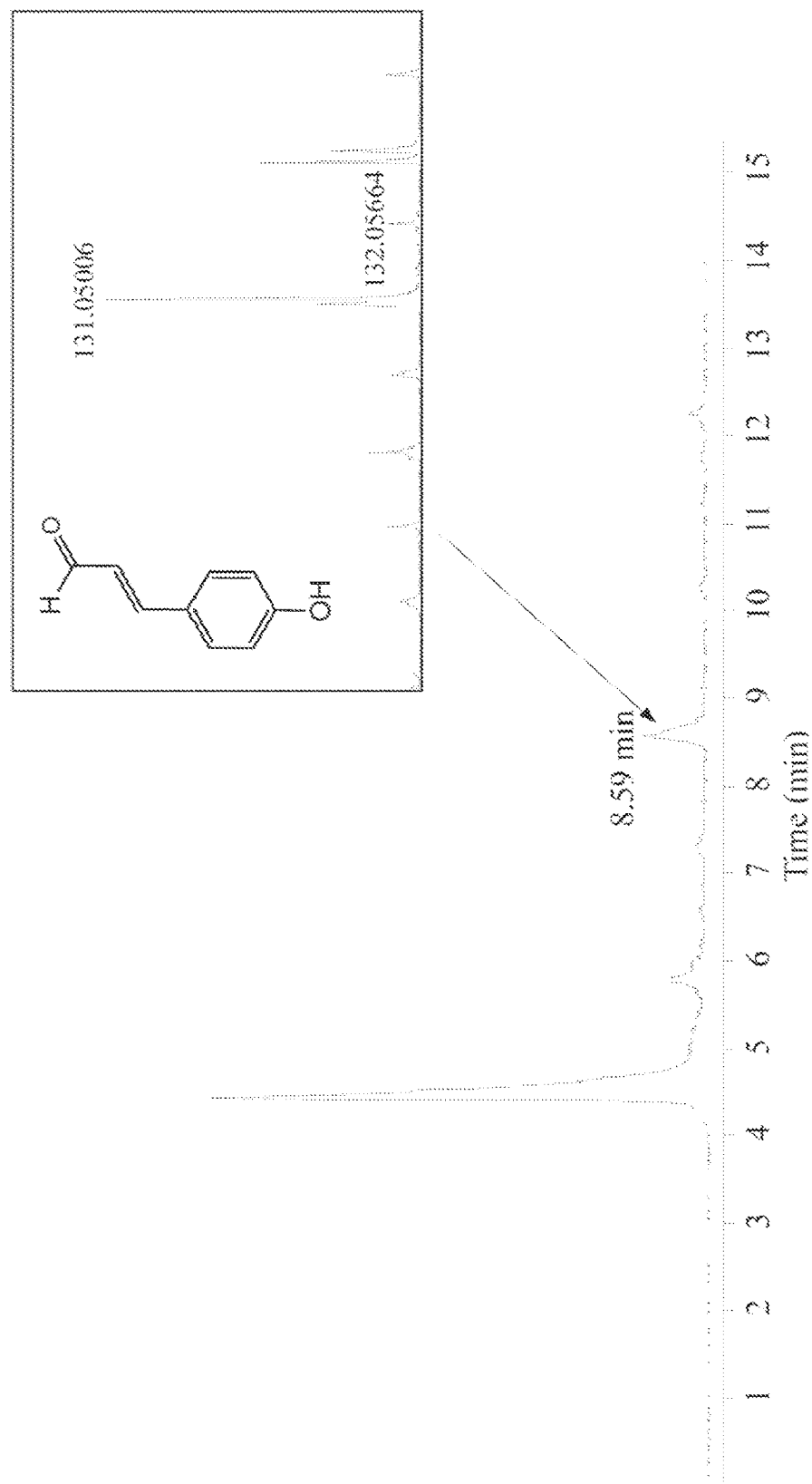
FIG. 26. LC-MS chromatogram of p-coumaraldehyde detected in methanol-soluble extracts of stems from lines expressing QsuB.

As previously described in Bokinsky et al. (42) and Eudes et al. (43)—aromatic amino acids, and aromatic acids and aldehydes, respectively—were analyzed using high-performance liquid chromatography (HPLC), electrospray ionization (ESI), and time-of-flight (TOF) mass spectrometry (MS). Aromatic alcohols were analyzed by HPLC—atmospheric pressure chemical ionization (APCI)—TOF MS. Their separation was conducted on an Agilent 1200 Series Rapid Resolution HPLC system (Agilent Technologies Inc., Santa Clara, Calif., USA) using a Phenomenex Kinetex XB-C18 (100 mm length, 2.1 mm internal diameter, and 2.6

μm particle size; Phenomenex, Torrance, Calif., USA). The mobile phase was composed of 0.1% formic acid in water (solvent A) and methanol (solvent B). The elution gradient was as follows: from 5% B to 25% B for 6 min, 25% B to 5% B for 1 min, and held at 5% B for a further 3 min. A flow rate of 0.5 mL/min was used throughout. The column compartment and sample tray were set to 50° C. and 4° C., respectively. The HPLC system was coupled to an Agilent Technologies 6210 LC/TOF mass spectrometer with a 1:4 post-column split. Mass spectrometric detection was conducted using APCI in the positive ion mode. MS experiments were carried out in the full scan mode, at 0.86 spectra/second, for the detection of $[M-H_2O+H]^+$ ions. Drying and nebulizing gases were set to 10 L/min and 25 psi, respectively, and a drying gas temperature of 330° C. was used throughout. The vaporizer and corona were set to 350° C. and 4 μA respectively, and a capillary voltage of 3,500 V was also used. Fragmentor and OCT 1 RF voltages were each set to 135 V, while the skimmer voltage was set to 50 V. Data acquisition and processing were performed by the MassHunter software package (Agilent Technologies Inc., Santa Clara, Calif., USA). Metabolites were quantified via 10-point calibration curves of authentic standard compounds for which the $R^2$ coefficients were 0.99. The p-coumaraldehyde content was estimated by integrating the area of the mass peak eluting at Rt=8.6 min ($[M-H]^-$=131.050238) and for which the ratio [theoretical mass/observed mass] was less than ±5 ppm (FIG. 26).

Carbohydrate and Lignin Assays

For each genotype (wild type, C4H::qsuB-1, and C4H::qsuB-9), samples consisted of equal mixtures of stem material from three independent cultures. Biomass was extracted sequentially by sonication (20 min) with 80% ethanol (three times), acetone (one time), chloroform-methanol (1:1, v/v, one time) and acetone (one time). For determination of carbohydrate composition, the biomass was acid-hydrolyzed as previously described (44). After $CaCO_3$ neutralization, monomeric sugars from the biomass hydrolyzates were separated by high-performance anion exchange chromatography with pulsed amperiometric detection using a PA20 column (Dionex, Sunnyvale, Calif., USA) and quantified as previously described (45). A calibration curve of monosaccharide standards was run for verification of response factors. The standard NREL biomass protocol was used to measure lignin and ash (46). All carbohydrate and lignin assays were conducted in triplicate. The thioacidolysis procedure was carried out as described (47, 48) and the lignin-derived monomers were identified by GC-MS as their trimethyl-silylated derivatives.

2D $^{13}C$-$^1H$ Heteronuclear Single Quantum Coherence (HSQC) NMR Spectroscopy For each genotype (wild type, C4H::qsuB-1 and C4H::qsuB-9), samples consisted of equal mixtures of stem material from three independent cultures. Samples were extracted and ball milled as previously described (49, 50). The gels were formed using DMSO-$d_6$/pyridine-$d_5$ (4:1) and sonicated until homogenous in a Branson 2510 table-top cleaner (Branson Ultrasonic Corporation, Danbury, Conn.). The temperature of the bath was closely monitored and maintained below 55° C. The homogeneous solutions were transferred to NMR tubes. HSQC spectra were acquired at 25° C. using a Bruker Avance-600 MHz instrument equipped with a 5 mm inverse-gradient $^1H/^{13}C$ cryoprobe using a hsqcetgpsisp2.2 pulse program (ns=400, ds=16, number of increments=256, $d_1$=1.0 s) (53). Chemical shifts were referenced to the central DMSO peak ($\delta_C/\delta_H$ 39.5/2.5 ppm). Assignment of the HSQC spectra was described elsewhere (51, 54). A semi-quantitative analysis of the volume integrals of the HSQC correlation peaks was performed using Bruker's Topspin 3.1 (Windows) processing software. A Guassian apodization in $F_2$ (LB=−0.50, GB=0.001) and squared cosine-bell in $F_1$ (LB=−0.10, GB=0.001) were applied prior to 2D Fourier Transformation.

Isolation of Cellulolytic Enzyme Lignin

For each genotype (wild type, C4H::qsuB-1 and C4H::qsuB-9), samples consisted of equal mixtures of stem material from three independent cultures. The extracted biomass was ball-milled for 3 h per 500 mg of sample (in 10 min on/10 min off cycles) using a PM100 ball mill (Retsch, Newtown, Pa.) vibrating at 600 rpm in zirconium dioxide vessels (50 mL) containing $ZrO_2$ ball bearings (10×10 mm). Ball-milled walls were digested four times over 3 d at 50° C. with the polysaccharidases Cellic CTec2 and HTec2 (Novozymes, Davis, Calif.) and pectinase from *Aspergillus niger* (Sigma-Aldrich, St. Louis, Mo.) in sodium citrate buffer (pH 5.0). The obtained cellulolytic lignin was washed with deionized water and lyophilized overnight.

Size Exclusion Chromatography

Lignin solutions, 1% (w/v), were prepared in analytical-grade 1-nethyl-2-pyrrolidinone (NMP). The polydispersity of dissolved lignin was determined using analytical techniques involving SEC UV-$F_{250/400}$ as previously described (53). An Agilent 1200 series binary LC system (G1312B) equipped with diode-array (G1315D) and fluorescence (G1321A) detectors was used. Separation was achieved with a Mixed-D column (5 μm particle size, 300 mm×7.5 mm i.d., linear molecular mass range of 200 to 400,000 u, Agilent Technologies Inc.) at 80° C. using a mobile phase of NMP at a flow rate of 0.5 ml/min. Absorbance of materials eluting from the column was detected using UV-F fluorescence ($Ex_{250}/Em_{450}$). Spectral intensities were area-normalized and molecular mass estimates were determined after calibration of the system with polystyrene standards.

Cell Wall Pretreatments and Saccharification

Ball-milled senesced stems (10 mg) were mixed with 340 μL of water, 340 μL of $H_2SO_4$ (1.2%, w/v), or 340 μL of NaOH (0.25%, w/v) for hot water, dilute acid, or dilute alkali pretreatments, respectively; shaken at 1,400 rpm (30° C. 30 min), and autoclaved at 120° C. V for 1 h. Samples pretreated with dilute acid were neutralized with 5 N NaOH (25 μL). Saccharification was initiated by adding 650 μL of 100 mM sodium citrate buffer pH 5 (for hot water- and dilute alkali-pretreated samples) or 625 μL of 80 mM sodium citrate buffer pH 6.2 (for dilute acid-pretreated samples) containing 80 μg/mL tetracycline and 1% w/w or 0.2% w/w Cellic CTec2 cellulase (Novozymes, Davis, Calif.). After 72 h of incubation at 50° C. with shaking (800 rpm), samples were centrifuged (20,000×g, 3 min) and 10 μL of the supernatant was collected for measurement of reducing sugars using the 3,5-dinitrosalicylic acid assay and glucose solutions as standards (54).

Subcellular Localization of QsuB

The schl-qsuB nucleotide sequence from the pTkan-pC4H::schl-qsuB construct was amplified using oligonucleotides 5'-

(SEQ ID NO: 48)
5'-GGGGACAAGTTTGTACAAAAAAGCAGGCTTCATGGCTTCGATCTCCT

CCT-3'; (attB1 site underlined)
and (SEQ ID NO: 49)
5'-GGGGACCACTTTGTACAAGAAAGCTGGGTCGTTTGGGATACCTCTCT CTAAATCTC-3'; (attB2 site underlined)

and cloned into the Gateway pDONR221-fl entry vector (Lalonde S, et al. (2010) Front Physiol 1:24). A sequence-verified entry clone was LR recombined with the pTKan-p35S-GWR1R2-YFP vector to generate the pTKan-p35S-schl-qsuB-YFP construct. Infiltration of 4-wo *N. benthamiana* leaves was done using the *Agrobacterium* strain GV3101, following the method described by Sparkes et al. (Nat Protoc 1(4):2019-2025). Plants transiently expressing the SCHL-QsuB-YFP fusion protein were analyzed by confocal laser scanning microscopy 2 d after the infiltration. The microscopy was performed using a Zeiss LSM 710 device (Carl Zeiss Microscopy, Jena, Germany) equipped with an argon laser (excitation at 514 nm and emission collected at 510 to 545 nm).

Lignin Histochemical Staining

Histochemical staining was performed as described by Pradhan-Mitra and Loqué ("Histochemical staining of *Arabidopsis thaliana* secondary cell wall elements," JoVe (in press)). Basal stem transverse sections (100 µm thick) were obtained using a vibratome. Sections were incubated for 3 min in phloroglucinol-HCl reagent (VWR International, Brisbane, Calif.), rinsed with water, and observed using bright field light microscopy (Leica Microsystems Inc., Buffalo Grove, Ill.).

Pyrolysis-Gas Chromatography Mass Spectrometry

Chemical composition of lignin in plant cell-wall samples were analyzed by pyrolysis-gas chromatography (GC)/mass spectrometry, (MS) using a previously described method with some modifications (Del Rio J C, et al. (2012) *J Agric Food Chem* 60(23):5922-5935). Pyrolysis of plant cell walls was performed with a Pyroprobe 5200 (CDS Analytical, Inc.) connected with GC/MS (Thermo Electron Corporation with Trace GC Ultra and Polaris-Q MS) equipped with an Agilent HP-5MS column (30 m×0.25 mm i.d., 0.25 µm film thickness). The pyrolysis was carried out at 550° C. The chromatograph was programmed from 50° C. (1 min) to 300° C. at a rate of 30° C./min; the final temperature was held for 10 min. Helium was used as the carrier gas at a constant flow rate of 1 mL/min. The mass spectrometer was operated in scan mode and the ion source was maintained at 300° C. The compounds were identified by comparing their mass spectra with those of the NIST library and those previously reported (Del Rio J C, Gutiérrez A. (2006) *J Agric Food Chem* 54(13):4600-4610; Ralph J, Hatfield R D (1991) *J Agric Food Chem* 39(8):1426-1437). Peak molar areas were calculated for the lignin degradation products, the summed areas were normalized. Analyses on all samples were conducted in duplicate and data were averaged and expressed as percentages.

In Vivo HCT Activity Assay

For the cloning of AtHCT, total *Arabidopsis* RNA (1 µg) were extracted using the Plant RNeasy extraction kit (Qiagen, Valencia, Calif.) and reverse-transcribed using the Transcriptor First Strand cDNA Synthesis Kit (Roche Applied Science, Indianapolis, Ind.). The obtained cDNA preparation was used to amplify AtHCT (GenBank accession number NP 199704.1) using the following oligonucleotides (SEQ ID NO: 50)
5'-GGG GAC AAG TTT GTA CAA AAA AGC AGG CTT C

ATGAAAATTA ACATCAGAGA TTCC-3';

(attB1 site underlined)
and (SEQ ID NO: 51)
5'-GGG GAC CAC TTT GTA CAA GAA AGC TGG GCTCATATCTC AAACAAAACTTCTCAAAC-3' (attB2 site underlined)

for cloning into the Gateway pDONR221-fl entry vector by BP recombination (Life Technologies, Foster City, Calif.). A sequence-verified AtHCT entry clone was LR recombined with the pDRf1-4CL5-GW vector (41) to generate the pDRf1-4CL5-AtHCT construct.

For For HCT activity assays, the pDRf1-4CL5-AtHCT and pDRf1-4CL5 vectors were transformed into the *S. cerevisiae* pad1 knockout (MATa his3Δ1 leu2Δ0 met15Δ0 ura3Δ0 Δpad1 ATCC 4005833) as previously described (41). Overnight cultures from single colonies harboring the pDRf1-4CL5-AtHCT and pDRf1-4CL5 vectors were grown in 2× yeast nitrogen base medium without amino acids (Difco, Detroit, Mich.) supplemented with 6% glucose and 2× dropout mix without uracil (Sunrise Science Products, San Diego, Calif.). Overnight cultures were used to inoculated 10 mL of fresh minimal medium at an $OD_{600}=0.1$. Substrates (p-coumarate, catechol or benzoates) were added to the medium 4 h later at a final concentration of 1 mM and the cultures were grown for 22 h. For the detection of the coumarate conjugate products, an aliquot of the culture medium was collected, cleared by centrifugation (20,000×g for 5 min at 4° C.), mixed with an equal volume of 50% (v/v) methanol water and filtered using Amicon Ultra centrifugal filters (3,000 Da MW cutoff regenerated cellulose membrane; Millipore, Billerica, Mass.) prior to HPLC-ESI-TOF MS analysis.

REFERENCES

1. Boerjan W, Ralph J, Baucher M (2003) Lignin biosynthesis. *Annu Rev Plant Biol* 54:519-546.
2. Boudet A-M (2007) Evolution and current status of research in phenolic compounds. *Phytochemistry* 68(22-24):2722-2735.
3. Keasling J D (2010) Manufacturing molecules through metabolic engineering. *Science* 330(6009):1355-1358.
4. Baucher M, Halpin, C, Petit-Conil, M, Boerjan W (2003) Lignin: Genetic engineering and impact on pulping. *Crit Rev Biochem Mol Biol* 38(4):305-350.
5. Chen F, Dixon R A (2007) Lignin modification improves fermentable sugar yields for biofuel production. *Nat Biotechnol* 25(7):759-761.
6. Taboada A, et al. (2010) Digestibility of silages in relation to their hydroxycinnamic acid content and lignin composition. *J Sci Food Agric* 90(7):1155-1162.
7. Fraser C M, Chapple C (2011) The phenylpropanoid pathway in *Arabidopsis*. *The Arabidopsis Book* 9:e152.

8. Tohge T, Watanabe M, Hoefgen R, Fernie A R (2013) Shikimate and phenylalanine biosynthesis in the green lineage. *Front Plant Sci* 4:62.
9. Umezawa T (2010) The cinnamate/monolignol pathway. *Phytochemistry Rev* 9(1):1-17.
10. Vanholme R, et al. (2013) Caffeoyl shikimate esterase (CSE) is an enzyme in the lignin biosynthetic pathway in *Arabidopsis*. *Science* 341(6150):1103-1106.
11. Li X, Weng Chapple C (2008) Improvement of biomass through lignin modification. *Plant J* 54(4):569-581.
12. Vanholme R, Morreel K, Ralph J, Boerjan W (2008) Lignin engineering. Curr Opin Plant Biol 11(3):278-285.
13. Bonawitz N D, Chapple C. (2013) Can genetic engineering of lignin deposition be accomplished without an unacceptable yield penalty? *Curr Opin Biotechnol* 24(2): 336-343.
14. Voelker S L, Lachenbruch B, Meinzer F C, Kitin P, Strauss S H (2011) Transgenic poplars with reduced lignin show impaired xylem conductivity, growth efficiency and survival. *Plant Cell Environ* 34(4):655-668.
15. Brosnan C A, Voinnet O (2011) Cell-to-cell and long-distance siRNA movement in plants: mechanisms and biological implications. *Curr Opin Plant Biol* 14(5):580-587.
16. Iwase A, Matsui K, Ohme-Takagi M (2009) Manipulation of plant metabolic pathways by transcription factors. *Plant Biotechnol* 26(1):29-38.
17. Fornalé S, et al. (2010) ZmMYB31 directly represses maize lignin genes and redirects the phenylpropanoid metabolic flux. *Plant J* 64(4):633-644.
18. Shen H, et al. (2012) Functional characterization of the switchgrass (*Panicum virgatum*) R2R3-MYB transcription factor PvMYB4 for improvement of lignocellulosic feedstocks. New Phytol 193(1):121-136.
19. Yan L, et al. (2013) The heterologous expression in *Arabidopsis thaliana* of sorghum transcription factor SbbHLH1 downregulates lignin synthesis. *J Exp Bot* 64(10):3021-3302.
20. Costa M A, et al. (2013) Transgenic Hybrid Poplar for Sustainable and Scalable Production of the Commodity/Specialty Chemical, 2-Phenylethanol. *PloS ONE* 8(12): e83169.
21. Eudes A, et al. (2012) Biosynthesis and incorporation of side-chain-truncated lignin monomers to reduce lignin polymerization and enhance saccharification. Plant Biotechnol J 10(5):609-620.
22. Koeduka T, et al. (2013) Enhancement of production of eugenol and its glycosides in transgenic aspen plants via genetic engineering. *Biochem Biophys Res Commun* 436 (1):73-78.
23. Zhang K, et al. (2012) An engineered monolignol 4-o-methyltransferase depresses lignin biosynthesis and confers novel metabolic capability in *Arabidopsis*. Plant Cell 24(7):3135-3152.
24. Zhang X, Gou M, Lin C J (2014) *Arabidopsis* kelch repeat F-box proteins regulate phenylpropanoid biosynthesis via controlling the turnover of phenylalanine ammonia-lyase. Plant Cell 25(12):4994-5010.
25. Teramoto H, Inui M, Yukawa H (2009) Regulation of expression of genes involved in quinate and shikimate utilization in *Corynebacterium glutamicum*. *Appl Environ Microbiol* 75(11):3461-3468.
26. Eudes A, Liang Y, Mitra P, Loqué D. (2014) Lignin bioengineering. Curr Opin Biotechnol 16 (in press).
27. Klein-Marcuschamer D, Oleskowicz-Popiel P, Simmons B A, Blanch H W (2012) The challenge of enzyme cost in the production of lignocellulosic biofuels. *Biotechnol Bioeng* 109(4):1083-1087.
28. Yang F, et al (2013) Engineering secondary cell wall deposition in plants. Plant Biotechnol J 11(3):325-335.
29. Lin H H, Chen J H, Huang C C, Wang C J (2007) Apoptotic effect of 3,4-dihydroxybenzoic acid on human gastric carcinoma cells involving JNK/p38 MAPK signaling activation. Int J Cancer 120(11):2306-2316.
30. Otsuka Y, et al. (2006) Efficient production of 2-pyrone 4,6-dicarboxylic acid as a novel polymer-based material from protocatechuate by microbial function. Appl Microbiol Biotechnol 71(5):608-614.
31. Sangha A K, et al. (2014) Chemical Factors that Control Lignin Polymerization. J Phys Chem B 118(1):164-170.
32. Ziebell A, et al. (2010) Increase in 4-coumaryl alcohol units during lignification in alfalfa (*Medicago sativa*) alters the extractability and molecular weight of lignin. J Biol Chem 285(50)38961-38968.
33. Ralph J, et al. (2006) Effects of coumarate 3-hydroxylase down-regulation on lignin structure. J Biol Chem 281 (13):8843-8853.
34. Moglia A, et al (2010) Production of novel antioxidative phenolic amides through heterologous expression of the plant's chlorogenic acid biosynthesis genes in yeast. Metab Eng 12(3):223-232.
35. Sander M, Petersen M (2011) Distinct substrate specificities and unusual substrate flexibilities of two hydroxycinnamoyltransferases, rosmarinic acid synthase and hydroxycinnamoyl-CoA:shikimate hydroxycinnamoyltransferase, from *Coleus blumei* Benth. Planta 233 (6): 1157-1171.
36. Yuan L, et al. (2009) AtAMT1; 4, a pollen-specific high-affinity ammonium transporter of the plasma membrane in *Arabidopsis*. Plant Cell Physiol 50(1):13-25.
37. Kim J G et al. (2009) *Xanthomonas* T3S Effector XopN Suppresses PAMP-Triggered Immunity and Interacts with a Tomato Atypical Receptor-Like Kinase and TFT1. Plant Cell 21(4):1305-1323.
38. Lebrun M, Leroux B, Sailland A (1992) Gène chimère pour la transformation des plantes. European patent application. Patent Application No. EP 508909A1.
39. Bechtold N, Pelletier G (1998) In planta *Agrobacterium*-mediated transformation of adult *Arabidopsis thaliana* plants by vacuum infiltration. *Methods in molecular biology* (Clifton, N.J.) 82:259-266.
40. Bradford M M (1976) A rapid and sensitive method for the quantitation of microgram quantities of protein utilizing the principle of protein-dye binding. *Anal Biochem* 72:248-254.
41. Eudes A, et al. (2.011) Production of tranilast [N-(3',4'-dimethoxycinnamoyl)-anthranilic acid] and its analogs in yeast *Saccharomyces cerevisiae*. *Appl Microbiol Biotechnol* 89(4):989-1000.
42. Bokinsky G, et al. (2013) HipA-triggered growth arrest and β-lactam tolerance in *Escherichia coli* are mediated by RelA-dependent ppGpp synthesis. J Bacteriol 195 (14):3173-3182.
43. Eudes A, et al. (2013) Production of hydroxycinnamoyl anthranilates from glucose in *Escherichia coli*. *Microb Cell Fact* 12:62.
44. Moxley G, Zhang Y H P (2007) More accurate determination of acid-labile carbohydrate composition in lignocellulose by modified quantitative saccharification. *Energy Fuels* 21(6)3684-3688.

45. ØBro J, Harholt J, Scheller H, Orfila (2004) Rhamnogalacturonan I in *Solanum tuberosum* tubers contains complex arabinogalactan structures. *Phytochemistry* 65(10): 1429-1438.
46. Sluiter A, Hames B, Ruiz R, Scarlata C, Sluiter J (2008) Determination of structural carbohydrates and lignin in biomass. In *Laboratory Analytical Procedure* (Technical Report, NREL/TP-510-42618), Golden, Colo.: National Renewable Energy Laboratory.
47. Lapierre C, Pollet B, Rolando C (1995) New insights into the molecular architecture of hardwood lignins by chemical degradative methods. *Res Chem Intermed* 21(3-5):397-412.
48. Lapierre C, et al. (1999) Structural alterations of lignins in transgenic poplars with depressed cinnamoyl alcohol dehydrogenase or caffeic acid O-methyltransferase activity have an opposite impact on the efficiency of industrial kraft pulping. *Plant Physiol* 119(1):153-164.
49. Kim H, Ralph J (2010) Solution-state 2D NMR of ball-milled plant cell wall gels in DMSO-d(6)/pyridine-d(5). *Org Biomol Chem* 8(3):576-591.
50. Mansfield S D, Kim H, Lu F, Ralph J (2012) Whole plant cell all characterization using solution-state 2D NMR. *Nat Protoc* 7(9):1579-1589.
51. Heikkinen S, Toikka M M, Karhunen P T, Kilpeläinen I A (2003) Quantitative 2D HSQC (Q-HSQC) via suppression of J-dependence of polarization transfer in NMR spectroscopy: application to wood lignin. *J Am Chem Soc* 125(14):4362-4367.
52. Yelle D J, Ralph J, Frihart C R (2008) Characterization of nonderivatized plant cell walls using high-resolution solution-state NMR spectroscopy. *Magn Reson Chem* 46(6):508-517.
53. George A, et al. (2011) The effect of ionic liquid cation and anion combinations on the macromolecular structure of lignins. *Green Chem* 13:3375-3385.
54. Miller G (1959) Use of dinitrosalicylic acid reagent for determination of reducing sugar. *Anal Chem* 31(3):426-428.

```
ILLUSTRATIVE SEQUENCES
MtAroK polynucleotide sequence
                                              SEQ ID NO: 1
ATGGCACCAAAAGCTGTTTTAGTGGGACTTCCTGGAAGTGGAAAGTCCAC

TATCGGTAGAAGGTTGGCTAAAGCATTAGGAGTTGGTTTGTTAGACACTG

ATGTGGCTATAGAACAAAGGACAGGAAGATCAATAGCAGACATTTTTGCT

ACAGATGGTGAACAGGAGTTCAGAAGGATAGAAGAGGATGTTGTGAGAGC

TGCATTGGCTGACCATGATGGTGTTCTTAGTTTGGGTGGAGGTGCAGTTA

CTTCCCCAGGAGTGAGAGCTGCACTTGCTGGTCACACAGTTGTGTATTTG

GAAATCTCAGCTGCAGAGGGAGTGAGAAGGACAGGTGGTAACACCGTGAG

ACCACTTTTGGCAGGTCCTGATAGGGCTGAAAAGTATAGAGCTTTGATGG

CAAAAAGGGCTCCTTTATACAGAAGGGTTGCTACTATGAGAGTGGATACA

AATAGAAGGAACCCAGGTGCAGTTGTTAGGCACATTTTATCCAGGTTGCA

GGTTCCATCTCCTTCTGAGGCAGCTACT

MtAroK amino acid sequence (Mycobacterium
tuberculosis shikimate kinase; NP_217055)
                                              SEQ ID NO: 2
MAPKAVLVGLPGSGKSTIGRRLAKALGVGLLDTDVAIEQRTGRSIADIFA

TDGEQEFRRIEEDVVRAALADHDGVLSLGGGAVTSPGVRAALAGHTVVYL

EISAAEGVRRTGGNTVRPLLAGPDRAEKYRALMAKRAPLYRRVATMRVDT

NRRNPGAVVRHILSRLQVPSPSEAAT

ScAro1 polynucleotide sequence
                                              SEQ ID NO: 3
ATGGTTCAGCTTGCTAAGGTGCCTATTTTGGGTAACGACATCATTCACGT

TGGATATAACATTCACGATCATTTGGTTGAGACTATTATCAAGCATTGTC

CATCTTCTACTTATGTTATTTGTAACGATACCAACCTTTCTAAGGTTCCT

TATTACCAACAGTTAGTGCTTGAGTTTAAGGCTTCTTTGCCAGAAGGAAG

TAGATTGTTAACTTATGTTGTGAAACCTGGAGAGACTTCTAAGTCAAGGG

AAACAAAAGCTCAATTGGAGGACTACCTTTTGGTTGAAGGATGTACCAGA

GATACTGTGATGGTTGCTATTGGTGGAGGTGTTATAGGTGATATGATTGG

ATTTGTGGCATCAACTTTCATGAGAGGTGTTAGGGTTGTGCAAGTGCCAA

CAAGTTTACTTGCTATGGTTGACAGTTCCATCGGAGGAAAGACAGCAATA

GATACCCCATTGGGAAAAAACTTTATTGGTGCTTTCTGGCAGCCTAAGTT

CGTGCTTGTTGATATCAAGTGGCTTGAGACATTGGCTAAGAGAGAATTTA

TCAACGGAATGGCAGAAGTTATCAAGACAGCTTGTATTTGGAACGCAGAT

GAGTTTACCAGATTGGAATCAAATGCTAGTTTGTTCTTAAACGTTGTGAA

CGGTGCAAAGAACGTGAAGGTTACTAACCAACTTACAAACGAGATCGATG

AAATCTCAAATACCGACATCGAAGCTATGCTTGATCACACTTACAAACTT

GTTTTGGAGTCTATCAAGGTGAAAGCAGAAGTTGTGTCTTCAGATGAGAG

AGAAAGTTCCTTGAGGAACTTGCTTAACTTCGGTCATTCAATCGGACACG

CTTACGAAGCAATCTTAACTCCACAAGCTCTTCATGGAGAATGTGTTTCT

ATTGGTATGGTGAAGGAGGCAGAATTGTCAAGATACTTCGGAATATTAAG

TCCTACACAGGTTGCAAGGTTGTCCAAAATTTTGGTTGCTTACGGTTTGC

CAGTGTCTCCTGATGAGAAGTGGTTCAAGGAATTAACACTTCATAAAAAG

ACCCCTTTAGACATCCTTTTGAAAAAGATGTCCATCGATAAAAAGAATGA

GGGTTCTAAAAAGAAAGTTGTGATCTTAGAATCTATCGGAAAGTGCTATG

GAGACTCCGCTCAATTTGTTTCTGATGAGGACCTTAGATTCATTTTGACA

GATGAAACCCTTGTTTACCCATTTAAAGATATACCTGCTGACCAACAGAA

GGTTGTGATTCCACCTGGTAGTAAATCCATTTCTAACAGAGCATTGATCT

TAGCTGCATTGGGTGAAGGACAGTGTAAGATAAAGAACCTTCTTCATTCA

GATGACACTAAGCACATGCTTACAGCAGTTCATGAATTGAAAGGTGCTAC

AATCTCTTGGGAGGATAACGGAGAAACCGTTGTGGTTGAAGGTCATGGAG

GTTCCACTTTGTCTGCTTGCGCAGATCCACTTTATTTGGGTAATGCTGGA

ACCGCATCAAGATTTTTAACTAGTCTTGCTGCTTTGGTTAACTCAACTTC

TTCACAAAAGTACATTGTGTTAACTGGTAATGCAAGAATGCAACAGAGGC

CAATCGCTCCTTTAGTTGATTCTCTTAGAGCAAACGGAACAAAGATCGAG

TACCTTAACAACGAAGGTTCACTTCCTATCAAGGTTTACACTGATAGTGT

GTTCAAAGGAGGTAGAATAGAATTAGCTGCAACAGTTAGTTCCCAATATG

TGTCTTCAATTCTTATGTGTGCTCCATACGCAGAAGAGCCTGTTACTTTA

GCTCTTGTGGGAGGAAAGCCAATCTCAAAATTGTACGTTGATATGACAAT
```

```
CAAGATGATGGAAAAGTTCGGAATCAACGTTGAGACTTCTACTACAGAAC
CATACACATACTACATCCCTAAGGGTCATTACATCAACCCTTCAGAGTAC
GTTATCGAAAGTGATGCTAGTTCCGCAACTTATCCATTAGCTTTCGCTGC
AATGACCGGAACCACTGTGACTGTTCCTAATATTGGATTTGAATCTCTTC
AAGGTGACGCTAGATTCGCAAGGGATGTTTTGAAGCCAATGGGTTGTAAA
ATCACTCAGACAGCTACCTCAACAACCGTTAGTGGTCCACCTGTGGGAAC
ATTAAAGCCACTTAAACACGTTGACATGGAACCTATGACAGATGCTTTCT
TGACCGCATGTGTGGTTGCTGCAATTTCACATGATAGTGACCCAAATTCT
GCTAACACTACAACCATAGAGGGAATAGCAAACCAAAGAGTTAAGGAATG
CAACAGGATCTTGGCTATGGCAACTGAGTTAGCTAAATTTGGTGTTAAAA
CTACAGAATTACCTGATGGAATCCAGGTGCACGGTCTTAATTCAATCAAG
GACTTGAAAGTTCCAAGTGATTCTTCAGGTCCTGTGGGAGTTTGTACTTA
TGATGACCATAGAGTGGCAATGTCATTCAGTTTGTTAGCTGGTATGGTTA
ATTCTCAAAACGAGAGGGATGAAGTGGCTAACCCAGTTAGAATTTTGGAA
AGGCACTGCACTGGAAAGACATGGCCTGGTTGGTGGGACGTTTTGCATAG
TGAATTAGGAGCTAAACTTGATGGTGCAGAGCCTTTAGAATGTACTTCTA
AGAAAAATTCCAAGAAATCTGTGGTTATTATCGGAATGAGAGCTGCAGGT
AAAACCACTATTTCCAAATGGTGCGCTTCTGCATTGGGATACAAATTGGT
TGATTTAGACGAGCTTTTTGAACAACAGCATAATAACCAATCAGTTAAGC
AGTTCGTGGTTGAGAACGGTTGGGAAAAATTTAGAGAAGAGGAAACTAGG
ATCTTCAAGGAAGTTATCCAAAACTACGGTGATGACGGATACGTTTTCTC
TACAGGAGGTGGAATTGTGGAGTCAGCTGAAAGTAGAAAGGCACTTAAAG
ATTTCGCTAGTTCCGGTGGATATGTGTTGCATTTACACAGGGACATTGAG
GAAACTATCGTTTTCTTGCAATCTGATCCATCAAGACCAGCTTATGTTGA
GGAAATTAGAGAAGTGTGGAACAGAAGGGAGGGTTGGTACAAGGAATGTT
CAAACTTCTCTTTCTTTGCTCCACACTGCTCTGCTGAGGCAGAATTTCAA
GCTCTTAGAAGGTCCTTCTCTAAATACATCGCAACTATAACAGGAGTTAG
AGAGATCGAAATACCATCCGGTAGGTCTGCTTTTGTTTGTTTGACCTTCG
ATGACTTAACCGAGCAGACTGAAAACTTAACTCCTATTTGTTATGGTTGC
GAGGCAGTGGAAGTTAGAGTGGACCATCTTGCTAATTACTCAGCAGATTT
CGTTTCCAAGCAATTGTCTATCCTTAGAAAGGCTACTGATAGTATCCCAA
TAATTTTCACAGTTAGGACCATGAAACAGGGTGGAAACTTTCCTGACGAG
GAATTTAAGACACTTAGAGAATTGTACGTATAGCTCTTAAGAATGGTGT
TGAGTTTCTTGACTTGGAATTAACTCTTCCTACAGATATCCAATACGAAG
TTATCAACAAGAGAGGAAACTAAGATCATAGGTTCCCATCACGATTTT
CAAGGATTATACTCTTGGGATGACGCTGAGTGGGAAAATAGATTCAACCA
GGCATTGACCTTAGATGTTGACGTGGTTAAGTTTGTGGGTACTGCTGTTA
ATTTCGAGGACAACCTTAGATTGGAACATTTTAGGGATACACACAAGAAC
AAGCCACTTATCGCAGTTAACATGACCTCAAAAGGATCAATCAGTAGAGT
GTTGAATAACGTTTTAACCCCTGTGACTTCCGATCTTTTTGCCAAACTCTG
CTGCACCTGGTCAACTTACCGTTGCTCAGATCAACAAGATGTACACTTCT
```

```
ATGGGTGGAATTGAGCCAAAAGAACTTTTCGTGGTTGGAAAGCCAATCGG
ACATTCAAGATCACCTATCTTGCATAACACTGGATACGAAATTTTAGGTC
TTCCTCATAAGTTCGATAAATTCGAGACAGAATCTGCTCAATTGGTTAAG
GAAAAATTACTTGATGGTAACAAGAACTTTGGTGGAGCTGCAGTTACTAT
CCCATTGAAATTGGATATCATGCAGTACATGGATGAATTGACAGACGCTG
CAAAGGTTATTGGTGCTGTGAATACCGTTATCCCACTTGGAAACAAGAAG
TTCAAGGGTGATAACACAGACTGGCTTGGAATAAGAAATGCTCTTATCAA
CAACGGTGTTCCTGAATATGTGGGTCACACTGCAGGATTGGTTATTGGTG
CTGGTGGAACATCAAGAGCTGCATTATACGCTCTTCATAGTTTGGGTTGT
AAGAAAATCTTTATCATCAACAGGACAACCTCTAAGTTAAAACCACTTAT
CGAGTCACTTCCTAGTGAATTTAACATCATCGGAATAGAGTCCACTAAGT
CTATTGAGGAAATCAAAGAACACGTTGGTGTGGCAGTTTCCTGCGTTCCA
GCTGATAAACCTTTGGATGACGAGTTGCTTTCAAAACTTGAAAGATTTTT
GGTTAAGGGTGCTCATGCTGCATTCGTGCCAACACTTTTGGAAGCTGCAT
ATAAGCCATCCGTGACCCCTGTTATGACTATCTCTCAGGATAAGTACCAG
TGGCACGTGGTTCCTGGATCTCAAATGTTGGTTCATCAGGGTGTGGCTCA
GTTTGAGAAGTGGACAGGATTCAAAGGACCATTTAAGGCTATTTTCGACG
CAGTTACCAAGGAG

ScArol amino acid sequence (Saccharomyces
cerevisiae Pentafunctional arom protein; CAA88208)
                                        SEQ ID NO: 4
MVQLAKVPILGNDIIHVGYNIHDHLVETIIKHCPSSTYVICNDTNLSKVP

YYQQLVLEFKASLPEGSRLLTYVVKPGETSKSRETKAQLEDYLLVEGCTR

DTVMVAIGGGVIGDMIGFVASTFMRGVRVVQVPTSLLAMVDSSIGGKTAI

DTPLGKNFIGAFWQPKFVLVDIKWLETLAKREFINGMAEVIKTACIWNAD

EFTRLESNASLFLNVVNGAKNVKVTNQLTNEIDEISNTDIEAMLDHTYKL

VLESIKVKAEVVSSDERESSLRNLLNFGHSIGHAYEAILTPQALHGECVS

IGMVKEAELSRYFGILSPTQVARLSKILVAYGLPVSPDEKWFKELTLHKK

TPLDILLKKMSIDKKNEGSKKKVVILESIGKCYGDSAQFVSDEDLRFILT

DETLVYPFKDIPADQQKVVIPPGSKSISNRALILAALGEGQCKIKNLLHS

DDTKHMLTAVHELKGATISWEDNGETVVVEGHGGSTLSACADPLYLGNAG

TASRFLTSLAALVNSTSSQKYIVLTGNARMQQRPIAPLVDSLRANGTKIE

YLNNEGSLPIKVYTDSVFKGGRIELAATVSSQYVSSILMCAPYAEEPVTL

ALVGGKPISKLYVDMTIKMMEKFGINVETSTTEPYTYYIPKGHYINPSEY

VIESDASSATYPLAFAAMTGTTVTVPNIGFESLQGDARFARDVLKPMGCK

ITQTATSTTVSGPPVGTLKPLKHVDMEPMTDAFLTACVVAAISHDSDPNS

ANTTTIEGIANQRVKECNRILAMATELAKFGVKTTELPDGIQVHGLNSIK

DLKVPSDSSGPVGVCTYDDHRVAMSFSLLAGMVNSQNERDEVANPVRILE

RHCTGKTWPGWWDVLHSELGAKLDGAEPLECTSKKNSKKSVVIIGMRAAG

KTTISKWCASALGYKLVDLDELFEQQHNNQSVKQFVVENGWEKFREEETR

IFKEVIQNYGDDGYVFSTGGGIVESAESRKALKDFASSGGYVLHLHRDIE

ETIVFLQSDPSRPAYVEEIREVWNRREGWYKECSNFSFFAPHCSAEAEFQ
```

-continued

ALRRSFSKYIATITGVREIEIPSGRSAFVCLTFDDLTEQTENLTPICYC
EAVEVRVDHLANYSADFVSKQLSILRKATDSIPIIFTVRTMKQGGNFPDE
EFKTLRELYDIALKNGVEFLDLELTLPTDIQYEVINKRGNTKIIGSHHDF
QGLYSWDDAEWENRFNQALTLDVDVVKFVGTAVNFEDNLRLEHFRDTHKN
KPLIAVNMTSKGSISRVLNNVLTPVTSDLLPNSAAPGQLTVAQINKMYTS
MGGIEPKELFVVGKPIGHSRSPILHNTGYEILGLPHKFDKFSTESAQLVK
EKLLDGNKNFGGAAVTIPLKLDIMQYMDELTDAAKVIGAVNTVIPLGNKK
FKGDNTDWLGIRNALINNGVPEYVGHTAGLVIGAGGTSRAALYALHSLGC
KKIFIINRTTSKLKPLIESLPSEFNIIGIESTKSIEEIKEHVGVAVSCVP
ADKPLDDELLSKLERFLVKGAHAAFVPTLLEAAYKPSVTPVMTISQDKYQ
WHVVPGSQMLVHQGVAQFEKWTGFKGPFKAIFDAVTKE

CgQsuB polynucleotide sequence
SEQ ID NO: 5
ATGAGAACAAGTATTGCAACCGTTTGTTTATCCGGAACTCTTGCTGAAAA
ATTGAGAGCAGCTGCAGACGCAGGATTCGATGGTGTTGAGATTTTTGAAC
AAGATTTGGTTGTGTCTCCACATTCAGCTGAACAAATCAGACAGAGGGCA
CAAGATTTAGGTCTTACATTGGACTTATTTCAGCCTTTCAGAGATTTTGA
AGGAGTTGAAGAGGAACAATTCTTAAAGAATCTTCACAGGTTGGAGGAAA
AATTTAAGTTAATGAACAGACTTGGTATCGAAATGATCTTGCTTTGTTCT
AACGTTGGAACAGCTACCATCAACGATGACGATCTTTTTGTGGAACAATT
GCATAGAGCTGCAGATTTGGCTGAGAAGTACAACGTTAAGATCGCTTATG
AAGCTCTTGCTTGGGGTAAATTCGTTAATGATTTTGAGCATGCTCACGCA
TTGGTTGAAAAAGTGAACCATAAGGCTTTGGGTACTTGCTTAGATACATT
CCACATATTAAGTAGAGGATGGGAGACTGATGAGGTTGAAAACATCCCAG
CTGAAAAAATATTTTTCGTGCAATTGGCTGATGCACCTAAGTTATCTATG
GATATCCTTTCTTGGTCAAGGCATCACAGAGTTTTTCCAGGAGAGGGTGA
CTTCGATTTGGTTAAGTTCATGGTGCATCTTGCTAAGACAGGATACGATG
GTCCTATATCTTTGGAGATTTTCAACGACTCATTTAGGAAAGCTGAAGTT
GGAAGAACTGCAATTGATGGTTTAAGGTCTCTTAGATGGTTGGAGGACCA
AACATGGCATGCACTTAACGCTGAAGATAGGCCATCAGCACTTGAGTTGA
GAGCTTTGCCAGAAGTTGCAGAGCCTGAGGGTGTGGATTTCATTGAGATC
GCTACAGGAAGGTTAGGTGAAACCATCAGAGTTTTACACCAGCTTGGTTT
TAGACTTGGTGGACATCACTGTTCTAAGCAGGATTATCAAGTTTGGACTC
AAGGAGATGTGAGGATCGTTGTGTGCGACAGAGGAGCAACAGGTGCTCCT
ACCACTATATCAGCTATGGGTTTCGACACCCCAGATCCTGAGGCTGCACA
TGCTAGGGCAGAACTTTTGAGAGCACAAACAATTGATAGACCACACATCG
AGGGAGAAGTTGATCTTAAGGGTGTGTACGCTCCTGACGGAGTTGAATTG
TTTTTTCGCAGGACCATCTCCTGATGGTATGCCAGAGTGGTTACCTGAATT
TGGTGTTGAGAAGCAAGAAGCTGGACTTATCGAAGCAATCGATCATGTTA
ACTTTGCTCAGCCTTGGCAACACTTCGATGAGGCAGTTTTGTTTTATACC
GCATTGATGGCTTTAGAAACTGTGAGAGAGGATGAATTTCCATCACCTAT -continued TGGTTTAGTTAGGAATCAGGTGATGAGATCACCCAAACGATGCTGTTAGAT
TACTTTTGTCAGTGGCACCTGAGGACGGAGAACAGGGTGATTTCTTAAAT
GCTGCATACCCAGAACATATAGCTCTTGCAACTGCTGATATTGTTGCAGT
GGCTGAAAGAGCTAGGAAAAGAGGTTTGGATTTCTTGCCAGTTCCTGAAA
ACTATTACGACGATGTGCAGGCTAGATTCGATTTGCCTCAAGAGTTTTTA
GACACACTTAAGGAAAACCATCTTCTTTATGACTGCGATGAGAACGGTGA
ATTTTTGCACTTCTACACTAGAACATTGGGAACATTATTTTTCGAGGTTG
TGGAAAGAAGGGGTGGATTTGCTGGATGGGGTGAAACCAATGCACCTGTT
AGGCTTGCTGCTCAATATAGAGAAGTTAGAGATTTAGAGAGAGGTATCCC
AAAC CgQsuB amino acid sequence (Corynebacterium
glutamicum dehydroshikimate dehydratase; BAF53460)
SEQ ID NO: 6
MRTSIATVCLSGTLAEKLRAAADAGFDGVEIFEQDLVVSPHSAEQIRQRA
QDLGLTLDLFQPFRDFEGVEEEQFLKNLHRLEEKFKLMNRLGIEMILLCS
NVGTATINDDDLFVEQLHRAADLAEKYNVKIAYEALAWGKFVNDFEHAHA
LVEKVNHKALGTCLDTFHILSRGWETDEVENIPAEKIFFVQLADAPKLSM
DILSWSRHHRVFPGEGDFDLVKFMVHLAKTGYDGPISLEIFNDSFRKAEV
GRTAIDGLRSLRWLEDQTWHALNAEDRPSALELRALPEVAEPEGVDFIEI
ATGRLGETIRVLHQLGFRLGGHHCSKQDYQVWTQGDVRIVVCDRGATGAP
TTISAMGFDTPDPEAAHARAELLPAQTIDRPHIEGEVDLKGVYAPDGVEL
FFAGPSPDGMPEWLPEFGVEKQEAGLIEAIDHVNFAQPWQHFDEAVLFYT
ALMALETVREDEFPSPIGLVRNQVMRSPNDAVRLLLSVAPEDGEQGDFLN
AAYPEHIALATADIVAVAERARKRGLDFLPVPENYYDDVQARFDLPQEFL
DTLKENHLLYDCDENGEFLHFYTRTLGTLFFEVVERRGGFAGWGETNAPV
RLAAQYREVRDLERGIPN PaDsDH polynucleotide sequence
SEQ ID NO: 7
ATGCCTTCAAAACTTGCTATCACCTCAATGTCTCTTGGTAGATGCTATGC
TGGTCACTCCTTCACTACTAAATTGGATATGGCTAGGAAATATGGTTACC
AAGGACTTGAATTGTTCCATGAGGATTTGGCTGACGTTGCATATAGACTT
AGTGGTGAAACACCATCCCCTTGTGGACCATCTCCTGCTGCACAGTTGAG
TGCTGCAAGACAAATACTTAGGATGTGTCAGGTTAGAAACATAGAAATTG
TGTGCTTACAGCCATTTTCTCAATACGATGGTTTGTTAGACAGAGAAGAG
CATGAAGAAGGCTTGAACAATTGGAGTTCTGGATAGAATTAGCTCACGA
GCTTGATACAGACATTATCCAGATTCCAGCAAATTTTCTTCCTGCTGAAG
AGGTTACCGAAGATATTTCTTTGATCGTTTCAGATTTGCAAGAGGTGGCT
GACATGGGTTTGCAGGCAAACCCACCTATTAGATTCGTTTATGAAGCTCT
TTGTTGGTCAACTAGAGTGGATACATGGGAAAGGAGTTGGGAGGTTGTGC
AAAGAGTTAATAGGCCTAACTTTGGTGTGTGCCTTGATACATTCAATATC
GCAGGAAGAGTTTACGCTGACCCAACCGTTGGCATCAGGTAGAACTCCTAA
CGCTGAAGAGGCAATTAGGAAGTCAATCGCTAGATTGGTTGAAAGGGTTG
ATGTTAGTAAAGTTTTCTATGTGCAAGTTGTGGACGCAGAGAAGTTGAAA -continued

AAGCCATTAGTTCCTGGACACAGATTCTACGATCCAGAACAACCTGCTAG

GATGTCTTGGTCAAGAAACTGCAGGTTGTTTTATGGTGAAAAAGATAGAG

GAGCTTACTTGCCAGTTAAGGAGATTGCTTGGGCATTTTTCAATGGTTTG

GGATTTGAAGGTTGGGTTTCCTTAGAGCTTTTCAACAGAAGGATGTCTGA

TACTGGTTTTGGAGTGCCTGAAGAGTTAGCTAGAAGGGGAGCAGTTTCCT

GGGCTAAACTTGTGAGAGATATGAAGATCACCGTTGACTCACCAACTCAA

CAGCAAGCTACACAGCAACCTATAAGAATGTTGAGTTTATCCGCTGCATT

A

PaDsDH amino acid sequence (Podospora anserina
dehydroshikimate dehydratase; CAD60599)
SEQ ID NO: 8

MPSKLAITSMSLGRCYAGHSFTTKLDMARKYGYQGLELFHEDLADVAYRL

SGETPSPCGPSPAAQLSAARQILRMCQVRNIEIVCLQPFSQYDGLLDREE

HERRLEQLEFWIELAHELDTDIIQIPANFLPAEEVTEDISLIVSDLQEVA

DMGLQANPPIRFVYEALCWSTRVDTWERSWEVVQRVNRPNFGVCLDTFNI

AGRVYADPTVASGRTPNAEEAIRKSIARLVERVDVSKVFYVQVVDAEKLK

KPLVPGHRFYDPEQPARMSWSRNCRLFYGEKDRGAYLPVKEIAWAFFNGL

GFEGWVSLELFNRRMSDTGFGVPEELARRGAVSWAKLVRDMKITVDSPTQ

QQATQQPIRMLSLSAAL

PhPAAS polynucleotide sequence
SEQ ID NO: 9

ATGGACACTATCAAGATCAACCCAGAGTTCGACGGACAGTTCTGCAAGAC

TACATCATTATTAGACCCAGAGGAGTTCAGGAGGAATGGACATATGATGG

TTGATTTTCTTGCTGACTACTTCCACAACATCGAAAAGTACCCAGTTAGA

TCCCAAGTGGAACCTGGTTATTTGGAGAGGTTGTTACCAGATTCAGCTCC

TATACAGCCAGAACCTATCGAGAAAATTTTGAAGGATGTTAGATCAGACA

TATTTCCAGGTTTAACACATTGGCAAAGTCCAAATTTCTTTGCTTACTTC

CCTTGCTCTTCAAGTACCGCAGGAATTTTAGGTGAAATGCTTTCAGCTGG

ATTGAACGTTGTGGGTTTTTCATGGATCGCTAGTCCAGCTGCAACTGAAT

TAGAGAGTATTGTTATGGATTGGCTTGGAAAATTGATTAATTTGCCTAAG

ACATATCTTTTCTCTGGTGGAGGTGGAGGTGTGATGCAGGGTACTACATG

CGAAGTTATGCTTTGTACTATCGTGGCTGCAAGAGATAAAATGTTGGAAA

AGTTTGGAAGGGAGAACATTGATAAGTTAGTTGTGTACGCATCAGACCAA

ACCCACTTTAGTTTCCAGAAAGCTGTTAAGATCTCAGGTATAAAACCAGA

AAACTTCAGAGCTATACCTACCACTAAGGCAACAGAATTCTCCCTTAACC

CAGAGTCTTTGAGAAGGGCTATCCAAGAGGATAAAAAGGCAGGACTTATC

CCTTTGTTTTTATGCACATCAATAGGTACAACCAGTACTACAGCAGTTGA

CCCACTTAAACCTTTGTGTGAAATAGCTGAAGAGTATGGAATTTGGGTTC

ATGTGGATGCTGCATACGCTGGTTCTGCATGCATTTGTCCTGAATTTCAG

CATTTCTTGGACGGTGTTGAGCACGCTAATTCCTTTTCTTTCAACGCACA

CAAGTGGTTGTTTACTACTCTTGATTGTTGCTGTCTTTGGTTGAAAGACC

CATCCTCTTTGACTAAGGCACTTTCAACAAACCCTGAAGTTTTGAGAAAC

GATGCTACCGACAGTGAGCAAGTTGTGGATTATAAAGACTGGCAGATTAC

TTTATCCAGAAGGTTTAGGTCTCTTAAGCTTTGGTTGGTTCTTAAGTCCT

ACGGAGTGGCTAATCTTAGAAACTTCATAAGGTCTCATATCGAAATGGCT

AAGCACTTTGAAGAGTTGGTTGCAATGGATGAAAGATTCGAGATCATGGC

ACCAAGGAATTTTTCCTTAGTTTGTTTCAGAGTGTCTCTTTTGGCTCTTG

AAAAGAAGTTTAATTTCGTTGATGAAACTCAAGTGAACGAGTTTAACGCT

AAGCTTCTTGAATCTATCATCTCAAGTGGTAACGTTTACATGACACATAC

CGTTGTGGAGGGAGTTTACATGATTAGATTCGCTGTGGGTGCACCTTTGA

CAGATTATCCTCACATTGATATGGCTTGGAATGTTGTTAGGAACCACGCT

ACTATGATGTTGAACGCA

PhPAAS amino acid sequence (Petunia hybrida
Phenylacetaldehyde synthase; ABB72475)
SEQ ID NO: 10

MDTIKINPEFDGQFCKTTSLLDPEEFRRNGHMMVDFLADYFHNIEKYPVR

SQVEPGYLERLLPDSAPIQPEPIEKILKDVRSDIFPGLTHWQSPNFFAYF

PCSSSTAGILGEMLSAGLNVVGFSWIASPAATELESIVMDWLGKLINLPK

TYLFSGGGGVMQGTTCEVMLCTIVAARDKMLEKFGRENIDKLVVYASDQ

THFSFQKAVKISGIKPENFRAIPTTKATEFSLNPESLRRAIQEDKKAGLI

PLFLCTSIGTTSTTAVDPLKPLCEIAEEYGIWVHVDAAYAGSACICPEFQ

HFLDGVEHANSFSFNAHKWLFTTLDCCCLWLKDPSSLTKALSTNPEVLRN

DATDSEQVVDYKDWQITLSRRFRSLKLWLVLKSYGVANLRNFIRSHIEMA

KHFEELVAMDERFEIMAPRNFSLVCFRVSLLALEKKFNFVDETQVNEFNA

KLLESIISSGNVYMTHTVVEGVYMIRFAVGAPLTDYPHIDMAWNVVRNHA

TMMLNA

ObCCMT1 polynucleotide sequence
SEQ ID NO: 11

ATGGCGAGAAAAGAGAACTATGTTGTTTCTAACATGAATGTTGAAAGTGT

GTTGTGCATGAAAGGTGGAAAAGGAGAAGATAGCTATGATAACAACTCTA

AGATGCAGGAGCAACATGCTCGATCAGTGCTCCACCTTCTGATGGAAGCT

CTCGACGGCGTGGGGCTGAGCTCGGTGGCGGCCGGCGCTTTCGTGGTGGC

GGATCTCGGCTGCTCCAGCGGAAGAAACGCCATAAACACGATGGAATTTA

TGATCAATCACCTGACTGAGCACTACACGGTGGCGGCGGAAGAGCCGCCG

GAATTCTCAGCCTTCTTCTGCGACCTCCCCTCCAACGACTTCAACACCCT

CTTTCAGCTCCTTCCGCCGTCTGACGGCAGCAGCGGTTCTTACTTCACTG

CCGGCGTGGCCGGTTCGTTTTACCGGAGGCTTTTCCCGGCGAAGTCTGTT

GATTTCTTTTACTCGGCATTTAGTTTGCACTGGCTATCTCAGATACCAAA

GGAGGTGATGGAGAAGGGATCGCGGCTTACAACGACGGAGAGTGACCA

TCAACGGTGCAAAAGAGCACCGTAAATGCATACAAGAAACAATTTCAA

AGTGATTTGGGTGTCTTCTTGAGATCCAGATCCAAAGAATTGAAACCGGG

AGGATCCATGTTCCTCATGCTCTTGGGTCGGACCAGCCCCGACCCGGCAG

ATCAGGGCGCATGGATTCTCACTTTCAGCACACGTTATCAAGATGCTTGG

AATGATCTTGTGCAAGAGGGCTTAATTTCGAGCGAAAAACGGGATACGTT

CAACATCCCGATATATACGCCCAGCCTAGAGGAGTTCAAAGAGGTGGTAG

AAAGAGATGGTGCATTCATAATCAACAAGCTCCAACTTTTCCACGGTGGC

AGCGCTCTCATCATCGATGATCCCAACGATGCGGTTGAGATTAGCCGTGC

CTATGTCAGCCTCTGTCGCAGCCTCACCGGAGGCTTAGTTGATGCCCACA

TAGGCGATCAGCTCGGCCATGAGCTCTTCTCGCGCTTATTAAGCCAAGCC

GTGGATCAGGCTAAGGAGCTAATGGACCAGTTTCAGCTCGTCCATATAGT

TGCATCCCTTACTTTAGCT

ObCCMT1 amino acid sequence (*Ocimum basilicum* cinnamate/p-coumarate carboxyl methyltransferases; ABV91100)
SEQ ID NO: 12
MARKENYVVSNMNVESVLCMKGGKGEDSYDNNSKMQEQHARSVLHLLMEA

LDGVGLSSVAAGAFVVADLGCSSGRNAINTMEFMINHLTEHYTVAAEEPP

EFSAFFCDLPSNDFNTLFQLLPPSDGSSGSYFTAGVAGSFYRRLFPAKSV

DFFYSAFSLHWLSQIPKEVMEKGSAAYNEGRVTINGAKESTVNAYKKQFQ

SDLGVFLRSRSKELKPGGSMFLMLLGRTSPDPADQGAWILTFSTRYQDAW

NDLVQEGLISSEKRDTFNIPIYTPSLEEFKEVVERDGAFIINKLQLFHGG

SALIIDDPNDAVEISRAYVSLCRSLTGGLVDAHIGDQLGHELFSRLLSQA

VDQAKELMDQFQLVHIVASLTLA

RgC2'H polynucleotide sequence
SEQ ID NO: 13
ATGGCACCAACCAAAGATTCAGTTATTCACATGGGAGCAGAGTCCTGGGA

TGAGATTTCCGAGTTCGTTACTAAAAAGGGACACGGTGTTAAGGGTCTTT

CTGAACTTGGTATTAAAACTCTTCCAAAGCAATTCCATCAGCCTCTTGAA

GAGAGGTTCAGTGAGAAAAAGATTTTGGAAAGAGCTTCAATCCCACTTAT

CGATATGAGTAAGTGGGACTCCCCTGAGGTTGTGAAGTCTATCTGTGATG

CTGCAGAACATTGGGGTTTCTTTCAAATAGTTAATCACGGAGTGCCATTG

GAGACTTTACAGAGAGTTAAAGAAGCTACACATAGGTTTTTCGCTTTGCC

TGCAGAAGAGAAAAATAAGTACTCTAAGGAAAACTCACCAATTAATAACG

TTAGATTCGGTTCTTCATTCGTTCCTCATGTTGAGAAAGCACTTGAATGG

AAGGATTTTCTTAGTATGTTCTATGTTTCCGAAGAGGAAACTAACACATA

CTGGCCACCTATTTGTAGAGACGAGATGTTAGAATACATGAGGAGTTCCG

AGGTTCTTATCAAAGATTGATGGAAGTGTTAGTTGTGAAGGGTCTTAAA

GTTAAGCAAATCGATGAGATAAGAGAACCAATGTTGGTGGGATCAAGAAG

AATTAATTTGAACTACTACCCTAAATGCCCAAATCCTGAACTTACATTGG

GTGTTGGAAGGCATAGTGATATTTCCACCTTTACTATCTTGTTACAAGAC

GAAATCGGTGGACTTCATGTTAGAAAGTTGGATGACACTGGTAACACCTG

GGTTCATGTTACCCCAATATCTGGTTCACTTATTATCAATATCGGAGATG

CTTTGCAGATAATGTCTAACGGAAGGTACAAGTCAATAGAACACATGGTT

GTGGCAAATGGAACACAAGACAGAATCTCTGTTCCTTTATTTGTGAACCC

AAAGCCTCAGGCTATACTTTGTCCATTCCCTGAGGTTTTGGCAAATGGAG

AAAAACCAGTTTATAAGCCTGTGTTGTGCTCTGATTACTCAAGGCATTTC

TACACAAAACCTCACGATGGTAAAAAGACAGTGGATTTCGCATTGATGAA

C

RgC2'H amino acid sequence (*Ruta graveolens* 2-oxoglutarate-dependent dioxygenase; Vialart et al, plant J 2012, 70:460-470)
SEQ ID NO: 14
MAPTKDSVIHMGAESWDEISEFVTKKGHGVKGLSELGIKTLPKQFHQPLE

ERFSEKKILERASIPLIDMSKWDSPEVVKSICDAAEHWGFFQIVNHGVPL

ETLQRVKEATHRFFALPAEEKNKYSKENSPINNVRFGSSFVPHVEKALEW

KDFLSMFYVSEEETNTYWPPICRDEMLEYMRSSEVLIKRLMEVLVVKGLK

VKQIDEIREPMLVGSRRINLNYYPKCPNPELTLGVGRHSDISTFTILLQD

EIGGLHVRKLDDTGNTWVHVTPISGSLIINIGDALQIMSNGRYKSIEHMV

VANGTQDRISVPLFVNPKPQAILCPFPEVLANGEKPVYKPVLCSDYSRHF

YTKPHDGKKTVDFALMN

Plastid targeting signal polynucleotide sequence
SEQ ID NO: 15
ATGGCTTCGATCTCCTCCTCAGTCGCGACCGTTAGCCGGACCGCCCCTGC

TCAGGCCAACATGGTGGCTCCGTTCACCGGCCTTAAGTCCAACGCCGCCT

TCCCCACCACCAAGAAGGCTAACGACTTCTCCACCCTTCCCAGCAACGGT

GGAAGAGTTCAATGCATGCAGGTGTGGCCGGCCTACGGCAACAAGAAGTT

CGAGACGCTGTCGTACCTGCCGCCGCTGTCGACGATGGCGCCCACCGTGA

TGATGGCCTCGTCGGCCACCGCCGTCGCTCCGTTCCAGGGGCTCAAGTCC

ACCGCCAGCCTCCCCGTCGCCCGCCGCTCCTCCAGAAGCCTCGGCAACGT

CAGCAACGGCGGAAGGATCCGGTGCATGCAG

Plastid targeting signal amino acid sequence
SEQ ID NO: 16
MASISSSVATVSRTAPAQANMVAPFTGLKSNAAFPTTKKANDFSTLPSNG

GRVQCMQVWPAYGNKKFETLSYLPPLSTMAPTVMMASSATAVAPFQGLKS

TASLPVARRSSRSLGNVSNGGRIRCMQ

IRX5 promoter polynucleotide sequence
SEQ ID NO: 17
ATGAAGCCATCCTCTACCTCGGAAAAACTTGTTGCGAGAAGAAGACATGC

GATGGCATGGATGCTTGGATCTTTGACATTGATGACACTCTTCTCTCAAC

CATTCCTTACCACAAGAGCAACGGTTGTTTCGGGTAAATAAACTAAACTT

AACCATATACATTAGCCTTGATTCGGTTTTTGGTTTGATTTATGGATATT

AAAGATCCGAATTATATTTGAACAAAAAAAAATGATTATGTCACATAAAA

AAAAATTGGCTTGAATTTTGGTTTAGATGGGTTTAAATGTCTACCTCTAA

TCATTTCATTTGTTTTCTGGTTAGCTTTAATTCGGTTTAGAATGAAACCG

GGATTGACATGTTACATTGATTTGAAACAGTGGTGAGCAACTGAACACGA

CCAAGTTCGAGGAATGGCAAAATTCGGGCAAGGCACCAGCGGTTCCACAC

ATGGTGAAGTTGTACCATGAGATCAGAGAGAGAGGTTTCAAGATCTTTTT

GATCTCTTCTCGTAAAGAGTATCTCAGATCTGCCACCGTCGAAAATCTTA

TTGAAGCCGGTTACCACAGCTGGTCTAACCTCCTTCTGAGGTTCGAATCA

TATTTAATAACCGCATTAAACCGAAATTTAAATTCTAATTTCACCAAATC

AAAAGTAAAACTAGAACACTTCAGATAAATTTTGTCGTTCTGTTGACTT

CATTTATTCTCTAAACACAAAGAACTATAGACCATAATCGAAATAAAAAC

CCTAAAAACCAAATTTATCTATTTAAAACAAACATTAGCTATTTGAGTTT

```
CTTTTAGGTAAGTTATTTAAGGTTTTGGAGACTTTAAGATGTTTTCAGCA
TTTATGGTTGTGTCATTAATTTGTTTAGTTTAGTAAAGAAAGAAAAGATA
GTAATTAAAGAGTTGGTTGTGAAATCATATTTAAAACATTAATAGGTATT
TATGTCTAATTTGGGGACAAAATAGTGGAATTCTTTATCATATCTAGCTA
GTTCTTATCGAGTTTGAACTCGGGTTATGATTATGTTACATGCATTGGTC
CATATAAATCTATGAGCAATCAATATAATTCGAGCATTTTGGTATAACAT
AATGAGCCAAGTATAACAAAAGTATCAAACCTATGCAGGGGAGAAGATGA
TGAAAAGAAGAGTGTGAGCCAATACAAAGCAGATTTGAGGACATGGCTTA
CAAGTCTTGGGTACAGAGTTTGGGGAGTGATGGGTGCACAATGGAACAGC
TTCTCTGGTTGTCCAGTTCCCAAGAGAACCTTCAAGCTCCCTAACTCCAT
CTACTATGTCGCCTGATTAAATCTTATTTACTAACAAAACAATAAGATCA
GAGTTTCATTCTGATTCTTGAGTCTTTTTTTCTCTCTCCCTCTTTTCAT
TTCTGGTTTATATAACCAATTCAAATGCTTATGATCCATGCATGAACCAT
GATCATCTTTGTGTTTTTTTTCCTTCTGTATTACCATTTTGGGCCTTTG
TGAAATTGATTTTGGGCTTTTGTTATATAATCTCCTCTTTCTCTTTCTCT
ACCTGATTGGATTCAAGAACATAGCCAGATTTGGTAAAGTTTATAAGATA
CAAAATATTAAGTAAGACTAAAGTAGAAATACATAATAACTTGAAAGCTA
CTCTAAGTTATACAAATTCTAAAGAACTCAAAAGAATAACAAACAGTAGA
AGTTGGAAGCTCAAGCAATTAAATTATATAAAAACACTAACTACACTGAG
CTGTCTCCTTCTTCCACCAAATCTTGTTGCTGTCTCTTGAAGCTTTCTTA
TGACACAAACCTTAGACCCAATTTCACTCACAGTTTGGTACAACCTCAGT
TTTCTTCACAACAAATTCAAACATCTTACCCTTATATTACCTCTTTATCT
CTTCAATCATCAAAACACATAGTCACATACATTTCTCTACCCCACCTTCT
GCTCTGCTTCCGAGAGCTCAGTGTACCTCGCC
```

AtC4H promoter polynucleotide sequence

SEQ ID NO: 18

```
CGGAATGAGAGACGAGAGCAATGTGCTAAGAGAAGAGATTGGGAAGAGAG
AAGAGAAGATAAAGGAAACGGAAAAGCATATGGAGGAGCTTCACATGGAG
CAAGTGAGGCTGAGAAGACGGTCAAGTGAGCTTACGGAAGAAGTGGAAAG
GACGAGAGTGTCTGCATCGGAAATGGCTGAGCAGAAAAGAGAAGCTATAA
GACAGCTTTGTATGTCTCTTGACCATTACAGAGATGGGTACGACAGACTT
TGGAGAGTTGTTGCAGGACATAAGAGTAAGAGAGTAGTGGTCTTATCAAC
TTGAAGTGTAAGAACAATGAGTCAATGACTACGTGCAGGACATTGGACAT
ACCGTGTGTTCTTTTGGATTGAAATGTTGTTTCGAAGGGCTGTTAGTTGA
TGTTGAAAATAGGTTGAAGTTGAATAATGCATGTTGATATAGTAAATATC
AATGGTAATATTTTCTCATTTCCCAAAACTCAAATGATATCATTTAACTA
TAAACTAACGTAAACTGTTGACAATACACTTATGGTTAAAAATTTGGAGT
CTTGTTTTAGTATACGTATCACCACCGCACGGTTTCAAAACCACATAATT
GTAAATGTTATTGGAAAATAGAACTCGCAATACGTATTGTATTTTGGTAA
ACATAGCTCTAAGCCTCTAATATATAAGCTCTCAACAATTCTGGCTAATG
GTCCCAAGTAAGAAAAGCCCATGTATTGTAAGGTCATGATCTCAAAAACG
AGGGTGAGGTGGAATACTAACATGAGGAGAAAGTAAGGTGACAAATTTTT
GGGGCAATAGTGGTGGATATGGTGGGGAGGTAGGTAGCATCATTTCTCCA
AGTCGCTGTCTTTCGTGGTAATGGTAGGTGTGTCTCTCTTTATATTATTT
ATTACTACTCATTGTAAATTTCTTTTTTCTACAATTTGTTTCTGACTCCA
AAATACGTCACAAATATAATACTAGGCAAATAATTATTTTATTATAAGTC
AATAGAGTGGTTGTTGTAAAATTGATTTTTTGATATTGAAAGAGTTCATG
GACGGATGTGTATGCGCCAAATGGTAAGCCCTTGTACTGTGCCGCGCGTA
TATTTTAACCACCACTAGTTGTTTCTCTTTTTCAAAAAACACAAAAAAAA
AATAATTTGTTTTCTTAACGGCGTCAAATCTGACGGCGTCTCAATACGTT
CAATTTTTTTCTTTCTTTCACATGGTTTCTCATAGCTTTGCATTGACCAT
AGGTAAAGGGATAAGGATAATGGTTTTTTCTCTTGTTTGTTTTATCCTTA
TTATTCAAAAGGATAAAAAACAGTGATATTTAGATTTCTTTGATTAAA
AAAGTCATTGAAATTCATATTTGATTTTTTGCTAAATGTCAACACAGAGA
CACAAACGTAATGCACTGTCGCCAATATTCATGGATCATGACAATAAATA
TCACTAGAATAATTAAAAATCAGTAGAATGCAAACAAAGCATTTTCTAAG
TAAAACAGTCTTTTATATTCACGTAATTGGAATTTCCTTTTTTTTTTTT
GTCGTAATTGGAATTTCCTTTATCAAACCCAAAGTCCAAAACAATCGGCA
ATGTTTTGCAAAATGTTCAAAACTATTGGCGGGTTGGTCTATCCGAATTG
AAGATCTTTTCTCCATATGATAGACCAACGAAATTCGGCATACGTGTTTT
TTTTTTTGTTTGAAAACCCTTTAAACAACCTTAATTCAAAATACTAATG
TAACTTTATTGAACGTGCATCTAAAAATTTTGAACTTTGCTTTTGAGAAA
TAATCAATGTACCAATAAAGAAGATGTAGTACATACATTATAATTAAATA
CAAAAAAGGAATCACCCATATAGTACATGGTAGACAATGAAAAACTTTAAA
ACATATACAATCAATAATACTCTTTGTGCATAACTTTTTTTGTCGTCTCG
AGTTTATATTTGAGTACTTATACAAACTATTAGATTACAAACTGTGCTCA
GATACATTAAGTTAATCTTATATACAAGAGCACTCGAGTGTTGTCCTTAA
GTTAATCTTAAGATATCTTGAGGTAAATAGAAATAGTTGACTCGTTTTTA
TCTTCTTCTTTTTTTACCATGAGCAAAAAGATGAAATAAGTTCAAAACG
TGACGAATCTATATGTTACTACTTAGTATGTGTCAATCATTAAATCGGGA
AAACTTCATCATTTCAGGAGTATTACAAAACTCCTAAGAGTGAGAACGAC
TACATAGTACATATTTTGATAAAAGACTTGAAAACTTGCTAAAACGAATT
TGCGAAAATATAATCATACAAGTGCCAGTGATTTTGATCGAATTATTCAT
AGCTTTGTAGGATGAACTTAATTAAATAATATCTCACAAAAGTATTGACA
GTAACCTAGTACTATACTATCTATGTTAGAATATGATTATGATATAATTT
ATCCCCTCACTTATTCATATGATTTTTGAAGCAACTACTTTCGTTTTTTT
AACATTTTCTTTTGTTGGTTATTGTTAATGAGCATATTTAGTCGTTTCTT
AATTCCACTGAAATAGAAAATACAAAGAGAACTTTAGTTAATAGATATGA
ACATAATCTCACATCCTCCTCCTACCTTCACCAAACACTTTTACATACAC
TTTGTGGTCTTTCTTTACCTACCACCATCAACAACAACACCAAGCCCCAC
TCACACACACGCAATCACGTTAAATTTAACGCCGTTTATTATCTCATCAT
TCACCAACTCCCACGTACCTAACGCCGTTTACCTTTTGCCGTTGGTCCTC
```

AtC3H promoter polynucleotide sequence

SEQ ID NO: 19

ATCGTAAGTTTTTTTGTGTGTGTTAACAATGTACTCACTACTCACTGT
TCCATATTTTTGATGTACGTATATCGAAAACATTCTGCCAACAAATGCAA
ACATAACAAAAGTCAAAAACAATAACATAACCGGGAATTAAACCAAAATG
TAATTGCTTTTTATTAGTGTCAGGCCTTCTGCTTAAAAATATTCTCGGCC
CAGAGCCCATTAACACCTATCTCAATTCATATTGAAGAAAATGACTATAT
TACTTGACAAAAACTTTAGTCAGAAAAATATGGAATCTCTTTCGGTACTG
CTAAGTGCTAACCTTAAATAGTATAGAATTCTTAGTTCATTCTCAAAAAC
ATAGCTATATGTAGATTATAAAAGTTCGATATTATTTCCTGCAAAAGATG
TTATAATGTTACAACTTACAAGAAAATGATGTATATGTAGATTTTATAAA
CTGGTACCGTAATTCATAAAAGATGGTGGTGGGTATGTATCAGTAACGGA
ACTTACATATGCGTGTGTATTACTATGTCTATATGGTGTATTCCTTTGTG
TGGAACAATGCACGTCAGAGTTGTTTATTTTCTTATAGAATTTAAGGAAT
CAATTATTGGATTTCTCAAGGTGAAAGTGGACTTCTTTGCACGCAAGGTC
TAGTTGCCGACTTGCCGTTGCATGTAACATGATTGTTGAAATAAAGTGAA
TTGAGAGAAGTTTGGCCAGACATTTTAAATTTAACCCAAAAAAAGTAGGG
CCTAACACAAAATATAACCTCTCTTTGTTCAAAGGAAATAACACCTACGT
CTTATAATTGAACCAAACATTGAATCATTGAACTCACCTATAATAATTAT
AATAACACGAATTCACAAGACACCTAAAAGAAAAAGTTCACAAAAACAAA
TAAAAATTTACCTCTCACCAAACACACTCACCTACCCGTCTGGTCCCACT
GACCCCAACATACAACACCGACTCTCTCCCACACCAATTTTTTTTTTGG
CGTTTTAAAACAAATAAACTATCTATTTTTTTTCTTACCAACTGATTAA
TTCGTGAATAATCTATTATCTTCTTCTTTTTTTGTGACGGATGATTAGT
GCGTGGGAAATCAAAATTTACAAAATTTGGGATGATTCCGATTTTTGCC
ATTCGATTAATTTTGGTTAAAAGATATACTATTCATTCACCAAGTTTTCA
GATGAGTCTAAAAGATAATATCATTTCACTAGTCACTTAAAAAAAGGGTT
AAAAGAACATCAATAATATCACTGGTTTCCTTAGGTGACCCAAAAAAGA
AGAAAAAGTCACTAGTTTCTTTTTGGAAATTTTACTGGGCATATAGACGA
AGTTGTAATGAGTGAGTTTAAATTTATCTATGGCACGCAGCTACGTCTGG
TCGGACTATACCAAGTTACCAACTCTCTCTACTTCATGTGATTGCCAATA
AAAGGTGACGTCTCTCTCTCTCACCAACCCCAAACCACTTTCCCCACT
CGCTCTCAAAACGCTTGCCACCCAAATCTATGGCTTACGGGGACATGTAT
TAACATATATCACTGAGTGAAAAGAAGGGTTTATTACCGTTGGACCAGTG
ATCAAACGTGTTTTATAAAAATTTGGAATTGAAAACATGATTTGACATTT
TTAATGATGGCAGCAGACGAAACCAACAACACTAAGTTTAACGTTCGTGG
AGTATACTTTTCTATTTTCGAAGAAGACATATAACTAAGCTGATTGTTAT
TCTTCATAGATTTCTTTTCACTGCGAATAAAAGTTTGTGAACATGTCACC
GTTTGAACACTCAACAATCATAAGCGTTTTACCTTTGTGGGGTGGAGAAG
ATGACAATGAGAAAGTCGTCGTACATATAATTTAAGAAAATACTATTCTG

ATTTCTCAAACCAACCAAACCTCTCCCTCTTATAAAATCCTCTCTCCCTT
CTTTATTTCTTCCTCAGCAGCTTCTTCTGCTTTCAATTACTCTCGCC

ACTCTGGAACGTGTAAATAATTATCTAAACAGATTGCGAATGTTCTCTAC
TTTTTTTTTTGTTTACATTAAAAATGCAAATTTTATAACATTTTACATCGC
GTAAATATTCCTGTTTTATCTATAATTAATGAAAGCTACTGAAAAAAAAC
ATCCAGGTCAGGTACATGTATTTCACCTCAACTTAGTAAATAACCAGTAA
AATCCAAAGTAATTACCTTTTCTCTGGAAATTTTCCTCAGTAGTTTATAC
CAGTCAAATTAAAACCTCAAATCTGAATGTTGAAAATTTGATATCCAAGA
AATTTTCTCATTGGAATAAAAGTTCAATCTGAAAATAGATATTTCTCTAC
CTCTGTTTTTTTTTTCTCCACCAACTTTCCCCTACTTATCACTATCAAT
AATCGACATTATCCATCTTTTTTATTGTCTTGAACTTTGCAATTTAATTG
CATACTAGTTTCTTGTTTTACATAAAAGAAGTTTGGTGGTAGCAAATATA
TATGTCTGAAATTGATTATTTAAAAACAAAAAAAGATAAATCGGTTCACC
AACCCCCTCCCTAATATAAATCAAAGTCTCCACCACATATATCTAGAAGA
ATTCTACAAGTGAATTCGATTTACACTTTTTTTTGTCCTTTTTTATTAAT
AAATCACTGACCCGAAAATAAAAATAGAAGCAAAACTTC

AtHCT promoter polynucleotide sequence

SEQ ID NO: 20

TTCTCTAGGTTTTGAAGCTTTCCTAGTTCTTTTGGAAGCGTGCCGGACAA
GTCATTGTCGTATAGAAACAGATTGATAAGTTCAGAGCAGTTTCCAAGCT
CTTTAGGGATCTCACCTGAGAGCATTGTAGAATAGACAGATAAAGACTGG
AGCTTGCTTAGTTGACCCAACGAAACAGGTAAAGAACCGGATATTTTCGT
TGCTGCTAACCCTAAGACCTTGAGATTCCTACAGTTTCCGATCTCCTCCG
GGATCTTCCCTGAAAGCTCTGAGTTTCCTCCGGCTCTTATGCTCTCAAGA
GTCGAGATCTTTCCGAGCTCCAACGGGAGATTCTCGGATAAGTAGTTATC
GAAAATCTCAAGATTCTTGAGGCTAACGCAGTCGCCGAGTTCCGGTGGGA
TCTTTCCTGTGAGGCCATTGGAGTTTAAACAAAGTTCTTGAAGATTCTTG
AGCTTCCCTAGACTCGAAGGTATTTCACCAACAAGACTATTTGAGCTTAA
ATCGATAACTATAAGCTCCGAACAATCTCCGATCTCAGAAGATATAGCTC
CGGTGAGATTAGTGTTGGAGATAACGAGTTTCTGAAGTGAAGTAAACGAA
GAAATGTTAGGAGGGAAAGGTAAAGCTAACTGAACAGAGACGACATTGAT
CTCTGTAACGAGTTTGTTGTCTGAGGAGGAACAAGTAATGTAAGGCCATT
GACATGGGTCAGAATCAGAAGGATTCCAGCCGGAGAAGACTGACGGTGGC
GGCGAGTTCGAGCTGTGAAGCCAAGAAATCAAAGCTGAGACTTCATTGGT
TGATGCAGAGGTCGAGGAGATGAAGAAAGCTAAAAACAGAGACAATGTAA
TGGAAAAATGAGAAACAGTTAAGGCTTTTTTCTTGGAATCGGCATTTGC
AAAGACATAAGAGTTTTTTCTTTGCATTTGGCTCTCAAATCCAAAACAA
GCCTTCTTGGTTCTGCATCGATCTGAGTCCTTTGGCTTAGGGTTTAGGGA
AGTTTTTGCTTTAGAGATAAGCAATAAGAAAGAATGATATATTTAAATATA
TAAAAGTACTAAACTTCATGTGCTCTGTCTTTTTCTTTTACCTCGGGGTT
CTGTTTCTAGCTTCAGATTAATTAATTACAGTCATTAACTTTTCTTTGAA
ATATGTTTGCCAAGAGCCCGAGACACTATCCATAGATGACAAAAGTCAAT
AGTTATATATACATAAAATATCACAAAACAAAAGGCATTGGTTATATATA

-continued

TACAGAATCATTTCACTTAGTAGTGTTTTTTCTTATAAGATTATGATAGA
AATATGGAAGCATGCATGTGGTTTTGCATTGTTTTCCTCAATTAAGTCAG
GATTGTGAGTTGGTTTGTTTTCGAGACCTGAACCGAGCGTTTAAGATTCT
TCCTCGTTTGAAGTAAACTCCATAATTGTCCACACCTAAGCTAAAAGAAA
GTAATAACAAGTTTAAATATTCATGACAAGGAAAATATTGCATTCAGAAA
ATTGTTAACAACGAAGTAAACATTTTTTTCAATCCGATGCCAATAGTCTC
TAGCGGCATCAAAAGTCCACAAACTCGATACCTCTGGGTAAATGAGCGAA
TGGGCCGGTCCGTTGTAGCCCAGAAGAGAAATTGTCCTCTAAATTCCATA
CTTCCATGAATTTTCTCTGTATATCCTCGTTTGATGTATGGTATATTTGT
TCCGCTCTAAATCATGACCAACCCAAGGTACTAAATTGTCATTTAAGCTT
TGATTGGTATTTGGTAGCATGGGTTACCATTGACCAACCCACGGTACTAG
TTGCTTTTCTTTTAGTTTTGCTTTTGCTTTATTTTCTTAGAGAGTGGGAG
GACAAAAGGTTTGGATCATTAAGCCAATGAATGCTTCAAAGAAATTGAAT
TTTTATTAGATCCTCAAACCAAGTTGGATCATCAAATAATGGCTAAGAAA
TAATTTTAGAACAGAAAGCAAAGAAAAGCTATCCGCAACAACAACCATTA
GTTAATAAATTAAAATGAAATGTGAAATTTATGACTAATTGAGGTATGTT
TTCATATAATATAGTATAGTTCGGATATAAATTCAACATAATTTATTTGT
GGTGTACTGAAAAAAAGACTTTCTTGGATTCTGACGTAATTCTCTTAACA
CGTGAGTTTACGCCGTTAGATGTTATTGGTGGTTGTTGTTATGCTCTGCT
ACGTGGTAATGAGTTAAGTTAAGCCAAACTTTGGCATTCGATTGACTAAC
TTGTACGGTAGCTATAACAATCAACTTGTCAATTTTTTTCCTTCTTCTT
CATTCGAACTTTATACTATTTAAGCCCATTAGTATTATTTGGGCCTTAGG
ACAGAGGGAACGGGTTTACCAACCCCGGATAGAAAAGTAGGACCGAGTGA
TGAGATGGACCAATGATAAACCTTCTGAGAGAGTTGGTCGACAGATGGAG
TAGGCGGGGTCGTGGGCGGTAGGTGAAGGATTACGACCTTTCCTTTTTT
GTTCACACCCACTTATATCTACCCCTCCTCGCTTCTCACACAATTTCTCA
GATCAAACTCAAACAAAATTTGTTTGTTCGTTTGATCTTTCTTAAAAAT

AtCCR1 promoter polynucleotide sequence

SEQ ID NO: 21

TTGCTTTCTCTGTCCATGATATGAGGCATTGACTTCTCACCTGTATTCAT
ATGGTATAGATTCCTCTTTTCAGGAGTCCAATACAAACGAGCTTGGTGAA
GAACTCGTTGGTAAGAGAGTTAATGTCTGGTGGCCACTCGACAAGAAGTA
AGTTTATTGTTAAACTTACTAACTTCATTTTTGATACTATATGATGAATG
ATAGCAATCTTACGATTTGTATTTGCACAGGTTTATGAAGGTGTCATAA
AATCTTATTGTAGAGTTAAGAAGATGCATCAAGTGAGTTAACTTCTCTAT
TTGGTATTTTAAAATTCTCTATTTATTGCATAACTGGTTTATATAGAATT
TTCCCACTGATGGTCTCGCAGGTAACATATTCTGATGGCGATGTTGAAGA
GCTTAATCTGAAAAAGAACGTTTTAAGATAATCGAGGATAAATCTTCAG
CCAGTGAGGTGAAAATTTCTTACATTCTATCATTCACCATTCTTTATATT
TACCAAAATTTCAATGTATCTGGTTTCCCTAATAAAATCTAAGCAGGATA
AGGAAGATGATCTGCTTGAGTCTACTCCTTTATCTGCCTTGTAAGTGAAA
CTTCCATAGTTCTATGATAACCCACAATTTATAATTTTAATTTAGCTTTA

-continued

GTCTTGAGTTTTTTGCTGTTATGTGCAGTATACAAAGGGAGAAATCCAAG
AAGAGGAAAATTGTGTCTAAGAATGTGGAACCGAGTAGTTCTCCAGAAGT
CAGGTATGAAAGTATATAAGAATTCTAGTTTTAGTTGTTTGAAAGTTTGA
TCCGTGAGTGAATTAGTTCACAATTATGGATGTAGATCCTCTATGCAAAC
AATGAAGAAGAAAGACTCTGTAACAGACTCCATTAAGCAAACAAAAAGAA
CCAAAGGTGCACTGAAGGCTGTAAGCAATGAACCAGAAAGCACTACAGGG
AAAAATCTTAAATCCTTGAAAAAGCTGAATGGTGAACCTGATAAAACAAG
AGGCAGAACTGGCAAAAAGCAGAAGGTGACTCAAGCTATGCACCGGAAAA
TCGAAAAGATTGTGATGAGCAGGAAGACCTCGAAACCAAAGATGAAGAA
GACAGTCTGAAATTGGGGAAAGAATCAGATGCAGAGCCTGATCGTATGGA
AGATCACCAAGAATTGCCTGAAAATCACAATGTAGAAACCAAAACTGATG
GAGAAGAGCAGGAGGCAGCGAAAGAGCCAACGGCAGAGTCTAAAACTAAT
GGAGAGGAGCCAAATGCAGAACCCGAAACTGATGGAAAAGAGCATAAATC
ATTGAAGGAGCCAAATGCAGAGCCCAAATCTGATGGAGAAGAGCAGGAGG
CAGCAAAAGAGCCAAATGCTGAGCTCAAAACTGATGGAGAAAATCAGGAG
GCAGCAAAAGAGCTAACTGCAGAACGCAAAACTGATGAGGAAGAGCACAA
GGTAGCTGATGAGGTAGAGCAAAAGTCACAGAAAGAGACAAATGTAGAAC
CGGAAGCTGAGGGAGAAGAGCAAAAGTCAGTGGAAGAGCCAAATGCAGAA
CCCAAGACCAAGGTAGAAGAGAAAGAGTCAGCAAAAGAGCAAACTGCAGA
CACAAAATTGATTGAGAAGGAGGATATGTCTAAGACAAAGGGAGAAGAGA
TTGATAAAGAAACATATTCAAGCATCCCTGAGACTGGTAAAGTAGGAAAC
GAAGCTGAAGAAGATGATCAGAGAGTGATTAAGGAACTGGAAGAAGAGTC
TGACAAGGCAGAAGTCAGTACTACGGTGCTTGAGGTTGATCCATGAATGA
AGGATTGTAGGTAAATGTTAATCCAGGAAAAAAAGATTGGTTCTTGTGG
TTTAGGTAACTTATGTATTAAGTGAAGCTGCTTGTTTAGAGACTAATGGT
GTGTTTTATGAGTAGATTCTTCTGACCTATGTCTCGTTATGGAACTAGTT
TGATCTTATGTCACCTTGCTAGCAGCAGATATTGATATTTATATATTTAA
GAGACATGCGCATGAGAATGAGGGTATGGAAAAGTCCATATCAGATGACA
CAAACAATGATCGTATGTGTAGTCACTTGTGCATTTCCAGTTTTGGACAT
AAAAATTCTGATATTGCATAGAAATGTTTTTAAATAACACTAATCCAAACC
TAAATAAAATATCTCTATACATCATCTAGAAATGTATGGCTTGATCAAGA
ATTGTAGATAATAATACCCTGAGTTAAATGATTGTAGGTATTATTTCAGT
TTTCAAATTGTCCAAATTTATGAGCTATATTAAAGATAATATTTTCAAT
AAGGTGTGTAGTTCTAAATGTTTCTTCTTCTTCCACCAACCCCTCTTTCT
ATATGTATGTTCTTTTTTCTAAAATAATTGTTTGTTCTTTTTTAGATATA
TCAAATTAAATATAAAAAATATTGACAAAACTTATTTACCATTGTTAGGT
GAACTTGGCAAGTGTGTAAATATAAAGATAACATTCCTTTTCGTTCTTTA
TATATACGAAACGTACCACAAATTTCTAACTAAAGCATTCATAGTCTCTC
GAAAGCCTCTTTTCAGAACCGAAGCTCTTTACTTTCGTCCACCGGGAAAT

AtCAD4 promoter polynucleotide sequence
SEQ ID NO: 22
CAGAAAGGTCTTCACACTCTGTTTTAGCTAGAGAGTTTTATCCATCTGAG

TTTTTAGTCTATTTTGTTTTATCTAGGAGTTGCTTTGTTTGTTCGAATTC

GGTCATTGCTTTTGCTGCTTTACTGGAGTCAAATTTGAAGGTAAAATATA

TGTTAAATATCTGGGTAGGTGGTTGTGGATGATGGAAAATCTGAACGTAT

CACTGTTAATGACAATGGAGAACTCGTTTCTACTCAGCATGCTATCACCG

AATACCGAGTGATTGAATCTTCACCACATGGTTAGTGAGACTGACTTCCA

TTTCTATTCAGTTAAACTTAAAGCAAATGATTTTGCCTTGAGTTTTTAGC

ACATTGTTGAATTGCAGGATACACATGGCTTGAGCTTCGCCCTTTAACCG

GGAGAAAACATCAGGTCTCTATAGATATTCAGTTTTTGTTTCAACTTTCT

CTCTTTTTTATGTTCTCTTAATACTAATCTGTTTTCAACTGTTCTTCGAT

TGCCACAGCTTCGTGTACACTGCGCTGAAGTGCTAGGAACACCGATAGTC

GGGGACTACAAATACGGTTGGCAAGCTCATAAAGCCCGGGAACCTTTTGT

CTCTTCTGAAAACAACCCAACCAAGCAATCATCATCTCCTTTTGGATTGG

ATCTGGATGGTGGAGATGTCTCTTCGAAACAGCCACACCTTCATCTCCAT

TCAAAGCAAATCGATCTGCCAAACATATCACAGCTCTTGGAGAAAATGCA

GGTCTCTTCAGACTCTGATATTTCGGATCTCGATAGCCTTAAATTCGATG

CTCCATTGCCTAGTCATATGCAACTAAGCTTTAATTTGTTGAAATCTAGA

GTCGAAACTTGTGACAAAAATTAGATTTTTTTCTTACCGAGCTTTCTTC

TTTGTGTTCATTGAGGCCCAAGTATTTGTGTATTTGGACCTGAATATTCT

CATACAAAGATAAATAATTATAATTAAATGATTTTTCGCATATAATCATT

ATTGTGGTATGATTAACACAGTTGGTGTGATGACTGATTGACACAATAAT

CACCGTTTGGATTCGATTCCTTTAATACTTGTCACTAGAGTTGTTTGACT

AAACAGCTAACTTGTCACTAGAGTTATTGTGTTTGTATTTTGATCTGTTA

TTAATCTGATTGGGTATAATTACAGATAGAGAGACATCTATATTGTAATT

AAGACAATCTTAAAGTGTAAACTAAAAAGATCTCTCTGACCTCTGGAAAA

CGAAAGGTGGGTGACACATCACTCTAGCTATGAATATGATGAATATTCAG

TACCTAACCGAACAAAGACTGGTTTGGTATTTTTATTGGAAAAAAGAGAT

AAATAATTGTGAATGTGAATTATCCTGTCTGAAAGGTAAGCTGATGACAT

GGCGTTATATGATTGGACGAGCTTCAGAACAAAAGAGTAGCGTCGAATCG

AATCTTTACCTACTACACTTTGAACTTTGAAGTACATTACCTACTTCCTC

CTTGATCGAACGTCTTTTCTCAAAACTATTTTATTTCCCCAATTAAAGTA

GTGGTGATAAATTCACAAAAATACAAACACTTTTATTTTTGACGTCAAAA

ACAAATACTTCTTTGAACAGGCTATTACAATATTTTTAAGAAAAAGTAA

GCAAAATAGTCCACAAACCAAAATCTGTAACATATTAAACGATTTATGTT

TTTTTTTTTTTTCTTAACTAGAGAACAATTCGGGCTTTTACTAAGGATG

ATGAGTGTAGTTACCGAATAGTGTATTCATATAATCTTTTAATGAGCTTA

AGATATGATATTATTTCGACTAATCAGATAAGAGTAGTTAGATAATTTCG

TAATAGAGCAACTCTTTCGCAAATAAAACCATTGTAAACATTACCAATTA

GTTTTTCTTTTTTTTGGTCACAACCAATTAGTTTGTTTGTTCTATTTTA

TGAAGTGCGTATTAAAGCTAACGTGTTTACAGTAACGCCACACAAATAAA

AATAAAAATAATTATGTACTTTATGGATTTATAGAAAAAACAAGAATAGT

CACCAAAAATTGATTGTGTCATATATCTTTTGTCAACTATTTTATCTTAT

TTTTCTATGGATATGTATGTCCAAAATGTTAGACAAAAAACCAAAAAATC

ATGTCCAAAATTTCGTTAGGCTGCCGATATCTCTGTTTCCCTTTCAACGA

CTATCTATTTAATTACCGTCGTCCACATTGTTTTTAATATCTTTATTCGA

GGTTGGTTTAGTTTTTTTTACCAAACTCACTTTGCTACGTTTTTGCCTTT

TTGGTATGGTTGTATTTGTACCACCGGGAAAAAAAGATAAGAGGTTTGG

TTGGTCGAGCTTACTGATTAAAAAATATACACGTCCACCAAATATTAAAA

CAATATATCCCATTTTTCCTCCTCTCTTTTGGTATTACATTAATATTTTA

TTATTTCCCCATTTGCTCTGTATATATAAACATATGTCAATAGAGTGCCT

CTACAGTCATGTTTCCATAGACATAATCTCTCACCATTGTTTTTCTCTGC

AAAACTAAAGAAACAAAAAAAGAAAAATCGGAGAAACCAAGAAAAAAGAA

AtCAD5 promoter polynucleotide sequence
SEQ ID NO: 23
CCTCGATAACTCTGATTGTTGTATTGTCCAAGTATTCACTAAACAACTTT

GCTAAAAGAGAAGATGCTGCTGGAGCAATTTCAGAAGGTTTTAGCACAAC

CGCATTACCAGCTGCAATAGCTCCAATGACTGGCTCGACAGACAATACTA

AGGAAAAAAACAAAGCACCATGAAGACATATAAACTTTAATAGTTTAGAA

ATTGAGACAAAATTGTCAATAAATAAAATTGAGCTTACAGAAAGGGAAAT

TCCAGGCTGAAATAACCAAAACAACTCCAAGCGGTTCTGAGACTATTTGT

GCAGACGAGGGAAATGTTGTCACAGAAGTTTTGACCTGAAAGGTCCAAGC

ATAGAAAAAGCAAGTGGTTTTAGAAAGGACACATATCAATGAAGCAGCAA

AGCTTGAACGGTCTAGTTACCGTTTCTGGAGCCATCCAGTTCTTTAACTC

TTTGATTGCAAGCATACAGGATGATTTTGTATTCGAAATCTAAAAAACGA

GAAAAATACCAAAGAGATTCAACAGTGGATAAGTGGAATGCAGTGAAGAA

ACGGGACATTGAAATTATATAAAAAACCTCAGCTAGAAAAGCTTCAAGCT

CAGGCTTAGAAAGATCTTGATACAAAGCTTCGGTGATGCATTTCTCCTTC

TCATCAATCATCCTAGCAATGTTTTGAAGCTGAGAAATTCTCCACTCGTA

GCTCTTCGTTCTGCCAGAGTTGAAGTTGCTTCTGAGCTCATCTACAAGCA

AAGCTGCTTCTTTTCCACTAAAGTCTGATGCTTGCTCCTTTACCACAGCA

GATAGTGTTGCATAACAAGTACTGATTCAAGACACCAAAACCGCAATGTG

AGAGACTTTAAGACTAAAAATCATGGATAAGACTAAAAAAACATGGATAA

GTATCAACTGTTCTCACGATTATTTATTCATACCACTGTACTTAAACTTA

AAACCCACTATACTAAATAGAAAGGTAATCATCAAAAAATCAGTATGTAA

AAACCACTTTTGTGAATAAAATATGTAAAATGGGTGAATAAAGAAATGTG

CTTACAATTTCAACCGATAAGGGATACAAGCATTGCTGCAATATCCACCA

CCACCACGACGAGATATCCGAAAAGGTGAAGTTGCAACATTTAATCTGCA

ACAAAAGAGGCCATTCATTAAAATGGTACTAATTAGATCTAATCATATCA

TATTGAATGACCAAATCATTCACAGAAGCATCCATTGCTCCAATTAACAT

TCTAGACCAAATTCAACTTAAAGGTAACTCTTTTATACAGGAAACCGAGA

AACCGAAAACGCAATTCACATAAAAAGGAAGGCTTGTTTGGAGAAGCAGA

ATCGAACAAGTCAATCTCAAACCCTGATGAGCAGGTTTTTCAAGTTACCT

GGCAGGAGAAAAACCCTTGGCAAAACAAAGGGTTTGAATATGATTAATCT

CTAGAAGCTTCGTCATGACTTGGGTTCAGTTAAAAATCTCAAATTGGAGA

CATTATTGGTGTTTATATATTTGAGAGAGAGAGCCAGAGAGGAGACGTTG

AATTGAATGAAGGGTGTGGTCGGAAGAGAAGACGTGTAGAAGAGACGAGA

CAAGTAAATTTAAGCATTGGCCCCATTTACAGCCACAAGTCCGCTACAAC

AAATTATTTCCAAGAAACTCTGAGATAACGTCGTGATGAAACGGCTCATG

CTGCTGTTGTGATTCGTGAATTAGAGGTTTATCTTTTGGGTTTTTGAATG

TTACTTAATTGGACGGTCGATTTTTCAAACTGGGTGTGAAATGTGAATGG

GTCATTCATAATGGGCTTTGTTTTAATGTGAAGCCATTCACACACTCTT

TGTCCTTCTTTTCTATTATTCATAACTGTCACTCTTTGTTCTTCGAAATA

GTAAAGAGCAAATCGATTCTTTGTTGATCTGGGCCGTAAAATTTCCATGG

TTGTGGGAAGTATTCTCGCAGCTGATCTGGGCCGTCAATGCTACAGTTTC

ATGTCAGAGAGAGGTCAAGAATCAACACGTGGCCAACCATGATTTTAAAC

CAAAGCAAAGACACGATTAGACCCCACATTGTTTGTTCACCAACCCCGT

GGACCCTCCTTTAGCCGACGTGTCCACGTCAATAGTGGTTTTTCTTCCTT

TCAAAGTACACAAATTCCATTCTTTCTCATTTTACTTTTTGGATTACGTT

GTTGTTATAAACTGGTAAAATGAATTATGAATGCAAATAAATTTCATTTA

AGTTTTGTTGGCTTCTAATATTTTTTCACCTAAAATTCTAATAAACTAC

ACAGCCATGAGCCATCGTATGAAAAGAAGAAGAAAAAAATGTCTTTTTC

TAGAAGGATCTTTCAACGACTAAAAAAGATTTTAAGCTTTTGACTAATTT

TGTCAATAATATACACAAATTTACACTCAATTATAGCCATCAAATGTGTG

CTATGCAGAAACACCAATTATTTCATCACACATACGCATACGTTACGTTT

CCAACTTTCTCTATATATATATAGTAATACACACACATAAACAGCAAA

AGCGTGAAAGCAGCAGATCAAGATAAGAAAGAAGAAAGAATCATCAAAAA

AtF5H promoter polynucleotide sequence
SEQ ID NO: 24

TGTGTGTCTTTTTGCGAGTAGTTGTTGGCTTCAGACAGTTCATAGCGGAG

TTACTCTATACGCGAAGTACTTGTCTCATACTGATAATTTTGATGGCAAT

TAAGGCTTTAAAAGCTTATGTATTTTCTTATAACCATTTTATTCTGTATA

TAGGGGGACAGAAACATAATAAGTAACAAATAGTGGTTTTATTTTTTTAA

ATATACAAAAACTGTTTAACCATTTTATTTCTTGGTTAGCAAAATTTTGA

TATATTCTTAAGAAACTAATATTTTAGGTTGATATATTGCAGTCACTAAA

TAGTTTTAAAAGACACGAAGTTGGTAAGAACAGGCATATATTATTCGATT

TAATTAGGAATGCTTATGTTAATCTGATTCGACTAATTAGAAACGACGAT

ACTATGAGCTCATAGATGGTCCCACGACCCACTCTCCCATTTGATCAATA

TTCAACTGAGCAATGAAACTAATTAAAAACGTGGTTAGATTAAAAAATA

AATTGTGCAGGTAGCGGATATATAATACTAGTAGGGGTTAAAAATAAAT

AAAACACCACAGTATTAAATTTTGTTTCAAAAGTATTATCAATAGTTTT

TTTGCTTCAAAAATATCACAAATTTTTGTATGAAATATTTCTTTAACGAA

AATAAATTAAATAAAATTTAAAATTTATATTTGGAGTTCTATTTTTAATT

TAGAGTTTTTATTGTTACCACATTTTTTGAATTATTCTAATATTAATTTG

TGATATTATTACAAAAAGTAAAAATATGATATTTTAGAATACTATTATCG

ATATTTGATATTATTGACCTTAGCTTTGTTTGGGTGGAGACATGTGATTA

TCTTATTACCTTTTTATTCCATGAAACTACAGAGTTCGCCAGGTACCATA

CATGCACACACCCTCGTGAAACGAGCGTGACTTAATATGATCTAGAACTT

AAATAGTACTACTAATTGTGTCATTTGAACTTTCTCCTATGTCGGTTTCA

CTTCATGTATCGCAGAACAGGTGGAATACAGTGTCCTTGAGTTTCACCCA

AATCGGTCCAATTTTGTGATATATATTGCGATACAGACATACAGCCTACA

GAGTTTTGTCTTAGCCCACTGGTTGGCAAACGAAATTGTCTTTATTTTTT

TATGTTTTGTTGTCAATGTGTCTTTGTTTTTAACTAGATTGAGGTTTAAT

TTTAATACATTTGTTAGTTTACAGATTATGCAGTGTAATCTGATAATGTA

AGTTGAACTGCGTTGGTCAAAGTCTTGTGTAACGCACTGTATCTAAATTG

TGAGTAACGACAAAATAATTAAAATTAAAGGGACCTTCAAGTATTATTAG

TATCTCTGTCTAAGATGCACAGGTATTCAGTAATAGTAATAAATAATTAC

TTGTATAATTAATATCTAATTAGTAAACCTTGTGTCTAAACCTAAATGAG

CATAAATCCAAAAGCAAAAATCTAAACCTAACTGAAAAAGTCATTACGAA

AAAAAGAAAAAAAAAGAGAAAAAACTACCTGAAAAGTCATGCACAACGT

TCATCTTGGCTAAATTTATTTAGTTTATTAAATACAAAAATGGCGAGTTT

CTGGAGTTTGTTGAAAATATATTTGTTTAGCCACTTTAGAATTTCTTGTT

TTAATTTGTTATTAAGATATATCGAGATAATGCGTTTATATCACCAATAT

TTTTTGCCAAACTAGTCCTATACAGTCATTTTTCAACAGCTATGTTCACTA

ATTTAAAACCCACTGAAAGTCAATCATGATTCGTCATATTTATATGCTCG

AATTCAGTAAAATCCGTTTGGTATACTATTTATTTCGTATAAGTATGTAA

TTCCACTAGATTTCCTTAAACTAAATTATATATTTACATAATTGTTTTCT

TTAAAAGTCTACAACAGTTATTAAGTTATAGGAAATTATTTCTTTTATTT

TTTTTTTTTTTAGGAAATTATTTCTTTTGCAACACATTTGTCGTTTGCA

AACTTTTAAAAGAAAATAAATGATTGTTATAATTGATTACATTTCAGTTT

ATGACAGATTTTTTTATCTAACCTTTAATGTTTGTTTCCTGTTTTTAGG

AAAATCATACCAAAATATATTTGTGATCACAGTAAATCACGGAATAGTTA

TGACCAAGATTTTCAAAGTAATACTTAGAATCCTATTAAATAAACGAAAT

TTTAGGAAGAAATAATCAAGATTTTAGGAAACGATTTGAGCAAGGATTTA

GAAGATTTGAATCTTTAATTAAATATTTTCATTCCTAAATAATTAATGCT

AGTGGCATAATATTGTAAATAAGTTCAAGTACATGATTAATTTGTTAAAA

TGGTTGAAAAATATATATGTAGATTTTTTCAAAAGGTATACTAATTAT

TTTCATATTTTCAAGAAAATATAAGAAATGGTGTGTACATATATGGATGA

AGAAATTTAAGTAGATAATACAAAAATGTCAAAAAAGGGACCACACAAT

TTGATTATAAAACCTACCTCTCTAATCACATCCCAAAATGGAGAACTTTG

CCTCCTGACAACATTTCAGAAAATAATCGAATCCAAAAAAAACACTCAAT

AtPAL1 promoter polynucleotide sequence
SEQ ID NO: 25

CAAATAGTACGATGTATTTAGTGATTTTATTTATGTACTTTGTTCATTAA

ATTAGTCATAATTGTTCTGATTTTTAGGGGTTTTGATCGAACCCTTAGAT

```
CAAAAGTTACCTTAATTGTTTTTTTAGCTAAGTACTTTATTAAAAATTTA
ATGTTTAGTTCTGATTGAGTAGTACTATAAAGGAGACATGTGTCAATCTT
GTCAATTGGTTTTGAGTTCAACAATATGCAATATTGCACATGCATTAACG
ACCAAAAGAAGATGCAATGCACTTAAATCATTGAAACTGATTTTGTTTTT
GTAGTGTATAAAATATCTATTTAATTACCAACGAAAGAAGTGAGCTTTTA
AAAACAAAGAGTCAGAAGATATATATAACTACAAAACCTACAGAAGATAA
GCTGGATTTCAAAAGAAGAGAAAGAGTAAACCAATAAATTGACCAAAGCA
AAATCGGATATTTGACATAAGTTTCCATTCACATTGACCCAAATCCACCA
GCATTTCAAATAAAGTTACTTAATATAATTTTTGTGTTTATAATATATTC
CGCCCACTCTTGCCTTCATTTGGACCTTATCCTAAAAGTCAAAACAGGTG
AAAAAAATGAGAATACAATTAACACGAAAAATGCAAAGACTGTTAAACC
GAAATCGAATTCTAGTGTAATCAATCCTTTTCCCAATGACAACTATAA
ATCAAAAGAAAAAATGTACTGATAAACGAAACTAAACGTATAAATTAAT
ATATTTCTTGACATAAATAGGAGGCTTTTGCCTGCTAGTCTGCTACGATG
GAAGGAAAAATGCATGCACACATGACACATGCAAAATGTTTCAATGAAGA
CGCATTGCCCAATTAACCAACACACCACTTCTTCCATTCCACCCATATTA
TTTATTTCTACCATTTTCTTTAATTTATTGTTTTTTCTTTGATTCATACA
CTGTTTATGACTATTACATTTTCCCTTTCGACTAATATTAACGCGTTTAA
ACCAAAGAATGGATTTGATAATGAAATTTTATTTATTAGCATATAGATA
ATGGATGGCTTCATGCTTGGTTTCCATGACAAGGAATGACACAAGATAAT
TATTTTGAATAAAATCATAAATATGATAATACTAGTTGTAAAAAACTTG
AGTGTTTCGTGTGTTATTTTTCGGTTTCTTGACTTTTTATATTTCTCGTT
TTTGTAATTTTAGGATGGATTATTTAGCTTGCTTTTCTCTTTTATTACTT
TCTAAAATTTTATTTATAAACTCATTTTTAATATATTGACAATCAATAAA
TGAGTTATCTTTTAATTAATAAAAAATTTGTAAACTCTTGTAAACAGATC
ATAGTCACTAAAAGCTATTATAAGTTATTTGTAGCTATATTTTTTTATTT
CATGAACTTAGGATAAGATACGAAAATGGAGGTTATATTTACATAAATGT
CACCACATTGCCTTTGTCATGCAAACGGCGTGTTGCGTCACTCGCCTCCT
ATTGGGAATCTTATAATCGCGTGAATATTATTAGAGTTTGCGATATTTCC
ACGTAATAGTTATCTTTCACAAATTTTATACTCAATTACAAAATCAACGA
AAATGTACATTTGTATCTTTAACTATTTACGTTTTTTTACGTATCAACT
TTCAGTTATATGTTTTGGATAATATATTTTTTACTTTTGACTTTTCAGT
TTTCACCTAATGATTGGGATATACATATGCATGCATAGTTCCCATTATTT
AAATGTAAGCTAAGTGCATATGAACTGTTAGTCAAAATTACGAAGTTTAT
TTGTACATATATAGTTATAACAAAATGGTAGAGTAAATTAAACAGAAC
ATCAAGAAGTACAAAAGACTGAACACAATAATTTACATGAAAACAAAC
ACTTAAAAAATCATCCGATAAAATCGAAATGATATCCCAAATGACAAAA
TAACAATATAGAAAATACAAAAACAAAAACAAAATATGAAAGAGTGTTAT
GGTGGGGACGTTAATTGACTCAATTACGTTCATACATTATACACACCTAC
TCCCATCACAATGAAACGCTTTACTCCAAAAAAAAAAAAAAACCACTCT
TCAAAAAATCTCGTAGTCTCACCAACCGCGAAATGCAACTATCGTCAGCC
ACCAGCCACGACCACTTTTACCACCGTGACGTTGACGAAAACCAAAGAAA
TTCACCACCGTGTTAAAATCAAATTAAAAATAACTCTCTTTTTGCGACTT
AAACCAAATCCACGAATTATAATCTCCACCACTAAAATCCATCACTCACT
CTCCATCTAACGGTCATCATTAATTCTCAACCAACTCCTTCTTTCTCACT
AATTTTCATTTTTTCTATAATCTTTATATGGAAGAAAAAAAGAAACTAGC
TATCTCTATACGCTTACCTACCAACAAACACTACCACCTTATTTAAACCA
CCCTTCATTCATCTAATTTTCCTCAGGAACAAATACAATTCCTTAACCAA
CAATATTACAAATAAGCTCCTATCTTCTTTCTTTCTTTTAGAGATCTTGT
AATCTCCTCTTAGTTAATCTTCTATTGTAAAACTAAGATCAAAAGTCTAA
```

AtPAL2 promoter polynucleotide sequence

SEQ ID NO: 26

```
GATTGATGGTTTAATAATCTGCCTCGTGATACATGGTGTTATCTTAAAAT
GGTCTCTCAATTAGTCTTTGTATTTGTATAAAATAAGGCCTAAAAATATC
ATCAATGGGGTCCTGTTAAAAACAAAAACAGATACACCTTTCACTAATAA
AAAAAAACTGTTACCGACAAGTCAAACAATATCTGCGGACAAAAAAATGA
AGAATGTTTAGTAAGAAATAGAAGATGTGGTAAAGAGCCATACACACATG
CAAGTGTTTTTCAATGAACCCATCTTACCAACCCACTACTTCTTTGAGCC
ATAATTGTTTGGTTCGGAGACCCTTTACATTTCCGTCTCAGCTTTATTTG
TTTACGCATTGATTTGTCTTAAATTATGTTAGATATTGTTTTTTGGCTAT
TTATTAGCAGCAATCAAGTTAAAAGAGTGGTTCGATATCACCATCGAACT
CTCCTTTAGATATTTTCTATATAAAACCAAACAAAAACAAAAAAATTGGT
CCGATCATCTAATATACAAGTTAGACGATTTCACGTTATGTTATTACAAC
CTACAACAAAATAGACTATGATCGAAATCATATTGAATCTTTTACCTTTC
AACGTAATACAAATCTGGCTTTACAAAGCAATAATTCATGTTTGTTTGTC
TAATTTAAATTTCCCTGTTTTTTTTCCCCTCTTTCTGTTTCCCATTTGAA
AGTAAAAGATCATTTAAGCACCTAACTCAATTTTATTTTATTTTAAACAC
CTAATGTCATGCTCCTTGGCTCCTTGTAATTAGTTGATCGTTTCAATTTA
GACCAGCAAAACATTTTAGTATGTTCGTAAATATTGCGTACATGCCATTT
CGTTTGTCATGCAAACGGTGTGTGTTTCTTTACTTAGCTTCTAGTTGGTG
TATATTGCGTCGCATTAATATCGGTTTACCTTCCTCCTGTCTACGTAATG
ATATATTCTCCACCACAAATTTAAATTCTTATTGAAATTTCCTAATTTTT
TAGGTAGCTCAAGGTCTCAAGTATACTACGTACCCTATTTTTTTGAATAT
CTATCTATATTATAACAAGAGTTTTTCTGAGCTAGTTAATGAGATGACAA
TATTCTACATAAATAAATGACCCTCGAAAGTTTCAAGTACTTTAGGATCT
GACCAAATCGGGGTAAAACATTTTGAAACTAATTACGTTCACATCTACCA
TCGATGATTGACAAGCTTATTGTCACCTTTTATGTTAAAGTGACATGGTC
TTGACGTTAATTTGCATGTTATTCTACATCTATAGTCCAAAGATAGCAAA
CCAAAGAAAAAATTGTCACAGAGGGTTCAATGTTACTTAGATAGAAATG
GTTCTTTACAATAATAAATTTATGTTCCATTCTTCATGGACCGATGGTAT
ATATATGACTATATATATGTTACAAGAAAACAAAAACTTATATTTTCTA
AATATGTCTTCATCCATGTCACTAGCTCATTGTGTATACATTTACTTGCT
```

-continued

TCTTTTTGTTCTATTTCATTTCCTCTAACAAATTATTCCTTATATTTTGT
GATGTACTGAATTATTATGAAAAAAAACCTTTACACTTGATAGAAGCA
TATTTGGAAACGTATATAATTTGTTTAATTGGAGTCACCAAAATTATACA
AATCTTGTAATATCATTAACATAATAGCAAACTAATTAAATATATGTTTT
GAGGTCAAATGTTCGGTTTAGTGTTGAAACTGAAAAAAATTATTGGTTAA
TAAAATTTCAAATAAAAGGACAGGTCTTTCTCACCAAAACAAATTTCAAG
TATAGATAAGAAAAATATAATAAGATAAACAATTGATGCTGGTTTGGTTC
GACTTCAACTAGTTAGTTGTATAAGAATATATTTTTTAATACATTTTTT
TAGCAACTTTTGTTTTGATACATATAAACAAATATTCACAATAAAACCA
AACTACAAATAGCAACTAAAATAATTTTTTGAAAACGAAATTAGTGGGGA
CGACCTTGAATTGACTGAACTACATTCCTACGTTCCACAACTACTCCCAT
TTCATTCCCAAACCATAATCAATCACTCGTATAAACATTTTTGTCTCCAA
AAAGTCTCACCAACCGCAAAACGCTTATTAGTTATTACCTTCTCAATTCC
TCAGCCACCAGCCACGACTACCTTTTCGATGCTTGAGGTTGATATTTGAC
GGAACACACAAATTTAACCAAACCAAACCAAAACCAAACGCGTTTTAAAT
CTAAAAACTAATTGACAAACTCTTTTTGCGACTCAAACCAAATTCACGTT
TTCCATTATCCACCATTAGATCACCAATCTTCATCCAACGGTCATCATTA
AACTCTCACCCACCCCTCATACTTCACTTTTTTTCTCCAAAAAATCAAAA
CTTGTGTTCTCTCTTCTCTCTTCTCTTGTCCTTACCTAACAACAACACTA
ACATTGTCCTTCTTATTTAAACGTCTCTTCTCTCTTCTTCCTCCTCAGAA
AACCAAAACCACCAACAATTCAAACTCTCTCTTTCTCCTTTCACCAAAC
AATACAAGAGATCTGATCTCATTCACCTAAACACAACTTCTTGAAAACCA

At4C11 promoter polynucleotide sequence

SEQ ID NO: 27
ACATAAGATTTGGATTATGAGAGGAGTTGAGAAGTTATATGATGGAAACT
GAAAAGTAAATCTTTTTGCAGAGCTGTAGAATCAATCAACATTTGATGAC
TTGGACTTCTTCACCATGTGTGTTGGTGTGGACCATTGAATTGACGGTTT
TGCCATTCACCAACAACAGCATGAGTTTTTGAGTCTTCATGTTTGGTAAA
GGTTAGGCTTATTAGGAGACACGGGTAAGAGACTAGAGAGAGACATTCTC
CAAACCTTTCTTTTGCATGTTTTGTAAGAAACATTTCCGAAAATGAAAGA
AATCTTACACAACATTCATATAATTTGTTTGAAATATAACAAAATGATAA
TTTATACTCTCAAGTAAAATGCCTAAACTTTTATCAATTGGAAAAGACAT
CACACACAAGCGTGAAGCGTATCTTATTACCAAACCCAACTAAGCATGGG
TCTCGATACTTGCCATAATTACTTTAATCCATTCTCTTTTTGAGAAATGT
ATAAAACATGACTTTGCATAAATAGTCTTTTACTAATTACTATGTAAATA
ATTCCTAAGACTGGTTTCATGGTACATATTATCGTTTTATCCTTGTTTTA
AGAATATTCAGATGTTTGGTCTATGGAATATAGTCTATTCTTCATGTTTA
AAACTATTATTTGATAAGAAAATATGTACTAATATGTTTTTGCATACAAA
TGTTGATCAGTTCGTAGCATTTGAATTAATACATTCTCAATCACTTTCAA
GCATTATTATGTAATAAATGATTCATGTCGAAAAGTAATAGTATCACTGT
CCATTACATTTGGCATATATATTTTTTTGTCAAAGCCTTACATTTGGCAT

-continued

ATTGACGAAGCAGTTTTGTATTCACTTATATTTTGACATCGCTTTCACAA
AAATAAATAGCTATATATGATTATTATCCATTAATTGTCTCTTTTCTTTT
GCTGACACAATTGGTTGTAAATGCAATGCCAATATCCATAGCATTTGTGT
GGTGAATCTTTTTCTAAGCCTAATAGTAAATAAATCTCAATACAAGAACC
CATTTACGAACAAATCAAACCAAGTTGTGATGGGTTAGTACTTAGTAGCC
CGTTTGAAATGTAGAATTTTTGATGAGATTTTACGTTTTATATAGATTTT
TCTCAGAAAACAAAAAATTCTTGCATCTTGCATTTTGGTCATTTGTAAAT
ATTTTTTTAGTCTTAAAAAAGACCCAAATTCTTATTAATTTCAAAATTTT
CGGTCTCTAATACCTCCGGTTTTAAAAAAAAACATATCAGTTGAAGGATG
AGTTTGGTGAAGGCTATATTGTCCATTGATTTTGGAGATATATGTATTAT
GGTCATGATTATTACGATTTTTATATAAAAGAATATTAAAAATGGTGGGG
TTGGTGAAGAAATGAAGATTTATCGTCAAATATTTCAATTTTTACTTGGA
CTATTGCTTCGGTTATATCGTCAACATGGGCCCACTCTTCCACCAAAGCC
CAATCAATATATCTCTCGCTATCTTCACCAACCCACTCTTCTTCTCTTAC
CAAACCCATTTCCTTTATTTCCAACCCTACCCCTTTATTTCTCAAGCTTT
ACACTTTTAGCCCATAACTTTCTTTTTATCCAAATGGATTTGACTGGTCT
CCAAAGTTGAATTAAATGGTTGTAGAAATAAAATAAAATTATACGGGTTC
AATTGTTCAATTGTTCATATACCGTTGACGTTCAATTGTTCATATACGGG
TTCCGTGGTCGTTGGTAATATATATGTCTTTTATGGAACCAAAATAGACC
AAATCAACAACAAATGAAGAAATTGTTAGAGTATGATACACTCATATATA
CCCAAATATAGCATATATTTATAATATAACTTTTGGCTATGTCATTTTAC
ATGATTTTTTGGCTTATCTATTAAAAGTATCATACAAACTGTTTTTACT
TCTTTTTTTCTTAGAATATATATGCCCAAAATGGAAAAGAACATATGCC
AAGGTTGATTTTATCGCTTATATGGTAAAAATTGGAAAAACATACAAATC
ATTACTTTATTTAATTAAATCATGTGAAGAAACATATTCAATTACGGTAA
TACGTTATCAAAACATTTTTTTTTACATTAATTGTTACATTTTTTTTTT
TGCAAATATTCTTAAATAACCATTCTTTTTTTATTTACTATAATTAACAT
AAAAATAAATAAAATATAACATTTCAACAAAGAAATTTGCTTATGAAAAA
TACAAAATCCAGTTAATTTTTCAGAAAAATACAAATTTGCTTATAAATAT
ATTACCACTAGTTTATGTGATTTTAAAAGAAAGAAATGCAGCTTACCAAA
CGCAACGTGAAAATTTGAGAAACCCATACTCAAAAAAGATTAAATGACAA
AATCACCCTCAGCAAAATCATGAAACAACAACACTAACATTTTCACCAAC
CCCACCGTCTACTCCGGTGAATTGTCTATATGAACTCCTCCGATACAACT
CCTGTTTCCTTCAGGCCAAAGCCTAAAATTCACACAACCAAAAAAACCAA
CCTTTTTTTTCCACCTAAATCTTTGAATATCACAATATTTACTATTTACA

AtCcoAOMT promoter polynucleotide sequence

SEQ ID NO: 28
ACACATTAAAACAAAAACCATTTCCACATAAAAAAAAACGATCCAGTAAA
TGAAATAGATTCAAGACCGATCGTCGAGCGGTAGAGAAAGTAAACAAAAC
AAAGACAGAGAATTGAAGAAACTGTGTACCTGCAAAAATACCAATCAGAT
GGGTCTCCGCCAAAGTAATCTGCTTAGAAGTTTTGTAAGAAAAAACAATT
AAAGGCGTTTCATTTATTGAATTTTCCGGTTGTTTGATTCTCAGGATGAG

```
ATTGCCTATTTCCTTCAAAAAGAACTCTTTAATTTACACAGAAAAGCTC
TGAAAATTTCCACAGAAAATGAAGAAAGAAAAGAGCGTAAAAGGGGAAAG
AGATGAAATGGGTTATTAAAAAAAGAAGCAGTGGATGAGGGAAGAGAGGA
TTAAGAGGCGTAGAGATTACATGTGATGAATGATACTATCTTTTCTTACA
AACACATTTTCGTGTAATTAAAATTTAATTTGGTTCCAAAGATTTTAATC
AAAAGAAGTTTGGTAAATTGAAACAGGCAGACATAATTTATTGTAAAGAG
TTTTTATTTATTTATTCATGACGTTGCTTGATGGTGCTTTACCAATTTTC
TTCTCCTACGTTAGATTTTTTTCACTTTTTTTTTGGTGTTTGTAATAAA
TGTGAAAAATGGACCGTTTAAAAACTTAAAGACGTTTGATTACTATATAA
AGTAATTGTTTATAATAGAAAGTTAATTGAGACGTGAAATGGTATAATAT
TATTGTGTAACAGTTGTGTACACGTAGCTCTCATGCAGTTTTAGTGGACC
CATATGGCTTGACTTGTATTCTGTTTTTGGGCTATTAAAGTCCAAAACAG
AGACCCCTCTCAAGCCCTTCCTATTAATCCATCTAGCTAATAGAAACTAT
AAACGTGTCCTCTCTCAATTAAATAAGCTAGAAACATACTCAACCATT
CGCATTACGCACTTCATAGCGGTAGGTTTAGATTTGTCTAAAATACTTAA
AAAAATTTTTGTCTAAGTTGTTGTCCGTTACAAAGTTTTTTTCTTTGTGA
CAACTTGACAACATTGACAAATAGAAAAATAAATTTCGATGAAACCTATG
AAATGGGCTATGGCCCAACTAAAAAGAGTGGGAAATTAAAGATGGGATGG
TTCAAGTGTATACTTCGAACTTCCGACATTAGGGTCAAAGGATTTTTAAA
AGGCAACCATTTGTTCCACTTTCTCGAACAAAACGAGCCATTTATTAAT
ATATAGTACGGCTGAATTGGTTTTGTTCGTCATTGTGTAAACACAAAGTC
ATTCGAATTATGTTAGGGTCCGTTGATAATATAGACGGCCCATCCCACGC
ACATATTAAGTGTTCAACTCCATAGAATATCATATGGGACACTGTTTTTA
ATTTATAATCACCATTTAAAATGTTTAAATGTTTATGCAAATTGGATGGC
TTCTTCACACAACATTTATTTATTGGCCTTTCATTCCATCAAAGTAAAAT
AGCTTTTCAAATACATTATACTCTATACTCCTATACATGTAAATAACCAT
ATGCATATATATTTTTTCAAATATAGGTCAACGCCATTTAATATAATTT
TAAAAAAATTTGTTCGGAAAATATCACATTTCTTTCACTAGACAAGCCTT
GTTACCACACAATGTATCAATATGATCTAAAGGGCAAACGAAAGATCCTG
ACATGAAACGTTTAATTCTCATTTTCTCCAAATTTTATTTTTTATGTGAA
GTAGATAAATTAGTATATATATATATATACCAAACTAGTGTGTTATGTTA
TGGCAAATGTTATATCAATTCGAAGGTTCCGCTATTGCAATATTCATTAA
TTTTTTCATACCAATACTATTTTTCTTTCTCTTTTATTTTGTTTTTAAT
AAATAAAAGAAATTAAGGATGATTAGTAAGGAAGTCGCCTACCAAGAGAT
TCACCTACCACGGTACACTTCAACACCGAAGCAGAGTTGTTGAATCCACT
TTTTATTCCCTTCTCTAATCTCTACTCACCAAGTCTCCACTTTTTTTCT
CTTTATTATACATTTAAATTATTTAATATACGCCAACTACATACATAT
CCAGTGTAATTTCTCGTTACGTCACACCCCTTTCGTAATCGTCTAATTTC
AGAAAAAATATCCAGAGGTTTAAATACATATTCCCATCATTAAATCTAGAC
ATAAACACATCATACTCACAAAATTTGGCAGCAAACAGTTACTACAGACC
CATAAATGAAAAAACGTATTCACTTGTTTTCAATTTTCACATAACCACTT
CCCTGAGTTTGGTCTCAATTTGATTGCCCCGCCGAGGCATTACTACGCCA
AGTGCGATTAAGGTCCCATACAGTGTAACGGGACCCACTATAAGACAGCG
ACCGACCAATTGCGTGTTAGGAGAGTTTCACCAACCCCGGACCGGTTTTT
ACCGGATATAACAGAACCGGTACGAACCGGTCTCATTATCTTCCATCTTC
TTTATATAGACCTCATGCCATGTGTGTGACTCACCAAGAAAAACACAATC
GTTTAATCTCACCCAAGAAGACAAAAACACAGAGAGAGAAAGAGAGAGAA
```

TcPAM amino acid sequence (*Taxus chinensis* phenylalanine aminomutase; AAT47186)

SEQ ID NO: 29

MGFAVESRSHVKDILGLINTFNEVKKITVDGTTPITVAHVAALARRHDVK
VALEAEQCRARVETCSSWVQRKAEDGADIYGVTTGFGACSSRRTNQLSEL
QESLIRCLLAGVFTKGCASSVDELPATATRSAMLLRLNSFTYGCSGIRWE
VMEALEKLLNSNVSPKVPLRGSVSASGDLIPLAYIAGLLIGKPSVVARIG
DDVEVPAPEALSRVGLRPFKLQAKEGLALVNGTSFATALASTVMYDANVL
LLLVETLCGMFCEVIFGREEFAHPLIHKVKPHPGQIESAELLEWLLRSSP
FQDLSREYYSIDKLKKPKQDRYALRSSPQWLAPLVQTIRDATTTVETEVN
SANDNPIIDHANDRALHGANFQGSAVGFYMDYVRIAVAGLGKLLFAQFTE
LMIEYYSNGLPGNLSLGPDLSVDYGLKGLDIAMAAYSSELQYLANPVTTH
VHSAEQHNQDINSLALISARKTEEALDILKLMIASHLTAMCQAVDLRQLE
EALVKVVENVVSTLADECGLPNDTKARLLYVAKAVPVYTYLESPCDPTLP
LLLGLEQSCFGSILALHKKDGIETDTLVDRLAEFEKRLSDRLENEMTAVR
VLYEKKGHKTADNNDALVRIQGSRFLPFYRFVREELDTGVMSARREQTPQ
EDVQKVFDAIADGRITVPLLHCLQGFLGQPNGCANGVESFQSVWNKSA

PDC amino acid sequence (*Pediococcus pentosaceus* Phenylacrylic decarboxylase; CAC16794)

SEQ ID NO: 30

MEKTFKTLDDFLGTHFIYTYDNGWEYEWYAKNDHTVDYRIHGGMVAGRWV
KDQEAHIAMLTEGIYKVAWTEPTGTDVALDFVPNEKKLNGTIFFPKWVEE
HPEITVTFQNEHIDLMEESREKYETYPKLVVPEFATITYMGDAGQDNDEV
IAEAPYEGMTDDIRAGKYFDENYKRINK

CHS amino acid sequence (*Physcomitrella patens* chalcone synthase; ABB84527)

SEQ ID NO: 31

MASAGDVTRAALPRAQPRAEGPACVLGIGTAVPPAEFLQSEYPDFFFNIT
NCGEKEALKAKFKRICDKSGIRKRHMFLTEEVLKANPGICTYMEPSLNVR
HDIVVVQVPKLAAEEAAQKAIKEWGGRKSDITHIVFATTSGVNMPGADHAL
AKLLGLKPTVKRVMMYQTGCFGGASVLRVAKDLAENNKGARVLAVASEVT
AVTYRAPSENHLDGLVGSALFGDGAGVYVVGSDPKPEVEKPLFEVHWAGE
TILPESDGAIDGHLTEAGLIFHLMKDVPGLISKNIEKFLNEARKPVGSPA
WNEMFWAVHPGGPAILDQVEAKLKLTKDKMCGSRDILSEFGNMSSASVLF
VLDQIRHRSVKMGASTLGEGSEFGFFIGFGPGLTLEVLVLRAAPNSA

CHS amino acid sequence (*Arabidopsis thaliana* chalcone synthase; AAA32771)

SEQ ID NO: 32

MVMAGASSLDEIRQAQRADGPAGILAIGTANPENHVLQAEYPDYYFRITN
SEHMTDLKEKFKRMCDKSTIRKRHMHLTEEFLKENPHMCAYMAPSLDTRQ

-continued

DIVVVEVPKLGKEAAVKAIKEWGQPKSKITHVVFCTTSGVDMPGADYQLT

KLLGLRPSVKRLMMYQQGCFAGGTVLRIAKDLAENNRGARVLVVCSEITA

VTFRGPSDTHLDSLVGQALFSDGAAALIVGSDPDTSVGEKPIFEMVSAAQ

TILPDSDGAIDGHLREVGLTFHLLKDVPGLISKNIVKSLDEAFKPLGISD

WNSLFWIAHPGGPAILDQVEIKLGLKEEKMRATRHVLSEYGNMSSACVLF

ILDEMRRKSAKDGVATTGEGLEWGVLFGFGPGLTVETVVLHSVPL

SPS amino acid sequence (*Vitis vinifera* stilbene synthase; ABE68894)
SEQ ID NO: 33

MASVEEFRNAQRAKGPATILAIGTATPDHCVYQSDYADFYFRVTKSEHMT

ALKKKFNRICDKSMIKKRYIHLTEEMLEEHPNIGAYMAPSLNIRQEIITA

EVPKLGKEAALKALKEWGQPKSKITHLVFCTTSGVEMPGADYKLANLLGL

EPSVRRVMLYHQGCYAGGTVLRTAKDLAENNAGARVLVVCSEITVVTFRG

PSEDALDSLVGQALFGDGSAAVIVGSDPDISIERPLFQLVSAAQTFIPNS

AGAIAGNLREVGLTFHLWPNVPTLISENIEKCLTQAFDPLGISDWNSLFW

IAHPGGPAILDAVEAKLNLDKKKLEATRHVLSEYGNMSSACVLFILDEMR

KKSLKGERATTGEGLDWGVLFGFGPGLTIETVVLHSIPMVTN

CUS amino acid sequence (*Oryza sativa* curcuminoid synthase short version; 3OIT_A)
SEQ ID NO: 34

MRRSQRADGLAAVLAIGTANPPNCVTQEEIPDFYFRVTNSDHLTALKDKF

KRICQEMGVQRRYLHHTEEMLSAHPEFVDRDAPSLDARLDIAADAVPELA

AEAAKKAIAEWGRPAADITHLVVTTNSGAHVPGVDFRLVPLLGLRPSVRR

TMLHLNGCFAGCAALRLAKDLAENSRGARVLVVAAELTLMYFTGPDEGCF

RTLLVQGLFGDGAAAVIVGADADDVERPLFEIVSAAQTIIPESDHALNMR

FTERRLDGVLGRQVPGLIGDNVERCLLDMFGPLLGGDGGGGWNDLFWAVH

PGSSTIMDQVDAALGLEPGKLAASRRVLSDYGNMSGATVIFALDELRRQR

KEAAAAGEWPELGVMMAFGPGMTVDAMLLHATSHVN

CUS amino acid sequence (*Oryza sativa* curcuminoid synthase long version; 3ALE_A)
SEQ ID NO: 35

MAPTTTMGSALYPLGEMRRSQRADGLAAVLAIGTANPPNCVTQEEIPDFY

FRVTNSDHLTALKDKFKRICQEMGVQRRYLHHTEEMLSAHPEFVDRDAPS

LDARLDIAADAVPELAAEAAKKAIAEWGRPAADITHLVVTTNSGAHVPGV

DFRLVPLLGLRPSVRRTMLHLNGCFAGCAALRLAKDLAENSRGARVLVVA

AELTLMYFTGPDEGCFRTLLVQGLFGDGAAAVIVGADADDVERPLFEIVS

AAQTIIPESDHALNMRFTERRLDGVLGRQVPGLIGDNVERCLLDMFGPLL

GGDGGGGWNDLFWAVHPGSSTIMDQVDAALGLEPGKLAASRRVLSDYGNM

SGATVIFALDELRRQRKEAAAAGEWPELGVMMAFGPGMTVDAMLLHATSH

VN

BAS amino acid sequence (*Rheum palmatum* benzalacetone synthase; AAK82824)
SEQ ID NO: 36

MATEEMKKLATVMAIGTANPPNCYYQADFPDFYFRVTNSDHLINLKQFK

RLCENSRIEKRYLHVTEEILKENPNIAAYEATSLNVRHKMQVKGVAELGK

EAALKAIKEWGQPKSKITHLIVCCLAGVDMPGADYQLTKLLDLDPSVKRF

MFYHLGCYAGGTVLRLAKDIAENNKGARVLIVCSEMTTTCFRGPSETHLD

SMIGQAILGDGAAAVIVGADPDLTVERPIFELVSTAQTIVPESHGAIEGH

LLESGLSFHLYKTVPTLISNNIKTCLSDAFTPLNISDWNSLFWIAHPGGP

AILDQVTAKVGLEKEKLKVTRQVLKDYGNMSSATVFFIMDEMRKKSLENG

QATTGEGLEWGVLFGFGPGITVETVVLRSVPVIS

AtPAP1 amino acid sequence (*Arabidopsis thaliana* R2R3 Myb transcription factor, AtMyb75; AAG42001)
SEQ ID NO: 37

MEGSSKGLRKGAWTTEEDSLLRQCINKYGEGKWHQVPVRAGLNRCRKSCR

LRWLNYLKPSIKRGKLSSDEVDLLLRLHRLLGNRWSLIAGRLPGRTANDV

KNYWNTHLSKKHEPCCKIKMKKRDITPIPTTPALKNNVYKPRPRSFTVNN

DCNHLNAPPKVDVNPPCLGLNINNVCDNSIIYNKDKKKDQLVNNLIDGDN

MWLEKFLEESQEVDILVPEATTTEKGDTLAFDVDQLWSLFDGETVKFD

AtPAP2 amino acid sequence (*Arabidopsis thaliana* R2R3 Myb transcription factor, AtMyb90; AAG42002)
SEQ ID NO: 38

MEGSSKGLRKGAWTAEEDSLLRLCIDKYGEGKWHQVPLRAGLNRCRKSCR

LRWLNYLKPSIKRGRLSNDEVDLLLRLHKLLGNRWSLIAGRLPGRTANDV

KNYWNTHLSKKHESSCCKSKMKKKNIISPPTTPVQKIGVFKPRPRSFSVN

NGCSHLNGLPEVDLIPSCLGLKKNNVCENSITCNKDDEKDDFVNNLMNGD

NMWLENLLGENQEADAIVPEATTAEHGATLAFDVEQLWSLFDGETVELD

AtTT2 amino acid sequence (*Arabidopsis thaliana* R2R3 Myb transcription factor, AtMyb123; AED93980)
SEQ ID NO: 39

MGKRATTSVRREELNRGAWTDHEDKILRDYITTHGEGKWSTLPNQAGLKR

CGKSCRLRWKNYLRPGIKRGNISSDEEELIIRLHNLLGNRWSLIAGRLPG

RTDNEIKNHWNSNLRKRLPKTQTKQPKRIKHSTNNENNVCVIRTKAIRCS

KTLLFSDLSLQKKSSTSPLPLKEQEMDQGGSSLNGDLEFDFDRIHSEFHP

PDLMDFDGLDCGNVTSLVSSNEILGELVPAQGNLDLNRPFTSCHHRGDDE

DWLRDFTC

NtAn2 amino acid sequence (*Nicotiana tabacum* R2R3 Myb transcription factor; ACO52470)
SEQ ID NO: 40

MNICTNKSSSGVKKGAWTEEEDVLLKKCIEKYGEGKWHQVPLRAGLNRCR

KSCRLRWLNYLRPHIKRGDFSFDEVDLILRLHKLLGNRWSLIAGRLPGRT

ANDVKNYWNSHLRKKLIAPHDQKESKQKAKKITIFRPRPRTFSKTNTCVK

SNTNTVDKDIEGSSEIIRFNDNLKPTTEELTDDGIQWWADLLANNYNNNG

IEEADNSSPTLLHEEMPLLS

MtLAP1 amino acid sequence (*Medicago truncatula* R2R3 Myb transcription factor; ACN79541)
SEQ ID NO: 41

MENTGGVRKGAWTYKEDELLKACINTYGEGKWNLVPQRSGLNRCRKSCRL

RWLNYLSPNINRGRFSEDEEDLILRLHKLLGNRWSLIAGRLPGRTANDVK

NYWHTNLAKKVVSEKEEEKENDKPKETMKAHEVIKPRPITLSSHSNWLKG

KNSIPRDLDYSENMASNQIGRECASTSKPDLGNAPIPCEMWCDSLWNLGE

HVDSEKIGSCSSLQEENLMEFPNVDDDSFWDFNLCDLNSLWDLP

ZmMYB-C amino acid sequence (*Zea mays* R2R3 Myb transcription factor; AAK09326)
SEQ ID NO: 42
MGRRACCAKEGVKRGAWTSKEDDALAAYVKAHGEGKWREVPQKAGLRRCG

KSCRLRWLNYLRPNIRRGNISYDEEDLIIRLHRLLGNRWSLIAGRLPGRT

DNEIKNYWNSTLGRRAGAGAGAGGSWVVVAPDTGSHATPAATSGACETGQ

NSAAHRADPDSAGTTTTSAAAVWAPKAVRCTGGLFFFHRDTTPAHAGETA

TPMAGGGGGGGEAGSSDDCSSAASVSLRVGSHDEPCFSGDGDGDWMDDV

RALASFLESDEDWLRCQTAGQLA

ZmMYC-Lc amino acid sequence (*Zea mays* BHLH transcription factor; ABD72707)
SEQ ID NO: 43
MALSASRVQQAEELLQRPAERQLMRSQLAAAARSINWSYALFWSISDTQP

GVLTWTDGFYNGEVKTRKISNSVELTSDQLVMQRSDQLRELYEALLSGEG

DRRAAPARPAGSLSPEDLGDTEWYYVVSMTYAFRPGQGLPGRSFASDEHV

WLCNAHLAGSKAFPRALLAKSASIQSILCIPVMGGVLELGTTDTVPEAPD

LVSRATAAFWEPQCPSSSPSGRANETGEAAADDGTFAFEELDHNNGMDDI

EAMTAAGGHGQEEELRLREAEALSDDASLEHITKEIEEFYSLCDEMDLQA

LPLPLEDGWTVDASNFEVPCSSPQPAPPPVDRATANVAADASRAPVYGSR

ATSFMAWTRSSQQSSCSDDAAPAAVVPAIEEPQRLLKKVVAGGGAWESCG

GATGAAQEMSGTGTKNHVMSERKRREKLNEMFLVLKSLLPSIKRVNKASI

LAETIAYLKELQRRVQELESSREPASRPSETTTRLITRPSRGNNESVRKE

VCAGSKRKSPELGRDDVERPPVLTMDAGTSNVTVTVSDKDVLLEVQCRWE

ELLMTRVFDAIKSLHLDVLSVQASAPDGFMGLKIRAQFAGSGAVVPWMIS

EALRKAIGKR

AtTT8 amino acid sequence (*Arabidopsis thaliana* BHLH transcription factor; AEE82802)
SEQ ID NO: 44
MDESSIIPAEKVAGAEKKELQGLLKTAVQSVDWTYSVFWQFCPQQRVLVW

GNGYYNGAIKTRKTTQPAEVTAEEAALERSQQLRELYETLLAGESTSEAR

ACTALSPEDLTETEWFYLMCVSFSFPPPSGMPGKAYARRKHVWLSGANEV

DSKTFSRAILAKSAKIQTVVCIPMLDGVVELGTTKKVREDVEFVELTKSF

FYDHCKTNPKPALSEHSTYEVHEEAEDEEEVEEEMTMSEEMRLGSPDDED

VSNQNLHSDLHIESTHTLDTHMDMMNLMEEGGNYSQTVTTLLMSHPTSLL

SDSVSTSSYIQSSFATWRVENGKEHQQVKTAPSSQWVLKQMIFRVPFLHD

NTKDKRLPREDLSHVVAERRRREKLNEKFITLRSMVPFVTKMDKVSILGD

TIAYVNHLRKRVHELENTHHEQQHKRTRTCKRKTSEEVEVSIIENDVLLE

MRCEYRDGLLLDILQVLHELGIETTAVHTSVNDHDFEAEIRAKVRGKKAS

IAEVKRAIHQVIIHDTNL

VvMyc1 amino acid sequence (*Vitis vinifera* BHLH transcription factor; ACC68685)
SEQ ID NO: 45
MAAPPNSRLQSMLQSAVQSVRWTYSLFWQICPQQGILVWGDGYYNGAIKT

RKTVQPMEVSAEEASLQRSQQLRELYESLSAGETNQPARRPCAALSPEDL

TESEWFYLMCVSFSFPPPGVGLPGKAYAKRHHIWLAGANEVDSKVFSRAIL

AKSARVQTVVCIPLMDGVVEFGTTEKVQEDLGFVQHVKSFFTDHHLHNHP

PKPALSEHSTSNPATSSDHSRFHSPPIQAAYAAADPPASNNQEEEEEEEE

EEEEEEEEEEEEEEEEAESDSEAETGRNNRRVRTQNTGTEGVAGSHTAAE

PSELIQLEMSEGIRLGSPDDGSNNLDSDFHMLAVSQPGSSVDHQRRADSY

RAESARRWPMLQDPLCSSGLQQPPPQPPTGPPPLDELSQEDTHYSQTVST

ILQHQPNRWSESSSSGCIAPYSSQSAFAKWTTRCDHHHHPMAVEGTSQWL

LKYILFSVPFLHTKYRDENSPKSRDGDSAGRFRKGTPQDELSANHVLAER

RRREKLNERFIILRSLVPFVTKMDKASILGDTIEYVKQLRKKIQDLEART

RQMEVEQRSRGSDSVRSKEHRIGSGSVDRNRAVVAGSDKRKLRIVEGSTG

AKPKVVDSPPAAVEGGTTTVEVSIIESDALLEMQCPYREGLLLDVMQMLR

ELRLETTTVQSSLTNGVFVAELRAKVKENASGKKASIMEVKRAINQIIPQ

C

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of engineering a plant having reduced lignin content, the method comprising:
   introducing into the plant an expression cassette comprising a polynucleotide that encodes a bacterial dehydroshikimate dehydratase or a *Podospora anserina* dehydroshikimate dehydratase (DsDH), wherein the polynucleotide is operably linked to a heterologous promoter, wherein the promoter is a secondary cell wall-specific promoter, a fiber cell-specific promoter, or a promoter from a gene in the lignin biosynthesis pathway; and
   culturing the plant under conditions in which the bacterial dehydroshikimate dehydratase is expressed.

2. The method of claim 1, wherein the polynucleotide encodes a *Corynebacterium glutamicum* dehydroshikimate dehydratase (QsuB).

3. The method of claim 1, wherein the promoter is from a gene in the lignin biosynthesis pathway.

4. The method of claim 1, wherein the plant is selected from the group consisting of *Arabidopsis*, poplar, *eucalyptus*, rice, corn, switchgrass, sorghum, millet, *miscanthus*, sugarcane, pine, alfalfa, wheat, soy, barley, turfgrass, tobacco, hemp, bamboo, rape, sunflower, willow, and *Brachypodium*.

5. A plant engineered by the method of claim 1.

6. A plant cell from the plant of claim 5.

7. A seed, flower, leaf, or fruit from the plant of claim 5, wherein the seed, flower, leaf, or fruit comprises the expression cassette.

8. A plant cell comprising a polynucleotide that encodes a bacterial dehydroshikimate dehydratase or a *Podospora anserina* dehydroshikimate dehydratase (DsDH), wherein the polynucleotide is operably linked to a heterologous promoter, wherein the promoter is a secondary cell wall-specific promoter, a fiber cell-specific promoter, or a promoter from a gene in the lignin biosynthesis pathway.

9. The plant cell of claim 8, wherein the polynucleotide encodes a *Corynebacterium glutamicum* dehydroshikimate dehydratase (QsuB).

10. A plant comprising the plant cell of claim 9, wherein the plant has reduced lignin content that is localized to the secondary cell wall tissue or fiber cells of the plant.

11. The method of claim 1, wherein the promoter is a secondary cell wall-specific promoter or a fiber cell-specific promoter.

12. The method of claim 11, wherein the promoter is an IRX5 promoter.

13. The method of claim 3, wherein the promoter is a cinnamate 4-hydroxylase (C4H), coumarate 3-hydroxylase (C3H), hydroxycinnamoyl-Coenzyme A shikimate/quinate hydroxycinnamoyltransferase (HCT), cinnamoyl-CoA reductase (CCR1), cinnamyl alcohol dehydrogenase 4 (CAD4), cinnamyl alcohol dehydrogenase 5 (CAD5), ferulate 5-hydroxylase (F5H), phenylalanine ammonia-lyase 1 (PAL1), phenylalanine ammonia-lyase 2 (PAL2), 4-coumarate CoA ligase 1 (4CL1), or caffeoyl/CoA-3-O-methyltransferase (CCoAMT) promoter.

14. The method of claim 13, wherein the promoter is a C4H promoter.

15. The method of claim 1, wherein the expression cassette comprises a polynucleotide that encodes a *Corynebacterium glutamicum* dehydroshikimate dehydratase (QsuB) and wherein the promoter is a C4H promoter.

* * * * *

SEQUENCE LISTING

```
<160> NUMBER OF SEQ ID NOS: 51

<210> SEQ ID NO 1
<211> LENGTH: 528
<212> TYPE: DNA
<213> ORGANISM: Mycobacterium tuberculosis
<220> FEATURE:
<221> NAME/KEY: misc_feature
<222> LOCATION: (1)..(528)
<223> OTHER INFORMATION: shikimate kinase (MtAroK, AroK)

<400> SEQUENCE: 1
atggcaccaa aagctgtttt agtgggactt cctggaagtg gaaagtccac tatcggtaga      60
aggttggcta aagcattagg agttggtttg ttagacactg atgtggctat agaacaaagg     120
acaggaagat caatagcaga cattttttgct acagatggtg aacaggagtt cagaaggata     180
```

```
gaagaggatg ttgtgagagc tgcattggct gaccatgatg gtgttcttag tttgggtgga      240
ggtgcagtta cttccccagg agtgagagct gcacttgctg gtcacacagt tgtgtatttg      300
gaaatctcag ctgcagaggg agtgagaagg acaggtggta acaccgtgag accacttttg      360
gcaggtcctg atagggctga aaagtataga gctttgatgg caaaaagggc tcctttatac      420
agaagggttg ctactatgag agtggataca aatagaagga acccaggtgc agttgttagg      480
cacattttat ccaggttgca ggttccatct ccttctgagg cagctact                   528
```

<210> SEQ ID NO 2
<211> LENGTH: 176
<212> TYPE: PRT
<213> ORGANISM: Mycobacterium tuberculosis
<220> FEATURE:
<221> NAME/KEY: MISC_FEATURE
<222> LOCATION: (1)..(176)
<223> OTHER INFORMATION: shikimate kinase (MtAroK, AroK)

<400> SEQUENCE: 2

```
Met Ala Pro Lys Ala Val Leu Val Gly Leu Pro Gly Ser Gly Lys Ser
1               5                   10                  15

Thr Ile Gly Arg Arg Leu Ala Lys Ala Leu Gly Val Gly Leu Leu Asp
            20                  25                  30

Thr Asp Val Ala Ile Glu Gln Arg Thr Gly Arg Ser Ile Ala Asp Ile
        35                  40                  45

Phe Ala Thr Asp Gly Glu Gln Glu Phe Arg Arg Ile Glu Glu Asp Val
    50                  55                  60

Val Arg Ala Ala Leu Ala Asp His Asp Gly Val Leu Ser Leu Gly Gly
65                  70                  75                  80

Gly Ala Val Thr Ser Pro Gly Val Arg Ala Ala Leu Ala Gly His Thr
                85                  90                  95

Val Val Tyr Leu Glu Ile Ser Ala Ala Glu Gly Val Arg Arg Thr Gly
            100                 105                 110

Gly Asn Thr Val Arg Pro Leu Leu Ala Gly Pro Asp Arg Ala Glu Lys
        115                 120                 125

Tyr Arg Ala Leu Met Ala Lys Arg Ala Pro Leu Tyr Arg Arg Val Ala
    130                 135                 140

Thr Met Arg Val Asp Thr Asn Arg Arg Asn Pro Gly Ala Val Val Arg
145                 150                 155                 160

His Ile Leu Ser Arg Leu Gln Val Pro Ser Pro Ser Glu Ala Ala Thr
                165                 170                 175
```

<210> SEQ ID NO 3
<211> LENGTH: 4764
<212> TYPE: DNA
<213> ORGANISM: Saccharomyces cerevisiae
<220> FEATURE:
<221> NAME/KEY: misc_feature
<222> LOCATION: (1)..(4764)
<223> OTHER INFORMATION: pentafunctional arom protein, pentafuntional
    AROM protein (ScAro1, ARO1, AROM)

<400> SEQUENCE: 3

```
atggttcagc ttgctaaggt gcctattttg ggtaacgaca tcattcacgt tggatataac      60
attcacgatc atttggttga gactattatc aagcattgtc catcttctac ttatgttatt      120
tgtaacgata ccaacctttc taaggttcct tattaccaac agttagtgct tgagtttaag      180
gcttctttgc cagaaggaag tagattgtta acttatgttg tgaaacctgg agagacttct      240
```

```
aagtcaaggg aaacaaaagc tcaattggag gactaccttt tggttgaagg atgtaccaga    300
gatactgtga tggttgctat tggtggaggt gttataggtg atatgattgg atttgtggca    360
tcaactttca tgagaggtgt tagggttgtg caagtgccaa caagtttact tgctatggtt    420
gacagttcca tcggaggaaa gacagcaata gatacccat tgggaaaaaa ctttattggt     480
gctttctggc agcctaagtt cgtgcttgtt gatatcaagt ggcttgagac attggctaag    540
agagaattta tcaacggaat ggcagaagtt atcaagacag cttgtatttg aacgcagat     600 gagtttacca gattggaatc aaatgctagt ttgttcttaa acgttgtgaa cggtgcaaag    660
aacgtgaagg ttactaacca acttacaaac gagatcgatg aaatctcaaa taccgacatc    720
gaagctatgc ttgatcacac ttacaaactt gttttggagt ctatcaaggt gaaagcagaa    780
gttgtgtctt cagatgagag agaaagttcc ttgaggaact tgcttaactt cggtcattca    840
atcggacacg cttacgaagc aatcttaact ccacaagctc ttcatggaga atgtgtttct    900
attggtatgg tgaaggaggc agaattgtca agatacttcg gaatattaag tcctacacag    960
gttgcaaggt tgtccaaaat tttggttgct tacggtttgc cagtgtctcc tgatgagaag   1020
tggttcaagg aattaacact tcataaaaag accccttttag acatcctttt gaaaaagatg   1080
tccatcgata aaaagaatga gggttctaaa agaaagttg tgatcttaga atctatcgga    1140
aagtgctatg gagactccgc tcaatttgtt tctgatgagg accttagatt cattttgaca    1200
gatgaaaccc ttgtttaccc atttaaagat atacctgctg accaacgaaa ggttgtgatt   1260
ccacctggta gtaaatccat ttctaacaga gcattgatct tagctgcatt gggtgaagga   1320
cagtgtaaga taaagaacct tcttcattca gatgacacta agcacatgct tacagcagtt   1380
catgaattga aggtgctac aatctcttgg gaggataacg agaaaccgt tgtggttgaa     1440 ggtcatggag gttccacttt gtctgcttgc gcagatccac tttatttggg taatgctgga   1500
accgcatcaa gattttaac tagtcttgct gctttggtta actcaacttc ttcacaaaag    1560
tacattgtgt taactggtaa tgcaagaatg caacagaggc caatcgctcc tttagttgat   1620
tctcttagag caaacggaac aaagatcgag taccttaaca acgaaggttc acttcctatc   1680
aaggtttaca ctgatagtgt gttcaaagga ggtagaatag aattagctgc aacagttagt   1740
tcccaatatg tgtcttcaat tcttatgtgt gctccatacg cagaagagcc tgttacttta   1800
gctcttgtgg gaggaaagcc aatctcaaaa ttgtacgttg atatgacaat caagatgatg   1860
gaaaagttcg gaatcaacgt tgagacttct actacagaac catacacata ctacatccct   1920
aagggtcatt acatcaaccc ttcagagtac gttatcgaaa gtgatgctag ttccgcaact   1980
tatccattag ctttcgctgc aatgaccgga accactgtga ctgttcctaa tattggattt   2040
gaatctcttc aaggtgacgc tagattcgca agggatgttt tgaagccaat gggttgtaaa   2100
atcactcaga cagctacctc aacaaccgtt agtggtccac ctgtgggaac attaaagcca   2160
cttaaacacg ttgacatgga acctatgaca gatgcttttct tgaccgcatg tgtggttgct   2220
gcaatttcac atgatagtga cccaaattct gctaacacta caaccataga gggaatagca   2280
aaccaaagag ttaaggaatg caacaggatc ttggctatgg caactgagtt agctaaattt   2340
ggtgttaaaa ctcagaaatt acctgatgga atccaggtgc acggtcttaa ttcaatcaag   2400
gacttgaaag ttccaagtga ttcttcaggt cctgtgggag tttgtactta tgatgaccat   2460
agagtggcaa tgtcattcag tttgttagct ggtatggtta attctcaaaa cgagagggat   2520
gaagtggcta acccagttag aattttgaa aggcactgca ctggaaagac atggcctggt    2580
tggtgggacg ttttgcatag tgaattagga gctaaacttg atggtgcaga gcctttagaa   2640
```

```
tgtacttcta agaaaaattc caagaaatct gtggttatta tcggaatgag agctgcaggt    2700
aaaaccacta tttccaaatg gtgcgcttct gcattgggat acaaattggt tgatttagac    2760 gagcttttg aacaacagca taataaccaa tcagttaagc agttcgtggt tgagaacggt     2820
tgggaaaaat ttagagaaga ggaaactagg atcttcaagg aagttatcca aaactacggt    2880
gatgacggat acgttttctc tacaggaggt ggaattgtgg agtcagctga agtagaaag     2940 gcacttaaag atttcgctag ttccggtgga tatgtgttgc atttacacag ggacattgag    3000
gaaactatcg ttttcttgca atctgatcca tcaagaccag cttatgttga ggaaattaga    3060
gaagtgtgga acagaaggga gggttggtac aaggaatgtt caaacttctc tttctttgct    3120
ccacactgct ctgctgaggc agaatttcaa gctcttagaa ggtccttctc taaatacatc    3180
gcaactataa caggagttag agagatcgaa ataccatccg gtaggtctgc ttttgtttgt    3240
ttgaccttcg atgacttaac cgagcagact gaaaacttaa ctcctatttg ttatggttgc    3300
gaggcagtgg aagttagagt ggaccatctt gctaattact cagcagattt cgtttccaag    3360
caattgtcta tccttagaaa ggctactgat agtatcccaa taatttcac agttaggacc     3420 atgaaacagg gtgaaaactt tcctgacgag gaatttaaga cacttagaga attgtacgat    3480
atagctctta agaatggtgt tgagtttctt gacttggaat taactcttcc tacagatatc    3540
caatacgaag ttatcaacaa gagaggaaac actaagatca taggttccca tcacgatttt    3600
caaggattat actcttggga tgacgctgag tgggaaaata gattcaacca ggcattgacc    3660
ttagatgttg acgtggttaa gtttgtgggt actgctgtta atttcgagga caaccttaga    3720
ttggaacatt ttagggatac acacaagaac aagccactta tcgcagttaa catgacctca    3780
aaaggatcaa tcagtagagt gttgaataac gttttaaccc ctgtgacttc cgatcttttg    3840
ccaaactctg ctgcacctgg tcaacttacc gttgctcaga tcaacaagat gtacacttct    3900
atgggtggaa ttgagccaaa agaacttttc gtggttggaa agccaatcgg acattcaaga    3960
tcacctatct tgcataacac tggatacgaa attttaggtc ttcctcataa gttcgataaa    4020
ttcgagacag aatctgctca attggttaag gaaaaattac ttgatggtaa caagaacttt    4080
ggtggagctg cagttactat cccattgaaa ttggatatca tgcagtacat ggatgaattg    4140
acagacgctg caaaggttat tggtgctgtg aataccgtta tcccacttgg aaacaagaag    4200
ttcaagggtg ataacacaga ctggcttgga ataagaaatg ctcttatcaa caacggtgtt    4260
cctgaatatg tgggtcacac tgcaggattg gttattggtg ctggtggaac atcaagagct    4320
gcattatacg ctcttcatag tttgggttgt aagaaaatct ttatcatcaa caggacaacc    4380
tctaagttaa aaccacttat cgagtcactt cctagtgaat taacatcat cggaatagag     4440 tccactaagt ctattgagga aatcaaagaa acgttggtg tggcagttc ctgcgttcca      4500 gctgataaac ctttggatga cgagttgctt tcaaaacttg aaagattttt ggttaagggt    4560
gctcatgctg cattcgtgcc aacacttttg gaagctgcat ataagccatc cgtgaccct     4620 gttatgacta tctctcagga taagtaccag tggcacgtgg ttcctggatc tcaaatgttg    4680
gttcatcagg gtgtggctca gtttgagaag tggacaggat tcaaaggacc atttaaggct    4740
attttcgacg cagttaccaa ggag                                           4764
```

<210> SEQ ID NO 4
<211> LENGTH: 1588
<212> TYPE: PRT
<213> ORGANISM: Saccharomyces cerevisiae
<220> FEATURE:

```
<221> NAME/KEY: MISC_FEATURE
<222> LOCATION: (1)..(1588)
<223> OTHER INFORMATION: pentafunctional arom protein, pentafuntional
      AROM protein (ScAro1, ARO1, AROM)

<400> SEQUENCE: 4
```

| Met | Val | Gln | Leu | Ala | Lys | Val | Pro | Ile | Leu | Gly | Asn | Asp | Ile | Ile | His |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Val Gly Tyr Asn Ile His Asp His Leu Val Glu Thr Ile Ile Lys His
            20                  25                  30

Cys Pro Ser Ser Thr Tyr Val Ile Cys Asn Asp Thr Asn Leu Ser Lys
                35                  40                  45

Val Pro Tyr Tyr Gln Gln Leu Val Leu Glu Phe Lys Ala Ser Leu Pro
 50                  55                  60

Glu Gly Ser Arg Leu Leu Thr Tyr Val Val Lys Pro Gly Glu Thr Ser
 65                  70                  75                  80

Lys Ser Arg Glu Thr Lys Ala Gln Leu Glu Asp Tyr Leu Leu Val Glu
                 85                  90                  95

Gly Cys Thr Arg Asp Thr Val Met Val Ala Ile Gly Gly Val Ile
                100                 105                 110

Gly Asp Met Ile Gly Phe Val Ala Ser Thr Phe Met Arg Gly Val Arg
            115                 120                 125

Val Val Gln Val Pro Thr Ser Leu Leu Ala Met Val Asp Ser Ser Ile
130                 135                 140

Gly Gly Lys Thr Ala Ile Asp Thr Pro Leu Gly Lys Asn Phe Ile Gly
145                 150                 155                 160

Ala Phe Trp Gln Pro Lys Phe Val Leu Val Asp Ile Lys Trp Leu Glu
                165                 170                 175

Thr Leu Ala Lys Arg Glu Phe Ile Asn Gly Met Ala Glu Val Ile Lys
            180                 185                 190

Thr Ala Cys Ile Trp Asn Ala Asp Glu Phe Thr Arg Leu Glu Ser Asn
            195                 200                 205

Ala Ser Leu Phe Leu Asn Val Val Asn Gly Ala Lys Asn Val Lys Val
210                 215                 220

Thr Asn Gln Leu Thr Asn Glu Ile Asp Glu Ile Ser Asn Thr Asp Ile
225                 230                 235                 240

Glu Ala Met Leu Asp His Thr Tyr Lys Leu Val Leu Glu Ser Ile Lys
                245                 250                 255

Val Lys Ala Glu Val Val Ser Ser Asp Glu Arg Glu Ser Ser Leu Arg
            260                 265                 270

Asn Leu Leu Asn Phe Gly His Ser Ile Gly His Ala Tyr Glu Ala Ile
            275                 280                 285

Leu Thr Pro Gln Ala Leu His Gly Glu Cys Val Ser Ile Gly Met Val
290                 295                 300

Lys Glu Ala Glu Leu Ser Arg Tyr Phe Gly Ile Leu Ser Pro Thr Gln
305                 310                 315                 320

Val Ala Arg Leu Ser Lys Ile Leu Val Ala Tyr Gly Leu Pro Val Ser
                325                 330                 335

Pro Asp Glu Lys Trp Phe Lys Glu Leu Thr Leu His Lys Lys Thr Pro
            340                 345                 350

Leu Asp Ile Leu Leu Lys Lys Met Ser Ile Asp Lys Lys Asn Glu Gly
            355                 360                 365

Ser Lys Lys Lys Val Val Ile Leu Glu Ser Ile Gly Lys Cys Tyr Gly
370                 375                 380

-continued

Asp Ser Ala Gln Phe Val Ser Asp Glu Asp Leu Arg Phe Ile Leu Thr
385                 390                 395                 400

Asp Glu Thr Leu Val Tyr Pro Phe Lys Asp Ile Pro Ala Asp Gln Gln
            405                 410                 415

Lys Val Val Ile Pro Pro Gly Ser Lys Ser Ile Ser Asn Arg Ala Leu
            420                 425                 430

Ile Leu Ala Ala Leu Gly Glu Gly Gln Cys Lys Ile Lys Asn Leu Leu
            435                 440                 445

His Ser Asp Asp Thr Lys His Met Leu Thr Ala Val His Glu Leu Lys
        450                 455                 460

Gly Ala Thr Ile Ser Trp Glu Asp Asn Gly Glu Thr Val Val Val Glu
465                 470                 475                 480

Gly His Gly Gly Ser Thr Leu Ser Ala Cys Ala Asp Pro Leu Tyr Leu
            485                 490                 495

Gly Asn Ala Gly Thr Ala Ser Arg Phe Leu Thr Ser Leu Ala Ala Leu
            500                 505                 510

Val Asn Ser Thr Ser Ser Gln Lys Tyr Ile Val Leu Thr Gly Asn Ala
        515                 520                 525

Arg Met Gln Gln Arg Pro Ile Ala Pro Leu Val Asp Ser Leu Arg Ala
530                 535                 540

Asn Gly Thr Lys Ile Glu Tyr Leu Asn Asn Glu Gly Ser Leu Pro Ile
545                 550                 555                 560

Lys Val Tyr Thr Asp Ser Val Phe Lys Gly Gly Arg Ile Glu Leu Ala
            565                 570                 575

Ala Thr Val Ser Ser Gln Tyr Val Ser Ser Ile Leu Met Cys Ala Pro
            580                 585                 590

Tyr Ala Glu Glu Pro Val Thr Leu Ala Leu Val Gly Gly Lys Pro Ile
            595                 600                 605

Ser Lys Leu Tyr Val Asp Met Thr Ile Lys Met Met Glu Lys Phe Gly
        610                 615                 620

Ile Asn Val Glu Thr Ser Thr Thr Glu Pro Tyr Thr Tyr Tyr Ile Pro
625                 630                 635                 640

Lys Gly His Tyr Ile Asn Pro Ser Glu Tyr Val Ile Glu Ser Asp Ala
            645                 650                 655

Ser Ser Ala Thr Tyr Pro Leu Ala Phe Ala Ala Met Thr Gly Thr Thr
            660                 665                 670

Val Thr Val Pro Asn Ile Gly Phe Glu Ser Leu Gln Gly Asp Ala Arg
        675                 680                 685

Phe Ala Arg Asp Val Leu Lys Pro Met Gly Cys Lys Ile Thr Gln Thr
        690                 695                 700

Ala Thr Ser Thr Thr Val Ser Gly Pro Pro Val Gly Thr Leu Lys Pro
705                 710                 715                 720

Leu Lys His Val Asp Met Glu Pro Met Thr Asp Ala Phe Leu Thr Ala
            725                 730                 735

Cys Val Val Ala Ala Ile Ser His Asp Ser Asp Pro Asn Ser Ala Asn
            740                 745                 750

Thr Thr Thr Ile Glu Gly Ile Ala Asn Gln Arg Val Lys Glu Cys Asn
        755                 760                 765

Arg Ile Leu Ala Met Ala Thr Glu Leu Ala Lys Phe Gly Val Lys Thr
        770                 775                 780

Thr Glu Leu Pro Asp Gly Ile Gln Val His Gly Leu Asn Ser Ile Lys
785                 790                 795                 800

Asp Leu Lys Val Pro Ser Asp Ser Ser Gly Pro Val Gly Val Cys Thr

```
                    805                 810                 815
Tyr Asp Asp His Arg Val Ala Met Ser Phe Ser Leu Leu Ala Gly Met
                820                 825                 830

Val Asn Ser Gln Asn Glu Arg Asp Glu Val Ala Asn Pro Val Arg Ile
                835                 840                 845

Leu Glu Arg His Cys Thr Gly Lys Thr Trp Pro Gly Trp Asp Val
    850                 855                 860

Leu His Ser Glu Leu Gly Ala Lys Leu Asp Gly Ala Glu Pro Leu Glu
865                 870                 875                 880

Cys Thr Ser Lys Lys Asn Ser Lys Lys Ser Val Val Ile Ile Gly Met
                885                 890                 895

Arg Ala Ala Gly Lys Thr Thr Ile Ser Lys Trp Cys Ala Ser Ala Leu
                900                 905                 910

Gly Tyr Lys Leu Val Asp Leu Asp Glu Leu Phe Glu Gln Gln His Asn
                915                 920                 925

Asn Gln Ser Val Lys Gln Phe Val Val Glu Asn Gly Trp Glu Lys Phe
            930                 935                 940

Arg Glu Glu Glu Thr Arg Ile Phe Lys Glu Val Ile Gln Asn Tyr Gly
945                 950                 955                 960

Asp Asp Gly Tyr Val Phe Ser Thr Gly Gly Ile Val Glu Ser Ala
                965                 970                 975

Glu Ser Arg Lys Ala Leu Lys Asp Phe Ala Ser Ser Gly Gly Tyr Val
            980                 985                 990

Leu His Leu His Arg Asp Ile Glu  Glu Thr Ile Val Phe  Leu Gln Ser
            995                 1000                1005

Asp Pro  Ser Arg Pro Ala Tyr  Val Glu Ile Arg  Glu Val Trp
    1010                1015                1020

Asn Arg  Arg Glu Gly Trp Tyr  Lys Glu Cys Ser Asn  Phe Ser Phe
    1025                1030                1035

Phe Ala  Pro His Cys Ser Ala  Glu Ala Glu Phe Gln  Ala Leu Arg
    1040                1045                1050

Arg Ser  Phe Ser Lys Tyr Ile  Ala Thr Ile Thr Gly  Val Arg Glu
    1055                1060                1065

Ile Glu  Ile Pro Ser Gly Arg  Ser Ala Phe Val Cys  Leu Thr Phe
    1070                1075                1080

Asp Asp  Leu Thr Glu Gln Thr  Glu Asn Leu Thr Pro  Ile Cys Tyr
    1085                1090                1095

Gly Cys  Glu Ala Val Glu Val  Arg Val Asp His Leu  Ala Asn Tyr
    1100                1105                1110

Ser Ala  Asp Phe Val Ser Lys  Gln Leu Ser Ile Leu  Arg Lys Ala
    1115                1120                1125

Thr Asp  Ser Ile Pro Ile Ile  Phe Thr Val Arg Thr  Met Lys Gln
    1130                1135                1140

Gly Gly  Asn Phe Pro Asp Glu  Glu Phe Lys Thr Leu  Arg Glu Leu
    1145                1150                1155

Tyr Asp  Ile Ala Leu Lys Asn  Gly Val Glu Phe Leu  Asp Leu Glu
    1160                1165                1170

Leu Thr  Leu Pro Thr Asp Ile  Gln Tyr Glu Val Ile  Asn Lys Arg
    1175                1180                1185

Gly Asn  Thr Lys Ile Ile Gly  Ser His His Asp Phe  Gln Gly Leu
    1190                1195                1200

Tyr Ser  Trp Asp Asp Ala Glu  Trp Glu Asn Arg Phe  Asn Gln Ala
    1205                1210                1215
```

Leu Thr Leu Asp Val Asp Val Val Lys Phe Val Gly Thr Ala Val
1220                1225                1230

Asn Phe Glu Asp Asn Leu Arg Leu Glu His Phe Arg Asp Thr His
1235                1240                1245

Lys Asn Lys Pro Leu Ile Ala Val Asn Met Thr Ser Lys Gly Ser
1250                1255                1260

Ile Ser Arg Val Leu Asn Asn Val Leu Thr Pro Val Thr Ser Asp
1265                1270                1275

Leu Leu Pro Asn Ser Ala Ala Pro Gly Gln Leu Thr Val Ala Gln
1280                1285                1290

Ile Asn Lys Met Tyr Thr Ser Met Gly Gly Ile Glu Pro Lys Glu
1295                1300                1305

Leu Phe Val Val Gly Lys Pro Ile Gly His Ser Arg Ser Pro Ile
1310                1315                1320

Leu His Asn Thr Gly Tyr Glu Ile Leu Gly Leu Pro His Lys Phe
1325                1330                1335

Asp Lys Phe Glu Thr Glu Ser Ala Gln Leu Val Lys Glu Lys Leu
1340                1345                1350

Leu Asp Gly Asn Lys Asn Phe Gly Gly Ala Ala Val Thr Ile Pro
1355                1360                1365

Leu Lys Leu Asp Ile Met Gln Tyr Met Asp Glu Leu Thr Asp Ala
1370                1375                1380

Ala Lys Val Ile Gly Ala Val Asn Thr Val Ile Pro Leu Gly Asn
1385                1390                1395

Lys Lys Phe Lys Gly Asp Asn Thr Asp Trp Leu Gly Ile Arg Asn
1400                1405                1410

Ala Leu Ile Asn Asn Gly Val Pro Glu Tyr Val Gly His Thr Ala
1415                1420                1425

Gly Leu Val Ile Gly Ala Gly Gly Thr Ser Arg Ala Ala Leu Tyr
1430                1435                1440

Ala Leu His Ser Leu Gly Cys Lys Lys Ile Phe Ile Ile Asn Arg
1445                1450                1455

Thr Thr Ser Lys Leu Lys Pro Leu Ile Glu Ser Leu Pro Ser Glu
1460                1465                1470

Phe Asn Ile Ile Gly Ile Glu Ser Thr Lys Ser Ile Glu Glu Ile
1475                1480                1485

Lys Glu His Val Gly Val Ala Val Ser Cys Val Pro Ala Asp Lys
1490                1495                1500

Pro Leu Asp Asp Glu Leu Leu Ser Lys Leu Glu Arg Phe Leu Val
1505                1510                1515

Lys Gly Ala His Ala Ala Phe Val Pro Thr Leu Leu Glu Ala Ala
1520                1525                1530

Tyr Lys Pro Ser Val Thr Pro Val Met Thr Ile Ser Gln Asp Lys
1535                1540                1545

Tyr Gln Trp His Val Val Pro Gly Ser Gln Met Leu Val His Gln
1550                1555                1560

Gly Val Ala Gln Phe Glu Lys Trp Thr Gly Phe Lys Gly Pro Phe
1565                1570                1575

Lys Ala Ile Phe Asp Ala Val Thr Lys Glu
1580                1585

<210> SEQ ID NO 5
<211> LENGTH: 1854

<212> TYPE: DNA
<213> ORGANISM: Corynebacterium glutamicum
<220> FEATURE:
<221> NAME/KEY: misc_feature
<222> LOCATION: (1)..(1854)
<223> OTHER INFORMATION: dehydroshikimate dehydratase (CgQsuB, QsuB)

<400> SEQUENCE: 5

```
atgagaacaa gtattgcaac cgtttgttta tccggaactc ttgctgaaaa attgagagca      60
gctgcagacg caggattcga tggtgttgag atttttgaac aagatttggt tgtgtctcca     120
cattcagctg aacaaatcag acagagggca caagattag gtcttacatt ggacttattt     180
cagccttca gagattttga aggagttgaa aggaacaat tcttaaagaa tcttcacagg     240
ttggaggaaa aatttaagtt aatgaacaga cttggtatcg aaatgatctt gctttgttct     300
aacgttggaa cagctaccat caacgatgac gatctttttg tggaacaatt gcatagagct     360
gcagatttgg ctgagaagta caacgttaag atcgcttatg aagctcttgc ttggggtaaa     420
ttcgttaatg atttgagca tgctcacgca ttggttgaaa aagtgaacca taaggctttg     480
ggtacttgct agatacatt ccacatatta agtagaggat gggagactga tgaggttgaa     540
aacatcccag ctgaaaaaat atttttcgtg caattggctg atgcacctaa gttatctatg     600
gatatccttt cttggtcaag gcatcacaga gttttccag gagagggtga cttcgatttg     660
gttaagttca tggtgcatct tgctaagaca ggatacgatg gtcctatatc tttggagatt     720
ttcaacgact catttaggaa agctgaagtt ggaagaactg caattgatgg tttaaggtct     780
cttagatggt tggaggacca aacatggcat gcacttaacg ctgaagatag gccatcagca     840
cttgagttga gagctttgcc agaagttgca gagcctgagg gtgtggattt cattgagatc     900
gctacaggaa ggttaggtga aaccatcaga gttttacacc agcttggtt tagacttggt     960
ggacatcact gttctaagca ggattatcaa gtttggactc aaggagatgt gaggatcgtt    1020
gtgtgcgaca gaggagcaac aggtgctcct accactatat cagctatggg tttcgacacc    1080
ccagatcctg aggctgcaca tgctagggca gaacttttga gagcacaaac aattgataga    1140
ccacacatcg agggagaagt tgatcttaag ggtgtgtacg ctcctgacgg agttgaattg    1200
tttttcgcag gaccatctcc tgatggtatg ccagagtggt tacctgaatt tggtgttgag    1260
aagcaagaag ctggacttat cgaagcaatc gatcatgtta actttgctca gccttggcaa    1320
cacttcgatg aggcagtttt gttttatacc gcattgatgg ctttagaaac tgtgagagag    1380
gatgaatttc catcacctat tggtttagtt aggaatcagg tgatgagatc accaaaacgat    1440
gctgttagat tactttttgc agtggcacct gaggacggaa acagggtgaa tttcttaaat    1500
gctgcatacc cagaacatat agctcttgca actgctgata ttgttgcagt ggctgaaaga    1560
gctaggaaaa gaggtttgga tttcttgcca gttcctgaaa actattacga cgatgtgcag    1620
gctagattcg atttgcctca agagttttta gacacactta ggaaaaacca tcttctttat    1680
gactgcgatg agaacggtga attttttgcac ttctacacta gaacattggg aacattattt    1740
ttcgaggttg tggaaagaag gggtggattt gctggatggg gtgaaaccaa tgcacctgtt    1800
aggcttgctg ctcaatatag agaagttaga gatttagaga gaggtatccc aaac         1854
```

<210> SEQ ID NO 6
<211> LENGTH: 618
<212> TYPE: PRT
<213> ORGANISM: Corynebacterium glutamicum
<220> FEATURE:
<221> NAME/KEY: MISC_FEATURE
<222> LOCATION: (1)..(618)

<223> OTHER INFORMATION: dehydroshikimate dehydratase (CgQsuB, QsuB)

<400> SEQUENCE: 6

```
Met Arg Thr Ser Ile Ala Thr Val Cys Leu Ser Gly Thr Leu Ala Glu
1               5                   10                  15

Lys Leu Arg Ala Ala Asp Ala Gly Phe Asp Gly Val Glu Ile Phe
            20                  25                  30

Glu Gln Asp Leu Val Val Ser Pro His Ser Ala Glu Gln Ile Arg Gln
        35                  40                  45

Arg Ala Gln Asp Leu Gly Leu Thr Leu Asp Leu Phe Gln Pro Phe Arg
    50                  55                  60

Asp Phe Glu Gly Val Glu Glu Gln Phe Leu Lys Asn Leu His Arg
65                  70                  75                  80

Leu Glu Glu Lys Phe Lys Leu Met Asn Arg Leu Gly Ile Glu Met Ile
                85                  90                  95

Leu Leu Cys Ser Asn Val Gly Thr Ala Thr Ile Asn Asp Asp Asp Leu
            100                 105                 110

Phe Val Glu Gln Leu His Arg Ala Ala Asp Leu Ala Glu Lys Tyr Asn
        115                 120                 125

Val Lys Ile Ala Tyr Glu Ala Leu Ala Trp Gly Lys Phe Val Asn Asp
    130                 135                 140

Phe Glu His Ala His Ala Leu Val Glu Lys Val Asn His Lys Ala Leu
145                 150                 155                 160

Gly Thr Cys Leu Asp Thr Phe His Ile Leu Ser Arg Gly Trp Glu Thr
                165                 170                 175

Asp Glu Val Glu Asn Ile Pro Ala Glu Lys Ile Phe Phe Val Gln Leu
            180                 185                 190

Ala Asp Ala Pro Lys Leu Ser Met Asp Ile Leu Ser Trp Ser Arg His
        195                 200                 205

His Arg Val Phe Pro Gly Glu Gly Asp Phe Asp Leu Val Lys Phe Met
    210                 215                 220

Val His Leu Ala Lys Thr Gly Tyr Asp Gly Pro Ile Ser Leu Glu Ile
225                 230                 235                 240

Phe Asn Asp Ser Phe Arg Lys Ala Glu Val Gly Arg Thr Ala Ile Asp
                245                 250                 255

Gly Leu Arg Ser Leu Arg Trp Leu Glu Asp Gln Thr Trp His Ala Leu
            260                 265                 270

Asn Ala Glu Asp Arg Pro Ser Ala Leu Glu Leu Arg Ala Leu Pro Glu
        275                 280                 285

Val Ala Glu Pro Glu Gly Val Asp Phe Ile Glu Ile Ala Thr Gly Arg
    290                 295                 300

Leu Gly Glu Thr Ile Arg Val Leu His Gln Leu Gly Phe Arg Leu Gly
305                 310                 315                 320

Gly His His Cys Ser Lys Gln Asp Tyr Gln Val Trp Thr Gln Gly Asp
                325                 330                 335

Val Arg Ile Val Val Cys Asp Arg Gly Ala Thr Gly Ala Pro Thr Thr
            340                 345                 350

Ile Ser Ala Met Gly Phe Asp Thr Pro Asp Pro Glu Ala Ala His Ala
        355                 360                 365

Arg Ala Glu Leu Leu Arg Ala Gln Thr Ile Asp Arg Pro His Ile Glu
    370                 375                 380

Gly Glu Val Asp Leu Lys Gly Val Tyr Ala Pro Asp Gly Val Glu Leu
385                 390                 395                 400
```

```
Phe Phe Ala Gly Pro Ser Pro Asp Gly Met Pro Glu Trp Leu Pro Glu
                405                 410                 415

Phe Gly Val Glu Lys Gln Glu Ala Gly Leu Ile Glu Ala Ile Asp His
            420                 425                 430

Val Asn Phe Ala Gln Pro Trp Gln His Phe Asp Glu Ala Val Leu Phe
        435                 440                 445

Tyr Thr Ala Leu Met Ala Leu Glu Thr Val Arg Glu Asp Glu Phe Pro
    450                 455                 460

Ser Pro Ile Gly Leu Val Arg Asn Gln Val Met Arg Ser Pro Asn Asp
465                 470                 475                 480

Ala Val Arg Leu Leu Leu Ser Val Ala Pro Glu Asp Gly Glu Gln Gly
                485                 490                 495

Asp Phe Leu Asn Ala Ala Tyr Pro Glu His Ile Ala Leu Ala Thr Ala
            500                 505                 510

Asp Ile Val Ala Val Ala Glu Arg Ala Arg Lys Arg Gly Leu Asp Phe
        515                 520                 525

Leu Pro Val Pro Glu Asn Tyr Tyr Asp Asp Val Gln Ala Arg Phe Asp
    530                 535                 540

Leu Pro Gln Glu Phe Leu Asp Thr Leu Lys Glu Asn His Leu Leu Tyr
545                 550                 555                 560

Asp Cys Asp Glu Asn Gly Glu Phe Leu His Phe Tyr Thr Arg Thr Leu
                565                 570                 575

Gly Thr Leu Phe Phe Glu Val Val Glu Arg Arg Gly Phe Ala Gly
            580                 585                 590

Trp Gly Glu Thr Asn Ala Pro Val Arg Leu Ala Ala Gln Tyr Arg Glu
        595                 600                 605

Val Arg Asp Leu Glu Arg Gly Ile Pro Asn
    610                 615

<210> SEQ ID NO 7
<211> LENGTH: 1101
<212> TYPE: DNA
<213> ORGANISM: Podospora anserina
<220> FEATURE:
<221> NAME/KEY: misc_feature
<222> LOCATION: (1)..(1101)
<223> OTHER INFORMATION: dehydroshikimate dehydratase (CgQsuB, QsuB)

<400> SEQUENCE: 7
atgccttcaa aacttgctat cacctcaatg tctcttggta gatgctatgc tggtcactcc      60
ttcactacta aattggatat ggctaggaaa tatggttacc aaggacttga attgttccat     120
gaggatttgg ctgacgttgc atatagactt agtggtgaaa caccatcccc ttgtggacca     180
tctcctgctg cacagttgag tgctgcaaga caaatactta ggatgtgtca ggttagaaac     240
atagaaattg tgtgcttaca gccatttttct caatacgatg gtttgttaga cagagaagag     300
catgaaagaa ggcttgaaca attggagttc tggatagaat tagctcacga gcttgataca     360
gacattatcc agattccagc aaattttctt cctgctgaag aggttaccga agatatttct     420
ttgatcgttt cagatttgca agaggtggct gacatgggtt tgcaggcaaa cccacctatt     480
agattcgttt atgaagctct tgttggtca actagagtgg atacatggga aaggagttgg     540
gaggttgtgc aaagagttaa taggcctaac tttggtgtgt gccttgatac attcaatatc     600
gcaggaagag tttacgctga cccaaccgtg gcatcaggta gaactcctaa cgctgaagag     660
gcaattagga agtcaatcgc tagattggtt gaaagggttg atgttagtaa agttttctat     720
gtgcaagttg tggacgcaga gaagttgaaa aagccattag ttcctggaca cagattctac     780
```

```
gatccagaac aacctgctag gatgtcttgg tcaagaaact gcaggttgtt ttatggtgaa    840
aaagatagag gagcttactt gccagttaag gagattgctt gggcattttt caatggtttg    900
ggatttgaag gttgggtttc cttagagctt ttcaacagaa ggatgtctga tactggtttt    960
ggagtgcctg aagagttagc tagaagggga gcagtttcct gggctaaact tgtgagagat    1020
atgaagatca ccgttgactc accaactcaa cagcaagcta cacagcaacc tataagaatg    1080
ttgagtttat ccgctgcatt a                                              1101

<210> SEQ ID NO 8
<211> LENGTH: 367
<212> TYPE: PRT
<213> ORGANISM: Podospora anserina
<220> FEATURE:
<221> NAME/KEY: MISC_FEATURE
<222> LOCATION: (1)..(367)
<223> OTHER INFORMATION: dehydroshikimate dehydratase (PaDsDH, DsDH)

<400> SEQUENCE: 8
```

Met Pro Ser Lys Leu Ala Ile Thr Ser Met Ser Leu Gly Arg Cys Tyr
1               5                   10                  15

Ala Gly His Ser Phe Thr Thr Lys Leu Asp Met Ala Arg Lys Tyr Gly
            20                  25                  30

Tyr Gln Gly Leu Glu Leu Phe His Glu Asp Leu Ala Asp Val Ala Tyr
        35                  40                  45

Arg Leu Ser Gly Glu Thr Pro Ser Pro Cys Gly Pro Ser Pro Ala Ala
    50                  55                  60

Gln Leu Ser Ala Ala Arg Gln Ile Leu Arg Met Cys Gln Val Arg Asn
65                  70                  75                  80

Ile Glu Ile Val Cys Leu Gln Pro Phe Ser Gln Tyr Asp Gly Leu Leu
                85                  90                  95

Asp Arg Glu Glu His Glu Arg Arg Leu Glu Gln Leu Glu Phe Trp Ile
            100                 105                 110

Glu Leu Ala His Glu Leu Asp Thr Asp Ile Ile Gln Ile Pro Ala Asn
        115                 120                 125

Phe Leu Pro Ala Glu Glu Val Thr Glu Asp Ile Ser Leu Ile Val Ser
    130                 135                 140

Asp Leu Gln Glu Val Ala Asp Met Gly Leu Gln Ala Asn Pro Pro Ile
145                 150                 155                 160

Arg Phe Val Tyr Glu Ala Leu Cys Trp Ser Thr Arg Val Asp Thr Trp
                165                 170                 175

Glu Arg Ser Trp Glu Val Val Gln Arg Val Asn Arg Pro Asn Phe Gly
            180                 185                 190

Val Cys Leu Asp Thr Phe Asn Ile Ala Gly Arg Val Tyr Ala Asp Pro
        195                 200                 205

Thr Val Ala Ser Gly Arg Thr Pro Asn Ala Glu Glu Ala Ile Arg Lys
    210                 215                 220

Ser Ile Ala Arg Leu Val Glu Arg Val Asp Val Ser Lys Val Phe Tyr
225                 230                 235                 240

Val Gln Val Val Asp Ala Glu Lys Leu Lys Lys Pro Leu Val Pro Gly
                245                 250                 255

His Arg Phe Tyr Asp Pro Glu Gln Pro Ala Arg Met Ser Trp Ser Arg
            260                 265                 270

Asn Cys Arg Leu Phe Tyr Gly Glu Lys Asp Arg Gly Ala Tyr Leu Pro
        275                 280                 285

```
Val Lys Glu Ile Ala Trp Ala Phe Phe Asn Gly Leu Gly Phe Glu Gly
        290                 295                 300

Trp Val Ser Leu Glu Leu Phe Asn Arg Arg Met Ser Asp Thr Gly Phe
305                 310                 315                 320

Gly Val Pro Glu Glu Leu Ala Arg Arg Gly Ala Val Ser Trp Ala Lys
                325                 330                 335

Leu Val Arg Asp Met Lys Ile Thr Val Asp Ser Pro Thr Gln Gln Gln
                340                 345                 350

Ala Thr Gln Gln Pro Ile Arg Met Leu Ser Leu Ser Ala Ala Leu
                355                 360                 365

<210> SEQ ID NO 9
<211> LENGTH: 1518
<212> TYPE: DNA
<213> ORGANISM: Petunia x hybrida
<220> FEATURE:
<221> NAME/KEY: misc_feature
<222> LOCATION: (1)..(1518)
<223> OTHER INFORMATION: phenylacetaldehyde synthase (PhPAAS, PAAS)

<400> SEQUENCE: 9
```

| | | | | | |
|---|---|---|---|---|---|
| atggacacta | tcaagatcaa | cccagagttc | gacggacagt | tctgcaagac | tacatcatta | 60 |
| ttagacccag | aggagttcag | gaggaatgga | catatgatgg | ttgattttct | tgctgactac | 120 |
| ttccacaaca | tcgaaaagta | cccagttaga | tcccaagtgg | aacctggtta | tttggagagg | 180 |
| ttgttaccag | attcagctcc | tatacagcca | gaacctatcg | agaaaatttt | gaaggatgtt | 240 |
| agatcagaca | tatttccagg | tttaacacat | tggcaaagtc | caaatttctt | tgcttacttc | 300 |
| ccttgctctt | caagtaccgc | aggaatttta | ggtgaaatgc | tttcagctgg | attgaacgtt | 360 |
| gtgggttttt | catggatcgc | tagtccagct | gcaactgaat | tagagagtat | tgttatggat | 420 |
| tggcttggaa | aattgattaa | tttgcctaag | acatatcttt | tctctggtgg | aggtggaggt | 480 |
| gtgatgcagg | gtactacatg | cgaagttatg | ctttgtacta | tcgtggctgc | aagagataaa | 540 |
| atgttggaaa | agtttggaag | ggagaacatt | gataagttag | ttgtgtacgc | atcagaccaa | 600 |
| acccactta | gtttccagaa | agctgttaag | atctcaggta | taaaaccaga | aaacttcaga | 660 |
| gctataccta | ccactaaggc | aacagaattc | tcccttaacc | cagagtcttt | gagaagggct | 720 |
| atccaagagg | ataaaaaggc | aggacttatc | cctttgtttt | tatgcacatc | aataggtaca | 780 |
| accagtacta | cagcagttga | cccacttaaa | cctttgtgtg | aaatagctga | agagtatgga | 840 |
| atttgggttc | atgtggatgc | tgcatacgct | ggttctgcat | gcatttgtcc | tgaatttcag | 900 |
| catttcttgg | acggtgttga | gcacgctaat | cctttttctt | tcaacgcaca | caagtggttg | 960 |
| tttactactc | ttgattgttg | ctgtctttgg | ttgaaagacc | catcctcttt | gactaaggca | 1020 |
| ctttcaacaa | accctgaagt | tttgagaaac | gatgctaccg | acagtgagca | agttgtggat | 1080 |
| tataaagact | ggcagattac | tttatccaga | aggtttaggt | ctcttaagct | ttggttggtt | 1140 |
| cttaagtcct | acggagtggc | taatcttaga | aacttcataa | ggtctcatat | cgaaatggct | 1200 |
| aagcactttg | aagagttggt | tgcaatggat | gaaagattcg | agatcatggc | accaaggaat | 1260 |
| ttttccttag | tttgtttcag | agtgtctctt | ttggctcttg | aaaagaagtt | taatttcgtt | 1320 |
| gatgaaactc | aagtgaacga | gtttaacgct | aagcttcttg | aatctatcat | ctcaagtggt | 1380 |
| aacgtttaca | tgacacatac | cgttgtggag | ggagtttaca | tgattagatt | cgctgtgggt | 1440 |
| gcacctttga | cagattatcc | tcacattgat | atggcttgga | atgttgttag | gaaccacgct | 1500 |
| actatgatgt | tgaacgca | | | | | 1518 |

<210> SEQ ID NO 10
<211> LENGTH: 506
<212> TYPE: PRT
<213> ORGANISM: Petunia x hybrida
<220> FEATURE:
<221> NAME/KEY: MISC_FEATURE
<222> LOCATION: (1)..(506)
<223> OTHER INFORMATION: phenylacetaldehyde synthase (PhPAAS, PAAS)

<400> SEQUENCE: 10

Met Asp Thr Ile Lys Ile Asn Pro Glu Phe Asp Gly Gln Phe Cys Lys
1               5                   10                  15

Thr Thr Ser Leu Leu Asp Pro Glu Glu Phe Arg Arg Asn Gly His Met
            20                  25                  30

Met Val Asp Phe Leu Ala Asp Tyr Phe His Asn Ile Glu Lys Tyr Pro
        35                  40                  45

Val Arg Ser Gln Val Glu Pro Gly Tyr Leu Glu Arg Leu Leu Pro Asp
    50                  55                  60

Ser Ala Pro Ile Gln Pro Glu Pro Ile Glu Lys Ile Leu Lys Asp Val
65                  70                  75                  80

Arg Ser Asp Ile Phe Pro Gly Leu Thr His Trp Gln Ser Pro Asn Phe
                85                  90                  95

Phe Ala Tyr Phe Pro Cys Ser Ser Thr Ala Gly Ile Leu Gly Glu
            100                 105                 110

Met Leu Ser Ala Gly Leu Asn Val Val Gly Phe Ser Trp Ile Ala Ser
            115                 120                 125

Pro Ala Ala Thr Glu Leu Glu Ser Ile Val Met Asp Trp Leu Gly Lys
130                 135                 140

Leu Ile Asn Leu Pro Lys Thr Tyr Leu Phe Ser Gly Gly Gly Gly Gly
145                 150                 155                 160

Val Met Gln Gly Thr Thr Cys Glu Val Met Leu Cys Thr Ile Val Ala
                165                 170                 175

Ala Arg Asp Lys Met Leu Glu Lys Phe Gly Arg Glu Asn Ile Asp Lys
            180                 185                 190

Leu Val Val Tyr Ala Ser Asp Gln Thr His Phe Ser Phe Gln Lys Ala
        195                 200                 205

Val Lys Ile Ser Gly Ile Lys Pro Glu Asn Phe Arg Ala Ile Pro Thr
    210                 215                 220

Thr Lys Ala Thr Glu Phe Ser Leu Asn Pro Glu Ser Leu Arg Arg Ala
225                 230                 235                 240

Ile Gln Glu Asp Lys Lys Ala Gly Leu Ile Pro Leu Phe Leu Cys Thr
                245                 250                 255

Ser Ile Gly Thr Thr Ser Thr Thr Ala Val Asp Pro Leu Lys Pro Leu
            260                 265                 270

Cys Glu Ile Ala Glu Glu Tyr Gly Ile Trp Val His Val Asp Ala Ala
        275                 280                 285

Tyr Ala Gly Ser Ala Cys Ile Cys Pro Glu Phe Gln His Phe Leu Asp
    290                 295                 300

Gly Val Glu His Ala Asn Ser Phe Ser Phe Asn Ala His Lys Trp Leu
305                 310                 315                 320

Phe Thr Thr Leu Asp Cys Cys Cys Leu Trp Leu Lys Asp Pro Ser Ser
                325                 330                 335

Leu Thr Lys Ala Leu Ser Thr Asn Pro Glu Val Leu Arg Asn Asp Ala
            340                 345                 350

Thr Asp Ser Glu Gln Val Val Asp Tyr Lys Asp Trp Gln Ile Thr Leu

```
              355                 360                 365
Ser Arg Arg Phe Arg Ser Leu Lys Leu Trp Leu Val Leu Lys Ser Tyr
    370                 375                 380

Gly Val Ala Asn Leu Arg Asn Phe Ile Arg Ser His Ile Glu Met Ala
385                 390                 395                 400

Lys His Phe Glu Glu Leu Val Ala Met Asp Glu Arg Phe Glu Ile Met
                405                 410                 415

Ala Pro Arg Asn Phe Ser Leu Val Cys Phe Arg Val Ser Leu Leu Ala
            420                 425                 430

Leu Glu Lys Lys Phe Asn Phe Val Asp Glu Thr Gln Val Asn Glu Phe
        435                 440                 445

Asn Ala Lys Leu Leu Glu Ser Ile Ile Ser Ser Gly Asn Val Tyr Met
    450                 455                 460

Thr His Thr Val Val Glu Gly Val Tyr Met Ile Arg Phe Ala Val Gly
465                 470                 475                 480

Ala Pro Leu Thr Asp Tyr Pro His Ile Asp Met Ala Trp Asn Val Val
                485                 490                 495

Arg Asn His Ala Thr Met Met Leu Asn Ala
            500                 505
```

<210> SEQ ID NO 11
<211> LENGTH: 1119
<212> TYPE: DNA
<213> ORGANISM: Ocimum basilicum
<220> FEATURE:
<221> NAME/KEY: misc_feature
<222> LOCATION: (1)..(1119)
<223> OTHER INFORMATION: cinnammate/p-coumarate carboxyl
      methyltransferase 1 (obCCMT1, CCMT1)

<400> SEQUENCE: 11

```
atggcgagaa aagagaacta tgttgtttct aacatgaatg ttgaaagtgt gttgtgcatg      60
aaaggtggaa aaggagaaga tagctatgat aacaactcta agatgcagga gcaacatgct     120
cgatcagtgc tccaccttct gatggaagct ctcgacggcg tggggctgag ctcggtggcg     180
gccggcgctt cgtggtggc ggatctcggc tgctccagcg aagaaacgc cataaacacg       240
atggaattta tgatcaatca cctgactgag cactacacgg tggcggcgga agagccgccg     300
gaattctcag ccttcttctg cgacctcccc tccaacgact tcaacaccct ctttcagctc     360
cttccgccgt ctgacggcag cagcggttct tacttcactg ccggcgtggc cggttcgttt     420
taccggaggc ttttcccggc gaagtctgtt gatttctttt actcggcatt tagttttgcac    480
tggctatctc agataccaaa ggaggtgatg gagaagggat cggcggctta caacgagggg     540
agagtgacca tcaacggtgc aaaagagagc accgtaaatg catacaagaa acaatttcaa     600
agtgatttgg gtgtcttctt gagatccaga tccaaagaat gaaaccggg aggatccatg      660
ttcctcatgc tcttgggtcg gaccagcccc gacccggcag atcagggcgc atggattctc     720
actttcagca cacgttatca agatgcttgg aatgatcttg caagagggg cttaatttcg     780
agcgaaaaac gggatacgtt caacatcccg atatatacgc ccagcctaga ggagttcaaa     840
gaggtggtag aaagagatgg tgcattcata atcaacaagc tccaactttt ccacggtggc     900
agcgctctca tcatcgatga tcccaacgat gcggttgaga ttagccgtgc ctatgtcagc     960
ctctgtcgca gcctcaccgg aggcttagtt gatgcccaca taggcgatca gctcggccat    1020
gagctcttct cgcgcttatt aagccaagcc gtggatcagg ctaaggagct aatggaccag    1080
tttcagctcg tccatatagt tgcatccctt actttagct                            1119
```

```
<210> SEQ ID NO 12
<211> LENGTH: 373
<212> TYPE: PRT
<213> ORGANISM: Ocimum basilicum
<220> FEATURE:
<221> NAME/KEY: MISC_FEATURE
<222> LOCATION: (1)..(373)
<223> OTHER INFORMATION: cinnammate/p-coumarate carboxyl
      methyltransferase 1 (obCCMT1, CCMT1)

<400> SEQUENCE: 12

Met Ala Arg Lys Glu Asn Tyr Val Val Ser Asn Met Asn Val Glu Ser
1               5                   10                  15

Val Leu Cys Met Lys Gly Gly Lys Gly Glu Asp Ser Tyr Asp Asn Asn
            20                  25                  30

Ser Lys Met Gln Glu Gln His Ala Arg Ser Val Leu His Leu Leu Met
        35                  40                  45

Glu Ala Leu Asp Gly Val Gly Leu Ser Ser Val Ala Ala Gly Ala Phe
    50                  55                  60

Val Val Ala Asp Leu Gly Cys Ser Ser Gly Arg Asn Ala Ile Asn Thr
65                  70                  75                  80

Met Glu Phe Met Ile Asn His Leu Thr Glu His Tyr Thr Val Ala Ala
                85                  90                  95

Glu Glu Pro Pro Glu Phe Ser Ala Phe Phe Cys Asp Leu Pro Ser Asn
            100                 105                 110

Asp Phe Asn Thr Leu Phe Gln Leu Leu Pro Pro Ser Asp Gly Ser Ser
        115                 120                 125

Gly Ser Tyr Phe Thr Ala Gly Val Ala Gly Ser Phe Tyr Arg Arg Leu
    130                 135                 140

Phe Pro Ala Lys Ser Val Asp Phe Phe Tyr Ser Ala Phe Ser Leu His
145                 150                 155                 160

Trp Leu Ser Gln Ile Pro Lys Glu Val Met Glu Lys Gly Ser Ala Ala
                165                 170                 175

Tyr Asn Glu Gly Arg Val Thr Ile Asn Gly Ala Lys Glu Ser Thr Val
            180                 185                 190

Asn Ala Tyr Lys Lys Gln Phe Gln Ser Asp Leu Gly Val Phe Leu Arg
        195                 200                 205

Ser Arg Ser Lys Glu Leu Lys Pro Gly Gly Ser Met Phe Leu Met Leu
    210                 215                 220

Leu Gly Arg Thr Ser Pro Asp Pro Ala Asp Gln Gly Ala Trp Ile Leu
225                 230                 235                 240

Thr Phe Ser Thr Arg Tyr Gln Asp Ala Trp Asn Asp Leu Val Gln Glu
                245                 250                 255

Gly Leu Ile Ser Ser Glu Lys Arg Asp Thr Phe Asn Ile Pro Ile Tyr
            260                 265                 270

Thr Pro Ser Leu Glu Glu Phe Lys Glu Val Val Glu Arg Asp Gly Ala
        275                 280                 285

Phe Ile Ile Asn Lys Leu Gln Leu Phe His Gly Gly Ser Ala Leu Ile
    290                 295                 300

Ile Asp Asp Pro Asn Asp Ala Val Glu Ile Ser Arg Ala Tyr Val Ser
305                 310                 315                 320

Leu Cys Arg Ser Leu Thr Gly Gly Leu Val Asp Ala His Ile Gly Asp
                325                 330                 335

Gln Leu Gly His Glu Leu Phe Ser Arg Leu Leu Ser Gln Ala Val Asp
            340                 345                 350
```

Gln Ala Lys Glu Leu Met Asp Gln Phe Gln Leu Val His Ile Val Ala
        355                 360                 365

Ser Leu Thr Leu Ala
    370

<210> SEQ ID NO 13
<211> LENGTH: 1101
<212> TYPE: DNA
<213> ORGANISM: Ruta graveolens
<220> FEATURE:
<221> NAME/KEY: misc_feature
<222> LOCATION: (1)..(1101)
<223> OTHER INFORMATION: 2-oxoglutarate-dependent dioxygenase (RgC2'H,
      C2'H)

<400> SEQUENCE: 13

| | | |
|---|---|---|
| atggcaccaa ccaaagattc agttattcac atgggagcag agtcctggga tgagatttcc | 60 |
| gagttcgtta ctaaaaaggg acacggtgtt aagggtcttt ctgaacttgg tattaaaact | 120 |
| cttccaaagc aattccatca gcctcttgaa gagaggttca gtgagaaaaa gattttggaa | 180 |
| agagcttcaa tcccacttat cgatatgagt aagtgggact cccctgaggt tgtgaagtct | 240 |
| atctgtgatg ctgcagaaca ttggggtttc tttcaaatag ttaatcacgg agtgccattg | 300 |
| gagactttac agagagttaa agaagctaca cataggtttt cgctttgcc tgcagaagag | 360 |
| aaaaataagt actctaagga aaactcacca attaataacg ttagattcgg ttcttcattc | 420 |
| gttcctcatg ttgagaaagc acttgaatgg aaggattttc ttagtatgtt ctatgttccc | 480 |
| gaagaggaaa ctaacacata ctggccacct atttgtagag acgagatgtt agaatacatg | 540 |
| aggagttccg aggttcttat caaaagattg atggaagtgt tagttgtgaa gggtcttaaa | 600 |
| gttaagcaaa tcgatgagat aagagaacca atgttggtgg gatcaagaag aattaatttg | 660 |
| aactactacc ctaaatgccc aaatcctgaa cttacattgg gtgttggaag gcatagtgat | 720 |
| atttccacct ttactatctt gttacaagac gaaatcggtg gacttcatgt tagaaagttg | 780 |
| gatgacactg gtaacacctg ggttcatgtt accccaatat ctggttcact tattatcaat | 840 |
| atcggagatg ctttgcagat aatgtctaac ggaaggtaca agtcaataga acacatggtt | 900 |
| gtggcaaatg aacacaagca cagaatctct gttcctttat ttgtgaaccc aaagcctcag | 960 |
| gctatacttt gtccattccc tgaggttttg gcaaatggag aaaaaccagt ttataagcct | 1020 |
| gtgttgtgct ctgattactc aaggcatttc tacacaaaac ctcacgatgg taaaaagaca | 1080 |
| gtggatttcg cattgatgaa c | 1101 |

<210> SEQ ID NO 14
<211> LENGTH: 367
<212> TYPE: PRT
<213> ORGANISM: Ruta graveolens
<220> FEATURE:
<221> NAME/KEY: MISC_FEATURE
<222> LOCATION: (1)..(367)
<223> OTHER INFORMATION: 2-oxoglutarate-dependent dioxygenase (RgC2'H,
      C2'H)

<400> SEQUENCE: 14

Met Ala Pro Thr Lys Asp Ser Val Ile His Met Gly Ala Glu Ser Trp
1               5                   10                  15

Asp Glu Ile Ser Glu Phe Val Thr Lys Lys Gly His Gly Val Lys Gly
            20                  25                  30

Leu Ser Glu Leu Gly Ile Lys Thr Leu Pro Lys Gln Phe His Gln Pro
        35                  40                  45

Leu Glu Glu Arg Phe Ser Glu Lys Lys Ile Leu Glu Arg Ala Ser Ile
 50                  55                  60

Pro Leu Ile Asp Met Ser Lys Trp Asp Ser Pro Glu Val Val Lys Ser
 65                  70                  75                  80

Ile Cys Asp Ala Ala Glu His Trp Gly Phe Phe Gln Ile Val Asn His
                 85                  90                  95

Gly Val Pro Leu Glu Thr Leu Gln Arg Val Lys Glu Ala Thr His Arg
            100                 105                 110

Phe Phe Ala Leu Pro Ala Glu Glu Lys Asn Lys Tyr Ser Lys Glu Asn
            115                 120                 125

Ser Pro Ile Asn Asn Val Arg Phe Gly Ser Ser Phe Val Pro His Val
130                 135                 140

Glu Lys Ala Leu Glu Trp Lys Asp Phe Leu Ser Met Phe Tyr Val Ser
145                 150                 155                 160

Glu Glu Glu Thr Asn Thr Tyr Trp Pro Pro Ile Cys Arg Asp Glu Met
                165                 170                 175

Leu Glu Tyr Met Arg Ser Ser Glu Val Leu Ile Lys Arg Leu Met Glu
            180                 185                 190

Val Leu Val Val Lys Gly Leu Lys Val Lys Gln Ile Asp Glu Ile Arg
            195                 200                 205

Glu Pro Met Leu Val Gly Ser Arg Arg Ile Asn Leu Asn Tyr Tyr Pro
210                 215                 220

Lys Cys Pro Asn Pro Glu Leu Thr Leu Gly Val Gly Arg His Ser Asp
225                 230                 235                 240

Ile Ser Thr Phe Thr Ile Leu Leu Gln Asp Glu Ile Gly Gly Leu His
                245                 250                 255

Val Arg Lys Leu Asp Asp Thr Gly Asn Thr Trp Val His Val Thr Pro
            260                 265                 270

Ile Ser Gly Ser Leu Ile Ile Asn Ile Gly Asp Ala Leu Gln Ile Met
            275                 280                 285

Ser Asn Gly Arg Tyr Lys Ser Ile Glu His Met Val Val Ala Asn Gly
290                 295                 300

Thr Gln Asp Arg Ile Ser Val Pro Leu Phe Val Asn Pro Lys Pro Gln
305                 310                 315                 320

Ala Ile Leu Cys Pro Phe Pro Glu Val Leu Ala Asn Gly Glu Lys Pro
                325                 330                 335

Val Tyr Lys Pro Val Leu Cys Ser Asp Tyr Ser Arg His Phe Tyr Thr
            340                 345                 350

Lys Pro His Asp Gly Lys Lys Thr Val Asp Phe Ala Leu Met Asn
            355                 360                 365

<210> SEQ ID NO 15
<211> LENGTH: 381
<212> TYPE: DNA
<213> ORGANISM: Artificial Sequence
<220> FEATURE:
<223> OTHER INFORMATION: synthetic plastid targeting signal, organelle
      targeting signal

<400> SEQUENCE: 15
atggcttcga tctcctcctc agtcgcgacc gttagccgga ccgcccctgc tcaggccaac      60
atggtggctc cgttcaccgg ccttaagtcc aacgccgcct tccccaccac caagaaggct     120
aacgacttct ccacccttcc cagcaacggt ggaagagttc aatgcatgca ggtgtggccg     180
gcctacggca acaagaagtt cgagacgctg tcgtacctgc cgccgctgtc gacgatggcg     240

```
cccaccgtga tgatggcctc gtcggccacc gccgtcgctc cgttccaggg gctcaagtcc      300
accgccagcc tccccgtcgc ccgccgctcc tccagaagcc tcggcaacgt cagcaacggc      360
ggaaggatcc ggtgcatgca g                                                381
```

```
<210> SEQ ID NO 16
<211> LENGTH: 127
<212> TYPE: PRT
<213> ORGANISM: Artificial Sequence
<220> FEATURE:
<223> OTHER INFORMATION: synthetic plastid targeting signal, organelle
      targeting signal

<400> SEQUENCE: 16

Met Ala Ser Ile Ser Ser Val Ala Thr Val Ser Arg Thr Ala Pro
1               5                   10                  15

Ala Gln Ala Asn Met Val Ala Pro Phe Thr Gly Leu Lys Ser Asn Ala
            20                  25                  30

Ala Phe Pro Thr Thr Lys Lys Ala Asn Asp Phe Ser Thr Leu Pro Ser
        35                  40                  45

Asn Gly Gly Arg Val Gln Cys Met Gln Val Trp Pro Ala Tyr Gly Asn
    50                  55                  60

Lys Lys Phe Glu Thr Leu Ser Tyr Leu Pro Pro Leu Ser Thr Met Ala
65                  70                  75                  80

Pro Thr Val Met Met Ala Ser Ser Ala Thr Ala Val Ala Pro Phe Gln
                85                  90                  95

Gly Leu Lys Ser Thr Ala Ser Leu Pro Val Ala Arg Arg Ser Ser Arg
            100                 105                 110

Ser Leu Gly Asn Val Ser Asn Gly Gly Arg Ile Arg Cys Met Gln
        115                 120                 125
```

```
<210> SEQ ID NO 17
<211> LENGTH: 1982
<212> TYPE: DNA
<213> ORGANISM: Arabidopsis thaliana
<220> FEATURE:
<221> NAME/KEY: promoter
<222> LOCATION: (1)..(1982)
<223> OTHER INFORMATION: scondary cell wall cellulose synthase
      CesA4/IRX5 promoter, IRX5 promoter, pIRX5

<400> SEQUENCE: 17
atgaagccat cctctacctc ggaaaaactt gttgcgagaa aagacatgc gatggcatgg      60 atgcttggat ctttgacatt gatgacactc ttctctcaac cattccttac cacaagagca      120
acggttgttt cgggtaaata aactaaactt aaccatatac attagccttg attcggtttt      180
tggtttgatt tatggatatt aaagatccga attatatttg aacaaaaaaa aatgattatg      240
tcacataaaa aaaaattggc ttgaatttg gtttagatgg gtttaaatgt ctacctctaa       300
tcatttcatt tgttttctgg ttagctttaa ttcggtttag aatgaaaccg ggattgacat      360
gttacattga tttgaaacag tggtgagcaa ctgaacacga ccaagttcga ggaatggcaa      420
aattcgggca aggcaccagc ggttccacac atggtgaagt tgtaccatga gatcagagag      480
agaggtttca agatcttttt gatctcttct cgtaaagagt atctcagatc tgccaccgtc      540
gaaaatctta ttgaagccgg ttaccacagc tggtctaacc tccttctgag gttcgaatca      600
tatttaataa ccgcattaaa ccgaaattta aattctaatt tcaccaaatc aaaaagtaaa      660
actagaacac ttcagataaa ttttgtcgtt ctgttgactt catttattct ctaaacacaa      720
```

```
agaactatag accataatcg aaataaaaac cctaaaaacc aaatttatct atttaaaaca      780
aacattagct atttgagttt cttttaggta agttatttaa ggttttggag actttaagat      840
gttttcagca tttatggttg tgtcattaat ttgtttagtt tagtaaagaa agaaaagata      900
gtaattaaag agttggttgt gaaatcatat ttaaaacatt aataggtatt tatgtctaat      960
ttggggacaa aatagtggaa ttctttatca tatctagcta gttcttatcg agtttgaact     1020
cgggttatga ttatgttaca tgcattggtc catataaatc tatgagcaat caatataatt     1080
cgagcatttt ggtataacat aatgagccaa gtataacaaa agtatcaaac ctatgcaggg     1140
gagaagatga tgaaaagaag agtgtgagcc aatacaaagc agatttgagg acatggctta     1200
caagtcttgg gtacagagtt tggggagtga tgggtgcaca atggaacagc ttctctggtt     1260
gtccagttcc caagagaacc ttcaagctcc ctaactccat ctactatgtc gcctgattaa     1320
atcttattta ctaacaaaac aataagatca gagtttcatt ctgattcttg agtctttttt     1380
ttctctctcc ctcttttcat ttctggttta tataaccaat tcaaatgctt atgatccatg     1440
catgaaccat gatcatcttt gtgttttttt ttccttctgt attaccatttt tgggcctttg     1500 tgaaattgat tttgggcttt tgttatataa tctcctctctt ctctttctct acctgattgg     1560
attcaagaac atagccagat ttggtaaagt ttataagata caaatatatta agtaagacta     1620 aagtagaaat acataataac ttgaaagcta ctctaagtta tacaaattct aaagaactca     1680
aaagaataac aaacagtaga agttggaagc tcaagcaatt aaattatata aaaacactaa     1740
ctacactgag ctgtctcctt cttccaccaa atcttgttgc tgtctcttga agctttctta     1800
tgacacaaac cttagaccca atttcactca cagtttggta caacctcagt tttcttcaca     1860
acaaattcaa acatcttacc cttatattac ctctttatct cttcaatcat caaaacacat     1920
agtcacatac atttctctac cccaccttct gctctgcttc cgagagctca gtgtacctcg     1980
cc                                                                     1982
```

<210> SEQ ID NO 18
<211> LENGTH: 2897
<212> TYPE: DNA
<213> ORGANISM: Arabidopsis thaliana
<220> FEATURE:
<221> NAME/KEY: promoter
<222> LOCATION: (1)..(2897)
<223> OTHER INFORMATION: cinnamate-4-hydroxylase (AtC4H, C4H) promoter

<400> SEQUENCE: 18

```
cggaatgaga gacgagagca atgtgctaag agaagagatt gggaagagag aagagaagat       60
aaaggaaacg gaaaagcata tggaggagct tcacatggag caagtgaggc tgagaagacg      120
gtcaagtgag cttacggaag aagtggaaag gacgagagtg tctgcatcgg aaatggctga      180
gcagaaaaga gaagctataa gacagctttg tatgtctctt gaccattaca gagatgggta      240
cgacagactt tggagagttg ttgcaggaca taagagtaag agagtagtgg tcttatcaac      300
ttgaagtgta agaacaatga gtcaatgact acgtgcagga cattggacat accgtgtgtt      360
cttttggatt gaaatgttgt ttcgaagggc tgttagttga tgttgaaaat aggttgaagt      420
tgaataatgc atgttgatat agtaaatatc aatggtaata ttttctcatt tcccaaaact      480
caaatgatat catttaacta taaactaacg taaactgttg acaatacact tatggttaaa      540
aatttggagt cttgttttag tatacgtatc accaccgcac ggtttcaaaa ccacataatt      600
gtaaatgtta ttgaaaaata gaactcgcaa tacgtattgt attttggtaa acatagctct      660
aagcctctaa tatataagct ctcaacaatt ctggctaatg gtcccaagta agaaaagccc      720
```

```
atgtattgta aggtcatgat ctcaaaaacg agggtgaggt ggaatactaa catgaggaga      780
aagtaaggtg acaaatttt ggggcaatag tggtggatat ggtggggagg taggtagcat      840
catttctcca agtcgctgtc tttcgtggta atggtaggtg tgtctctctt tatattattt      900
attactactc attgtaaatt tcttttttct acaatttgtt tctgactcca aaatacgtca      960
caaatataat actaggcaaa taattatttt attataagtc aatagagtgg ttgttgtaaa     1020
attgatttt tgatattgaa agagttcatg gacggatgtg tatgcgccaa atggtaagcc     1080
cttgtactgt gccgcgcgta tattttaacc accactagtt gtttctcttt ttcaaaaaac     1140
acaaaaaaaa aataatttgt tttcttaacg gcgtcaaatc tgacggcgtc tcaatacgtt     1200
caatttttt ctttctttca catggtttct catagctttg cattgaccat aggtaaaggg     1260
ataaggataa tggttttttc tcttgtttgt tttatcctta ttattcaaaa aggataaaaa     1320
aacagtgata tttagatttc tttgattaaa aaagtcattg aaattcatat ttgatttttt     1380
gctaaatgtc aacacagaga cacaaacgta atgcactgtc gccaatattc atggatcatg     1440
acaataaata tcactagaat aattaaaaat cagtagaatg caaacaaagc attttctaag     1500
taaaacagtc ttttatattc acgtaattgg aatttccttt tttttttttt gtcgtaattg     1560
gaatttcctt tatcaaaccc aaagtccaaa acaatcggca atgttttgca aaatgttcaa     1620
aactattggc gggttggtct atccgaattg aagatctttt ctccatatga tagaccaacg     1680
aaattcggca tacgtgtttt ttttttttgtt ttgaaaaccc tttaaacaac cttaattcaa     1740
aatactaatg taactttatt gaacgtgcat ctaaaaattt tgaactttgc ttttgagaaa     1800
taatcaatgt accaataaag aagatgtagt acatacatta taattaaata caaaaaagga     1860
atcaccatat agtacatggt agacaatgaa aaactttaaa acatatacaa tcaataatac     1920
tctttgtgca taactttttt tgtcgtctcg agtttatatt tgagtactta tacaaactat     1980
tagattacaa actgtgctca gatacattaa gttaatctta tatacaagag cactcgagtg     2040
ttgtccttaa gttaatctta agatatcttg aggtaaatag aaatagttga ctcgtttta     2100
tcttcttctt tttttaccat gagcaaaaaa gatgaaataa gttcaaaacg tgacgaatct     2160
atatgttact acttagtatg tgtcaatcat taaatcggga aaacttcatc atttcaggag     2220
tattacaaaa ctcctaagag tgagaacgac tacatagtac atattttgat aaaagacttg     2280
aaaacttgct aaaacgaatt tgcgaaaata taatcataca agtgccagtg attttgatcg     2340
aattattcat agctttgtag gatgaactta attaaataat atctcacaaa agtattgaca     2400
gtaacctagt actatactat ctatgttaga atatgattat gatataattt atcccctcac     2460
ttattcatat gatttttgaa gcaactactt tcgtttttt aacatttct ttt tgttggtt     2520
attgttaatg agcatattta gtcgtttctt aattccactg aaatagaaaa tacaaagaga     2580
actttagtta atagatatga acataatctc acatcctcct cctaccttca ccaaacactt     2640
ttacatacac tttgtggtct ttctttacct accaccatca acaacaacac caagccccac     2700
tcacacacac gcaatcacgt taaatttaac gccgtttatt atctcatcat tcaccaactc     2760
ccacgtacct aacgccgttt accttttgcc gttggtcctc atttctcaaa ccaaccaaac     2820
ctctccctct tataaaatcc tctctcccctt ctttatttct tcctcagcag cttcttctgc     2880
tttcaattac tctcgcc                                                   2897

<210> SEQ ID NO 19
<211> LENGTH: 2589
<212> TYPE: DNA
```

<213> ORGANISM: Arabidopsis thaliana
<220> FEATURE:
<221> NAME/KEY: promoter
<222> LOCATION: (1)..(2589)
<223> OTHER INFORMATION: 4-hydroxycinnamate 3-hydroxylase (AtC3H, C3'H) promoter

<400> SEQUENCE: 19

```
atcgtaagtt tttttgtgtg tgtgttaaca atgtactcac tactcactgt tccatatttt    60
tgatgtacgt atatcgaaaa cattctgcca acaaatgcaa acataacaaa agtcaaaaac   120
aataacataa ccgggaatta aaccaaaatg taattgcttt ttattagtgt caggccttct   180
gcttaaaaat attctcggcc cagagcccat taacacctat ctcaattcat attgaagaaa   240
atgactatat tacttgacaa aaactttagt cagaaaaata tggaatctct ttcggtactg   300
ctaagtgcta accttaaata gtatagaatt cttagttcat tctcaaaaac atagctatat   360
gtagattata aaagttcgat attatttcct gcaaaagatg ttataatgtt acaacttaca   420
agaaaatgat gtatatgtag atttttataaa ctggtaccgt aattcataaa agatggtggt   480
gggtatgtat cagtaacgga acttacatat gcgtgtgtat tactatgtct atatggtgta   540
ttcctttgtg tggaacaatg cacgtcagag ttgtttattt tcttatagaa tttaaggaat   600
caattattgg atttctcaag gtgaaagtgg acttctttgc acgcaaggtc tagttgccga   660
cttgccgttg catgtaacat gattgttgaa ataaagtgaa ttgagagaag tttggccaga   720
cattttaaat ttaacccaaa aaaagtaggg cctaacacaa aatataaccct ctctttgttc   780
aaaggaaata acacctacgt cttataattg aaccaaacat tgaatcattg aactcaccta   840
taataattat aataacacga attcacaaga cacctaaaag aaaaagttca caaaaacaaa   900
taaaaatta cctctcacca aacacactca cctacccgtc tggtcccact gaccccaaca   960
tacaacaccg actctctccc acaccaattt ttttttttgg cgttttaaaa caaataaact  1020
atctattttt ttttcttacc aactgattaa ttcgtgaata atctattatc ttcttctttt  1080
ttttgtgacg gatgattagt gcgtggggaa atcaaaattt acaaaatttg ggatgattcc  1140
gattttgtcc attcgattaa ttttggttaa aagatatact attcattcac caagttttca  1200
gatgagtcta aaagataata tcatttcact agtcacttaa aaaagggtt aaaagaacat   1260
caataatatc actggtttcc ttaggtgacc caaaaaaaga agaaaaagtc actagtttct   1320
ttttggaaat tttactgggc atatagacga agttgtaatg agtgagttta aatttatcta   1380
tggcacgcag ctacgtctgg tcggactata ccaagttacc aactctctct acttcatgtg  1440
attgccaata aaaggtgacg tctctctctc tctcaccaac cccaaaccac tttccccact  1500
cgctctcaaa acgcttgcca cccaaatcta tggcttacgg ggacatgtat taacatatat  1560
cactgagtga aaagaagggt ttattaccgt tggaccagtg atcaaacgtg ttttataaaa  1620
atttggaatt gaaacatga tttgacattt ttaatgatgg cagcagacga aaccaacaac   1680
actaagttta acgttcgtgg agtatacttt tctattttcg aagaagacat ataactaagc  1740
tgattgttat tcttcataga tttcttttca ctgcgaataa aagtttgtga acatgtcacc  1800
gtttgaacac tcaacaatca taagcgtttt acctttgtgg ggtggagaag atgacaatga  1860
gaaagtcgtc gtacatataa tttaagaaaa tactattctg actctggaac gtgtaaataa  1920
ttatctaaac agattgcgaa tgttctctac tttttttttg tttacattaa aaatgcaaat  1980
tttataacat tttacatcgc gtaaatattc ctgttttatc tataattaat gaaagctact  2040
gaaaaaaaac atccaggtca ggtacatgta tttcacctca acttagtaaa taaccagtaa  2100
```

```
aatccaaagt aattacctttt tctctggaaa ttttcctcag tagtttatac cagtcaaatt    2160
aaaacctcaa atctgaatgt tgaaaatttg atatccaaga aatttctca ttggaataaa     2220 agttcaatct gaaaatagat atttctctac ctctgttttt ttttttctcc accaactttc    2280
ccctacttat cactatcaat aatcgacatt atccatcttt tttattgtct tgaactttgc    2340
aatttaattg catactagtt tcttgtttta cataaaagaa gtttggtggt agcaaatata    2400
tatgtctgaa attgattatt taaaaacaaa aaaagataaa tcggttcacc aacccctcc    2460 ctaatataaa tcaaagtctc caccacatat atctagaaga attctacaag tgaattcgat    2520
ttacactttt ttttgtcctt tttattaat aaatcactga cccgaaaata aaaatagaag     2580
caaaacttc                                                             2589
```

<210> SEQ ID NO 20
<211> LENGTH: 2600
<212> TYPE: DNA
<213> ORGANISM: Arabidopsis thaliana
<220> FEATURE:
<221> NAME/KEY: promoter
<222> LOCATION: (1)..(2600)
<223> OTHER INFORMATION: htdrooxycinnamoyl-CoA shikimate/quinate
    hydroxycinnamoyltransferase (AtHCT, HCT) promoter

<400> SEQUENCE: 20

```
ttctctaggt tttgaagctt tcctagttct tttggaagcg tgccggacaa gtcattgtcg      60
tatagaaaca gattgataag ttcagagcag tttccaagct ctttagggat ctcacctgag     120
agcattgtag aatagacaga taaagactgg agcttgctta gttgacccaa cgaaacaggt     180
aaagaaccgg atattttcgt tgctgctaac cctaagacct tgagattcct acagtttccg     240
atctcctccg ggatcttccc tgaaagctct gagtttcctc cggctcttat gctctcaaga     300
gtcgagatct ttccgagctc caacgggaga ttctcggata agtagttatc gaaaatctca     360
agattcttga ggctaacgca gtcgccgagt tccggtggga tctttcctgt gaggccattg     420
gagtttaaac aaagttcttg aagattcttg agcttcccta gactcgaagg tatttcacca     480
acaagactat ttgagcttaa atcgataact ataagctccg aacaatctcc gatctcagaa     540
gatatagctc cggtgagatt agtgttggag ataacgagtt tctgaagtga agtaaacgaa     600
gaaatgttag gagggaaagg taaagctaac tgaacagaga cgacattgat ctctgtaacg     660
agtttgttgt ctgaggagga acaagtaatg taaggccatt gacatgggtc agaatcagaa     720
ggattccagc cggagaagac tgacggtggc ggcgagttcg agctgtgaag ccaagaaatc     780
aaagctgaga cttcattggt tgatgcagag gtcgaggaga tgaagaaagc taaaaacaga     840
gacaatgtaa tggaaaaatg agaaacagtt aaggcttttt tcttggaat cggcatttgc     900 aaagacataa gagttttttt ctttgcattt ggctctcaaa tccaaaacaa gccttcttgg     960
ttctgcatcg atctgagtcc tttggcttag ggtttaggga gttttttgct ttagagataa    1020
gcaataagaa agaatgatat attaaatata taaaagtact aaacttcatg tgctctgtct    1080 tttttttttta cctcggggtt ctgtttctag cttcagatta attaattaca gtcattaact    1140
tttctttgaa atatgtttgc caagagcccg agacactatc catagatgac aaaagtcaat    1200
agttatatat acataaaata tcacaaaaca aaaggcattg ttatatata tacagaatca    1260 tttcacttag tagtgttttt tcttataaga ttatgataga aatatggaag catgcatgtg    1320
gttttgcatt gttttcctca attaagtcag gattgtgagt tggtttgttt tcgagacctg    1380
aaccgagcgt ttaagattct tcctcgtttg aagtaaactc cataattgtc cacacctaag    1440
```

```
ctaaaagaaa gtaataacaa gtttaaatat tcatgacaag gaaatatattg cattcagaaa   1500 attgttaaca acgaagtaaa cattttttc aatccgatgc caatagtctc tagcggcatc     1560
aaaagtccac aaactcgata cctctgggta aatgagcgaa tgggccggtc cgttgtagcc   1620
cagaagagaa attgtcctct aaattccata cttccatgaa ttttctctgt atatcctcgt   1680
ttgatgtatg gtatatttgt tccgctctaa atcatgacca acccaaggta ctaaattgtc   1740
atttaagctt tgattggtat tggtagcat gggttaccat tgaccaaccc acggtactag    1800
ttgcttttct tttagttttg cttttgcttt attttcttag agagtgggag gacaaaaggt   1860
ttggatcatt aagccaatga atgcttcaaa gaaattgaat ttttattaga tcctcaaacc   1920
aagttggatc atcaaataat ggctaagaaa taattttaga acagaaagca aagaaaagct   1980
atccgcaaca acaaccatta gttaataaat taaaatgaaa tgtgaaattt atgactaatt   2040
gaggtatgtt ttcatataat atagtatagt tcggatataa attcaacata atttatttgt   2100
ggtgtactga aaaaaagact ttcttggatt ctgacgtaat tctcttaaca cgtgagttta   2160
cgccgttaga tgttattggt ggttgttgtt atgctctgct acgtggtaat gagttaagtt   2220
aagccaaact ttggcattcg attgactaac ttgtacggta gctataacaa tcaacttgtc   2280
aatttttttt ccttcttctt cattcgaact ttatactatt taagcccatt agtattattt   2340
gggccttagg acagagggaa cgggtttacc aaccccggat agaaaagtag gaccgagtga   2400
tgagatggac caatgataaa ccttctgaga gagttggtcg acagatggag taggcggggt   2460
cgtggggcgg taggtgaagg attacgacct ttccttttt gttcacaccc acttatatct   2520
acccctcctc gcttctcaca caatttctca gatcaaactc aaaacaaaat ttgtttgttc   2580
gtttgatctt tcttaaaaat                                               2600
```

<210> SEQ ID NO 21
<211> LENGTH: 2600
<212> TYPE: DNA
<213> ORGANISM: Arabidopsis thaliana
<220> FEATURE:
<221> NAME/KEY: promoter
<222> LOCATION: (1)..(2600)
<223> OTHER INFORMATION: hydroxycinnamoyl-CoA NADPH oxidoreductase
      (AtCCR1, CCR) promoter

<400> SEQUENCE: 21

```
ttgctttctc tgtccatgat atgaggcatt gacttctcac ctgtattcat atggtataga     60
ttcctctttt caggagtcca atacaaacga gcttggtgaa gaactcgttg gtaagagagt    120
taatgtctgg tggccactcg acaagaagta agtttattgt taaacttact aacttcattt    180
ttgatactat atgatgaatg atagcaatct tacgatttgt atttgcacag gttttatgaa    240
ggtgtcataa aatcttattg tagagttaag aagatgcatc aagtgagtta acttctctat    300
ttggtatttt aaaattctct atttattgca taactggttt atatagaatt ttcccactga    360
tggtctcgca ggtaacatat tctgatgcg atgttgaaga gcttaatctg aaaaagaac     420 gttttaagat aatcgaggat aaatcttcag ccagtgaggt gaaaatttct tacattctat    480
cattcaccat tctttatatt taccaaaatt tcaatgtatc tggtttccct aataaaatct   540
aagcaggata aggaagatga tctgcttgag tctactcctt tatctgcctt gtaagtgaaa   600
cttccatagt tctatgataa cccacaattt ataattttaa tttagcttta gtcttgagtt   660
ttttgctgtt atgtgcagta tacaaaggga gaaatccaag aagaggaaaa ttgtgtctaa   720
gaatgtggaa ccgagtagtt ctccagaagt caggtatgaa agtatataag aattctagtt   780
```

```
ttagttgttt gaaagtttga tccgtgagtg aattagttca caattatgga tgtagatcct      840
ctatgcaaac aatgaagaag aaagactctg taacagactc cattaagcaa acaaaaagaa      900
ccaaaggtgc actgaaggct gtaagcaatg aaccagaaag cactacaggg aaaaatctta      960
aatccttgaa aaagctgaat ggtgaacctg ataaaacaag aggcagaact ggcaaaaagc     1020
agaaggtgac tcaagctatg caccggaaaa tcgaaaaaga ttgtgatgag caggaagacc     1080
tcgaaaccaa agatgaagaa gacagtctga aattggggaa agaatcagat gcagagcctg     1140
atcgtatgga agatcaccaa gaattgcctg aaaatcacaa tgtagaaacc aaaactgatg     1200
gagaagagca ggaggcagcg aaagagccaa cggcagagtc taaaactaat ggagaggagc     1260
caaatgcaga acccgaaact gatggaaaag agcataaatc attgaaggag ccaaatgcag     1320
agcccaaatc tgatggagaa gagcaggagg cagcaaaaga gccaaatgct gagctcaaaa     1380
ctgatggaga aaatcaggag gcagcaaaag agctaactgc agaacgcaaa actgatgagg     1440
aagagcacaa ggtagctgat gaggtagagc aaaagtcaca gaaagagaca aatgtagaac     1500
cggaagctga gggagaagag caaaagtcag tggaagagcc aaatgcagaa cccaagacca     1560
aggtagaaga gaaagagtca gcaaaagagc aaactgcaga cacaaaattg attgagaagg     1620
aggatatgtc taagacaaag ggagaagaga ttgataaaga aacatattca agcatccctg     1680
agactggtaa agtaggaaac gaagctgaag aagatgatca gagagtgatt aaggaactgg     1740
aagaagagtc tgacaaggca gaagtcagta ctacggtgct tgaggttgat ccatgaatga     1800
aggattgtta ggtaaatgtt aatccaggaa aaaagattg gttcttgtgg tttaggtaac     1860
ttatgtatta agtgaagctg cttgtttaga gactaatggt gtgttttatg agtagattct     1920
tctgacctat gtctcgttat ggaactagtt tgatcttatg tcaccttgct agcagcagat     1980
attgatatt atatattaa gagacatgcg catgagaatg agggtatgga aaagtccata     2040
tcagatgaca caaacaatga tcgtatgtgt agtcacttgt gcatttccag ttttggacat     2100
aaaattctga tattgcatag aaatgttttt aaataacact aatccaaacc taaataaaat     2160
atctctatac atcatctaga aatgtatggc ttgatcaaga attgtagata ataatacct     2220
gagttaaatg attgtaggta ttatttcagt tttcaaaatt gtccaaattt atgagctata     2280
ttaaagataa tattttcaat aaggtgtgta gttctaaatg tttcttcttc ttccaccaac     2340
ccctcttct atatgtatgt tcttttttct aaaataattg tttgttcttt tttagatata     2400
tcaaattaaa tataaaaat attgacaaaa cttatttacc attgttaggt gaacttggca     2460
agtgtgtaaa tataaagata acattccttt tcgttcttta tatatacgaa acgtaccaca     2520
aatttctaac taaagcattc atagtctctc gaaagcctct tttcagaacc gaagctcttt     2580
actttcgtcc accgggaaat                                                 2600
```

<210> SEQ ID NO 22
<211> LENGTH: 2600
<212> TYPE: DNA
<213> ORGANISM: Arabidopsis thaliana
<220> FEATURE:
<221> NAME/KEY: promoter
<222> LOCATION: (1)..(2600)
<223> OTHER INFORMATION: hydroxycinnamyl alcoholdehydrogenase AtCAD4, CAD) promoter

<400> SEQUENCE: 22

```
cagaaaggtc ttcacactct gttttagcta gagagtttta tccatctgag tttttagtct       60
attttgtttt atctaggagt tgctttgttt gttcgaattc ggtcattgct tttgctgctt      120
```

```
tactggagtc aaatttgaag gtaaaatata tgttaaatat ctgggtaggt ggttgtggat      180
gatggaaaat ctgaacgtat cactgttaat gacaatggag aactcgtttc tactcagcat      240
gctatcaccg aataccgagt gattgaatct tcaccacatg gttagtgaga ctgacttcca      300
tttctattca gttaaactta aagcaaatga ttttgcctrg agttttttagc acattgttga      360 attgcaggat acacatggct tgagcttcgc cctttaaccg ggagaaaaca tcaggtctct      420
atagatattc agttttttgtt tcaactttct ctcttttta tgttctctta atactaatct       480
gttttcaact gttcttcgat tgccacagct tcgtgtacac tgcgctgaag tgctaggaac      540
accgatagtc ggggactaca aatacggttg gcaagctcat aaagcccggg aacctttttgt     600 ctcttctgaa acaacccaa ccaagcaatc atcatctcct tttggattgg atctggatgg       660
tggagatgtc tcttcgaaac agccacacct tcatctccat tcaaagcaaa tcgatctgcc      720
aaacatatca cagctcttgg agaaaatgca ggtctcttca gactctgata tttcggatct      780
cgatagcctt aaattcgatg ctccattgcc tagtcatatg caactaagct ttaatttgtt      840
gaaatctaga gtcgaaactt gtgacaaaaa ttagattttt ttcttaccg agctttcttc       900 tttgtgttca ttgaggccca agtatttgtg tatttggacc tgaatattct catacaaaga     960
taaataatta taattaaatg atttttcgca tataatcatt attgtggtat gattaacaca      1020
gttggtgtga tgactgattg acacaataat caccgtttgg attcgattcc tttaatactt      1080
gtcactagag ttgtttgact aaacagctaa cttgtcacta gagttattgt gtttgtattt      1140
tgatctgtta ttaatctgat tgggtataat tacagataga gagacatcta tattgtaatt      1200 aagcaatct taaagtgtaa actaaaaaga tctctctgac ctctggaaaa cgaaaggtgg       1260
gtgacacatc actctagcta tgaatatgat gaatattcag tacctaaccg aacaaagact     1320
ggtttggtat tttattgga aaaaagagat aaataattgt gaatgtgaat tatcctgtct       1380
gaaaggtaag ctgatgacat ggcgttatat gattggacga gcttcagaac aaaagagtag     1440
cgtcgaatcg aatctttacc tactacactt tgaactttga agtacattac ctacttcctc      1500
cttgatcgaa cgtctttct caaaactatt ttatttcccc aattaaagta gtggtgataa      1560
attcacaaaa atacaaacac ttttatttt gacgtcaaaa acaaatactt ctttgaacag      1620
gctattacaa tatttttaag aaaaaagtaa gcaaaatagt ccacaaacca aaatctgtaa     1680
catattaaac gatttatgtt ttttttttt tttcttaact agagaacaat tcgggctttt      1740
actaaggatg atgagtgtag ttaccgaata gtgtattcat ataatctttt aatgagctta    1800
agatatgata ttatttcgac taatcagata agagtagtta gataatttcg taatagagca    1860
actctttcgc aaataaaacc attgtaaaca ttaccaatta gttttctttt tttttggtc      1920 acaaccaatt agtttgtttg ttctatttta tgaagtgcgt attaaagcta acgtgtttac    1980
agtaacgcca cacaaataaa aataaaaata attatgtact ttatggattt atagaaaaaa    2040
caagaatagt caccaaaaat tgattgtgtc atatatcttt tgtcaactat tttatcttat     2100
ttttctatgg atatgtatgt ccaaaatgtt agacaaaaaa ccaaaaaatc atgtccaaaa    2160
tttcgttagg ctgccgatat ctctgttttcc ctttcaacga ctatctattt aattaccgtc   2220
gtccacattg tttttaatat ctttattcga ggttggttta gttttttta ccaaactcac      2280 tttgctacgt ttttgccttt tggtatggt tgtatttgta ccaccgggaa aaaaagata       2340 agaggtttgg ttggtcgagc ttactgatta aaaaatatac acgtccacca aatattaaaa   2400
caatatatcc cattttcct cctctctttt ggtattacat taatatttta ttatttcccc      2460
atttgctctg tatatataaa catatgtcaa tagagtgcct ctacagtcat gtttccatag    2520
```

```
acataatctc tcaccattgt ttttctctgc aaaactaaag aaacaaaaaa agaaaaatcg    2580
gagaaaccaa gaaaaaagaa                                                2600
```

```
<210> SEQ ID NO 23
<211> LENGTH: 2600
<212> TYPE: DNA
<213> ORGANISM: Arabidopsis thaliana
<220> FEATURE:
<221> NAME/KEY: promoter
<222> LOCATION: (1)..(2600)
<223> OTHER INFORMATION: hydroxycinnamyl alcoholdehydrogenase AtCAD5,
      CAD) promoter

<400> SEQUENCE: 23
```

```
cctcgataac tctgattgtt gtattgtcca agtattcact aaacaacttt gctaaaagag      60
aagatgctgc tggagcaatt tcagaaggtt ttagcacaac cgcattacca gctgcaatag     120
ctccaatgac tggctcgaca gacaatacta aggaaaaaaa caaagcacca tgaagacata     180
taaactttaa tagtttagaa attgagacaa aattgtcaat aaataaaatt gagcttacag     240
aaagggaaat tccaggctga aataaccaaa acaactccaa gcggttctga gactatttgt     300
gcagacgagg gaaatgttgt cacagaagtt ttgacctgaa aggtccaagc atagaaaaag     360
caagtggttt tagaaaggac acatatcaat gaagcagcaa agcttgaacg gtctagttac     420
cgtttctgga gccatccagt tctttaactc tttgattgca agcatacagg atgattttgt     480
attcgaaatc taaaaaacga gaaaaatacc aaagagattc aacagtggat aagtggaatg     540
cagtgaagaa acgggacatt gaaattatat aaaaaacctc agctagaaaa gcttcaagct     600
caggcttaga aagatcttga tacaaagctt cggtgatgca tttctccttc tcatcaatca     660
tcctagcaat gttttgaagc tgagaaattc tccactcgta gctcttcgtt ctgccagagt     720
tgaagttgct tctgagctca tctacaagca aagctgcttc ttttccacta aagtctgatg     780
cttgctcctt taccacagca gatagtgttg cataacaagt actgattcaa gacaccaaaa     840
ccgcaatgtg agagacttta agactaaaaa tcatggataa gactaaaaaa acatggataa     900
gtatcaactg ttctcacgat tatttattca taccactgta cttaaactta aaacccacta     960
tactaaatag aaaggtaatc atcaaaaaat cagtatgtaa aaaccacttt tgtgaataaa    1020
atatgtaaaa tgggtgaata aagaaatgtg cttacaattt caaccgataa gggatacaag    1080
cattgctgca atatccacca ccaccacgac gagatatccg aaaaggtgaa gttgcaacat    1140
ttaatctgca acaaaagagg ccattcatta aaatggtact aattagatct aatcatatca    1200
tattgaatga ccaaatcatt cacagaagca tccattgctc aattaacat tctagaccaa     1260 attcaactta aaggtaactc ttttatacag gaaaccgaga aaccgaaaac gcaattcaca    1320
taaaaaggaa ggcttgtttg gagaagcaga atcgaacaag tcaatctcaa accctgatga    1380
gcaggttttt caagttacct ggcaggagaa aaacccttgg caaaacaaag ggtttgaata    1440
tgattaatct ctagaagctt cgtcatgact tgggttcagt taaaaatctc aaattggaga    1500
cattattggt gtttatatat ttgagagaga gagccagaga ggagacgttg aattgaatga    1560
agggtgtggt cggaagagaa gacgtgtaga agagacgaga caagtaaatt taagcattgg    1620
ccccatttac agccacaagt ccgctacaac aaattatttc caagaaactc tgagataacg    1680
tcgtgatgaa acggctcatg ctgctgttgt gattcgtgaa ttagaggttt atcttttggg    1740
tttttgaatg ttacttaatt ggacggtcga ttttcaaac tgggtgtgaa atgtgaatgg     1800
gtcattcata atgggctttt gttttaatgt gaagccattc acacactctt tgtccttctt    1860
```

```
ttctattatt cataactgtc actctttgtt cttcgaaata gtaaagagca aatcgattct    1920
ttgttgatct gggccgtaaa atttccatgg ttgtgggaag tattctcgca gctgatctgg    1980
gccgtcaatg ctacagtttc atgtcagaga gaggtcaaga atcaacacgt ggccaaccat    2040
gattttaaac caaagcaaac acacgattag accccacatt gtttgttcac caaccccgt     2100 ggaccctcct ttagccgacg tgtccacgtc aatagtggtt tttcttcctt tcaaagtaca    2160
caaattccat tctttctcat tttactttt ggattacgtt gttgttataa actggtaaaa     2220
tgaattatga atgcaaataa atttcattta agttttgttg cttctaata ttttttttcac    2280 ctaaaattct aataaactac acagccatga gccatcgtat gaaaagaaga agaaaaaaaa    2340 tgtcttttc tagaaggatc tttcaacgac taaaaaagat tttaagcttt tgactaattt     2400
tgtcaataat atacacaaat ttacactcaa ttatagccat caaatgtgtg ctatgcagaa    2460
acaccaatta tttcatcaca catacgcata cgttacgttt ccaactttct ctatatatat    2520
atatagtaat acacacacat aaacagcaaa agcgtgaaag cagcagatca agataagaaa    2580
gaagaaagaa tcatcaaaaa                                                2600

<210> SEQ ID NO 24
<211> LENGTH: 2600
<212> TYPE: DNA
<213> ORGANISM: Arabidopsis thaliana
<220> FEATURE:
<221> NAME/KEY: promoter
<222> LOCATION: (1)..(2600)
<223> OTHER INFORMATION: ferulate 5-hydroxylase (AtF5H, F5h) promoter

<400> SEQUENCE: 24
tgtgtgtctt tttgcgagta gttgttggct tcagacagtt catagcggag ttactctata     60
cgcgaagtac ttgtctcata ctgataattt tgatggcaat taaggcttta aaagcttatg    120
tattttctta taaccatttt attctgtata taggggaca gaaacataat aagtaacaaa     180
tagtggtttt attttttaa atatacaaaa actgtttaac cattttattt cttggttagc     240
aaaattttga tatattctta agaaactaat attttaggtt gatatattgc agtcactaaa    300
tagttttaaa agacacgaag ttggtaagaa caggcatata ttattcgatt taattaggaa    360
tgcttatgtt aatctgattc gactaattag aaacgacgat actatgagct catagatggt    420
cccacgaccc actctcccat ttgatcaata ttcaactgag caatgaaact aattaaaaac    480
gtggttagat taaaaaaata aattgtgcag gtagcggata tataatacta gtagggtta    540 aaaataaaat aaaacaccac agtattaaat ttttgtttca aaagtattat caatagtttt    600
tttgcttcaa aaatatcaca aattttgta tgaaatattt ctttaacgaa aataaattaa    660
ataaaattta aaatttatat ttggagttct attttttaatt tagagttttt attgttacca   720
cattttttga attattctaa tattaatttg tgatattatt acaaaaagta aaatatgat     780 atttagaat actattatcg atatttgata ttattgaccc tagctttgtt tgggtggaga    840
catgtgatta tcttattacc tttttattcc atgaaactac agagttcgcc aggtaccata    900
catgcacaca ccctcgtgaa acgagcgtga cttaatatga tctagaactt aaatagtact    960
actaattgtg tcatttgaac tttctcctat gtcggtttca cttcatgtat cgcagaacag   1020
gtggaataca gtgtccttga gtttcaccca aatcggtcca attttgtgat atatattgcg   1080
atacagacat acagcctaca gagttttgtc ttagcccact ggttggcaaa cgaaattgtc   1140 tttattttt tatgttttgt tgtcaatgtg tctttgtttt taactagatt gaggtttaat    1200
```

```
tttaatacat tgttagttt acagattatg cagtgtaatc tgataatgta agttgaactg      1260
cgttggtcaa agtcttgtgt aacgcactgt atctaaattg tgagtaacga caaaataatt      1320
aaaattaaag ggaccttcaa gtattattag tatctctgtc taagatgcac aggtattcag      1380
taatagtaat aaataattac ttgtataatt aatatctaat tagtaaacct tgtgtctaaa      1440
cctaaatgag cataaatcca aaagcaaaaa tctaaaccta actgaaaaag tcattacgaa      1500
aaaaagaaaa aaaaaagaga aaaaactacc tgaaaagtca tgcacaacgt tcatcttggc      1560
taaatttatt tagtttatta aatacaaaaa tggcgagttt ctggagtttg ttgaaaatat      1620
atttgtttag ccactttaga atttcttgtt ttaatttgtt attaagatat atcgagataa      1680
tgcgtttata tcaccaatat ttttgccaaa ctagtcctat acagtcattt ttcaacagct      1740
atgttcacta atttaaaacc cactgaaagt caatcatgat tcgtcatatt tatatgctcg      1800
aattcagtaa aatccgtttg gtatactatt tatttcgtat aagtatgtaa ttccactaga      1860
tttccttaaa ctaaattata tatttacata attgttttct ttaaaagtct acaacagtta      1920
ttaagttata ggaaattatt tcttttattt tttttttttt ttaggaaatt attttctttg      1980
caacacattt gtcgtttgca aacttttaaa agaaaataaa tgattgttat aattgattac      2040
atttcagttt atgacagatt ttttttatct aacctttaat gtttgtttcc tgtttttagg      2100
aaaatcatac caaatatat ttgtgatcac agtaaatcac ggaatagtta tgaccaagat      2160
tttcaaagta atacttagaa tcctattaaa taaacgaaat tttaggaaga aataatcaag      2220
attttaggaa acgatttgag caaggattta gaagatttga atctttaatt aaatattttc      2280
attcctaaat aattaatgct agtggcataa tattgtaaat aagttcaagt acatgattaa      2340
tttgttaaaa tggttgaaaa atatatatat gtagattttt tcaaaaggta tactaattat      2400 tttcatatt tcaagaaaat ataagaaatg gtgtgtacat atatggatga agaaatttaa      2460
gtagataata caaaaatgtc aaaaaagggg accacacaat ttgattataa aacctacctc      2520
tctaatcaca tcccaaaatg gagaactttg cctcctgaca acatttcaga aaataatcga      2580
atccaaaaaa aacactcaat                                                  2600
```

<210> SEQ ID NO 25
<211> LENGTH: 2600
<212> TYPE: DNA
<213> ORGANISM: Arabidopsis thaliana
<220> FEATURE:
<221> NAME/KEY: promoter
<222> LOCATION: (1)..(2600)
<223> OTHER INFORMATION: phenylalanine ammonia-lyase (AtPAL1, PAL) promoter

<400> SEQUENCE: 25

```
caaatagtac gatgtattta gtgatttat ttatgtactt tgttcattaa attagtcata        60
attgttctga ttttaggggg ttttgatcga acccttagat caaaagttac cttaattgtt       120
tttttagcta agtactttat taaaaattta atgtttagtt ctgattgagt agtactataa       180
aggagacatg tgtcaatctt gtcaattggt tttgagttca acaatatgca atattgcaca       240
tgcattaacg accaaaagaa gatgcaatgc acttaaatca ttgaaactga ttttgttttt       300
gtagtgtata aaatatctat ttaattacca acgaaagaag tgagcttta aaaacaaaga        360 gtcagaagat atatataact acaaaaccta cagaagataa gctggatttc aaaagaagag       420
aaagagtaaa ccaataaaatt gaccaaagca aaatcggata tttgacataa gtttccattc      480
acattgaccc aaatccacca gcatttcaaa taaagttact aatataatt tttgtgttta        540
```

```
taatatattc cgcccactct tgccttcatt tggaccttat cctaaaagtc aaaacaggtg    600
aaaaaaatga gaatacaatt aacacgaaaa atgcaaaaga ctgttaaacc gaaatcgaat    660
tctagtgtaa tcaatccttt tcccaatgat acaactataa atcaaaaaga aaaaatgtac    720
tgataaacga aactaaacgt ataaattaat atatttcttg acataaatag gaggcttttg    780
cctgctagtc tgctacgatg gaaggaaaaa tgcatgcaca catgacacat gcaaaatgtt    840
tcaatgaaga cgcattgccc aattaaccaa cacaccactt cttccattcc acccatatta    900
tttatttcta ccatttcctt taatttattg ttttttcttt gattcataca ctgtttatga    960
ctattacatt ttccctttcg actaatatta acgcgtttaa accaaagaat ggatttgata   1020
atgaaatttt attttattag catatagata atggatggct tcatgcttgg tttccatgac   1080
aaggaatgac acaagataat tatttttgaat aaaatcataa atatgataat actagttgta   1140
aaaaaacttg agtgtttcgt gtgttatttt tcggtttctt gacttttat atttctcgtt    1200 tttgtaattt taggatggat tatttagctt gcttttctct tttattactt tctaaaattt   1260
tatttataaa ctcattttta atatattgac aatcaataaa tgagttatct tttaattaat   1320
aaaaaatttg taaactcttg taaacagatc atagtcacta aaagctatta taagttattt   1380
gtagctatat tttttattt catgaactta ggataagata cgaaaatgga ggttatattt    1440
acataaatgt caccacattg cctttgtcat gcaaacggcg tgttgcgtca ctcgcctcct   1500
attgggaatc ttataatcgc gtgaatatta ttagagtttg cgatatttcc acgtaatagt   1560
tatctttcac aaattttata ctcaattaca aaatcaacga aaatgtacat ttgtatcttt   1620
aactatttac gtttttttta cgtatcaact ttcagttata tgttttggat aatatatttt   1680
tttacttttg acttttcagt tttcacctaa tgattgggat atacatatgc atgcatagtt   1740
cccattattt aaatgtaagc taagtgcata tgaactgtta gtcaaaatta cgaagtttat   1800
ttgtacatat atatagttat aacaaaatgg tacagtaaat taaacagaac atcaagaaag   1860
tacaaaagac tgaacacaat aatttacatg aaaacaaaac acttaaaaaa tcatccgata   1920
aaatcgaaat gatatcccaa atgacaaaaa taacaatata gaaaatacaa aaacaaaaac   1980
aaaatatgaa agagtgttat ggtggggacg ttaattgact caattacgtt catacattat   2040
acacacctac tcccatcaca atgaaacgct ttactccaaa aaaaaaaaaa aaaccactct   2100
tcaaaaaatc tcgtagtctc accaaccgcg aaatgcaact atcgtcagcc accagccacg   2160
accactttta ccaccgtgac gttgacgaaa accaaagaaa ttcaccaccg tgttaaaatc   2220
aaattaaaaa taactctctt tttgcgactt aaaccaaatc cacgaattat aatctccacc   2280
actaaaatcc atcactcact ctccatctaa cggtcatcat taattctcaa ccaactcctt   2340
ctttctcact aattttcatt ttttctataa tctttatatg gaagaaaaaa agaaactagc   2400
tatctctata cgcttaccta ccaacaaaca ctaccacctt atttaaacca cccttcattc   2460
atctaatttt cctcaggaac aaatacaatt ccttaaccaa caatattaca aataagctcc   2520
tatcttcttt ctttctttta gagatcttgt aatctcctct tagttaatct tctattgtaa   2580
aactaagatc aaaagtctaa                                                2600
```

<210> SEQ ID NO 26
<211> LENGTH: 2600
<212> TYPE: DNA
<213> ORGANISM: Arabidopsis thaliana
<220> FEATURE:
<221> NAME/KEY: promoter
<222> LOCATION: (1)..(2600)
<223> OTHER INFORMATION: phenylalanine ammonia-lyase (AtPAL2, PAL)

promoter

<400> SEQUENCE: 26

```
gattgatggt ttaataatct gcctcgtgat acatggtgtt atcttaaaat ggtctctcaa      60
ttagtctttg tatttgtata aaataaggcc taaaaatatc atcaatgggg tcctgttaaa     120
aacaaaaaca gatacacctt tcactaataa aaaaaaactg ttaccgacaa gtcaaacaat     180
atctgcggac aaaaaaatga agaatgttta gtaagaaata gaagatgtgg taaagagcca     240
tacacacatg caagtgtttt tcaatgaacc catcttacca acccactact tctttgagcc     300
ataattgttt ggttcggaga ccctttacat ttccgtctca gctttatttg tttacgcatt     360
gatttgtctt aaattatgtt agatattgtt ttttggctat ttattagcag caatcaagtt     420
aaaagagtgg ttcgatatca ccatcgaact ctcctttaga tattttctat ataaaaccaa     480
acaaaaacaa aaaaattggt ccgatcatct aatatacaag ttagacgatt tcacgttatg     540
ttattacaac ctacaacaaa atagactatg atcgaaatca tattgaatct tttacctttc     600
aacgtaatac aaatctggct ttacaaagca ataattcatg tttgtttgtc taatttaaat     660
ttccctgttt ttttccccct ctttctgttt cccatttgaa agtaaaagat catttaagca     720
cctaactcaa ttttatttta ttttaaacac ctaatgtcat gctccttggc tccttgtaat     780
tagttgatcg tttcaattta gaccagcaaa acattttagt atgttcgtaa atattgcgta     840
catgccattt cgtttgtcat gcaaacggtg tgtgttctt tacttagctt ctagttggtg      900
tatattgcgt cgcattaata tcggtttacc ttcctcctgt ctacgtaatg atatattctc     960
caccacaaat ttaaattctt attgaaattt cctaattttt taggtagctc aaggtctcaa    1020
gtatactacg taccctattt ttttgaatat ctatctatat tataacaaga gttttttctga   1080
gctagttaat gagatgacaa tattctacat aaataaatga ccctcgaaag tttcaagtac    1140
tttaggatct gaccaaatcg gggtaaaaca ttttgaaact aattacgttc acatctacca    1200
tcgatgattg acaagcttat tgtcaccttt tatgttaaag tgacatggtc ttgacgttaa    1260
tttgcatgtt attctacatc tatagtccaa agatagcaaa ccaagaaaaa aaattgtcac    1320
agagggttca atgttactta gatagaaatg gttctttaca ataataaatt tatgttccat    1380
tcttcatgga ccgatggtat atatatgact atatatatgt tacaagaaaa acaaaaactt    1440
atattttcta aatatgtctt catccatgtc actagctcat tgtgtataca tttacttgct    1500
tcttttttgtt ctatttcatt tcctctaaca aattattcct tatattttgt gatgtactga   1560
attattatga aaaaaaacct ttacacttga tagagaagca tatttggaaa cgtatataat    1620
ttgttttaatt ggagtcacca aaattataca aatcttgtaa tatcattaac ataatagcaa   1680
actaattaaa tatatgtttt gaggtcaaat gttcggttta gtgttgaaac tgaaaaaaat    1740
tattggttaa taaaatttca aataaaagga caggtctttc tcaccaaaac aaatttcaag    1800
tatagataag aaaaatataa taagataaac aattcatgct ggtttggttc gacttcaact    1860
agttagttgt ataagaatat attttttttaa tacatttttt tagcaacttt tgttttttgat   1920
acatataaac aaatattcac aataaaacca aactacaaat agcaactaaa ataattttttt   1980
gaaaacgaaa ttagtgggga cgaccttgaa ttgactgaac tacattccta cgttccacaa    2040
ctactcccat ttcattccca aaccataatc aatcactcgt ataaacattt tgtctccaa     2100
aaagtctcac caaccgcaaa acgcttatta gttattacct tctcaattcc tcagccacca    2160
gccacgacta ccttttcgat gcttgaggtt gatatttgac ggaacacaca aatttaacca    2220
aaccaaacca aaaccaaacg cgttttaaat ctaaaaacta attgacaaac tcttttttgcg   2280
```

```
actcaaacca aattcacgtt ttccattatc caccattaga tcaccaatct tcatccaacg    2340
gtcatcatta aactctcacc caccctcat acttcacttt ttttctccaa aaaatcaaaa     2400
cttgtgttct ctcttctctc ttctcttgtc cttacctaac aacaacacta acattgtcct    2460
tcttatttaa acgtctcttc tctcttcttc ctcctcagaa aaccaaaaac caccaacaat    2520
tcaaactctc tctttctcct ttcaccaaac aatacaagag atctgatctc attcacctaa    2580
acacaacttc ttgaaaacca                                                 2600

<210> SEQ ID NO 27
<211> LENGTH: 2600
<212> TYPE: DNA
<213> ORGANISM: Arabidopsis thaliana
<220> FEATURE:
<221> NAME/KEY: promoter
<222> LOCATION: (1)..(2600)
<223> OTHER INFORMATION: 4-hydroxycinnamate CoA-ligase (At4CL1, 4CL)
      promoter

<400> SEQUENCE: 27
acataagatt tggattatga gaggagttga gaagttatat gatggaaact gaaaagtaaa    60 tcttttgca gagctgtaga atcaatcaac atttgatgac ttggacttct tcaccatgtg     120
tgttggtgtg gaccattgaa ttgacggttt tgccattcac caacaacagc atgagttttt    180
gagtcttcat gtttggtaaa ggttaggctt attaggagac acgggtaaga gactagagag    240
agacattctc caaaccttc ttttgcatgt tttgtaagaa acatttccga aaatgaaaga     300
aatcttacac aacattcata taatttgttt gaaatataaa aaaatgataa tttatactct    360
caagtaaaat gcctaaactt ttatcaattg gaaaagacat cacacacaag cgtgaagcgt    420
atcttattac caaacccaac taagcatggg tctcgatact tgccataatt actttaatcc    480
attctctttt tgagaaatgt ataaaacatg actttgcata aatagtcttt tactaattac    540
tatgtaaata attcctaaga ctggtttcat ggtacatatt atcgttttat ccttgtttta    600
agaatattca gatgtttggt ctatggaata tagtctattc ttcatgttta aaactattat    660
ttgataagaa aatatgtact aatatgtttt tgcatacaaa tgttgatcag ttcgtagcat    720
ttgaattaat acattctcaa tcactttcaa gcattattat gtaataaatg attcatgtcg    780
aaaagtaata gtatcactgt ccattacatt tggcatatat attttttgt caaagcctta    840 catttggcat attgacgaag cagttttgta ttcacttata ttttgacatc gctttcacaa    900
aaataaatag ctatatatga ttattatcca ttaattgtct cttttctttt gctgacacaa    960
ttggttgtaa atgcaatgcc aatatccata gcatttgtgt ggtgaatctt tttctaagcc    1020
taatagtaaa taaatctcaa tacaagaacc catttacgaa caaatcaaac caagttgtga    1080
tgggttagta cttagtagcc cgtttgaaat gtagaatttt tgatgagatt ttacgtttta    1140
tatagatttt tctcagaaaa caaaaaattc ttgcatcttg cattttggtc atttgtaaat    1200
atttttttag tcttaaaaaa gacccaaatt cttattaatt tcaaaatttt cggtctctaa    1260
tacctccggt tttaaaaaaa aacatatcag ttgaaggatg agtttggtga aggctatatt    1320
gtccattgat tttggagata tatgtattat ggtcatgatt attacgattt ttatataaaa    1380
gaatattaaa aatggtgggg ttggtgaaga aatgaagatt tatcgtcaaa tatttcaatt    1440
tttacttgga ctattgcttc ggttatatcg tcaacatggg cccactcttc caccaaagcc    1500
caatcaatat atctctcgct atcttcacca acccactctc cttctcttac caaacccatt    1560 tccttttattt ccaaccctac ccctttattt ctcaagcttt acacttttag cccataactt    1620
```

```
tcttttatc caaatggatt tgactggtct ccaaagttga attaaatggt tgtagaaata    1680
aaataaaatt atacgggttc aattgttcaa ttgttcatat accgttgacg ttcaattgtt    1740
catatacggg ttccgtggtc gttggtaata tatatgtctt ttatggaacc aaaatagacc    1800
aaatcaacaa caaatgaaga aattgttaga gtatgataca ctcatatata cccaaatata    1860
gcatatattt ataatataac ttttggctat gtcattttac atgattttt tggcttatct    1920 attaaaagta tcatacaaac tgttttact tcttttttt cttagaatat atatgcccaa    1980
aatggaaaag aacatatgcc aaggttgatt ttatcgctta tatggtaaaa attggaaaaa    2040
catacaaatc attactttat ttaattaaat catgtgaaga aacatattca attacggtaa    2100
tacgttatca aaacatttt ttttacatta attgttacat ttttttttt tgcaaatatt    2160 cttaaataac cattcttttt ttatttacta taattaacat aaaaataaat aaatataac    2220 atttcaacaa agaaatttgc ttatgaaaaa tacaaaatcc agttaatttt tcagaaaaat    2280
acaaatttgc ttataaatat attaccacta gtttatgtga ttttaaaaga aagaaatgca    2340
gcttaccaaa cgcaacgtga aaatttgaga aacccatact caaaaaagat taaatgacaa    2400
aatcaccctc agcaaaatca tgaaacaaca acactaacat tttcaccaac cccaccgtct    2460
actccggtga attgtctata tgaactcctc cgatacaact cctgtttcct tcaggccaaa    2520
gcctaaaatt cacacaacca aaaaaaccaa cctttttttt ccacctaaat ctttgaatat    2580
cacaatattt actatttaca                                                2600
```

<210> SEQ ID NO 28
<211> LENGTH: 2600
<212> TYPE: DNA
<213> ORGANISM: Arabidopsis thaliana
<220> FEATURE:
<221> NAME/KEY: promoter
<222> LOCATION: (1)..(2600)
<223> OTHER INFORMATION: caffeoyl-CoA O-methyltransferase (AtCCoAOMT, CCoAOMT) promoter

<400> SEQUENCE: 28

```
acacattaaa acaaaaacca tttccacata aaaaaaaacg atccagtaaa tgaaatagat      60
tcaagaccga tcgtcgagcg gtagagaaag taaacaaaac aaagacagag aattgaagaa     120
actgtgtacc tgcaaaaata ccaatcagat gggtctccgc caaagtaatc tgcttagaag     180
ttttgtaaga aaaacaatt aaaggcgttt catttattga attttccggt tgtttgattc     240
tcaggatgag attgcctatt tccttcaaaa aagaactctt taatttacac agaaaagctc     300
tgaaaatttc cacagaaaat gaagaaagaa aagagcgtaa aaggggaaag agatgaaatg     360
ggttattaaa aaaagaagca gtggatgagg gaagagagga ttaagaggcg tagagattac     420
atgtgatgaa tgatactatc ttttcttaca aacacatttt cgtgtaatta aaatttaatt     480
tggttccaaa gattttaatc aaaagaagtt tggtaaattg aaacaggcag acataattta     540
ttgtaaagag ttttattta tttattcatg acgttgcttg atggtgcttt accaatttc     600 ttctcctacg ttagattttt ttcacttttt tttttggtgt tgtaataaa tgtgaaaaat     660 ggaccgttta aaaacttaaa gacgtttgat tactatataa agtaattgtt tataatagaa     720
agttaattga gacgtgaaat ggtataatat tattgtgtaa cagttgtgta cacgtagctc     780
tcatgcagtt ttagtggacc catatggctt gacttgtatt ctgttttggg gctattaaag     840
tccaaaacag agacccctct caagcccttc ctattaatcc atctagctaa tagaaactat     900
aaacgtgtcc tctctctcaa ttaaataagc tagaaacata ctcaaccatt cgcattacgc     960
```

-continued

```
acttcatagc ggtaggttta gatttgtcta aaatacttaa aaaaattttt gtctaagttg    1020
ttgtccgtta caaagttttt ttctttgtga caacttgaca acattgacaa atagaaaaat    1080
aaatttcgat gaaacctatg aaatgggcta tggcccaact aaaaagagtg ggaaattaaa    1140
gatgggatgg ttcaagtgta tacttcgaac ttccgacatt agggtcaaag gattttaaa    1200 aggcaaccat ttgttccact ttctcgaaca aaaacgagcc atttattaat atatagtacg    1260
gctgaattgg ttttgttcgt cattgtgtaa acacaaagtc attcgaatta tgttagggtc    1320
cgttgataat atagacggcc catcccacgc acatattaag tgttcaactc catagaatat    1380
catatgggac actgttttta atttataatc accatttaaa atgtttaaat gtttatgcaa    1440
attggatggc ttcttcacac aacatttatt tattggcctt tcattccatc aaagtaaaat    1500
agcttttcaa atacattata ctctatactc ctatacatgt aaataaccat atgcatatat    1560 attttttttca aatataggtc aacgccattt aatataattt taaaaaaatt tgttcggaaa    1620
atatcacatt tctttcacta gacaagcctt gttaccacac aatgtatcaa tatgatctaa    1680
agggcaaacg aaagatcctg acatgaaacg tttaattctc attttctcca aatttttattt    1740 tttatgtgaa gtagataaat tagtatatat atatatatac caaactagtg tgttatgtta    1800
tggcaaatgt tatatcaatt cgaaggttcc gctattgcaa tattcattaa ttttttcata    1860
ccaatactat ttttctttct cttttatttt gttttttaat aaataaaaga aattaaggat    1920
gattagtaag gaagtcgcct accaagagat tcacctacca cggtacactt caacaccgaa    1980
gcagagttgt tgaatccact ttttattccc ttctctaatc tctactcacc aagtctccac    2040
ttttttttct ctttattata tacatttaaa ttatttaata tacgccaact acatacatat    2100
ccagtgtaat ttctcgttac gtcacacccc tttcgtaatc gtctaatttc agaaaaatat    2160
ccagaggttt aaatacatat tcccatcatt aaatctagac ataaacacat catactcaca    2220
aaatttggca gcaaacagtt actacagacc cataaatgaa aaaacgtatt cacttgtttt    2280 caatttttcac ataaccactt ccctgagttt ggtctcaatt tgattgcccc gccgaggcat    2340
tactacgcca agtgcgatta aggtcccata cagtgtaacg ggacccacta taagacagcg    2400
accgaccaat tgcgtgttag gagagtttca ccaaccccgg accggttttt accggatata    2460
acagaaccgg tacgaaccgg tctcattatc ttccatcttc tttatataga cctcatgcca    2520
tgtgtgtgac tcaccaagaa aaacacaatc gtttaatctc acccaagaag acaaaaacac    2580
agagagagaa agagagagaa                                                 2600
```

<210> SEQ ID NO 29
<211> LENGTH: 698
<212> TYPE: PRT
<213> ORGANISM: Taxus canadensis
<220> FEATURE:
<221> NAME/KEY: MISC_FEATURE
<222> LOCATION: (1)..(698)
<223> OTHER INFORMATION: phenylalanine aminomutase (TcPAM, PAM)

<400> SEQUENCE: 29

Met Gly Phe Ala Val Glu Ser Arg Ser His Val Lys Asp Ile Leu Gly
1               5                   10                  15

Leu Ile Asn Thr Phe Asn Glu Val Lys Lys Ile Thr Val Asp Gly Thr
            20                  25                  30

Thr Pro Ile Thr Val Ala His Val Ala Leu Ala Arg Arg His Asp
        35                  40                  45

Val Lys Val Ala Leu Glu Ala Glu Gln Cys Arg Ala Arg Val Glu Thr

```
            50                  55                  60
Cys Ser Ser Trp Val Gln Arg Lys Ala Glu Asp Gly Ala Asp Ile Tyr
 65                  70                  75                  80

Gly Val Thr Thr Gly Phe Gly Ala Cys Ser Ser Arg Arg Thr Asn Gln
                     85                  90                  95

Leu Ser Glu Leu Gln Glu Ser Leu Ile Arg Cys Leu Leu Ala Gly Val
                100                 105                 110

Phe Thr Lys Gly Cys Ala Ser Ser Val Asp Glu Leu Pro Ala Thr Ala
                115                 120                 125

Thr Arg Ser Ala Met Leu Leu Arg Leu Asn Ser Phe Thr Tyr Gly Cys
                130                 135                 140

Ser Gly Ile Arg Trp Glu Val Met Glu Ala Leu Glu Lys Leu Leu Asn
145                 150                 155                 160

Ser Asn Val Ser Pro Lys Val Pro Leu Arg Gly Ser Val Ser Ala Ser
                165                 170                 175

Gly Asp Leu Ile Pro Leu Ala Tyr Ile Ala Gly Leu Leu Ile Gly Lys
                180                 185                 190

Pro Ser Val Val Ala Arg Ile Gly Asp Asp Val Glu Val Pro Ala Pro
                195                 200                 205

Glu Ala Leu Ser Arg Val Gly Leu Arg Pro Phe Lys Leu Gln Ala Lys
                210                 215                 220

Glu Gly Leu Ala Leu Val Asn Gly Thr Ser Phe Ala Thr Ala Leu Ala
225                 230                 235                 240

Ser Thr Val Met Tyr Asp Ala Asn Val Leu Leu Leu Val Glu Thr
                    245                 250                 255

Leu Cys Gly Met Phe Cys Glu Val Ile Phe Gly Arg Glu Glu Phe Ala
                260                 265                 270

His Pro Leu Ile His Lys Val Lys Pro His Pro Gly Gln Ile Glu Ser
                275                 280                 285

Ala Glu Leu Leu Glu Trp Leu Leu Arg Ser Ser Pro Phe Gln Asp Leu
                290                 295                 300

Ser Arg Glu Tyr Tyr Ser Ile Asp Lys Leu Lys Lys Pro Lys Gln Asp
305                 310                 315                 320

Arg Tyr Ala Leu Arg Ser Ser Pro Gln Trp Leu Ala Pro Leu Val Gln
                325                 330                 335

Thr Ile Arg Asp Ala Thr Thr Thr Val Glu Thr Glu Val Asn Ser Ala
                340                 345                 350

Asn Asp Asn Pro Ile Ile Asp His Ala Asn Asp Arg Ala Leu His Gly
                355                 360                 365

Ala Asn Phe Gln Gly Ser Ala Val Gly Phe Tyr Met Asp Tyr Val Arg
                370                 375                 380

Ile Ala Val Ala Gly Leu Gly Lys Leu Leu Phe Ala Gln Phe Thr Glu
385                 390                 395                 400

Leu Met Ile Glu Tyr Tyr Ser Asn Gly Leu Pro Gly Asn Leu Ser Leu
                405                 410                 415

Gly Pro Asp Leu Ser Val Asp Tyr Gly Leu Lys Gly Leu Asp Ile Ala
                420                 425                 430

Met Ala Ala Tyr Ser Ser Glu Leu Gln Tyr Leu Ala Asn Pro Val Thr
                435                 440                 445

Thr His Val His Ser Ala Glu Gln His Asn Gln Asp Ile Asn Ser Leu
                450                 455                 460

Ala Leu Ile Ser Ala Arg Lys Thr Glu Glu Ala Leu Asp Ile Leu Lys
465                 470                 475                 480
```

```
Leu Met Ile Ala Ser His Leu Thr Ala Met Cys Gln Ala Val Asp Leu
                485                 490                 495

Arg Gln Leu Glu Glu Ala Leu Val Lys Val Val Glu Asn Val Val Ser
            500                 505                 510

Thr Leu Ala Asp Glu Cys Gly Leu Pro Asn Asp Thr Lys Ala Arg Leu
        515                 520                 525

Leu Tyr Val Ala Lys Ala Val Pro Val Tyr Thr Tyr Leu Glu Ser Pro
    530                 535                 540

Cys Asp Pro Thr Leu Pro Leu Leu Gly Leu Gln Ser Cys Phe
545                 550                 555                 560

Gly Ser Ile Leu Ala Leu His Lys Lys Asp Gly Ile Glu Thr Asp Thr
                565                 570                 575

Leu Val Asp Arg Leu Ala Glu Phe Glu Lys Arg Leu Ser Asp Arg Leu
            580                 585                 590

Glu Asn Glu Met Thr Ala Val Arg Val Leu Tyr Glu Lys Lys Gly His
        595                 600                 605

Lys Thr Ala Asp Asn Asn Asp Ala Leu Val Arg Ile Gln Gly Ser Arg
    610                 615                 620

Phe Leu Pro Phe Tyr Arg Phe Val Arg Glu Glu Leu Asp Thr Gly Val
625                 630                 635                 640

Met Ser Ala Arg Arg Glu Gln Thr Pro Gln Glu Asp Val Gln Lys Val
                645                 650                 655

Phe Asp Ala Ile Ala Asp Gly Arg Ile Thr Val Pro Leu Leu His Cys
            660                 665                 670

Leu Gln Gly Phe Leu Gly Gln Pro Asn Gly Cys Ala Asn Gly Val Glu
        675                 680                 685

Ser Phe Gln Ser Val Trp Asn Lys Ser Ala
    690                 695

<210> SEQ ID NO 30
<211> LENGTH: 178
<212> TYPE: PRT
<213> ORGANISM: Pediococcus pentosaceus
<220> FEATURE:
<221> NAME/KEY: MISC_FEATURE
<222> LOCATION: (1)..(178)
<223> OTHER INFORMATION: phenylacrylic acid decarboxylase (PDC)

<400> SEQUENCE: 30

Met Glu Lys Thr Phe Lys Thr Leu Asp Asp Phe Leu Gly Thr His Phe
1               5                   10                  15

Ile Tyr Thr Tyr Asp Asn Gly Trp Glu Tyr Glu Trp Tyr Ala Lys Asn
            20                  25                  30

Asp His Thr Val Asp Tyr Arg Ile His Gly Gly Met Val Ala Gly Arg
        35                  40                  45

Trp Val Lys Asp Gln Glu Ala His Ile Ala Met Leu Thr Glu Gly Ile
    50                  55                  60

Tyr Lys Val Ala Trp Thr Glu Pro Thr Gly Thr Asp Val Ala Leu Asp
65                  70                  75                  80

Phe Val Pro Asn Glu Lys Lys Leu Asn Gly Thr Ile Phe Phe Pro Lys
                85                  90                  95

Trp Val Glu Glu His Pro Glu Ile Thr Val Thr Phe Gln Asn Glu His
            100                 105                 110

Ile Asp Leu Met Glu Glu Ser Arg Glu Lys Tyr Glu Thr Tyr Pro Lys
        115                 120                 125
```

```
Leu Val Val Pro Glu Phe Ala Thr Ile Thr Tyr Met Gly Asp Ala Gly
            130                 135                 140

Gln Asp Asn Asp Glu Val Ile Ala Glu Ala Pro Tyr Glu Gly Met Thr
145                 150                 155                 160

Asp Asp Ile Arg Ala Gly Lys Tyr Phe Asp Glu Asn Tyr Lys Arg Ile
                165                 170                 175

Asn Lys

<210> SEQ ID NO 31
<211> LENGTH: 397
<212> TYPE: PRT
<213> ORGANISM: Physcomitrella patens
<220> FEATURE:
<221> NAME/KEY: MISC_FEATURE
<222> LOCATION: (1)..(397)
<223> OTHER INFORMATION: chalcone synthase (CHS)

<400> SEQUENCE: 31

Met Ala Ser Ala Gly Asp Val Thr Arg Ala Ala Leu Pro Arg Ala Gln
1               5                   10                  15

Pro Arg Ala Glu Gly Pro Ala Cys Val Leu Gly Ile Gly Thr Ala Val
                20                  25                  30

Pro Pro Ala Glu Phe Leu Gln Ser Glu Tyr Pro Asp Phe Phe Phe Asn
            35                  40                  45

Ile Thr Asn Cys Gly Glu Lys Glu Ala Leu Lys Ala Lys Phe Lys Arg
 50                 55                  60

Ile Cys Asp Lys Ser Gly Ile Arg Lys Arg His Met Phe Leu Thr Glu
65                  70                  75                  80

Glu Val Leu Lys Ala Asn Pro Gly Ile Cys Thr Tyr Met Glu Pro Ser
                85                  90                  95

Leu Asn Val Arg His Asp Ile Val Val Gln Val Pro Lys Leu Ala
            100                 105                 110

Ala Glu Ala Ala Gln Lys Ala Ile Lys Glu Trp Gly Gly Arg Lys Ser
        115                 120                 125

Asp Ile Thr His Ile Val Phe Ala Thr Thr Ser Gly Val Asn Met Pro
130                 135                 140

Gly Ala Asp His Ala Leu Ala Lys Leu Leu Gly Leu Lys Pro Thr Val
145                 150                 155                 160

Lys Arg Val Met Met Tyr Gln Thr Gly Cys Phe Gly Gly Ala Ser Val
                165                 170                 175

Leu Arg Val Ala Lys Asp Leu Ala Glu Asn Asn Lys Gly Ala Arg Val
            180                 185                 190

Leu Ala Val Ala Ser Glu Val Thr Ala Val Thr Tyr Arg Ala Pro Ser
        195                 200                 205

Glu Asn His Leu Asp Gly Leu Val Gly Ser Ala Leu Phe Gly Asp Gly
210                 215                 220

Ala Gly Val Tyr Val Val Gly Ser Asp Pro Lys Pro Glu Val Glu Lys
225                 230                 235                 240

Pro Leu Phe Glu Val His Trp Ala Gly Glu Thr Ile Leu Pro Glu Ser
                245                 250                 255

Asp Gly Ala Ile Asp Gly His Leu Thr Glu Ala Gly Leu Ile Phe His
            260                 265                 270

Leu Met Lys Asp Val Pro Gly Leu Ile Ser Lys Asn Ile Glu Lys Phe
        275                 280                 285

Leu Asn Glu Ala Arg Lys Pro Val Gly Ser Pro Ala Trp Asn Glu Met
290                 295                 300
```

```
Phe Trp Ala Val His Pro Gly Gly Pro Ala Ile Leu Asp Gln Val Glu
305                 310                 315                 320

Ala Lys Leu Lys Leu Thr Lys Asp Lys Met Gln Gly Ser Arg Asp Ile
                325                 330                 335

Leu Ser Glu Phe Gly Asn Met Ser Ser Ala Ser Val Leu Phe Val Leu
            340                 345                 350

Asp Gln Ile Arg His Arg Ser Val Lys Met Gly Ala Ser Thr Leu Gly
        355                 360                 365

Glu Gly Ser Glu Phe Gly Phe Phe Ile Gly Phe Gly Pro Gly Leu Thr
370                 375                 380

Leu Glu Val Leu Val Leu Arg Ala Ala Pro Asn Ser Ala
385                 390                 395

<210> SEQ ID NO 32
<211> LENGTH: 395
<212> TYPE: PRT
<213> ORGANISM: Arabidopsis thaliana
<220> FEATURE:
<221> NAME/KEY: MISC_FEATURE
<222> LOCATION: (1)..(395)
<223> OTHER INFORMATION: chalcone synthase (CHS)

<400> SEQUENCE: 32

Met Val Met Ala Gly Ala Ser Ser Leu Asp Glu Ile Arg Gln Ala Gln
1               5                   10                  15

Arg Ala Asp Gly Pro Ala Gly Ile Leu Ala Ile Gly Thr Ala Asn Pro
            20                  25                  30

Glu Asn His Val Leu Gln Ala Glu Tyr Pro Asp Tyr Tyr Phe Arg Ile
        35                  40                  45

Thr Asn Ser Glu His Met Thr Asp Leu Lys Glu Lys Phe Lys Arg Met
    50                  55                  60

Cys Asp Lys Ser Thr Ile Arg Lys Arg His Met His Leu Thr Glu Glu
65                  70                  75                  80

Phe Leu Lys Glu Asn Pro His Met Cys Ala Tyr Met Ala Pro Ser Leu
                85                  90                  95

Asp Thr Arg Gln Asp Ile Val Val Glu Val Pro Lys Leu Gly Lys
            100                 105                 110

Glu Ala Ala Val Lys Ala Ile Lys Glu Trp Gly Gln Pro Lys Ser Lys
            115                 120                 125

Ile Thr His Val Val Phe Cys Thr Thr Ser Gly Val Asp Met Pro Gly
        130                 135                 140

Ala Asp Tyr Gln Leu Thr Lys Leu Leu Gly Leu Arg Pro Ser Val Lys
145                 150                 155                 160

Arg Leu Met Met Tyr Gln Gln Gly Cys Phe Ala Gly Gly Thr Val Leu
                165                 170                 175

Arg Ile Ala Lys Asp Leu Ala Glu Asn Asn Arg Gly Ala Arg Val Leu
            180                 185                 190

Val Val Cys Ser Glu Ile Thr Ala Val Thr Phe Arg Gly Pro Ser Asp
        195                 200                 205

Thr His Leu Asp Ser Leu Val Gly Gln Ala Leu Phe Ser Asp Gly Ala
    210                 215                 220

Ala Ala Leu Ile Val Gly Ser Asp Pro Asp Thr Ser Val Gly Glu Lys
225                 230                 235                 240

Pro Ile Phe Glu Met Val Ser Ala Ala Gln Thr Ile Leu Pro Asp Ser
                245                 250                 255
```

-continued

Asp Gly Ala Ile Asp Gly His Leu Arg Glu Val Gly Leu Thr Phe His
                260                 265                 270

Leu Leu Lys Asp Val Pro Gly Leu Ile Ser Lys Asn Ile Val Lys Ser
            275                 280                 285

Leu Asp Glu Ala Phe Lys Pro Leu Gly Ile Ser Asp Trp Asn Ser Leu
290                 295                 300

Phe Trp Ile Ala His Pro Gly Pro Ala Ile Leu Asp Gln Val Glu
305                 310                 315                 320

Ile Lys Leu Gly Leu Lys Glu Lys Met Arg Ala Thr Arg His Val
                325                 330                 335

Leu Ser Glu Tyr Gly Asn Met Ser Ser Ala Cys Val Leu Phe Ile Leu
            340                 345                 350

Asp Glu Met Arg Arg Lys Ser Ala Lys Asp Gly Val Ala Thr Thr Gly
                355                 360                 365

Glu Gly Leu Glu Trp Gly Val Leu Phe Gly Phe Gly Pro Gly Leu Thr
            370                 375                 380

Val Glu Thr Val Val Leu His Ser Val Pro Leu
385                 390                 395

<210> SEQ ID NO 33
<211> LENGTH: 392
<212> TYPE: PRT
<213> ORGANISM: Vitis vinifera
<220> FEATURE:
<221> NAME/KEY: MISC_FEATURE
<222> LOCATION: (1)..(392)
<223> OTHER INFORMATION: stilbene synthase (SPS)

<400> SEQUENCE: 33

Met Ala Ser Val Glu Glu Phe Arg Asn Ala Gln Arg Ala Lys Gly Pro
1               5                   10                  15

Ala Thr Ile Leu Ala Ile Gly Thr Ala Thr Pro Asp His Cys Val Tyr
            20                  25                  30

Gln Ser Asp Tyr Ala Asp Phe Tyr Phe Arg Val Thr Lys Ser Glu His
        35                  40                  45

Met Thr Ala Leu Lys Lys Lys Phe Asn Arg Ile Cys Asp Lys Ser Met
50                  55                  60

Ile Lys Lys Arg Tyr Ile His Leu Thr Glu Glu Met Leu Glu Glu His
65                  70                  75                  80

Pro Asn Ile Gly Ala Tyr Met Ala Pro Ser Leu Asn Ile Arg Gln Glu
                85                  90                  95

Ile Ile Thr Ala Glu Val Pro Lys Leu Gly Lys Glu Ala Ala Leu Lys
            100                 105                 110

Ala Leu Lys Glu Trp Gly Gln Pro Lys Ser Lys Ile Thr His Leu Val
        115                 120                 125

Phe Cys Thr Thr Ser Gly Val Glu Met Pro Gly Ala Asp Tyr Lys Leu
130                 135                 140

Ala Asn Leu Leu Gly Leu Glu Pro Ser Val Arg Arg Val Met Leu Tyr
145                 150                 155                 160

His Gln Gly Cys Tyr Ala Gly Gly Thr Val Leu Arg Thr Ala Lys Asp
                165                 170                 175

Leu Ala Glu Asn Asn Ala Gly Ala Arg Val Leu Val Val Cys Ser Glu
            180                 185                 190

Ile Thr Val Val Thr Phe Arg Gly Pro Ser Glu Asp Ala Leu Asp Ser
        195                 200                 205

Leu Val Gly Gln Ala Leu Phe Gly Asp Gly Ser Ala Ala Val Ile Val

```
            210                 215                 220
Gly Ser Asp Pro Asp Ile Ser Ile Glu Arg Pro Leu Phe Gln Leu Val
225                 230                 235                 240

Ser Ala Ala Gln Thr Phe Ile Pro Asn Ser Ala Gly Ala Ile Ala Gly
                245                 250                 255

Asn Leu Arg Glu Val Gly Leu Thr Phe His Leu Trp Pro Asn Val Pro
            260                 265                 270

Thr Leu Ile Ser Glu Asn Ile Glu Lys Cys Leu Thr Gln Ala Phe Asp
        275                 280                 285

Pro Leu Gly Ile Ser Asp Trp Asn Ser Leu Phe Trp Ile Ala His Pro
    290                 295                 300

Gly Gly Pro Ala Ile Leu Asp Ala Val Glu Ala Lys Leu Asn Leu Asp
305                 310                 315                 320

Lys Lys Lys Leu Glu Ala Thr Arg His Val Leu Ser Glu Tyr Gly Asn
                325                 330                 335

Met Ser Ser Ala Cys Val Leu Phe Ile Leu Asp Glu Met Arg Lys Lys
            340                 345                 350

Ser Leu Lys Gly Glu Arg Ala Thr Thr Gly Glu Gly Leu Asp Trp Gly
        355                 360                 365

Val Leu Phe Gly Phe Gly Pro Gly Leu Thr Ile Glu Thr Val Val Leu
    370                 375                 380

His Ser Ile Pro Met Val Thr Asn
385                 390

<210> SEQ ID NO 34
<211> LENGTH: 386
<212> TYPE: PRT
<213> ORGANISM: Oryza sativa
<220> FEATURE:
<221> NAME/KEY: MISC_FEATURE
<222> LOCATION: (1)..(386)
<223> OTHER INFORMATION: curcuminoid synthase (CUS) short version

<400> SEQUENCE: 34

Met Arg Arg Ser Gln Arg Ala Asp Gly Leu Ala Ala Val Leu Ala Ile
1               5                   10                  15

Gly Thr Ala Asn Pro Pro Asn Cys Val Thr Gln Glu Glu Ile Pro Asp
                20                  25                  30

Phe Tyr Phe Arg Val Thr Asn Ser Asp His Leu Thr Ala Leu Lys Asp
            35                  40                  45

Lys Phe Lys Arg Ile Cys Gln Glu Met Gly Val Gln Arg Arg Tyr Leu
        50                  55                  60

His His Thr Glu Glu Met Leu Ser Ala His Pro Glu Phe Val Asp Arg
65                  70                  75                  80

Asp Ala Pro Ser Leu Asp Ala Arg Leu Asp Ile Ala Ala Asp Ala Val
                85                  90                  95

Pro Glu Leu Ala Ala Glu Ala Ala Lys Lys Ala Ile Ala Glu Trp Gly
                100                 105                 110

Arg Pro Ala Ala Asp Ile Thr His Leu Val Val Thr Thr Asn Ser Gly
            115                 120                 125

Ala His Val Pro Gly Val Asp Phe Arg Leu Val Pro Leu Leu Gly Leu
        130                 135                 140

Arg Pro Ser Val Arg Arg Thr Met Leu His Leu Asn Gly Cys Phe Ala
145                 150                 155                 160

Gly Cys Ala Ala Leu Arg Leu Ala Lys Asp Leu Ala Glu Asn Ser Arg
                165                 170                 175
```

```
Gly Ala Arg Val Leu Val Ala Ala Glu Leu Thr Leu Met Tyr Phe
            180                 185                 190

Thr Gly Pro Asp Glu Gly Cys Phe Arg Thr Leu Leu Val Gln Gly Leu
        195                 200                 205

Phe Gly Asp Gly Ala Ala Val Ile Val Gly Ala Asp Ala Asp
210                 215                 220

Val Glu Arg Pro Leu Phe Glu Ile Val Ser Ala Ala Gln Thr Ile Ile
225                 230                 235                 240

Pro Glu Ser Asp His Ala Leu Asn Met Arg Phe Thr Glu Arg Leu
                245                 250                 255

Asp Gly Val Leu Gly Arg Gln Val Pro Gly Leu Ile Gly Asp Asn Val
            260                 265                 270

Glu Arg Cys Leu Leu Asp Met Phe Gly Pro Leu Leu Gly Gly Asp Gly
            275                 280                 285

Gly Gly Gly Trp Asn Asp Leu Phe Trp Ala Val His Pro Gly Ser Ser
        290                 295                 300

Thr Ile Met Asp Gln Val Asp Ala Ala Leu Gly Leu Glu Pro Gly Lys
305                 310                 315                 320

Leu Ala Ala Ser Arg Arg Val Leu Ser Asp Tyr Gly Asn Met Ser Gly
                325                 330                 335

Ala Thr Val Ile Phe Ala Leu Asp Glu Leu Arg Arg Gln Arg Lys Glu
            340                 345                 350

Ala Ala Ala Ala Gly Glu Trp Pro Glu Leu Gly Val Met Met Ala Phe
                355                 360                 365

Gly Pro Gly Met Thr Val Asp Ala Met Leu Leu His Ala Thr Ser His
        370                 375                 380

Val Asn
385

<210> SEQ ID NO 35
<211> LENGTH: 402
<212> TYPE: PRT
<213> ORGANISM: Oryza sativa
<220> FEATURE:
<221> NAME/KEY: MISC_FEATURE
<222> LOCATION: (1)..(402)
<223> OTHER INFORMATION: curcuminoid synthase (CUS) long version

<400> SEQUENCE: 35

Met Ala Pro Thr Thr Met Gly Ser Ala Leu Tyr Pro Leu Gly Glu
1               5                   10                  15

Met Arg Arg Ser Gln Arg Ala Asp Gly Leu Ala Ala Val Leu Ala Ile
                20                  25                  30

Gly Thr Ala Asn Pro Pro Asn Cys Val Thr Gln Glu Glu Ile Pro Asp
            35                  40                  45

Phe Tyr Phe Arg Val Thr Asn Ser Asp His Leu Thr Ala Leu Lys Asp
    50                  55                  60

Lys Phe Lys Arg Ile Cys Gln Glu Met Gly Val Gln Arg Arg Tyr Leu
65                  70                  75                  80

His His Thr Glu Glu Met Leu Ser Ala His Pro Glu Phe Val Asp Arg
                85                  90                  95

Asp Ala Pro Ser Leu Asp Ala Arg Leu Asp Ile Ala Ala Asp Ala Val
            100                 105                 110

Pro Glu Leu Ala Ala Glu Ala Ala Lys Lys Ala Ile Ala Glu Trp Gly
        115                 120                 125
```

Arg Pro Ala Ala Asp Ile Thr His Leu Val Val Thr Thr Asn Ser Gly
130                 135                 140

Ala His Val Pro Gly Val Asp Phe Arg Leu Val Pro Leu Leu Gly Leu
145                 150                 155                 160

Arg Pro Ser Val Arg Arg Thr Met Leu His Leu Asn Gly Cys Phe Ala
            165                 170                 175

Gly Cys Ala Ala Leu Arg Leu Ala Lys Asp Leu Ala Glu Asn Ser Arg
            180                 185                 190

Gly Ala Arg Val Leu Val Val Ala Glu Leu Thr Leu Met Tyr Phe
        195                 200                 205

Thr Gly Pro Asp Glu Gly Cys Phe Arg Thr Leu Leu Val Gln Gly Leu
210                 215                 220

Phe Gly Asp Gly Ala Ala Val Ile Val Gly Ala Asp Ala Asp
225                 230                 235                 240

Val Glu Arg Pro Leu Phe Glu Ile Val Ser Ala Ala Gln Thr Ile Ile
                245                 250                 255

Pro Glu Ser Asp His Ala Leu Asn Met Arg Phe Thr Gly Arg Arg Leu
            260                 265                 270

Asp Gly Val Leu Gly Arg Gln Val Pro Gly Leu Ile Gly Asp Asn Val
            275                 280                 285

Glu Arg Cys Leu Leu Asp Met Phe Gly Pro Leu Leu Gly Gly Asp Gly
290                 295                 300

Gly Gly Gly Trp Asn Asp Leu Phe Trp Ala Val His Pro Gly Ser Ser
305                 310                 315                 320

Thr Ile Met Asp Gln Val Asp Ala Ala Leu Gly Leu Glu Pro Gly Lys
            325                 330                 335

Leu Ala Ala Ser Arg Arg Val Leu Ser Asp Tyr Gly Asn Met Ser Gly
            340                 345                 350

Ala Thr Val Ile Phe Ala Leu Asp Glu Leu Arg Arg Gln Arg Lys Glu
            355                 360                 365

Ala Ala Ala Ala Gly Glu Trp Pro Glu Leu Gly Val Met Met Ala Phe
            370                 375                 380

Gly Pro Gly Met Thr Val Asp Ala Met Leu Leu His Ala Thr Ser His
385                 390                 395                 400

Val Asn

<210> SEQ ID NO 36
<211> LENGTH: 384
<212> TYPE: PRT
<213> ORGANISM: Rheum palmatum
<220> FEATURE:
<221> NAME/KEY: MISC_FEATURE
<222> LOCATION: (1)..(384)
<223> OTHER INFORMATION: benzalactone synthase (BAS)

<400> SEQUENCE: 36

Met Ala Thr Glu Glu Met Lys Lys Leu Ala Thr Val Met Ala Ile Gly
1               5                   10                  15

Thr Ala Asn Pro Pro Asn Cys Tyr Tyr Gln Ala Asp Phe Pro Asp Phe
            20                  25                  30

Tyr Phe Arg Val Thr Asn Ser Asp His Leu Ile Asn Leu Lys Gln Lys
        35                  40                  45

Phe Lys Arg Leu Cys Glu Asn Ser Arg Ile Glu Lys Arg Tyr Leu His
    50                  55                  60

Val Thr Glu Glu Ile Leu Lys Glu Asn Pro Asn Ile Ala Ala Tyr Glu
65                  70                  75                  80

```
Ala Thr Ser Leu Asn Val Arg His Lys Met Gln Val Lys Gly Val Ala
                85                  90                  95

Glu Leu Gly Lys Glu Ala Ala Leu Lys Ala Ile Lys Glu Trp Gly Gln
            100                 105                 110

Pro Lys Ser Lys Ile Thr His Leu Ile Val Cys Cys Leu Ala Gly Val
        115                 120                 125

Asp Met Pro Gly Ala Asp Tyr Gln Leu Thr Lys Leu Leu Asp Leu Asp
    130                 135                 140

Pro Ser Val Lys Arg Phe Met Phe Tyr His Leu Gly Cys Tyr Ala Gly
145                 150                 155                 160

Gly Thr Val Leu Arg Leu Ala Lys Asp Ile Ala Glu Asn Asn Lys Gly
                165                 170                 175

Ala Arg Val Leu Ile Val Cys Ser Glu Met Thr Thr Thr Cys Phe Arg
            180                 185                 190

Gly Pro Ser Glu Thr His Leu Asp Ser Met Ile Gly Gln Ala Ile Leu
        195                 200                 205

Gly Asp Gly Ala Ala Ala Val Ile Val Gly Ala Asp Pro Asp Leu Thr
    210                 215                 220

Val Glu Arg Pro Ile Phe Glu Leu Val Ser Thr Ala Gln Thr Ile Val
225                 230                 235                 240

Pro Glu Ser His Gly Ala Ile Glu Gly His Leu Leu Glu Ser Gly Leu
                245                 250                 255

Ser Phe His Leu Tyr Lys Thr Val Pro Thr Leu Ile Ser Asn Asn Ile
            260                 265                 270

Lys Thr Cys Leu Ser Asp Ala Phe Thr Pro Leu Asn Ile Ser Asp Trp
        275                 280                 285

Asn Ser Leu Phe Trp Ile Ala His Pro Gly Gly Pro Ala Ile Leu Asp
    290                 295                 300

Gln Val Thr Ala Lys Val Gly Leu Glu Lys Glu Lys Leu Lys Val Thr
305                 310                 315                 320

Arg Gln Val Leu Lys Asp Tyr Gly Asn Met Ser Ser Ala Thr Val Phe
                325                 330                 335

Phe Ile Met Asp Glu Met Arg Lys Lys Ser Leu Glu Asn Gly Gln Ala
            340                 345                 350

Thr Thr Gly Glu Gly Leu Glu Trp Gly Val Leu Phe Gly Phe Gly Pro
        355                 360                 365

Gly Ile Thr Val Glu Thr Val Val Leu Arg Ser Val Pro Val Ile Ser
    370                 375                 380

<210> SEQ ID NO 37
<211> LENGTH: 248
<212> TYPE: PRT
<213> ORGANISM: Arabidopsis thaliana
<220> FEATURE:
<221> NAME/KEY: MISC_FEATURE
<222> LOCATION: (1)..(248)
<223> OTHER INFORMATION: R2R3 Myb transcription factor (AtMyb75), AtPAP1

<400> SEQUENCE: 37

Met Glu Gly Ser Ser Lys Gly Leu Arg Lys Gly Ala Trp Thr Thr Glu
1               5                   10                  15

Glu Asp Ser Leu Leu Arg Gln Cys Ile Asn Lys Tyr Gly Glu Gly Lys
            20                  25                  30

Trp His Gln Val Pro Val Arg Ala Gly Leu Asn Arg Cys Arg Lys Ser
        35                  40                  45
```

```
Cys Arg Leu Arg Trp Leu Asn Tyr Leu Lys Pro Ser Ile Lys Arg Gly
     50                  55                  60

Lys Leu Ser Ser Asp Glu Val Asp Leu Leu Arg Leu His Arg Leu
 65              70                  75                  80

Leu Gly Asn Arg Trp Ser Leu Ile Ala Gly Arg Leu Pro Gly Arg Thr
                 85                  90                  95

Ala Asn Asp Val Lys Asn Tyr Trp Asn Thr His Leu Ser Lys Lys His
            100                 105                 110

Glu Pro Cys Cys Lys Ile Lys Met Lys Lys Arg Asp Ile Thr Pro Ile
            115                 120                 125

Pro Thr Thr Pro Ala Leu Lys Asn Asn Val Tyr Lys Pro Arg Pro Arg
        130                 135                 140

Ser Phe Thr Val Asn Asn Asp Cys Asn His Leu Asn Ala Pro Pro Lys
145                 150                 155                 160

Val Asp Val Asn Pro Pro Cys Leu Gly Leu Asn Ile Asn Asn Val Cys
                165                 170                 175

Asp Asn Ser Ile Ile Tyr Asn Lys Asp Lys Lys Asp Gln Leu Val
            180                 185                 190

Asn Asn Leu Ile Asp Gly Asp Asn Met Trp Leu Glu Lys Phe Leu Glu
            195                 200                 205

Glu Ser Gln Glu Val Asp Ile Leu Val Pro Glu Ala Thr Thr Thr Glu
210                 215                 220

Lys Gly Asp Thr Leu Ala Phe Asp Val Asp Gln Leu Trp Ser Leu Phe
225                 230                 235                 240

Asp Gly Glu Thr Val Lys Phe Asp
                245

<210> SEQ ID NO 38
<211> LENGTH: 249
<212> TYPE: PRT
<213> ORGANISM: Arabidopsis thaliana
<220> FEATURE:
<221> NAME/KEY: MISC_FEATURE
<222> LOCATION: (1)..(249)
<223> OTHER INFORMATION: R2R3 Myb transcription factor (AtMyb90), AtPAP2

<400> SEQUENCE: 38

Met Glu Gly Ser Ser Lys Gly Leu Arg Lys Gly Ala Trp Thr Ala Glu
 1               5                  10                  15

Glu Asp Ser Leu Leu Arg Leu Cys Ile Asp Lys Tyr Gly Glu Gly Lys
             20                  25                  30

Trp His Gln Val Pro Leu Arg Ala Gly Leu Asn Arg Cys Arg Lys Ser
         35                  40                  45

Cys Arg Leu Arg Trp Leu Asn Tyr Leu Lys Pro Ser Ile Lys Arg Gly
     50                  55                  60

Arg Leu Ser Asn Asp Glu Val Asp Leu Leu Arg Leu His Lys Leu
 65              70                  75                  80

Leu Gly Asn Arg Trp Ser Leu Ile Ala Gly Arg Leu Pro Gly Arg Thr
                 85                  90                  95

Ala Asn Asp Val Lys Asn Tyr Trp Asn Thr His Leu Ser Lys Lys His
            100                 105                 110

Glu Ser Ser Cys Cys Lys Ser Lys Met Lys Lys Asn Ile Ile Ser
            115                 120                 125

Pro Pro Thr Thr Pro Val Gln Lys Ile Gly Val Phe Lys Pro Arg Pro
        130                 135                 140

Arg Ser Phe Ser Val Asn Asn Gly Cys Ser His Leu Asn Gly Leu Pro
```

```
            145                 150                 155                 160
Glu Val Asp Leu Ile Pro Ser Cys Leu Gly Leu Lys Lys Asn Asn Val
                165                 170                 175

Cys Glu Asn Ser Ile Thr Cys Asn Lys Asp Asp Glu Lys Asp Asp Phe
                180                 185                 190

Val Asn Asn Leu Met Asn Gly Asp Asn Met Trp Leu Glu Asn Leu Leu
                195                 200                 205

Gly Glu Asn Gln Glu Ala Asp Ala Ile Val Pro Glu Ala Thr Thr Ala
                210                 215                 220

Glu His Gly Ala Thr Leu Ala Phe Asp Val Glu Gln Leu Trp Ser Leu
225                 230                 235                 240

Phe Asp Gly Glu Thr Val Glu Leu Asp
                245

<210> SEQ ID NO 39
<211> LENGTH: 258
<212> TYPE: PRT
<213> ORGANISM: Arabidopsis thaliana
<220> FEATURE:
<221> NAME/KEY: MISC_FEATURE
<222> LOCATION: (1)..(258)
<223> OTHER INFORMATION: R2R3 Myb transcription factor (AtMyb123), AtTT2

<400> SEQUENCE: 39

Met Gly Lys Arg Ala Thr Thr Ser Val Arg Arg Glu Glu Leu Asn Arg
1               5                   10                  15

Gly Ala Trp Thr Asp His Glu Asp Lys Ile Leu Arg Asp Tyr Ile Thr
                20                  25                  30

Thr His Gly Glu Gly Lys Trp Ser Thr Leu Pro Asn Gln Ala Gly Leu
            35                  40                  45

Lys Arg Cys Gly Lys Ser Cys Arg Leu Arg Trp Lys Asn Tyr Leu Arg
50                  55                  60

Pro Gly Ile Lys Arg Gly Asn Ile Ser Ser Asp Glu Glu Glu Leu Ile
65                  70                  75                  80

Ile Arg Leu His Asn Leu Leu Gly Asn Arg Trp Ser Leu Ile Ala Gly
                85                  90                  95

Arg Leu Pro Gly Arg Thr Asp Asn Glu Ile Lys Asn His Trp Asn Ser
                100                 105                 110

Asn Leu Arg Lys Arg Leu Pro Lys Thr Gln Thr Lys Gln Pro Lys Arg
            115                 120                 125

Ile Lys His Ser Thr Asn Asn Glu Asn Asn Val Cys Val Ile Arg Thr
130                 135                 140

Lys Ala Ile Arg Cys Ser Lys Thr Leu Leu Phe Ser Asp Leu Ser Leu
145                 150                 155                 160

Gln Lys Lys Ser Ser Thr Ser Pro Leu Pro Leu Lys Glu Gln Glu Met
                165                 170                 175

Asp Gln Gly Gly Ser Ser Leu Met Gly Asp Leu Glu Phe Asp Phe Asp
            180                 185                 190

Arg Ile His Ser Glu Phe His Phe Pro Asp Leu Met Asp Phe Asp Gly
        195                 200                 205

Leu Asp Cys Gly Asn Val Thr Ser Leu Val Ser Ser Asn Glu Ile Leu
    210                 215                 220

Gly Glu Leu Val Pro Ala Gln Gly Asn Leu Asp Leu Asn Arg Pro Phe
225                 230                 235                 240

Thr Ser Cys His His Arg Gly Asp Asp Glu Asp Trp Leu Arg Asp Phe
                245                 250                 255
```

Thr Cys

```
<210> SEQ ID NO 40
<211> LENGTH: 220
<212> TYPE: PRT
<213> ORGANISM: Nicotiana tabacum
<220> FEATURE:
<221> NAME/KEY: MISC_FEATURE
<222> LOCATION: (1)..(220)
<223> OTHER INFORMATION: R2R3 Myb transcription factor, NtAn2

<400> SEQUENCE: 40
```

Met Asn Ile Cys Thr Asn Lys Ser Ser Ser Gly Val Lys Lys Gly Ala
1               5                   10                  15

Trp Thr Glu Glu Glu Asp Val Leu Leu Lys Lys Cys Ile Glu Lys Tyr
            20                  25                  30

Gly Glu Gly Lys Trp His Gln Val Pro Leu Arg Ala Gly Leu Asn Arg
        35                  40                  45

Cys Arg Lys Ser Cys Arg Leu Arg Trp Leu Asn Tyr Leu Arg Pro His
    50                  55                  60

Ile Lys Arg Gly Asp Phe Ser Phe Asp Glu Val Asp Leu Ile Leu Arg
65                  70                  75                  80

Leu His Lys Leu Leu Gly Asn Arg Trp Ser Leu Ile Ala Gly Arg Leu
                85                  90                  95

Pro Gly Arg Thr Ala Asn Asp Val Lys Asn Tyr Trp Asn Ser His Leu
            100                 105                 110

Arg Lys Lys Leu Ile Ala Pro His Asp Gln Lys Glu Ser Lys Gln Lys
        115                 120                 125

Ala Lys Lys Ile Thr Ile Phe Arg Pro Arg Pro Arg Thr Phe Ser Lys
    130                 135                 140

Thr Asn Thr Cys Val Lys Ser Asn Thr Asn Val Asp Lys Asp Ile
145                 150                 155                 160

Glu Gly Ser Ser Glu Ile Ile Arg Phe Asn Asp Asn Leu Lys Pro Thr
                165                 170                 175

Thr Glu Glu Leu Thr Asp Asp Gly Ile Gln Trp Trp Ala Asp Leu Leu
            180                 185                 190

Ala Asn Asn Tyr Asn Asn Asn Gly Ile Glu Glu Ala Asp Asn Ser Ser
        195                 200                 205

Pro Thr Leu Leu His Glu Glu Met Pro Leu Leu Ser
    210                 215                 220

```
<210> SEQ ID NO 41
<211> LENGTH: 244
<212> TYPE: PRT
<213> ORGANISM: Medicago truncatula
<220> FEATURE:
<221> NAME/KEY: MISC_FEATURE
<222> LOCATION: (1)..(244)
<223> OTHER INFORMATION: R2R3 Myb transcription factor, MtLAP1

<400> SEQUENCE: 41
```

Met Glu Asn Thr Gly Gly Val Arg Lys Gly Ala Trp Thr Tyr Lys Glu
1               5                   10                  15

Asp Glu Leu Leu Lys Ala Cys Ile Asn Thr Tyr Gly Glu Gly Lys Trp
            20                  25                  30

Asn Leu Val Pro Gln Arg Ser Gly Leu Asn Arg Cys Arg Lys Ser Cys
        35                  40                  45

Arg Leu Arg Trp Leu Asn Tyr Leu Ser Pro Asn Ile Asn Arg Gly Arg

```
                    50                  55                  60
Phe Ser Glu Asp Glu Glu Asp Leu Ile Leu Arg Leu His Lys Leu Leu
 65                  70                  75                  80

Gly Asn Arg Trp Ser Leu Ile Ala Gly Arg Leu Pro Gly Arg Thr Ala
                 85                  90                  95

Asn Asp Val Lys Asn Tyr Trp His Thr Asn Leu Ala Lys Lys Val Val
            100                 105                 110

Ser Glu Lys Glu Glu Lys Glu Asn Asp Lys Pro Lys Glu Thr Met
        115                 120                 125

Lys Ala His Glu Val Ile Lys Pro Arg Pro Ile Thr Leu Ser Ser His
    130                 135                 140

Ser Asn Trp Leu Lys Gly Lys Asn Ser Ile Pro Arg Asp Leu Asp Tyr
145                 150                 155                 160

Ser Glu Asn Met Ala Ser Asn Gln Ile Gly Arg Glu Cys Ala Ser Thr
                165                 170                 175

Ser Lys Pro Asp Leu Gly Asn Ala Pro Ile Pro Cys Glu Met Trp Cys
            180                 185                 190

Asp Ser Leu Trp Asn Leu Gly Glu His Val Asp Ser Glu Lys Ile Gly
        195                 200                 205

Ser Cys Ser Ser Leu Gln Glu Glu Asn Leu Met Glu Phe Pro Asn Val
    210                 215                 220

Asp Asp Asp Ser Phe Trp Asp Phe Asn Leu Cys Asp Leu Asn Ser Leu
225                 230                 235                 240

Trp Asp Leu Pro

<210> SEQ ID NO 42
<211> LENGTH: 273
<212> TYPE: PRT
<213> ORGANISM: Zea mays
<220> FEATURE:
<221> NAME/KEY: MISC_FEATURE
<222> LOCATION: (1)..(273)
<223> OTHER INFORMATION: R2R3 Myb transcription factor, ZmMYB-C

<400> SEQUENCE: 42

Met Gly Arg Arg Ala Cys Cys Ala Lys Glu Gly Val Lys Arg Gly Ala
  1               5                  10                  15

Trp Thr Ser Lys Glu Asp Asp Ala Leu Ala Ala Tyr Val Lys Ala His
             20                  25                  30

Gly Glu Gly Lys Trp Arg Glu Val Pro Gln Lys Ala Gly Leu Arg Arg
         35                  40                  45

Cys Gly Lys Ser Cys Arg Leu Arg Trp Leu Asn Tyr Leu Arg Pro Asn
 50                  55                  60

Ile Arg Arg Gly Asn Ile Ser Tyr Asp Glu Glu Asp Leu Ile Ile Arg
 65                  70                  75                  80

Leu His Arg Leu Leu Gly Asn Arg Trp Ser Leu Ile Ala Gly Arg Leu
                 85                  90                  95

Pro Gly Arg Thr Asp Asn Glu Ile Lys Asn Tyr Trp Asn Ser Thr Leu
            100                 105                 110

Gly Arg Arg Ala Gly Ala Gly Ala Gly Gly Ser Trp Val Val
        115                 120                 125

Val Ala Pro Asp Thr Gly Ser His Ala Thr Pro Ala Ala Thr Ser Gly
    130                 135                 140

Ala Cys Glu Thr Gly Gln Asn Ser Ala Ala His Arg Ala Asp Pro Asp
145                 150                 155                 160
```

```
Ser Ala Gly Thr Thr Thr Ser Ala Ala Val Trp Ala Pro Lys
            165                 170                 175

Ala Val Arg Cys Thr Gly Gly Leu Phe Phe Phe His Arg Asp Thr Thr
        180                 185                 190

Pro Ala His Ala Gly Glu Thr Ala Thr Pro Met Ala Gly Gly Gly
            195                 200                 205

Gly Gly Gly Gly Glu Ala Gly Ser Ser Asp Asp Cys Ser Ala Ala
        210                 215                 220

Ser Val Ser Leu Arg Val Gly Ser His Asp Glu Pro Cys Phe Ser Gly
225                 230                 235                 240

Asp Gly Asp Gly Asp Trp Met Asp Asp Val Arg Ala Leu Ala Ser Phe
                245                 250                 255

Leu Glu Ser Asp Glu Asp Trp Leu Arg Cys Gln Thr Ala Gly Gln Leu
            260                 265                 270

Ala

<210> SEQ ID NO 43
<211> LENGTH: 610
<212> TYPE: PRT
<213> ORGANISM: Zea mays
<220> FEATURE:
<221> NAME/KEY: MISC_FEATURE
<222> LOCATION: (1)..(610)
<223> OTHER INFORMATION: BHLH transcription factor, ZmMYC-Lc

<400> SEQUENCE: 43

Met Ala Leu Ser Ala Ser Arg Val Gln Gln Ala Glu Glu Leu Leu Gln
1               5                   10                  15

Arg Pro Ala Glu Arg Gln Leu Met Arg Ser Gln Leu Ala Ala Ala Ala
            20                  25                  30

Arg Ser Ile Asn Trp Ser Tyr Ala Leu Phe Trp Ser Ile Ser Asp Thr
        35                  40                  45

Gln Pro Gly Val Leu Thr Trp Thr Asp Gly Phe Tyr Asn Gly Glu Val
    50                  55                  60

Lys Thr Arg Lys Ile Ser Asn Ser Val Glu Leu Thr Ser Asp Gln Leu
65                  70                  75                  80

Val Met Gln Arg Ser Asp Gln Leu Arg Glu Leu Tyr Glu Ala Leu Leu
                85                  90                  95

Ser Gly Glu Gly Asp Arg Arg Ala Ala Pro Ala Arg Pro Ala Gly Ser
            100                 105                 110

Leu Ser Pro Glu Asp Leu Gly Asp Thr Glu Trp Tyr Tyr Val Val Ser
        115                 120                 125

Met Thr Tyr Ala Phe Arg Pro Gly Gln Gly Leu Pro Gly Arg Ser Phe
    130                 135                 140

Ala Ser Asp Glu His Val Trp Leu Cys Asn Ala His Leu Ala Gly Ser
145                 150                 155                 160

Lys Ala Phe Pro Arg Ala Leu Leu Ala Lys Ser Ala Ser Ile Gln Ser
                165                 170                 175

Ile Leu Cys Ile Pro Val Met Gly Gly Val Leu Glu Leu Gly Thr Thr
            180                 185                 190

Asp Thr Val Pro Glu Ala Pro Asp Leu Val Ser Arg Ala Thr Ala Ala
        195                 200                 205

Phe Trp Glu Pro Gln Cys Pro Ser Ser Pro Ser Gly Arg Ala Asn
    210                 215                 220

Glu Thr Gly Glu Ala Ala Ala Asp Asp Gly Thr Phe Ala Phe Glu Glu
225                 230                 235                 240
```

```
Leu Asp His Asn Asn Gly Met Asp Asp Ile Glu Ala Met Thr Ala Ala
                245                 250                 255

Gly Gly His Gly Gln Glu Glu Glu Leu Arg Leu Arg Glu Ala Glu Ala
            260                 265                 270

Leu Ser Asp Asp Ala Ser Leu Glu His Ile Thr Lys Glu Ile Glu Glu
        275                 280                 285

Phe Tyr Ser Leu Cys Asp Glu Met Asp Leu Gln Ala Leu Pro Leu Pro
    290                 295                 300

Leu Glu Asp Gly Trp Thr Val Asp Ala Ser Asn Phe Glu Val Pro Cys
305                 310                 315                 320

Ser Ser Pro Gln Pro Ala Pro Pro Val Asp Arg Ala Thr Ala Asn
                325                 330                 335

Val Ala Ala Asp Ala Ser Arg Ala Pro Val Tyr Gly Ser Arg Ala Thr
                340                 345                 350

Ser Phe Met Ala Trp Thr Arg Ser Gln Gln Ser Ser Cys Ser Asp
                355                 360                 365

Asp Ala Ala Pro Ala Ala Val Val Pro Ala Ile Glu Glu Pro Gln Arg
                370                 375                 380

Leu Leu Lys Lys Val Val Ala Gly Gly Ala Trp Glu Ser Cys Gly
385                 390                 395                 400

Gly Ala Thr Gly Ala Ala Gln Glu Met Ser Gly Thr Gly Thr Lys Asn
                405                 410                 415

His Val Met Ser Glu Arg Lys Arg Arg Glu Lys Leu Asn Glu Met Phe
                420                 425                 430

Leu Val Leu Lys Ser Leu Leu Pro Ser Ile His Arg Val Asn Lys Ala
            435                 440                 445

Ser Ile Leu Ala Glu Thr Ile Ala Tyr Leu Lys Glu Leu Gln Arg Arg
450                 455                 460

Val Gln Glu Leu Glu Ser Ser Arg Glu Pro Ala Ser Arg Pro Ser Glu
465                 470                 475                 480

Thr Thr Thr Arg Leu Ile Thr Arg Pro Ser Arg Gly Asn Asn Glu Ser
                485                 490                 495

Val Arg Lys Glu Val Cys Ala Gly Ser Lys Arg Lys Ser Pro Glu Leu
                500                 505                 510

Gly Arg Asp Asp Val Glu Arg Pro Pro Val Leu Thr Met Asp Ala Gly
                515                 520                 525

Thr Ser Asn Val Thr Val Thr Val Ser Asp Lys Asp Val Leu Leu Glu
        530                 535                 540

Val Gln Cys Arg Trp Glu Glu Leu Leu Met Thr Arg Val Phe Asp Ala
545                 550                 555                 560

Ile Lys Ser Leu His Leu Asp Val Leu Ser Val Gln Ala Ser Ala Pro
                565                 570                 575

Asp Gly Phe Met Gly Leu Lys Ile Arg Ala Gln Phe Ala Gly Ser Gly
                580                 585                 590

Ala Val Val Pro Trp Met Ile Ser Glu Ala Leu Arg Lys Ala Ile Gly
            595                 600                 605

Lys Arg
    610

<210> SEQ ID NO 44
<211> LENGTH: 518
<212> TYPE: PRT
<213> ORGANISM: Arabidopsis thaliana
<220> FEATURE:
```

```
<221> NAME/KEY: MISC_FEATURE
<222> LOCATION: (1)..(518)
<223> OTHER INFORMATION: BHLH transcription factor, AtTT8

<400> SEQUENCE: 44
```

Met Asp Glu Ser Ser Ile Ile Pro Ala Glu Lys Val Ala Gly Ala Glu
1               5                   10                  15

Lys Lys Glu Leu Gln Gly Leu Leu Lys Thr Ala Val Gln Ser Val Asp
            20                  25                  30

Trp Thr Tyr Ser Val Phe Trp Gln Phe Cys Pro Gln Gln Arg Val Leu
        35                  40                  45

Val Trp Gly Asn Gly Tyr Tyr Asn Gly Ala Ile Lys Thr Arg Lys Thr
    50                  55                  60

Thr Gln Pro Ala Glu Val Thr Ala Glu Ala Ala Leu Glu Arg Ser
65                  70                  75                  80

Gln Gln Leu Arg Glu Leu Tyr Glu Thr Leu Leu Ala Gly Glu Ser Thr
                85                  90                  95

Ser Glu Ala Arg Ala Cys Thr Ala Leu Ser Pro Glu Asp Leu Thr Glu
                100                 105                 110

Thr Glu Trp Phe Tyr Leu Met Cys Val Ser Phe Ser Phe Pro Pro Pro
            115                 120                 125

Ser Gly Met Pro Gly Lys Ala Tyr Ala Arg Arg Lys His Val Trp Leu
        130                 135                 140

Ser Gly Ala Asn Glu Val Asp Ser Lys Thr Phe Ser Arg Ala Ile Leu
145                 150                 155                 160

Ala Lys Ser Ala Lys Ile Gln Thr Val Val Cys Ile Pro Met Leu Asp
                165                 170                 175

Gly Val Val Glu Leu Gly Thr Thr Lys Lys Val Arg Glu Asp Val Glu
            180                 185                 190

Phe Val Glu Leu Thr Lys Ser Phe Phe Tyr Asp His Cys Lys Thr Asn
        195                 200                 205

Pro Lys Pro Ala Leu Ser Glu His Ser Thr Tyr Glu Val His Glu Glu
    210                 215                 220

Ala Glu Asp Glu Glu Val Glu Glu Glu Met Thr Met Ser Glu Glu
225                 230                 235                 240

Met Arg Leu Gly Ser Pro Asp Asp Glu Asp Val Ser Asn Gln Asn Leu
                245                 250                 255

His Ser Asp Leu His Ile Glu Ser Thr His Thr Leu Asp Thr His Met
            260                 265                 270

Asp Met Met Asn Leu Met Glu Glu Gly Gly Asn Tyr Ser Gln Thr Val
        275                 280                 285

Thr Thr Leu Leu Met Ser His Pro Thr Ser Leu Leu Ser Asp Ser Val
    290                 295                 300

Ser Thr Ser Ser Tyr Ile Gln Ser Ser Phe Ala Thr Trp Arg Val Glu
305                 310                 315                 320

Asn Gly Lys Glu His Gln Gln Val Lys Thr Ala Pro Ser Ser Gln Trp
                325                 330                 335

Val Leu Lys Gln Met Ile Phe Arg Val Pro Phe Leu His Asp Asn Thr
            340                 345                 350

Lys Asp Lys Arg Leu Pro Arg Glu Asp Leu Ser His Val Val Ala Glu
        355                 360                 365

Arg Arg Arg Arg Glu Lys Leu Asn Glu Lys Phe Ile Thr Leu Arg Ser
    370                 375                 380

Met Val Pro Phe Val Thr Lys Met Asp Lys Val Ser Ile Leu Gly Asp

```
                385                 390                 395                 400
        Thr Ile Ala Tyr Val Asn His Leu Arg Lys Arg Val His Glu Leu Glu
                        405                 410                 415

Asn Thr His His Glu Gln Gln His Lys Arg Thr Arg Thr Cys Lys Arg
                        420                 425                 430

Lys Thr Ser Glu Glu Val Glu Ser Ile Ile Glu Asn Asp Val Leu
                        435                 440                 445

Leu Glu Met Arg Cys Glu Tyr Arg Asp Gly Leu Leu Leu Asp Ile Leu
                450                 455                 460

Gln Val Leu His Glu Leu Gly Ile Glu Thr Thr Ala Val His Thr Ser
        465                 470                 475                 480

Val Asn Asp His Asp Phe Glu Ala Glu Ile Arg Ala Lys Val Arg Gly
                        485                 490                 495

Lys Lys Ala Ser Ile Ala Glu Val Lys Arg Ala Ile His Gln Val Ile
                        500                 505                 510

Ile His Asp Thr Asn Leu
                        515

<210> SEQ ID NO 45
<211> LENGTH: 701
<212> TYPE: PRT
<213> ORGANISM: Vitis vinifera
<220> FEATURE:
<221> NAME/KEY: PEPTIDE
<222> LOCATION: (1)..(701)
<223> OTHER INFORMATION: BHLH transcription factor (VvMyc1)

<400> SEQUENCE: 45

Met Ala Ala Pro Pro Asn Ser Arg Leu Gln Ser Met Leu Gln Ser Ala
        1               5                   10                  15

Val Gln Ser Val Arg Trp Thr Tyr Ser Leu Phe Trp Gln Ile Cys Pro
                        20                  25                  30

Gln Gln Gly Ile Leu Val Trp Gly Asp Gly Tyr Tyr Asn Gly Ala Ile
                        35                  40                  45

Lys Thr Arg Lys Thr Val Gln Pro Met Glu Val Ser Ala Glu Glu Ala
                50                  55                  60

Ser Leu Gln Arg Ser Gln Gln Leu Arg Glu Leu Tyr Glu Ser Leu Ser
        65                  70                  75                  80

Ala Gly Glu Thr Asn Gln Pro Ala Arg Arg Pro Cys Ala Ala Leu Ser
                        85                  90                  95

Pro Glu Asp Leu Thr Glu Ser Glu Trp Phe Tyr Leu Met Cys Val Ser
                        100                 105                 110

Phe Ser Phe Pro Pro Gly Val Gly Leu Pro Gly Lys Ala Tyr Ala Lys
                        115                 120                 125

Arg His His Ile Trp Leu Ala Gly Ala Asn Glu Val Asp Ser Lys Val
                        130                 135                 140

Phe Ser Arg Ala Ile Leu Ala Lys Ser Ala Arg Val Gln Thr Val Val
        145                 150                 155                 160

Cys Ile Pro Leu Met Asp Gly Val Val Glu Phe Gly Thr Thr Glu Lys
                        165                 170                 175

Val Gln Glu Asp Leu Gly Phe Val Gln His Val Lys Ser Phe Phe Thr
                        180                 185                 190

Asp His His Leu His Asn His Pro Pro Lys Pro Ala Leu Ser Glu His
                        195                 200                 205

Ser Thr Ser Asn Pro Ala Thr Ser Ser Asp His Ser Arg Phe His Ser
                        210                 215                 220
```

```
Pro Pro Ile Gln Ala Ala Tyr Ala Ala Asp Pro Pro Ala Ser Asn
225                 230                 235                 240

Asn Gln Glu Glu Glu Glu Glu Glu Glu Glu Glu Glu Glu Glu Glu
            245                 250                 255

Glu Glu Glu Glu Glu Glu Glu Glu Glu Ala Glu Ser Asp Ser Glu
            260                 265                 270

Ala Glu Thr Gly Arg Asn Asn Arg Arg Val Arg Thr Gln Asn Thr Gly
            275                 280                 285

Thr Glu Gly Val Ala Gly Ser His Thr Ala Ala Glu Pro Ser Glu Leu
            290                 295                 300

Ile Gln Leu Glu Met Ser Glu Gly Ile Arg Leu Gly Ser Pro Asp Asp
305                 310                 315                 320

Gly Ser Asn Asn Leu Asp Ser Asp Phe His Met Leu Ala Val Ser Gln
                325                 330                 335

Pro Gly Ser Ser Val Asp His Gln Arg Arg Ala Asp Ser Tyr Arg Ala
            340                 345                 350

Glu Ser Ala Arg Arg Trp Pro Met Leu Gln Asp Pro Leu Cys Ser Ser
            355                 360                 365

Gly Leu Gln Gln Pro Pro Gln Pro Thr Gly Pro Pro Leu
370                 375                 380

Asp Glu Leu Ser Gln Glu Asp Thr His Tyr Ser Gln Thr Val Ser Thr
385                 390                 395                 400

Ile Leu Gln His Gln Pro Asn Arg Trp Ser Glu Ser Ser Ser Ser Gly
                405                 410                 415

Cys Ile Ala Pro Tyr Ser Ser Gln Ser Ala Phe Ala Lys Trp Thr Thr
            420                 425                 430

Arg Cys Asp His His His His Pro Met Ala Val Glu Gly Thr Ser Gln
            435                 440                 445

Trp Leu Leu Lys Tyr Ile Leu Phe Ser Val Pro Phe Leu His Thr Lys
450                 455                 460

Tyr Arg Asp Glu Asn Ser Pro Lys Ser Arg Asp Gly Asp Ser Ala Gly
465                 470                 475                 480

Arg Phe Arg Lys Gly Thr Pro Gln Asp Glu Leu Ser Ala Asn His Val
            485                 490                 495

Leu Ala Glu Arg Arg Arg Arg Glu Lys Leu Asn Glu Arg Phe Ile Ile
            500                 505                 510

Leu Arg Ser Leu Val Pro Phe Val Thr Lys Met Asp Lys Ala Ser Ile
            515                 520                 525

Leu Gly Asp Thr Ile Glu Tyr Val Lys Gln Leu Arg Lys Lys Ile Gln
            530                 535                 540

Asp Leu Glu Ala Arg Thr Arg Gln Met Glu Val Glu Gln Arg Ser Arg
545                 550                 555                 560

Gly Ser Asp Ser Val Arg Ser Lys Glu His Arg Ile Gly Ser Gly Ser
            565                 570                 575

Val Asp Arg Asn Arg Ala Val Val Ala Gly Ser Asp Lys Arg Lys Leu
            580                 585                 590

Arg Ile Val Glu Gly Ser Thr Gly Ala Lys Pro Lys Val Val Asp Ser
            595                 600                 605

Pro Pro Ala Ala Val Glu Gly Thr Thr Thr Val Glu Val Ser Ile
            610                 615                 620

Ile Glu Ser Asp Ala Leu Leu Glu Met Gln Cys Pro Tyr Arg Glu Gly
625                 630                 635                 640
```

Leu Leu Leu Asp Val Met Gln Met Leu Arg Glu Leu Arg Leu Glu Thr
            645                 650                 655

Thr Thr Val Gln Ser Ser Leu Thr Asn Gly Val Phe Val Ala Glu Leu
        660                 665                 670

Arg Ala Lys Val Lys Glu Asn Ala Ser Gly Lys Lys Ala Ser Ile Met
        675                 680                 685

Glu Val Lys Arg Ala Ile Asn Gln Ile Ile Pro Gln Cys
690                 695                 700

<210> SEQ ID NO 46
<211> LENGTH: 23
<212> TYPE: DNA
<213> ORGANISM: Artificial Sequence
<220> FEATURE:
<223> OTHER INFORMATION: synthetic PCR amplification phosphorylated
      primer F-p35S for promoter p35S

<400> SEQUENCE: 46
gtcaacatgg tggagcacga cac                                              23

<210> SEQ ID NO 47
<211> LENGTH: 39
<212> TYPE: DNA
<213> ORGANISM: Artificial Sequence
<220> FEATURE:
<223> OTHER INFORMATION: synthetic PCR amplification phosphorylated
      primer R-p35S for promoter p35S

<400> SEQUENCE: 47
cgagaatcta gattgtcctc tccaaatgaa atgaacttc                             39

<210> SEQ ID NO 48
<211> LENGTH: 50
<212> TYPE: DNA
<213> ORGANISM: Artificial Sequence
<220> FEATURE:
<223> OTHER INFORMATION: synthetic amplification oligonucleotide for
      schl-qsuB

<400> SEQUENCE: 48
ggggacaagt ttgtacaaaa aagcaggctt catggcttcg atctcctcct                 50

<210> SEQ ID NO 49
<211> LENGTH: 56
<212> TYPE: DNA
<213> ORGANISM: Artificial Sequence
<220> FEATURE:
<223> OTHER INFORMATION: synthetic amplification oligonucleotide for
      schl-qsuB

<400> SEQUENCE: 49
ggggaccact ttgtacaaga aagctgggtc gtttgggata cctctctcta aatctc          56

<210> SEQ ID NO 50
<211> LENGTH: 55
<212> TYPE: DNA
<213> ORGANISM: Artificial Sequence
<220> FEATURE:
<223> OTHER INFORMATION: synthetic amplification oligonucleotide for
      hydrooxycinnamoyl-CoA shikimate/quinate
      hydroxycinnamoyltransferase (AtHCT, HCT)

<400> SEQUENCE: 50
ggggacaagt ttgtacaaaa aagcaggctt catgaaaatt aacatcagag attcc           55

```
<210> SEQ ID NO 51
<211> LENGTH: 58
<212> TYPE: DNA
<213> ORGANISM: Artificial Sequence
<220> FEATURE:
<223> OTHER INFORMATION: synthetic amplification oligonucleotide for
      hydrooxycinnamoyl-CoA shikimate/quinate
      hydroxycinnamoyltransferase (AtHCT, HCT)

<400> SEQUENCE: 51
ggggaccact ttgtacaaga aagctgggtc tcatatctca aacaaaaact tctcaaac          58
```